United States Patent
Phenix et al.

(10) Patent No.: US 11,951,212 B2
(45) Date of Patent: *Apr. 9, 2024

(54) PHARMACEUTICAL COMPOSITIONS FOR THE TREATMENT OF CYSTIC FIBROSIS TRANSMEMBRANE CONDUCTANCE REGULATOR MEDIATED DISEASES

(71) Applicant: Vertex Pharmaceuticals Incorporated, Boston, MA (US)

(72) Inventors: Brian Dean Phenix, Acton, MA (US); Laurent Jean-Claude Bagnol, Burlington, MA (US); Geoffrey Glen Brodeur, Somerville, MA (US); Sachin Chandran, Somerville, MA (US); Eleni Dokou, Cambridge, MA (US); Lori Ann Ferris, Medford, MA (US); Dragutin Knezic, Watertown, MA (US); Katie Lynn McCarty, Watertown, MA (US); Ales Medek, Winchester, MA (US); Sara A. Waggener, N. Billerica, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/204,679

(22) Filed: Mar. 17, 2021

(65) Prior Publication Data

US 2021/0308053 A1   Oct. 7, 2021

Related U.S. Application Data

(63) Continuation of application No. 16/232,540, filed on Dec. 26, 2018, now Pat. No. 10,980,746, which is a continuation of application No. 14/686,117, filed on Apr. 14, 2015, now Pat. No. 10,206,877.

(60) Provisional application No. 62/059,287, filed on Oct. 3, 2014, provisional application No. 61/979,848, filed on Apr. 15, 2014.

(51) Int. Cl.

| | |
|---|---|
| *A61K 31/404* | (2006.01) |
| *A61K 9/14* | (2006.01) |
| *A61K 9/16* | (2006.01) |
| *A61K 9/20* | (2006.01) |
| *A61K 31/443* | (2006.01) |
| *A61K 31/47* | (2006.01) |
| *A61K 31/4709* | (2006.01) |
| *A61K 31/4725* | (2006.01) |
| *A61K 45/06* | (2006.01) |
| *C07D 209/04* | (2006.01) |
| *C07D 215/00* | (2006.01) |
| *C07D 215/56* | (2006.01) |
| *C07D 405/12* | (2006.01) |

(52) U.S. Cl.
CPC ............... *A61K 9/14* (2013.01); *A61K 9/146* (2013.01); *A61K 9/16* (2013.01); *A61K 9/1652* (2013.01); *A61K 9/2054* (2013.01); *A61K 9/2077* (2013.01); *A61K 31/404* (2013.01); *A61K 31/443* (2013.01); *A61K 31/47* (2013.01); *A61K 31/4709* (2013.01); *A61K 31/4725* (2013.01); *A61K 45/06* (2013.01); *C07D 209/04* (2013.01); *C07D 215/00* (2013.01); *C07D 215/56* (2013.01); *C07D 405/12* (2013.01)

(58) Field of Classification Search
CPC . A61K 9/14; A61K 9/146; A61K 9/16; A61K 9/1652; A61K 9/2054; A61K 9/2077; A61K 31/404; A61K 31/443; A61K 31/47; A61K 31/4709; A61K 45/06; C07D 209/04; C07D 215/00; C07D 405/12
See application file for complete search history.

(56) References Cited

U.S. PATENT DOCUMENTS

| | | | |
|---|---|---|---|
| 4,138,397 | A | 2/1979 | Böhme |
| 5,304,121 | A | 4/1994 | Sahatjian |
| 5,886,026 | A | 3/1999 | Hunter et al. |
| 6,099,562 | A | 8/2000 | Ding et al. |
| 6,426,331 | B1 | 7/2002 | McKinney et al. |
| 6,479,483 | B2 | 11/2002 | Bös et al. |
| 6,770,637 | B2 | 8/2004 | Godel et al. |
| 6,777,400 | B2 | 8/2004 | Biggadike et al. |
| 6,992,096 | B2 | 1/2006 | Karp et al. |
| 7,202,262 | B2 | 4/2007 | Karp et al. |
| 7,304,080 | B2 | 12/2007 | Karp et al. |

(Continued)

FOREIGN PATENT DOCUMENTS

| | | |
|---|---|---|
| CN | 1512987 A | 7/2004 |
| CN | 1898221 A | 1/2007 |

(Continued)

OTHER PUBLICATIONS

Nazih, A. and Heissler D. (2002) "One-pot Conversion of t-Butyl Carbamates to Amides with Acyl Halide-Methanol Mixtures" *Synthesis* 2:203-206.

(Continued)

*Primary Examiner* — Alma Pipic
(74) *Attorney, Agent, or Firm* — Finnegan, Henderson, Farabow, Garrett & Dunner, LLP

(57) ABSTRACT

The present invention features compositions comprising a plurality of therapeutic agents wherein the presence of one therapeutic agent enhances the properties of at least one other therapeutic agent. In one embodiment, the therapeutic agents are cystic fibrosis transmembrane conductance regulators (CFTR) such as a CFTR corrector or CFTR potentiator for the treatment of CFTR mediated diseases such as cystic fibrosis. Methods and kits thereof are also disclosed.

37 Claims, 15 Drawing Sheets

(56) References Cited

U.S. PATENT DOCUMENTS

| | | |
|---|---|---|
| 7,407,976 B2 | 8/2008 | Miller et al. |
| 7,419,991 B2 | 9/2008 | Karp et al. |
| 7,495,103 B2 | 2/2009 | Hadida-Ruah et al. |
| 7,553,855 B2 | 6/2009 | Young et al. |
| 7,582,665 B2 | 9/2009 | Takemoto et al. |
| 7,598,412 B2 | 10/2009 | Hadida Ruah et al. |
| 7,645,789 B2 | 1/2010 | Hadida Ruah et al. |
| 7,659,268 B2 | 2/2010 | Hadida-Ruah et al. |
| 7,671,221 B2 | 3/2010 | Hadida Ruah et al. |
| 7,691,902 B2 | 4/2010 | Hadida Ruah et al. |
| 7,728,023 B2 | 6/2010 | Takeuchi et al. |
| 7,741,321 B2 | 6/2010 | Hadida Ruah et al. |
| 7,754,739 B2 | 7/2010 | Hadida Ruah et al. |
| 7,772,259 B2 | 8/2010 | Karp et al. |
| 7,776,905 B2 | 8/2010 | Hadida Ruah et al. |
| 7,846,951 B2 | 12/2010 | Miller et al. |
| 7,893,094 B2 | 2/2011 | Pollard et al. |
| 7,906,516 B2 | 3/2011 | Tsaklakidis et al. |
| 7,956,052 B2 | 6/2011 | Hadida Ruah et al. |
| 7,973,038 B2 | 7/2011 | Hadida Ruah et al. |
| 7,973,169 B2 | 7/2011 | Hadida Ruah et al. |
| 7,977,322 B2 | 7/2011 | Ruah et al. |
| 7,999,113 B2 | 8/2011 | Hadida-Ruah et al. |
| 8,012,999 B2 | 9/2011 | Hadida Ruah et al. |
| 8,039,491 B2 | 10/2011 | Hadida Ruah et al. |
| 8,076,357 B2 | 12/2011 | Young et al. |
| 8,101,767 B2 | 1/2012 | Ruah et al. |
| 8,124,781 B2 | 2/2012 | Siesel |
| 8,163,772 B2 | 4/2012 | DeMattei et al. |
| 8,188,283 B2 | 5/2012 | Binch et al. |
| 8,227,615 B2 | 7/2012 | Hadida-Ruah et al. |
| 8,232,302 B2 | 7/2012 | Miller et al. |
| 8,242,149 B2 | 8/2012 | Ruah et al. |
| 8,299,099 B2 | 10/2012 | Ruah et al. |
| 8,314,239 B2 | 11/2012 | Binch et al. |
| 8,314,256 B2 | 11/2012 | Ruah et al. |
| 8,318,733 B2 | 11/2012 | Hadida-Ruah et al. |
| 8,324,207 B2 | 12/2012 | Hadida Ruah et al. |
| 8,324,242 B2 | 12/2012 | Ruah et al. |
| 8,344,147 B2 | 1/2013 | Ambhaikar et al. |
| 8,354,427 B2 | 1/2013 | Van Goor |
| 8,362,253 B2 | 1/2013 | DeMattei et al. |
| 8,367,660 B2 | 2/2013 | Binch et al. |
| 8,389,727 B2 | 3/2013 | Zhang et al. |
| 8,399,479 B2 | 3/2013 | Binch et al. |
| 8,404,849 B2 | 3/2013 | Sun et al. |
| 8,404,865 B2 | 3/2013 | Ambhaikar et al. |
| 8,410,132 B2 | 4/2013 | Binch et al. |
| 8,410,274 B2 | 4/2013 | Hurter et al. |
| 8,415,387 B2 | 4/2013 | Ruah et al. |
| 8,431,605 B2 | 4/2013 | Hadida Ruah et al. |
| 8,436,014 B2 | 5/2013 | Zhang et al. |
| 8,461,156 B2 | 6/2013 | Hadida Ruah et al. |
| 8,461,342 B2 | 6/2013 | Siesel |
| 8,461,352 B2 | 6/2013 | Ambhaikar et al. |
| 8,471,029 B2 | 6/2013 | Arekar et al. |
| 8,476,442 B2 | 7/2013 | DeMattei et al. |
| 8,507,524 B2 | 8/2013 | Ruah et al. |
| 8,507,534 B2 | 8/2013 | Keshavarz-Shokri et al. |
| 8,507,687 B2 | 8/2013 | Keshavarz-Shokri et al. |
| 8,513,282 B2 | 8/2013 | Binch et al. |
| 8,524,767 B2 | 9/2013 | Miller et al. |
| 8,524,910 B2 | 9/2013 | Hadida Ruah et al. |
| 8,541,453 B2 | 9/2013 | Hadida-Ruah et al. |
| 8,552,006 B2 | 10/2013 | Binch et al. |
| 8,552,034 B2 | 10/2013 | Verwijs et al. |
| 8,563,573 B2 | 10/2013 | Ruah et al. |
| 8,563,593 B2 | 10/2013 | Alargova et al. |
| 8,575,209 B2 | 11/2013 | Ruah et al. |
| 8,586,615 B2 | 11/2013 | Hadida-Ruah et al. |
| 8,592,602 B2 | 11/2013 | Siesel |
| 8,598,181 B2 | 12/2013 | Hadida Ruah et al. |
| 8,598,205 B2 | 12/2013 | Binch et al. |
| 8,604,203 B2 | 12/2013 | Binch et al. |
| 8,609,703 B2 | 12/2013 | Ruah et al. |
| 8,614,325 B2 | 12/2013 | Yang et al. |
| 8,614,327 B2 | 12/2013 | Sheth et al. |
| 8,623,894 B2 | 1/2014 | DeMattei et al. |
| 8,623,905 B2 | 1/2014 | Ruah et al. |
| 8,629,162 B2 | 1/2014 | Hadida-Ruah et al. |
| 8,633,189 B2 | 1/2014 | Binch et al. |
| 8,642,609 B2 | 2/2014 | Makings et al. |
| 8,653,103 B2 | 2/2014 | Keshavarz-Shokri et al. |
| 8,674,108 B2 | 3/2014 | Luisi et al. |
| 8,710,075 B2 | 4/2014 | Binch et al. |
| 8,716,338 B2 | 5/2014 | Young |
| 8,722,704 B2 | 5/2014 | Hadida Ruah et al. |
| 8,741,922 B2 | 6/2014 | Zhang et al. |
| 8,741,925 B2 | 6/2014 | Hadida-Ruah et al. |
| 8,741,933 B2 | 6/2014 | Hadida Ruah et al. |
| 8,741,939 B2 | 6/2014 | Hadida Ruah et al. |
| 8,742,122 B2 | 6/2014 | Keshavarz-Shokri et al. |
| 8,748,612 B2 | 6/2014 | Binch et al. |
| 8,754,222 B2 | 6/2014 | Ambhaikar et al. |
| 8,754,224 B2 | 6/2014 | Hurter et al. |
| 8,759,335 B2 | 6/2014 | Hadida Ruah et al. |
| 8,765,957 B2 | 7/2014 | DeMattei et al. |
| 8,785,476 B2 | 7/2014 | Arekar et al. |
| 8,785,640 B2 | 7/2014 | Binch et al. |
| 8,796,308 B2 | 8/2014 | Yang et al. |
| 8,796,312 B2 | 8/2014 | Hadida Ruah et al. |
| 8,802,700 B2 | 8/2014 | Sheth et al. |
| 8,802,844 B2 | 8/2014 | Gallardo-Godoy |
| 8,802,868 B2 | 8/2014 | Keshavarz-Shokri et al. |
| 8,816,093 B2 | 8/2014 | Siesel |
| 8,822,451 B2 | 9/2014 | Ruah et al. |
| 8,829,204 B2 | 9/2014 | Hadida-Ruah et al. |
| 8,835,639 B2 | 9/2014 | DeMattei et al. |
| 8,846,718 B2 | 9/2014 | Keshavarz-Shokri et al. |
| 8,846,753 B2 | 9/2014 | Hadida Ruah et al. |
| 8,853,254 B2 | 10/2014 | Hadida Ruah et al. |
| 8,853,415 B2 | 10/2014 | Hadida Ruah et al. |
| 8,883,206 B2 | 11/2014 | Doukou et al. |
| 8,884,018 B2 | 11/2014 | Ambhaikar et al. |
| 8,889,875 B2 | 11/2014 | Ruah et al. |
| 8,912,199 B2 | 12/2014 | Hadida Ruah et al. |
| 8,952,049 B2 | 2/2015 | Ruah et al. |
| 8,952,050 B2 | 2/2015 | Ruah et al. |
| 8,962,856 B2 | 2/2015 | Hadida-Ruah et al. |
| 8,969,382 B2 | 3/2015 | Binch et al. |
| 8,969,386 B2 | 3/2015 | Hadida-Ruah et al. |
| 8,969,574 B2 | 3/2015 | Keshavarz-Shokri et al. |
| 8,993,600 B2 | 3/2015 | Hadida Ruah et al. |
| 8,999,976 B2 | 4/2015 | Binch et al. |
| 9,012,473 B2 | 4/2015 | Hadida Ruah et al. |
| 9,012,496 B2 | 4/2015 | Alargova et al. |
| 9,012,652 B2 | 4/2015 | Siesel |
| 9,035,072 B2 | 5/2015 | Belmont et al. |
| 9,045,425 B2 | 6/2015 | Luisi et al. |
| 9,051,303 B2 | 6/2015 | Keshavarz-Shokri et al. |
| 9,051,324 B2 | 6/2015 | Binch et al. |
| 9,079,916 B2 | 7/2015 | Hadida-Ruah et al. |
| 9,090,619 B2 | 7/2015 | Hadida-Ruah et al. |
| 9,102,672 B2 | 8/2015 | Hadida-Ruah et al. |
| 9,127,162 B2 | 9/2015 | Harders et al. |
| 9,139,530 B2 | 9/2015 | Hurter et al. |
| 9,150,552 B2 | 10/2015 | Keshavarz-Shokri et al. |
| 9,192,606 B2 | 11/2015 | Young |
| 9,216,969 B2 | 12/2015 | Ruah et al. |
| 9,241,934 B2 | 1/2016 | Verwijs et al. |
| 9,249,131 B2 | 2/2016 | Hadida Ruah et al. |
| 9,254,291 B2 | 2/2016 | Looker et al. |
| 9,314,455 B2 | 4/2016 | Keshavarz-Shokri et al. |
| 9,321,725 B2 | 4/2016 | Miller et al. |
| 9,351,962 B2 | 5/2016 | Ruah et al. |
| 9,371,287 B2 | 6/2016 | DeMattei et al. |
| 9,399,648 B2 | 7/2016 | Gallardo-Godoy |
| 9,434,717 B2 | 9/2016 | Keshavarz-Shokri et al. |
| 9,504,683 B2 | 11/2016 | Hadida Ruah et al. |
| 9,522,145 B2 | 12/2016 | Hadida Ruah et al. |
| 9,550,761 B2 | 1/2017 | Hadida-Ruah et al. |
| 9,670,163 B2 | 6/2017 | Hurter et al. |
| 9,701,639 B2 | 7/2017 | Strohmeier et al. |
| 9,725,440 B2 | 8/2017 | Hadida-Ruah et al. |

(56) References Cited

U.S. PATENT DOCUMENTS

| | | |
|---|---|---|
| 9,732,080 B2 | 8/2017 | Hadida-Ruah et al. |
| 9,751,839 B2 | 9/2017 | DeMattei et al. |
| 9,751,890 B2 | 9/2017 | Hadida Ruah et al. |
| 9,758,510 B2 | 9/2017 | Hadida Ruah et al. |
| 9,776,968 B2 | 10/2017 | Siesel |
| 9,840,499 B2 | 12/2017 | Keshavarz-Shokri et al. |
| 9,931,334 B2 | 4/2018 | Hurter et al. |
| 9,974,781 B2 | 5/2018 | Hadida Ruah et al. |
| 10,022,352 B2 | 7/2018 | Hadida Ruah et al. |
| 10,058,546 B2 | 8/2018 | Alargova et al. |
| 10,071,979 B2 | 9/2018 | Tanoury et al. |
| 10,076,513 B2 | 9/2018 | Verwijs et al. |
| 10,081,621 B2 | 9/2018 | Keshavarz-Shokri et al. |
| 10,206,877 B2 | 2/2019 | Phenix et al. |
| 10,231,932 B2 | 3/2019 | Swinney et al. |
| 10,239,867 B2 | 3/2019 | Hadida Ruah et al. |
| 10,272,046 B2 | 4/2019 | Dokou et al. |
| 10,302,602 B2 | 5/2019 | Borsje et al. |
| 10,537,565 B2 | 1/2020 | Hurter et al. |
| 10,597,384 B2 | 3/2020 | Keshavarz-Shokri et al. |
| 10,626,111 B2 | 4/2020 | Hadida Ruah et al. |
| 10,646,481 B2 | 5/2020 | William et al. |
| 10,662,192 B2 | 5/2020 | Hadida-Ruah et al. |
| 10,906,891 B2 | 2/2021 | Keshavarz-Shokri et al. |
| 10,975,061 B2 | 4/2021 | Hadida Ruah et al. |
| 10,980,746 B2 | 4/2021 | Phenix et al. |
| 10,987,348 B2 | 4/2021 | Hadida Ruah et al. |
| 11,052,075 B2 | 7/2021 | Verwijs et al. |
| 11,084,804 B2 | 8/2021 | Hadida Ruah et al. |
| 11,578,062 B2 | 2/2023 | Keshavarz-Shokri et al. |
| 11,639,347 B2 | 5/2023 | Hadida Ruah et al. |
| 2003/0125315 A1 | 7/2003 | Mjalli et al. |
| 2003/0219489 A1 | 11/2003 | Curatolo et al. |
| 2004/0105820 A1 | 6/2004 | Weers et al. |
| 2005/0070718 A1 | 3/2005 | Lubisch et al. |
| 2005/0113423 A1 | 5/2005 | Van Goor et al. |
| 2005/0215614 A1 | 9/2005 | Singh et al. |
| 2005/0222271 A1 | 10/2005 | Huang |
| 2006/0003005 A1 | 1/2006 | Cao et al. |
| 2006/0004010 A1 | 1/2006 | Habashita et al. |
| 2006/0035943 A1 | 2/2006 | Karp et al. |
| 2006/0148863 A1 | 7/2006 | Karp et al. |
| 2006/0148864 A1 | 7/2006 | Karp et al. |
| 2006/0217448 A1 | 9/2006 | Kelly et al. |
| 2007/0218138 A1 | 9/2007 | Bittorf et al. |
| 2008/0081814 A1 | 4/2008 | Cezanne et al. |
| 2008/0132560 A1 | 6/2008 | Chow et al. |
| 2008/0138803 A1 | 6/2008 | Galvan-Goldman et al. |
| 2008/0260820 A1 | 10/2008 | Borrelly et al. |
| 2009/0105272 A1 | 4/2009 | Grootenhuis et al. |
| 2009/0176839 A1 | 7/2009 | Keshavarz-Shokri et al. |
| 2009/0246820 A1 | 10/2009 | Singh et al. |
| 2009/0270465 A1 | 10/2009 | Albright et al. |
| 2010/0036130 A1 | 2/2010 | Siesel |
| 2010/0074949 A1 | 3/2010 | Rowe et al. |
| 2010/0125090 A1 | 5/2010 | Hadida Ruah et al. |
| 2010/0144798 A1 | 6/2010 | Van Goor et al. |
| 2010/0256184 A1 | 10/2010 | Rowe et al. |
| 2011/0064811 A1 | 3/2011 | Hurter et al. |
| 2011/0098311 A1 | 4/2011 | Van Goor et al. |
| 2011/0098484 A1 | 4/2011 | Saitoh et al. |
| 2011/0177999 A1 | 7/2011 | Singh et al. |
| 2011/0251253 A1 | 10/2011 | Keshavarz-Shokri et al. |
| 2011/0257223 A1 | 10/2011 | Van Goor et al. |
| 2011/0288122 A1 | 11/2011 | Van Goor et al. |
| 2012/0035179 A1 | 2/2012 | Hadida-Ruah et al. |
| 2012/0046330 A1 | 2/2012 | Alargova et al. |
| 2012/0064157 A1 | 3/2012 | Dokou et al. |
| 2012/0122921 A1 | 5/2012 | DeMattei et al. |
| 2012/0122922 A1 | 5/2012 | Young et al. |
| 2012/0184583 A1 | 7/2012 | Van Goor et al. |
| 2012/0220625 A1 | 8/2012 | Rowe et al. |
| 2012/0232059 A1 | 9/2012 | Hadida-Ruah et al. |
| 2012/0258983 A1 | 10/2012 | Rowe et al. |
| 2013/0012536 A1 | 1/2013 | Hadida Ruah et al. |
| 2013/0018071 A1 | 1/2013 | Arekar et al. |
| 2013/0085158 A1 | 4/2013 | Keshavarz-Shokri et al. |
| 2013/0090354 A1 | 4/2013 | Van Goor et al. |
| 2013/0095181 A1 | 4/2013 | Verwijs et al. |
| 2013/0131107 A1 | 5/2013 | Van Goor et al. |
| 2013/0143919 A1 | 6/2013 | Van Goor et al. |
| 2013/0158071 A1 | 6/2013 | Van Goor et al. |
| 2013/0186801 A1 | 7/2013 | Verwijs et al. |
| 2013/0224293 A1 | 8/2013 | Dokou et al. |
| 2013/0231368 A1 | 9/2013 | Zhang et al. |
| 2013/0245010 A1 | 9/2013 | Hadida Ruah et al. |
| 2013/0245011 A1 | 9/2013 | Hadida Ruah et al. |
| 2013/0303484 A1 | 11/2013 | Grootenhuis et al. |
| 2013/0331567 A1 | 12/2013 | Hadida-Ruah et al. |
| 2014/0023706 A1 | 1/2014 | Verwijs et al. |
| 2014/0094499 A1 | 4/2014 | Alargova et al. |
| 2014/0112988 A1 | 4/2014 | Rowe et al. |
| 2014/0142138 A1 | 5/2014 | Van Goor et al. |
| 2014/0155431 A1 | 6/2014 | Hadida-Ruah et al. |
| 2014/0155626 A1 | 6/2014 | Hadida-Ruah et al. |
| 2014/0163011 A1 | 6/2014 | Hadida-Ruah et al. |
| 2014/0163068 A1 | 6/2014 | Verwijs et al. |
| 2014/0221424 A1 | 8/2014 | Zha |
| 2014/0235668 A1 | 8/2014 | Binch et al. |
| 2014/0243289 A1 | 8/2014 | Grootenhuis et al. |
| 2014/0303204 A1 | 10/2014 | Binch et al. |
| 2014/0303205 A1 | 10/2014 | Yang et al. |
| 2014/0315948 A1 | 10/2014 | Rowe et al. |
| 2014/0323521 A1 | 10/2014 | Van Goor et al. |
| 2014/0329855 A1 | 11/2014 | Arekar et al. |
| 2014/0336393 A1 | 11/2014 | Ambhaikar et al. |
| 2014/0343098 A1 | 11/2014 | Sheth et al. |
| 2014/0350281 A1 | 11/2014 | DeMattei et al. |
| 2015/0010628 A1 | 1/2015 | Dokou et al. |
| 2015/0024047 A1 | 1/2015 | Dokou et al. |
| 2015/0031722 A1 | 1/2015 | Hadida-Ruah et al. |
| 2015/0065487 A1 | 3/2015 | Hadida-Ruah et al. |
| 2015/0065497 A1 | 3/2015 | Hadida-Ruah et al. |
| 2015/0065500 A1 | 3/2015 | Hadida-Ruah et al. |
| 2015/0080431 A1 | 3/2015 | Van Goor et al. |
| 2015/0094304 A1 | 4/2015 | Ruah et al. |
| 2015/0119441 A1 | 4/2015 | Hadida Ruah et al. |
| 2015/0150879 A2 | 6/2015 | Van Goor et al. |
| 2015/0174098 A1 | 6/2015 | Ruah et al. |
| 2015/0182517 A1 | 7/2015 | Alargova et al. |
| 2015/0231142 A1 | 8/2015 | Van Goor et al. |
| 2015/0246031 A1 | 9/2015 | Dokou et al. |
| 2015/0293078 A1 | 10/2015 | Singh et al. |
| 2015/0336898 A1 | 11/2015 | Grootenhuis et al. |
| 2016/0022664 A2 | 1/2016 | Van Goor et al. |
| 2016/0022665 A2 | 1/2016 | Van Goor et al. |
| 2016/0039800 A1 | 2/2016 | Young |
| 2016/0067239 A9 | 3/2016 | Van Goor et al. |
| 2016/0143898 A1 | 5/2016 | Hadida Ruah et al. |
| 2016/0151335 A1 | 6/2016 | Tait et al. |
| 2016/0166540 A1 | 6/2016 | Looker et al. |
| 2016/0221952 A1 | 8/2016 | Yang et al. |
| 2016/0228414 A1 | 8/2016 | Hadida Ruah et al. |
| 2016/0318931 A1 | 11/2016 | Hadida Ruah et al. |
| 2016/0324788 A1 | 11/2016 | Verwijs |
| 2016/0324846 A1 | 11/2016 | Verwijs et al. |
| 2016/0354316 A1 | 12/2016 | Swinney et al. |
| 2017/0100340 A1 | 4/2017 | Dokou et al. |
| 2017/0107205 A1 | 4/2017 | Hadida Ruah et al. |
| 2017/0107206 A1 | 4/2017 | Hadida Ruah et al. |
| 2018/0008546 A1 | 1/2018 | Verwijs et al. |
| 2018/0153874 A1 | 6/2018 | Van Goor et al. |
| 2018/0280349 A1 | 10/2018 | Van Goor et al. |
| 2019/0038615 A1 | 2/2019 | Van Goor et al. |
| 2019/0070155 A1 | 3/2019 | Verwijs et al. |
| 2019/0076419 A1 | 3/2019 | Hadida Ruah et al. |
| 2019/0210991 A1 | 7/2019 | Tamoury et al. |
| 2019/0274959 A1 | 9/2019 | Dokou et al. |
| 2020/0085750 A1 | 3/2020 | Verwijs |
| 2020/0115366 A1 | 4/2020 | Hadida Ruah et al. |
| 2020/0197380 A1 | 6/2020 | Verwijs et al. |
| 2020/0338063 A1 | 10/2020 | Verwijs et al. |
| 2020/0377484 A1 | 12/2020 | Keshavarz-Shokri et al. |
| 2021/0023070 A1 | 1/2021 | Rowe et al. |

(56) References Cited

U.S. PATENT DOCUMENTS

| | | |
|---|---|---|
| 2021/0024505 A1 | 1/2021 | Hadida Ruah et al. |
| 2021/0238158 A1 | 8/2021 | Tanoury et al. |
| 2021/0340128 A1 | 11/2021 | Keshavarz-Shokri et al. |
| 2022/0031679 A1 | 2/2022 | Verwijs et al. |
| 2022/0153729 A1 | 5/2022 | Hadida Ruah et al. |
| 2022/0354797 A1 | 11/2022 | Verwijs |
| 2022/0411410 A1 | 12/2022 | Hadida Ruah et al. |
| 2023/0127655 A1 | 4/2023 | Hadida Ruah et al. |

FOREIGN PATENT DOCUMENTS

| | | |
|---|---|---|
| CN | 101006076 A | 7/2007 |
| CN | 101151257 A | 3/2008 |
| CN | 101287732 A | 10/2008 |
| CN | 101460489 A | 6/2009 |
| CN | 101605543 A | 12/2009 |
| DE | 27 35 433 A1 | 2/1978 |
| EA | 4925 B1 | 10/2004 |
| EA | 6155 B1 | 10/2005 |
| EP | 1 380 576 A1 | 1/2004 |
| EP | 1 864 978 A1 | 12/2007 |
| JP | 61-103861 A | 5/1986 |
| JP | 7-45466 B2 | 5/1995 |
| JP | 2004-131393 A | 4/2004 |
| JP | 2008-531534 A | 8/2008 |
| JP | 2009-506114 A | 3/2009 |
| JP | 2009-530416 A | 8/2009 |
| RU | 2005115965 A | 1/2006 |
| RU | 2005128828 A | 5/2006 |
| TW | 1244393 B | 12/2005 |
| WO | WO 1995/06046 A1 | 3/1995 |
| WO | WO 1996/19444 A1 | 6/1996 |
| WO | WO 1998/47868 A1 | 10/1998 |
| WO | WO 1998/58925 A1 | 12/1998 |
| WO | WO 2001/19830 A1 | 3/2001 |
| WO | WO 2001/47916 A1 | 7/2001 |
| WO | WO 2002/11883 A1 | 2/2002 |
| WO | WO 2002/12236 A1 | 2/2002 |
| WO | WO 2002/16349 A1 | 2/2002 |
| WO | WO 2003/002533 A1 | 1/2003 |
| WO | WO 2003/007945 A1 | 1/2003 |
| WO | WO 2003/055482 A1 | 7/2003 |
| WO | WO 2004/028480 A2 | 4/2004 |
| WO | WO 2004/035571 A1 | 4/2004 |
| WO | WO 2004/037806 A1 | 5/2004 |
| WO | WO 2004/041277 A1 | 5/2004 |
| WO | WO 2004/056745 A2 | 7/2004 |
| WO | WO 2004/080972 A1 | 9/2004 |
| WO | WO 2004/091502 A2 | 10/2004 |
| WO | WO 2004/110352 A2 | 12/2004 |
| WO | WO 2004/111014 A2 | 12/2004 |
| WO | WO 2005/016884 A1 | 2/2005 |
| WO | WO 2005/026137 A2 | 3/2005 |
| WO | WO 2005/035514 A2 | 4/2005 |
| WO | WO 2005/037802 A1 | 4/2005 |
| WO | WO 2005/049018 A1 | 6/2005 |
| WO | WO 2005/063746 A1 | 7/2005 |
| WO | WO 2005/075435 A1 | 8/2005 |
| WO | WO 2005/094374 A2 | 10/2005 |
| WO | WO 2005/120497 A2 | 12/2005 |
| WO | WO 2006/002421 A1 | 1/2006 |
| WO | WO 2006/014012 A2 | 2/2006 |
| WO | WO 2006/044456 A1 | 4/2006 |
| WO | WO 2006/044502 A2 | 4/2006 |
| WO | WO 2006/044503 A2 | 4/2006 |
| WO | WO 2006/044505 A2 | 4/2006 |
| WO | WO 2006/044682 A1 | 4/2006 |
| WO | WO 2006/099256 A2 | 9/2006 |
| WO | WO 2006/101740 A2 | 9/2006 |
| WO | WO 2006/110483 A1 | 10/2006 |
| WO | WO 2006/127588 A2 | 11/2006 |
| WO | WO 2007/021982 A2 | 2/2007 |
| WO | WO 2007/044560 A2 | 4/2007 |
| WO | WO 2007/056341 A1 | 5/2007 |
| WO | WO 2007/075567 A1 | 7/2007 |
| WO | WO 2007/075901 A2 | 7/2007 |
| WO | WO 2007/075946 A1 | 7/2007 |
| WO | WO 2007/079139 A2 | 7/2007 |
| WO | WO 2007/087066 A2 | 8/2007 |
| WO | WO 2007/109605 A2 | 9/2007 |
| WO | WO 2007/117715 A2 | 10/2007 |
| WO | WO 2008/051805 A2 | 5/2008 |
| WO | WO 2008/065732 A1 | 6/2008 |
| WO | WO 2008/127399 A2 | 10/2008 |
| WO | WO 2008/147952 A1 | 12/2008 |
| WO | WO 2009/006315 A1 | 1/2009 |
| WO | WO 2009/023509 A2 | 2/2009 |
| WO | WO 2009/036412 A1 | 3/2009 |
| WO | WO 2009/038683 A2 | 3/2009 |
| WO | WO 2009/038913 A2 | 3/2009 |
| WO | WO 2009/066775 A1 | 5/2009 |
| WO | WO 2009/073757 A1 | 6/2009 |
| WO | WO 2009/076141 A2 | 6/2009 |
| WO | WO 2009/076593 A1 | 6/2009 |
| WO | WO 2010/037066 A2 | 4/2010 |
| WO | WO 2010/053471 A1 | 5/2010 |
| WO | WO 2010/054138 A2 | 5/2010 |
| WO | WO 2011/019413 A1 | 2/2011 |
| WO | WO 2011/050325 A1 | 4/2011 |
| WO | WO 2011/119984 A1 | 9/2011 |
| WO | WO 2011/127290 A2 | 10/2011 |
| WO | WO 2011/133751 A1 | 10/2011 |
| WO | WO 2011/133951 A1 | 10/2011 |
| WO | WO 2011/133953 A1 | 10/2011 |
| WO | WO 2012/027247 A1 | 3/2012 |
| WO | WO 2012/027731 A2 | 3/2012 |
| WO | WO 2012/170061 A1 | 12/2012 |
| WO | WO 2013/070961 A1 | 5/2013 |
| WO | WO 2013/130669 A1 | 9/2013 |
| WO | WO 2013/185112 A1 | 12/2013 |
| WO | WO 2014/014841 A1 | 1/2014 |
| WO | WO 2015/073231 A1 | 5/2014 |
| WO | WO 2015/160787 A1 | 10/2015 |
| WO | WO 2016/081556 A1 | 5/2016 |
| WO | WO 2016/086103 A1 | 6/2016 |
| WO | WO 2016/086136 A1 | 6/2016 |
| WO | WO 2016/160945 A1 | 10/2016 |
| WO | WO 2018/183367 A1 | 10/2018 |

OTHER PUBLICATIONS

Notice of Allowance and Fee(s) Due for U.S. Appl. No. 16/530,240, dated Mar. 1, 2021.
Notice of Allowance and Fee(s) Due for U.S. Appl. No. 16/789,945, dated Mar. 30, 2021.
U.S. Appl. No. 17/174,764, filed Feb. 12, 2021, by Marinus Jacobus Verwijs.
U.S. Appl. No. 17/181,931, filed Feb. 22, 2021, by Sara S. Hadida Ruah et al.
U.S. Appl. No. 17/217,323, filed Mar. 30, 2021, by Sara S. Hadida Ruah et al.
Alhalaweh, A. et al. (2015) "Physical stability of drugs after storage above and below the glass transition temperature: Relationship to glass-forming ability" *Int J Pharm*, 495(1):312-317.
Aridor, M. and W.E. Balch (1999) "Integration of endoplasmic reticulum signaling in health and disease" *Nature Med*, 5(7):745-751.
Baghel, S. et al. (2016) "Polymeric Amorphous Solid Dispersions: A Review of Amorphization, Crystallization, Stabilization, Solid-State Characterization, and Aqueous Solubilization of Biopharmaceutical Classification System Class II Drugs" *J Pharm Sci*, 105(9): 2527-2544.
Balbach, S et al., Pharmaceutical evaluation of early development candidates "The 100 mg approach", International Journal of Pharmaceutics, 2004, vol. 275, pp. 1-12.
Beare, N.A. and J.F. Hartwig (Jan. 1, 2002) "Palladium-Catalyzed Arylation of Malonates and Cyanoesters Using Sterically Hindered Trialkyl- and Ferrocenyldialkylphosphine Ligands" *J Org Chem*, 67:541-555.
Bennett, J.C. and F. Plum (Eds.) (1996) *Cecil Textbook of Medicine*. 20th edition, vol. 2, pp. 1992-1996.

(56) References Cited

OTHER PUBLICATIONS

Bennett, J.C. and F. Plum (Eds.) (1996) *Cecil Textbook of Medicine.* 20th edition, vol. 2, pp. 2050-2057.
Berge, S.M. et al. (1977) "Pharmaceutical Salts" *J Pharm Sci*, 66(1):1-19.
Bjornsson, T.D. et al. (2003) "The conduct of in vitro and in vivo drug-drug interaction studies: A Pharmaceutical Research and Manufacturers of America (PhRMA) perspective" *Drug Metab Dispos*, 31(7):815-832.
Bombieri et al., "Recommendations for the classification of diseases of CFTR-related disorders," *J. Cyst Fibros* 10:2 S86-S102 (2011).
Bombieri, C. et al. (1998) "Complete mutational screening of the CFTR gene in 120 patients with pulmonary disease" *Hum Genet*, 103:718-722.
Braun, J. et al. (1999) "No association between the deltaF508 cystic fibrosis mutation and type 2 diabetes mellitus" *Exp Clin Endocrinol Diabetes*, 107(8):568-569. Abstract; PubMed PMID:10612489 [online]. Retrieved from http://www.ncbi.nlm.nih.gov/pubmed/10612489, on Sep. 24, 2012.
Brittain, H.G. (Ed.) *Polymorphism in Pharmaceutical Solids*. Marcel Dekker, 1999; p. 236.
Bross, P. et al. (1999) "Protein Misfolding and Degradation in Genetic Diseases" *Human Mut*, 14:186-198.
Byrn, S. et al. (1995) "Pharmaceutical Solids: A Strategic Approach to Regulatory Considerations" *Pharmaceutical Research*, 12(7):945-954.
Caira, M.R. (1998) "Crystalline Polymorphism of Organic Compounds" in *Topics of Current Chemistry*, 198:163-208.
Chen, R. et al. (2004) "Improved Dissolution of an Insoluble Drug Using a 4-Fluid Nozzle Spray-Drying Technique" *Chem Pharm Bull*, 52(9):1066-1070.
Chiou, W.L. and S. Riegelman (Sep. 1971) "Pharmaceutical Applications of Solid Dispersion Systems" *J Pharm Sci*, 60(9):1281-1302.
Chueshov, V.I. (Ed.) (2002) *Manufacturing Technologies of Drugs.* vol. 2. Kharkov:MTK-Kniga, Publishing House NPAU; excerpt, 7 pages.
Conti, S. et al. (2007) "Matrices containing NaCMC and HPMC 1. Dissolution performance characterization" *Intl J Pharma*, 333:136-142.
Cutting, G.R. et al. (1990) "A cluster of cystic fibrosis mutations in the first nucleotide-binding fold of the cystic fibrosis conductance regulator protein" *Nature*, 346:366-369.
Dahl, M. and B.G. Nordestgaard (2009) "Markers of early disease and prognosis in COPD" *Intl J COPD*, 4:157-167.
Dahl, M. et al. (Oct. 9, 2005) "Asthma and COPD in cystic fibrosis intron-8 5T carriers. A population-based study" *Respiratory Research*, 6:113, doi: 10.1186/1465-9921-6-113, 9 pages.
Dalemans, W. et al. (Dec. 1991) "Altered chloride ion channel kinetics associated with the ΔF508 cystic fibrosis mutation" *Nature*, 354:526-528.
Database Registry (Nov. 18, 1988) "6-Quinolineacetic acid, α-cyano-, ethyl ester" RN 117646-35-2, Retrieved from STN International [online]; retrieved on Feb. 13, 2015 (1 page).
Database Registry (May 19, 2004) "1,3-Benzodioxole-5-acetic acid, α-cyano-" RN 683220-08-8, Retrieved from STN International [online]; retrieved on Feb. 13, 2015 (1 page).
Datta, S., Grant, D. "Crystal structures of drugs: advances in determination, prediction and engineering," Nat. Rev. Drug. Discov. 3, 42-57 (2004).
Dean, M. et al. (Jun. 1990) "Multiple mutations in highly conserved residues are found in mildly affected cystic fibrosis patients" *Cell*, 61:863-870.
Decision of the European Commission to grant a marketing authorization for Symkevi, Summary of Product Characteristics for Symkevi, and EMA Assessment Report for Symkevi, Oct. 31, 2018, 203 pages.
Developing Solid Oral Dosage Forms (2009), p. 120.

Dong, Z. and Choi, D. S. (2008) "Hydroxypropyl Methylcellulose Acetate Succinate: Potential Drug-Excipient Incompatibility" *AAPS PharmSciTech*, 9(3): 991-997.
EMA, Committee for Proprietary Medicinal Products (CPMP); "Note for Guidance on Fixed Combination Medicinal Products", 1996, 5 pages.
Freireich, E.J. et al. (1966) "Quantitative comparison of toxicity of anticancer agents in mouse, rat, hamster, dog, monkey, and man" *Cancer Chemother Rep*, 50(4):219-244.
Friesen, D.T. et al. (2008) "Hydroxypropyl Methylcellulose Acetate Succinate-Based Spray-Dried Dispersions: An Overview" *Mol Pharma*, 5(6):1003-1019.
Fude, Cui (2002) *Pharmaceutics*. 1st Ed. China Medical Science Press, p. 443, 445-446. Chinese with English translation.
Fude, Cui (Feb. 2004) Pharmaceutics. 5th Ed. People's Medical Publishing House; p. 113-119, 334. Chinese with English translation.
Galietta, L.J.V. et al. (Jun. 1998) "An improved method to obtain highly differentiated monolayers of human bronchial epithelial cells" *In Vitro Cell Dev Biol*, 34:478-481.
González, J. E. et al. (Oct. 1995) "Voltage Sensing by Fluorescence Resonance Energy Transfer in Single Cells" *Biophys J*, 69(4):1272-1280.
González, J.E. et al. (Apr. 1997) "Improved indicators of cell membrane potential that use fluorescence resonance energy transfer" *Chem Biol*, 4(4):269-277.
González, J.E. et al. (1999) "Cell-based assays and instrumentation for screening ion-channel targets" *Drug Discov Today*, 4(9):431-439.
Gregory, R.J. et al. (Sep. 1990) "Expression and characterization of the cystic fibrosis transmembrane conductance regulator" *Nature*, 347:382-386.
Hancock, B. and Zografi, G. (1997) "Characteristics and significance of the amorphous state in pharmaceutical systems" *J Pharm Sci*, 86(1):1-12.
Hancock, B. C. and M. Parks (2000) "What Is the True Solubility Advantage of Amorphous Pharmaceuticals?" *Pharm Res*, 17(4):397-404.
Huang, Y. and Dai, W. G. (2014) "Fundamental aspects of solid dispersion technology for poorly soluble drugs" *Acta Pharm Sin B*, 4(1):18-25.
International Patent Application No. PCT/US2007/008975, filed Apr. 9, 2007, by Vertex Pharmaceuticals, Inc.: International Preliminary Report on Patentability and Written Opinion, dated Oct. 8, 2008.
International Patent Application No. PCT/US2007/008975, filed Apr. 9, 2007, by Vertex Pharmaceuticals, Inc.: International Search Report, dated Nov. 8, 2007.
International Patent Application No. PCT/US2008/012689, filed Nov. 12, 2008, by Vertex Pharmaceuticals, Inc.: International Preliminary Report on Patentability and Written Opinion, dated May 10, 2011.
International Patent Application No. PCT/US2008/012689, filed Nov. 12, 2008, by Vertex Pharmaceuticals, Inc.: International Search Report, dated Aug. 21, 2009.
International Patent Application No. PCT/US2009/063475, filed Nov. 6, 2009, by Vertex Pharmaceuticals, Inc.: International Search Report, dated Sep. 23, 2010.
International Patent Application No. PCT/US2009/063475, filed Nov. 6, 2009, by Vertex Pharmaceuticals, Inc.: International Preliminary Report on Patentability and Written Opinion, dated May 10, 2011.
International Patent Application No. PCT/US2011/030032, filed Mar. 25, 2011, by Vertex Pharmaceuticals, Inc.: International Preliminary Report on Patentability, dated Sep. 25, 2012.
International Patent Application No. PCT/US2011/030032, filed Mar. 25, 2011, by Vertex Pharmaceuticals, Inc.: International Search Report, dated Aug. 2, 2011.
International Patent Application No. PCT/US2011/033396, filed Apr. 21, 2011, by Vertex Pharmaceuticals, Inc.: International Preliminary Report on Patentability and Written Opinion, dated Oct. 23, 2012.

(56) References Cited

OTHER PUBLICATIONS

International Patent Application No. PCT/US2011/033396, filed Apr. 21, 2011, by Vertex Pharmaceuticals, Inc.: International Search Report, dated Nov. 11, 2011.
International Patent Application No. PCT/US2011/033687, filed Apr. 22, 2011, by Vertex Pharmaceuticals, Inc.: International Search Report and Written Opinion, dated Aug. 30, 2011.
International Patent Application No. PCT/US2011/048565, filed Aug. 22, 2011, by Vertex Pharmaceuticals, Inc.: International Search Report and Written Opinion, dated Mar. 20, 2012.
International Patent Application No. PCT/US2011/051725, filed Sep. 15, 2011, by Vertex Pharmaceuticals, Inc.: International Search Report and Written Opinion, dated May 24, 2012.
International Patent Application No. PCT/US2012/064217, filed Nov. 8, 2012, by Vertex Pharmaceuticals, Inc.: International Search Report and Written Opinion, dated Jan. 15, 2013.
International Patent Application No. PCT/US2013/050557, filed Jul. 15, 2013, by Vertex Pharmaceuticals Inc.: International Search Report and Written Opinion, dated Sep. 30, 2013.
International Patent Application No. PCT/US2015/025722, filed Apr. 14, 2015, by Vertex Pharmaceuticals Inc.: International Search Report and Written Opinion, dated Jul. 3, 2015.
Ishiguro, H. et al. (2006) "Dysfunction of pancreatic $HCO_3^-$ secretion and pathogenesis of cystic fibrosis/chronic pancreatitis" *J Japan Pancreas Soc*, 21(1):13-25. Japanese with English abstract.
Jenkins, R. and R.L. Snyder (1996) *Introduction to X-Ray Powder Diffractometry*. New York, NY: John Wiley & Sons, Inc.; pp. 23-26.
Jermain, S. V. et al. (2018) "Amorphous solid dispersions and nanocrystal technologies for poorly water-soluble drug delivery—An update" *Int J Pharm*, 535(1-2):379-392.
Jones, A. and J.M. Helm (Jan. 1, 2009) "Emerging Treatments in Cystic Fibrosis" *Drugs*, 69(14):1903-1910.
Kalydeco Prescribing Information, Revised Aug. 28, 2012, 13 pages.
Kamal, A. et al. (2005) "Ultrasonic activated efficient method for the cleavage of epoxides with aromatic amines" *Ultrasonics Sonochemistry*, 12(6):429-431.
Kawakami (Jan. 2010) "Formulation of a Poorly Water-soluble Drug by Decrystallization" Chapter 5 in *New Development of Property Evaluation and Formulation Design of Poorly Water Soluble Drugs*. CMC Publishing Co., Ltd.; pp. 212-244. Japanese with English abstract.
Kerem, B-S. et al. (Sep. 1989) "Identification of the cystic fibrosis gene: Genetic analysis" *Science*, 245:1073-1080.
Kerem, B-S. et al. (Nov. 1990) "Identification of mutations in regions corresponding to the two putative nucleotide (ATP)-binding folds of the cystic fibrosis gene" *Proc. Natl. Acad. Sci. USA*, 87:8447-8451.
Kerem, E. et al. (2005) "Standards of care for patients with cystic fibrosis: a European consensus" *J Cystic Fibr*, 4:7-26.
Kerns, E.H. and L. Di (2008) *Drug-like Properties: Concepts, Structure Design and Methods: from ADME to Toxicity Optimization*. London, UK: Academic Press; pp. 122-136 and 197-208.
King, F.D. (Ed.) "Bioisosteres, Conformational Restriction and Pro-drugs—Case History: An Example of a Conformational Restriction Approach" in *Medical Chemistry: Principles and Practice*. 1994; Chapter 14, pp. 206-209.
Konno, H. et al. (2008) "Effect of polymer type on the dissolution profile of amorphous solid dispersions containing felodipine" *Eur J Pharma Biopharma*, 70:493-499.
Krippendorff, B-F. et al. (2007) "Optimizing Classification of Drug-Drug Interaction Potential for CYP450 Isoenzyme Inhibition Assays in Early Drug Discovery" *J Biomol Screen*, 12(1):92-99.
Larock, R.C. and Yum, E.K. (1991) "Synthesis of Indoles via Palladium-Catalyzed Heteroannulation of Internal Alkynes" *J. Am. Chem. Soc.* 113:6689-6690.
Leuner, C. and J. Dressman (2000) "Improving drug solubility for oral delivery using solid dispersions" *Eur J Pharm Biopharm*, 50:47-60.

Levin, M. and A.S. Verkman (Apr. 2005) "CFTR-Regulated Chloride Transport at the Ocular Surface in Living Mice Measured by Potential Differences" *Investigative Ophthalmology & Visual Science*, 46:1428-1434.
Miyamatsu, H. et al. (1974) "A New Nonsteroidal Antiinflammatory Agent. 3. Analogs of 2-Substituted 5-Benzothiazoleacetic Acids and Their Derivatives" *J Med Chem*, 17(5):491-496.
Morello, J-P et al. (2000) "Pharmacological chaperones: A new twist on receptor folding" *TiPS*, 21:466-469.
Newman, A. et al. (2012) "Assessing the performance of amorphous solid dispersions" *J Pharm Sci*, 101(4):1355-1377.
Notice of Allowance and Fee(s) Due for U.S. Appl. No. 16/530,240, dated Nov. 12, 2020.
Notice of Allowance and Fee(s) Due for U.S. Appl. No. 16/276,887, dated Nov. 20, 2020.
Notice of Allowance and Fee(s) Due for U.S. Appl. No. 16/232,540, dated Dec. 15, 2020.
Pasyk, E.A. and J.K. Foskett (May 1995) "Mutant (Δ F508) cystic fibrosis transmembrane conductance regulator $CI^-$ channel is functional when retained in endoplasmic reticulum of mammalian cells" *J Biol Chem*, 270(21):12347-12350.
Pettit, R.S. (2012) "Cystic Fibrosis Transmembrane Conductance Regulator—Modifying Medications: The Future of Cystic Fibrosis Treatment" *Annals of Pharmacotherapy*, 46:1065-1075.
Prichard, M. N., Shipman Jr., C. "A three-dimensional model to analyze drug-drug interactions," Antiviral Res. Oct.-Nov. 1990;14(4-5):181-205.
Quinton, P.M. (1990) "Cystic fibrosis: a disease in electrolyte transport" *FASEB J*, 4:2709-2717.
Rahman, Z. et al. (2013) "Tacrolimus Properties and Formulations: Potential Impact of Product Quality on Safety and Efficacy" 1-39.
Remington, The Science and Practice of Pharmacy, 20th edition, 2000, p. 1970.
Rich, D.P. et al. (Sep. 1990) "Expression of cystic fibrosis transmembrane conductance regulator corrects defective chloride channel regulation in cystic fibrosis airway epithelial cells" *Nature*, 347:358-363.
Riordan, J.R. et al. (Sep. 1989) "Identification of the cystic fibrosis gene: cloning and characterization of the complementary DNA" *Science*, 245:1066-1073.
Riley, R.J. et al. (2007) "Time-dependent CYP inhibition" *Expert Opin Drug Metab Toxicol*, 3:51-66.
Rutishauser, J. and M. Spiess (2002) "Endoplasmic reticulum storage diseases" *Swiss Med Wkly*, 132:211-222.
Sasaki (1975) "Molecular Skeleton Synthesis: Its Creative Ways and Attitudes" *Maruzen Publishing Co., Ltd.*, pp. 206-209.
Satoshi (2005) "Advances in male infertility therapy" *Urology View*, 3(6):58-61. Japanese with English abstract.
Shastry, B.S. (2003) "Neurodegenerative disorders of protein aggregation" *Neurochem Intl*, 43:1-7.
Singhal, D. et al., Drug polymorphism and dosage form design: a practical perspective, Advanced Drug Delivery Reviews, 2004, vol. 56, pp. 335-347.
Stankovic, M. et al. (2008) "The CFTR M470V gene variant as a potential modifier of COPD severity: study of Serbian population" *Genetic Testing*, 12(3):357-362.
Stauffer, S.R et al. (Jan. 1, 2001) "Palladium-Catalyzed Arylation of Ethyl Cyanoacetate. Fluorescence Resonance Energy Transfer as a Tool for Reaction Discovery" *J Am Chem Soc*, 123(19):4641-4642.
Suzuki, H. et al. (1983) "A simple one-pot conversion of aryl halides into arylacetonitriles" *Chem Lett*, p. 193-194.
Tanno, F. et al. (2004) "Evaluation of Hypromellose Acetate Succinate (HPMCAS) as a Carrier in Solid Dispersions" *Drug Dev Ind Pharm*, 30(1):9-17.
Teichert et al. (2004) "One-Pot Homolytic Aromatic Substitutions/HWE Olefinations under Microwave Conditions for the Formation of a Small Oxindole Library" *Org Lett*, 6 (20):3477-3480.
The Associated Press (Sep. 24, 2003) "FDA mulls drug to slow late-stage Alzheimer's" [online]. *CNN.com*. Retrieved from: http://www.cnn.com/2003/HEALTH/condtions/09/24/alzheimers.drug.ap/indexhtml, on Sep. 24, 2003.
The Free Online Dictionary, Definition of Amorphous [online]. Retrieved from: http://www.thefreedictionary.com/amorphous, on May 1, 2012.

(56) References Cited

OTHER PUBLICATIONS

Tzetis, M. et al. (2001) "CFTR gene mutations—including three novel nucleotide substitutions—and haplotype background in patients with asthma, disseminated bronchiectasis and chronic obstructive pulmonary disease" *Hum Genet*, 108:216-221.
U.S. Appl. No. 16/704,713, filed Dec. 5, 2019, by Patricia Hurter et al.
U.S. Appl. No. 16/789,945, filed Feb. 13, 2020, by Sara S. Hadida Ruah et al.
U.S. Appl. No. 16/842,230, filed Apr. 7, 2020, by Sara S. Hadida Ruah et al.
U.S. Appl. No. 16/842,480, filed Apr. 7, 2020, by William Rowe et al.
U.S. Appl. No. 17/003,051, filed Aug. 26, 2020, by Gerald J. Tanoury et al.
U.S. Appl. No. 17/104,903, filed Nov. 25, 2020, by Ali Keshavarz-Shokri et al.
Van Goor, F. et al. (2006) "Rescue of deltaF508-CFTR trafficking and gating in human cystic fibrosis airway primary cultures by small molecules" *Am J Physiol Lung Cell Mol Physiol*, 290(6):L1117-L1130.
Vasiliou, V. et al. (Apr. 2009) "Human ATP-binding cassette (ABC) transporter family" *Hum Genomics*, 3(3):281-290.
Vehring, R. (May 2008) "Pharmaceutical Particle Engineering via Spray Drying" *Pharm Res*, 25(5):999-1022.
Vertex Pharmaceuticals, Inc. (Apr. 5, 2012) "A phase 2, multicenter, double-blinded, placebo controlled, 3-part study to evaluate safety, efficacy, pharmacokinetics, and pharmacodynamics of VX-661 monotherapy and VX-661/VX-770 cotherapy in subjects with cystic fibrosis, homozygous for the F508del-CFTR mutation" [online]. *Clinicaltrials.gov*. Retrieved from: http://clinicaltrials.gov/archive/NCT01531673/2012_04-05; Identifier: NCT01531673.
Vertex Pharmaceuticals, Inc. (Apr. 18, 2013) "Treatment with VX-661 and Ivacaftor in a Phase 2 Study Resulted in Statistically Significant Improvements in Lung Function in People with Cystic Fibrosis Who Have Two Copies of the F508del Mutation" [online]. Cambridge, Mass.: *Business Wire*. Retrieved from: http://investors.vrtx.com/releasedetail.cfm?ReleaseID=757597.
Vertex Pharmaceuticals, Inc. (Jul. 18, 2013) "A Phase 2, Multicenter, Double-Blinded, Placebo Controlled, 3-Part Study to Evaluate Safety, Efficacy, Pharmacokinetics, and Pharmacodynamics of VX-661 Monotherapy and VX-661/VX-770 Cotherapy in Subjects With Cystic Fibrosis, Homozygous for the F508del-CFTR Mutation" [online]. *ClinicalTrials.gov*. Retrieved from: http://clinicaltrials.gov/archive/NCT01531673/2013_07_18; Identifier: NCT01531673.
Vertex Pharmaceuticals, Inc. (Jul. 18, 2013) "Study of VX-661 Alone and in Combination with VX-770 in Subjects Homozygous to the F508del-CFTR Mutation" [online]. *ClinicalTrials.gov*. Retrieved from: _http://clinicaltrials.gov/archive/NCT01531673/2013_07_18; Identifier: NCT01531673.
Vertex Pharmaceuticals, Inc. (Mar. 25, 2014) "An Open-Label, Phase 1 Study in Healthy Adult Subjects to Examine the Effects of Multiple-Dose Ciprofloxacin on Ivacaftor and VX-661 in Combination with Ivacaftor" [online]. *ClinicalTrials.gov*. Retrieved from: https://clinicaltrials.gov/ct2/show/NCT02015507?term=vx-661&rank=4; Identifier: NCT02015507.
Vertex Pharmaceuticals, Inc. (May 1, 2014) "Addition of VX-661 to KALYDECO® (ivacaftor) Improves Lung Function in People with CF Who Are Heterozygous for the F508del and G551D Mutations in 28-day Phase 2 Proof-of-Concept Study" [online]. Boston: *Business Wire*. Retrieved from: http://investors.vrtx.com/releasedetail.cfm?ReleaseID=844677.
Vertex Pharmaceuticals, Inc. (Oct. 17, 2014) "Study to Evaluate Safety and Efficacy of VX-661 in Combination With Ivacaftor in Subjects With Cystic Fibrosis, Homozygous for the F508del-CFTR Mutation With an Open-Label Expansion" [online] *ClinicalTrials.gov*. Retrieved from: https://clinicaltrials.gov/ct2/show/NCT02070744?term=vx-661&rank=6; Identifier: NCT02070744.
Vertex Pharmaceuticals, Inc. (Mar. 23, 2015) "Vertex Announces Data from 12-Week Phase 2 Safety Study of VX-661 in Combination with Ivacaftor in People with Cystic Fibrosis Who Have Two Copies of the F508del Mutation" [online]. Boston: *Business Wire*. Retrieved from: http://investors.vrtx.com/releasedetail.cfm?ReleaseID=902790.
Vertex Pharmaceuticals, Inc. (May 5, 2015) "Study of VX-661 Alone and in Combination with Ivacaftor in Subjects Homozygous or Heterozygous to the F508del-Cystic Fibrosis Transmembrane Conductance Regulator (CFTR) Mutation" [online]. *ClinicalTrials.gov*, Identifier: NCT01531673. Retrieved from: https://clinicaltrials.gov/ct2/show/NCT01531673?term=vx-661&rank=3 (5 pages).
Wallis, C. (2001) "Mucolytic therapy in cystic fibrosis" *J R Soc Med*, 94(Suppl 40):17-24.
Wang, F. et al. (Mar. 1998) "Actions of genistein on cystic fibrosis transmembrane conductance regulator channel gating. Evidence for two binding sites with opposite effects" *J Gen Physiol*, 111(3):477-490.
Yu, H. et al. (2010) "VX-770, an investigational CFTR potentiator, acts on multiple CFTR forms in vitro" *Pediatric Pulmonology*, 45(33):318-319, Abstract 280.
Yu, H. et al. (2012) "Ivacaftor potentiation of multiple CFTR channels with gating mutations" *J Cystic Fibrosis*, 11(3):237-245.
Article 56 E, Travaux Preparatoires (EPC 1973), pp. 17-21.
Judgment for X ZR 89/007, pp. 1-22, Dec. 16, 2008.
Judgment for [2007] EWCA Civ 741, pp. 1-18, Jul. 19, 2017.
Rogge, R Thoughts on the concept of novelty according to currently applicable patent law, pp. 931-940, 1996 English translation appended thereto.
U.S. Appl. No. 17/692,235, filed Mar. 11, 2022, by Sara S. Hadida Ruah et al.
Cour D'Appel de Paris, Arret Du Oct. 29, 2019, *SAS Ethypharm v. Merck Sharp & Dohme Corp*, No. 126/2019, 22 pages.
Tribunal de Grande Instance de Paris, *SAS Mylan v. S.A.S. Astrazeneca*, Jul. 1, 2016, No. 15/05880, pp. 1-30.
U.S. Appl. No. 17/992,294, filed Nov. 22, 2022, by Ali Keshavarz-Shokri et al.
U.S. Appl. No. 18/108,053, filed Feb. 10, 2023, by Sara S. Hadida Ruah et al.
Vertex Pharmaceuticals, Inc. (Apr. 7, 2014) "Study of VX-661 Alone and in Combination with Ivacaftor in Subjects Homozygous or Heterozygous to the F508del-Cystic Fibrosis Transmembrane Conductance Regulator (CFTR) Mutation" [online]. *ClinicalTrials.gov*. Retrieved from: https://www.clinicaltrials.gov/ct2/history/NCT01531673?V_19=View#StudyPageTop; Identifier: NCT01531673.

PHARMACEUTICAL COMPOSITIONS FOR THE TREATMENT OF CYSTIC FIBROSIS TRANSMEMBRANE CONDUCTANCE REGULATOR MEDIATED DISEASES

CROSS-REFERENCE TO RELATED APPLICATIONS

This application is a continuation of U.S. application Ser. No. 16/232,540, filed Dec. 26, 2018, now U.S. Pat. No. 10,980,746, which is a continuation of U.S. application Ser. No. 14/686,117, filed Apr. 14, 2015, now U.S. Pat. No. 10,206,877, which claims priority to U.S. provisional application No. 61/979,848, filed on Apr. 15, 2014, and 62/059,287, filed on Oct. 3, 2014, all of which are incorporated herein by reference.

FIELD OF THE INVENTION

The present invention features combination compositions and methods of treating Cystic Fibrosis Transmembrane Conductance Regulator (CFTR) mediated diseases related thereto.

BACKGROUND OF THE INVENTION

Cystic fibrosis (CF) is a recessive genetic disease that affects approximately 30,000 children and adults in the United States and approximately 30,000 children and adults in Europe. Despite progress in the treatment of CF, there is no cure.

In patients with CF, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245:1073-1080; Kerem, B-S et al. (1990) Proc. Natl. Acad. Sci. USA 87:8447-8451). To date, greater than 1000 disease causing mutations in the CF gene have been identified (http://www.genet.sickkids.on.ca/cftr/app). The most prevalent mutation is a deletion of phenylalanine at position 508 of the CFTR amino acid sequence, and is commonly referred to as ΔF508-CFTR. This mutation occurs in approximately 70% of the cases of cystic fibrosis and is associated with a severe disease.

The deletion of residue 508 in ΔF508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to ΔF508-CFTR, other disease causing mutations in CFTR that result in defective trafficking, synthesis, and/or channel gating could be up- or down-regulated to alter anion secretion and modify disease progression and/or severity.

Accordingly, there is a need for novel treatments of CFTR mediated diseases.

SUMMARY OF THE INVENTION

The present invention relates to pharmaceutical compositions wherein the properties of one therapeutic agent are improved by the presence of another therapeutic agent, kits, and methods of treatment thereof. In one embodiment, the present invention features pharmaceutical compositions comprising (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound 1) and N-[2,4-bis(1,1-dimethylethyl)-5-hydroxyphenyl]-1,4-dihydro-4-oxoquinoline-3-carboxamide (Compound 2), wherein the composition has improved properties.

In one aspect, the present invention features a spray dried dispersion comprising a plurality of therapeutic agents, wherein the dispersion is substantially free of a polymer.

In one embodiment, the plurality of therapeutic agents consists of a first therapeutic agent and a second therapeutic agent.

In one embodiment, the ratio of the first agent to the second agent is from about 1:10 to about 10:1 by weight. In one embodiment, the ratio of the first agent to the second agent is about 1:1 by weight. In one embodiment, the ratio of the first agent to the second agent is about 1:3 by weight. In one embodiment, the ratio of the first agent to the second agent is about 1:6 by weight. In one embodiment, the ratio of the first agent to the second agent is about 2:3 by weight.

In one embodiment, the first agent is a CFTR corrector. In one embodiment, the second agent is a CFTR potentiator. In one embodiment, the first agent is a CFTR corrector and the second agent is a CFTR potentiator. In one embodiment, the first agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide. In one embodiment, the second agent is N-[2,4-bis(1,1-dimethylethyl)-5-hydroxyphenyl]-1,4-dihydro-4-oxoquinoline-3-carboxamide. In one embodiment, the first agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, and the second agent is N-[2,4-bis(1,1-dimethylethyl)-5-hydroxyphenyl]-1,4-dihydro-4-oxoquinoline-3-carboxamide.

In one embodiment, the spray dried dispersion has a Tg of from about 80° C. to about 180° C.

In one embodiment, the spray dried dispersion is substantially amorphous.

In another aspect the present invention features a spray dried dispersion consisting of a plurality of therapeutic agents.

In one embodiment, there are two therapeutic agents, a first therapeutic agent and a second therapeutic agent.

In one embodiment, the ratio of the first agent to the second agent is from about 1:10 to about 10:1 by weight. In one embodiment, the ratio of the first agent to the second agent is about 1:1 by weight. In one embodiment, the ratio of the first agent to the second agent is about 1:3 by weight. In one embodiment, the ratio of the first agent to the second agent is about 1:6 by weight. In one embodiment, the ratio of the first agent to the second agent is about 2:3 by weight.

In one embodiment, the first agent is a CFTR corrector. In one embodiment, the second agent is a CFTR potentiator. In one embodiment, the first agent is a CFTR corrector and the second agent is a CFTR potentiator. In one embodiment, the first agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide. In one embodiment, the second agent is N-[2,4-bis(1,1-dimethylethyl)-5-hydroxyphenyl]-1,4-dihydro-4-oxoquinoline-3-carboxamide. In one embodiment, the first agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide; and the second agent is N-[2,4-bis(1,1-dimethylethyl)-5-hydroxyphenyl]-1,4-dihydro-4-oxoquinoline-3-carboxamide.

In one aspect, the present invention features a spray dried dispersion comprising a particle, wherein the particle comprises a plurality of therapeutic agents, and the particle is substantially free of a polymer.

In one embodiment, the particle consists essentially of a first agent and a second agent.

In one embodiment, the ratio of the first agent to the second agent is from about 1:10 to about 10:1 by weight. In one embodiment, the ratio of the first agent to the second agent is about 1:1 by weight. In one embodiment, the ratio of the first agent to the second agent is about 1:3 by weight. In one embodiment, the ratio of the first agent to the second agent is about 1:6 by weight. In one embodiment, the ratio of the first agent to the second agent is about 2:3 by weight.

In one embodiment, the first agent is a CFTR corrector. In one embodiment, the second agent is a CFTR potentiator. In one embodiment, the first agent is a CFTR corrector and the second agent is a CFTR potentiator. In one embodiment, the first agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide. In one embodiment, the second agent is N-[2,4-bis(1,1-dimethylethyl)-5-hydroxyphenyl]-1,4-dihydro-4-oxoquinoline-3-carboxamide. In one embodiment, the first agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, and the second agent is N-[2,4-bis(1,1-dimethylethyl)-5-hydroxyphenyl]-1,4-dihydro-4-oxoquinoline-3-carboxamide.

In one embodiment, the particle has a mean particle diameter of about 5 microns to about 100 microns. In one embodiment, the particle has a mean particle diameter of about 5 microns to about 30 microns. In one embodiment, the particle has a mean particle diameter of about 15 microns.

In one embodiment, the spray dried dispersion has a Tg of from about 80° C. to about 180° C.

In one embodiment, the spray dried dispersion is substantially amorphous.

In one aspect, the present invention features a pharmaceutical composition comprising any of the preceding spray dried dispersion of the present invention.

In one embodiment, the pharmaceutical composition is a tablet.

In one embodiment, the tablet comprises from about 25 mg to about 125 mg of Compound 1. In one embodiment, the tablet comprises about 100 mg of Compound 1. In one embodiment, the tablet comprises about 50 mg of Compound 1.

In one embodiment, the tablet comprises from about 100 mg to about 200 mg of Compound 2. In one embodiment, the tablet comprises about 150 mg of Compound 2.

In one embodiment, the tablet comprises one or more excipients selected from a filler, a disintegrant, a lubricant, or any combination thereof. In one embodiment, the tablet comprises from about 100 mg to about 300 mg of a filler. In one embodiment, the filler comprises microcrystalline cellulose. In one embodiment, the tablet comprises from about 12 mg to about 36 mg of a disintegrant. In one embodiment, the disintegrant comprises croscarmellose sodium. In one embodiment, the tablet comprises from about 1 mg to about 5 mg of a lubricant. In one embodiment, the lubricant comprises magnesium stearate.

In one embodiment, the tablet comprises an additional therapeutic agent.

In one embodiment, the additional therapeutic agent is another CFTR corrector different from Compound 1. In one embodiment, the additional therapeutic agent is another CFTR potentiator different from Compound 2.

In one embodiment, the additional therapeutic agent is selected from

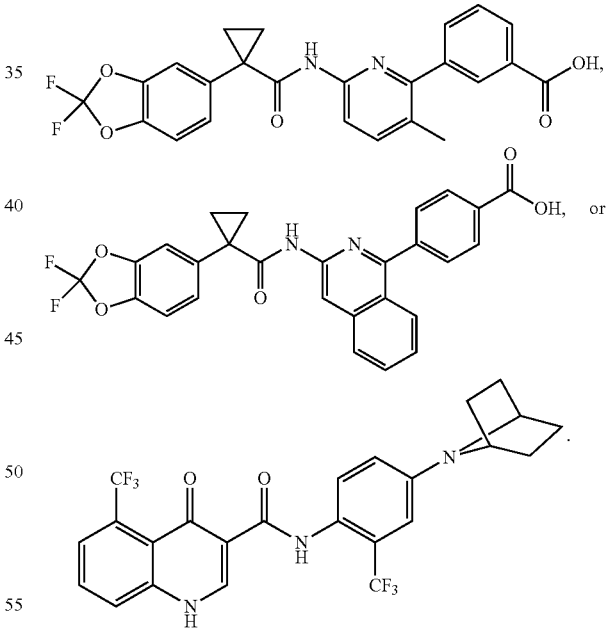

In aspect, the present invention features a pharmaceutical composition comprising an amorphous form of Compound 1, and an amorphous form of Compound 2.

In one embodiment, the pharmaceutical composition is a tablet.

In one embodiment, the tablet comprises from about 25 mg to about 125 mg of Compound 1. In one embodiment, the tablet comprises about 100 mg of Compound 1. In one embodiment, the tablet comprises about 50 mg of Compound 1.

In one embodiment, the tablet comprises from about 100 mg to about 200 mg of Compound 2. In one embodiment, the tablet comprises about 150 mg of Compound 2.

In one embodiment, the ratio of Compound 1 to Compound 2 is from about 1:10 to about 10:1 by weight. In one embodiment, the ratio of Compound 1 to Compound 2 is about 1:1 by weight. In one embodiment, the ratio of Compound 1 to Compound 2 is about 1:3 by weight. In one embodiment, the ratio of Compound 1 to Compound 2 is about 1:6 by weight. In one embodiment, the ratio of Compound 1 to Compound 2 is about 2:3 by weight.

In one embodiment, the pharmaceutical composition comprises from about 5 wt % to about 15 wt % of Compound 1. In one embodiment, the pharmaceutical composition comprises from about 15 wt % to about 45 wt % of Compound 2.

In one embodiment, the pharmaceutical composition further comprises one or more excipients selected from a filler, a disintegrant, a lubricant, or any combination thereof.

In one embodiment, the pharmaceutical composition comprises from about 30 wt % to about 50 wt % of a filler. In one embodiment, the filler comprises microcrystalline cellulose. In one embodiment, the pharmaceutical composition comprises from about 1 wt % to about 10 wt % of a disintegrant. In one embodiment, the disintegrant comprises croscarmellose sodium. In one embodiment, the pharmaceutical composition comprises about 1 wt % of a lubricant. In one embodiment, the lubricant comprises magnesium stearate.

In another aspect, the present invention features a pharmaceutical composition comprising a first spray dried dispersion and a second spray dried dispersion, wherein the first spray dried dispersion comprises an amorphous form of Compound 1, and the second spray dried dispersion comprises an amorphous form of Compound 2.

In one embodiment, the first spray dried dispersion further comprises a polymer. In one embodiment, the first spray dried dispersion comprises from about 70 wt % to about 90 wt % of Compound 1 and from about 10 wt % to about 30 wt % of the polymer. In one embodiment, the polymer comprises hydroxypropyl methylcellulose.

In one embodiment, the second spray dried dispersion further comprises a polymer. In one embodiment, the second spray dried dispersion comprises from about 70 wt % to about 90 wt % of Compound 2 and from about 10 wt % to about 30 wt % of the polymer.

In one embodiment, the pharmaceutical composition comprises from about 5 wt % to about 20 wt % of the first spray dried dispersion. In one embodiment, the pharmaceutical composition comprises from about 15 wt % to about 60 wt % of the second spray dried dispersion.

In one embodiment, the pharmaceutical composition is a tablet. In one embodiment, the tablet comprises about 25 mg to 125 mg of Compound 1. In one embodiment, the tablet comprises about 100 mg of Compound 1. In one embodiment, the tablet comprises about 50 mg of Compound 1. In one embodiment, the tablet comprises about 100 mg to 200 mg of Compound 2. In one embodiment, the tablet comprises about 150 mg of Compound 2.

In one embodiment, the tablet comprises one or more excipients selected from a filler, a disintegrant, a lubricant, or any combination thereof.

In one embodiment, the tablet comprises from about 30 wt % to about 50 wt % of a filler. In one embodiment, the filler comprises microcrystalline cellulose. In one embodiment, the tablet comprises from about 1 wt % to about 10 wt % of a disintegrant. In one embodiment, the disintegrant comprises croscarmellose sodium. In one embodiment, the tablet comprises about 1 wt % of a lubricant. In one embodiment, the lubricant comprises magnesium stearate.

In one embodiment, the tablet comprises from about 30 mg to about 85 mg of the first spray dried dispersion. In one embodiment, the tablet comprises from about 150 mg to about 250 mg of the second spray dried dispersion.

In one embodiment, the tablet comprises from about 100 mg to about 300 mg of a filler. In one embodiment, the tablet comprises from about 12 mg to about 36 mg of a disintegrant. In one embodiment, the tablet comprises from about 1 mg to about 5 mg of a lubricant.

In one embodiment, the pharmaceutical composition further comprises an additional therapeutic agent. In one embodiment, the additional therapeutic agent is another CFTR corrector different from Compound 1. In one embodiment, the additional therapeutic agent is another CFTR potentiator different from Compound 2. In one embodiment, the additional therapeutic agent is selected from

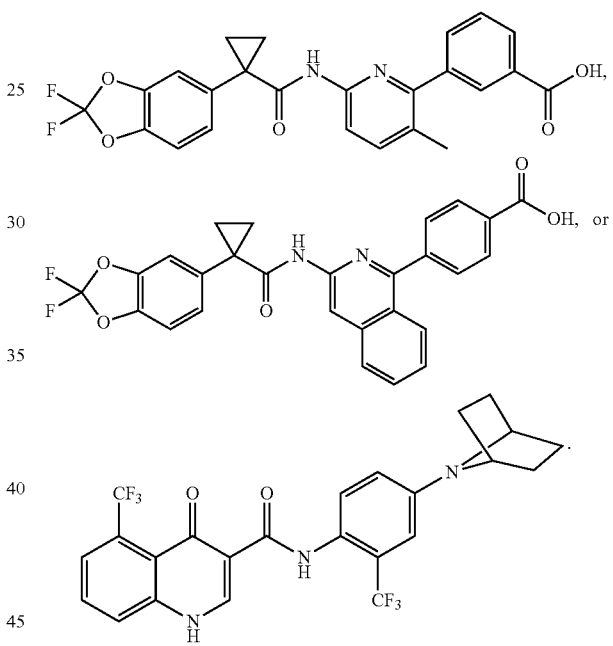

In one aspect, the present invention features a method of treating cystic fibrosis in a patient comprising administering to the patient any of the spray dried dispersions or pharmaceutical compositions previously described.

In one embodiment, the patient is orally administered the spray dried dispersion or pharmaceutical composition.

In one embodiment, the patient is further administered an additional therapeutic agent. In one embodiment, the additional therapeutic agent is administered before, after, or concurrently with any of the spray dried dispersions or pharmaceutical compositions previously described.

In one embodiment, the patient is homozygous in the ΔF508 CFTR mutation. In one embodiment, the patient is heterozygous in the ΔF508 CFTR mutation.

In one aspect, the present invention features a kit comprising any of the spray dried dispersions or pharmaceutical compositions previously described.

In one embodiment, the kit further comprises an additional therapeutic agent. In one embodiment, the additional therapeutic agent is a CFTR corrector. In one embodiment, the additional therapeutic agent is a CFTR potentiator. In one embodiment, the additional therapeutic agent is selected from

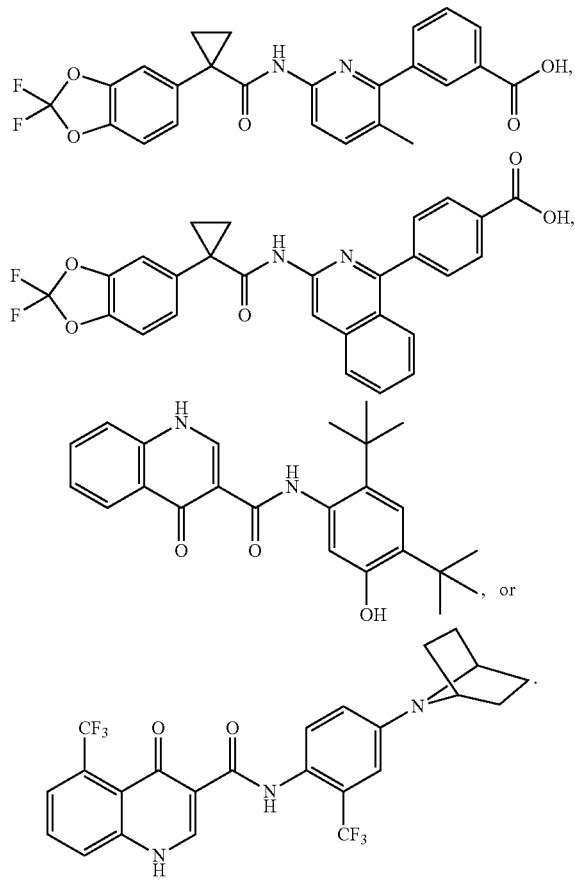

In one embodiment, the additional therapeutic agent and any of the spray dried dispersions or the pharmaceutical compositions previously described are stored in separate containers. In one embodiment, the additional therapeutic agent and any of the spray dried dispersions or pharmaceutical compositions previously described are stored in the same container.

In one embodiment, the container is a bottle, vial, blister pack, or any combination thereof.

In one aspect, the present invention features a method of generating a spray dried dispersion comprising: providing a mixture of a plurality of therapeutic agents and a solvent, wherein the mixture is substantially free of polymer; and forcing the mixture through a nozzle under spray drying conditions to generate the spray dried dispersion.

In one embodiment, the plurality of therapeutic agents consists of a first agent and a second agent.

In one embodiment, the ratio of the first agent to the second agent in the mixture is from about 1:10 to about 10:1 by weight. In one embodiment, the ratio of the first agent to the second agent in the mixture is about 1:1 by weight. In one embodiment, the ratio of the first agent to the second agent is about 1:3 by weight. In one embodiment, the ratio of the first agent to the second agent in the mixture is about 1:6 by weight. In one embodiment, the ratio of the first agent to the second agent in the mixture is about 2:3 by weight.

In one embodiment, the first agent is a CFTR corrector. In one embodiment, the second agent is a CFTR potentiator. In one embodiment, the first agent is a CFTR corrector and the second agent is a CFTR potentiator. In one embodiment, the first agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide. In one embodiment, the second agent is N-[2,4-bis(1,1-dimethylethyl)-5-hydroxyphenyl]-1,4-dihydro-4-oxoquinoline-3-carboxamide. In one embodiment, the first agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, and the second agent is N-[2,4-bis(1,1-dimethylethyl)-5-hydroxyphenyl]-1,4-dihydro-4-oxoquinoline-3-carboxamide.

In one embodiment, the method further comprises filtering the mixture before it is forced through the nozzle. In one embodiment, the method further comprises applying heat to the mixture as it enters the nozzle. In one embodiment, the nozzle comprises an inlet and an outlet, and the inlet is heated to a temperature that is greater than the boiling point of the solvent. It is understood that in certain embodiments, the temperature may be below the boiling point of the solvent, such as, for example under high pressure conditions.

In one embodiment, the spray dryer is heated to a temperature of from about 50° C. to about 150° C. In one embodiment, the spray dryer is heated to a temperature of from about 90° C. to about 150° C. In one embodiment, the mixture is forced through the nozzle by a pressurized gas. In one embodiment, the pressurized gas is inert to the first agent, the second agent, and the solvent. In one embodiment, the pressurized gas comprises molecular nitrogen. In one embodiment, the pressurized gas has a positive pressure of from about 1,000 psi to about 2,000 psi. In one embodiment, the pressurized gas has a positive pressure of about 1,500 psi. In one embodiment, the pressurized gas has a positive pressure of from about 90 psi to about 150 psi. In one embodiment, the pressurized gas has a positive pressure of about 120 psi.

In one embodiment, the method further comprises drying the spray dried dispersion. In one embodiment, the spray dried dispersion is dried under reduced pressure. In one embodiment, the spray dried dispersion is dried at a temperature of from about 50° C. to about 100° C.

In one embodiment, the solvent comprises a polar organic solvent. In one embodiment, the polar organic solvent comprises methylethyl ketone, methyltertbutyl ether, methanol, IPA, THF, DCM, or any combination thereof. In one embodiment, the solvent further comprises water. In one embodiment, the ratio of the polar organic solvent to water is from about 70:30 to about 95:5 by volume. In one embodiment, the ratio of the polar organic solvent to water is about 90:10 by volume.

In another aspect, the present invention features a spray dried dispersion comprising a plurality of particles that are substantially free of polymer, wherein the particles comprise both a CFTR corrector and a CFTR potentiator, wherein the ratio of CFTR corrector to CFTR potentiator is from about 10:1 to about 1:10; the particles have a mean particle diameter of about microns or greater; the particles have a Tg of from about 80° C. to about 180° C.; the particles are substantially amorphous; and the plurality of particles is substantially free of a polymer.

In another aspect, the present invention features a spray dried dispersion generated by providing a mixture that consists essentially of a plurality of therapeutic agents and a solvent; and forcing the mixture through a nozzle under spray drying conditions to generate the spray dried dispersion, wherein the mixture is substantially free of a polymer.

In another aspect, the present invention features a biological medium comprising Compound 1 and Compound 2. In one embodiment, the biological medium is an in vitro biological medium. In one embodiment, the biological medium is an in vivo biological medium.

BRIEF DESCRIPTION OF THE FIGURES

The following figures are provided by way of example and are not intended to limit the scope of the claimed invention.

DETAILED DESCRIPTION

Figure 1:
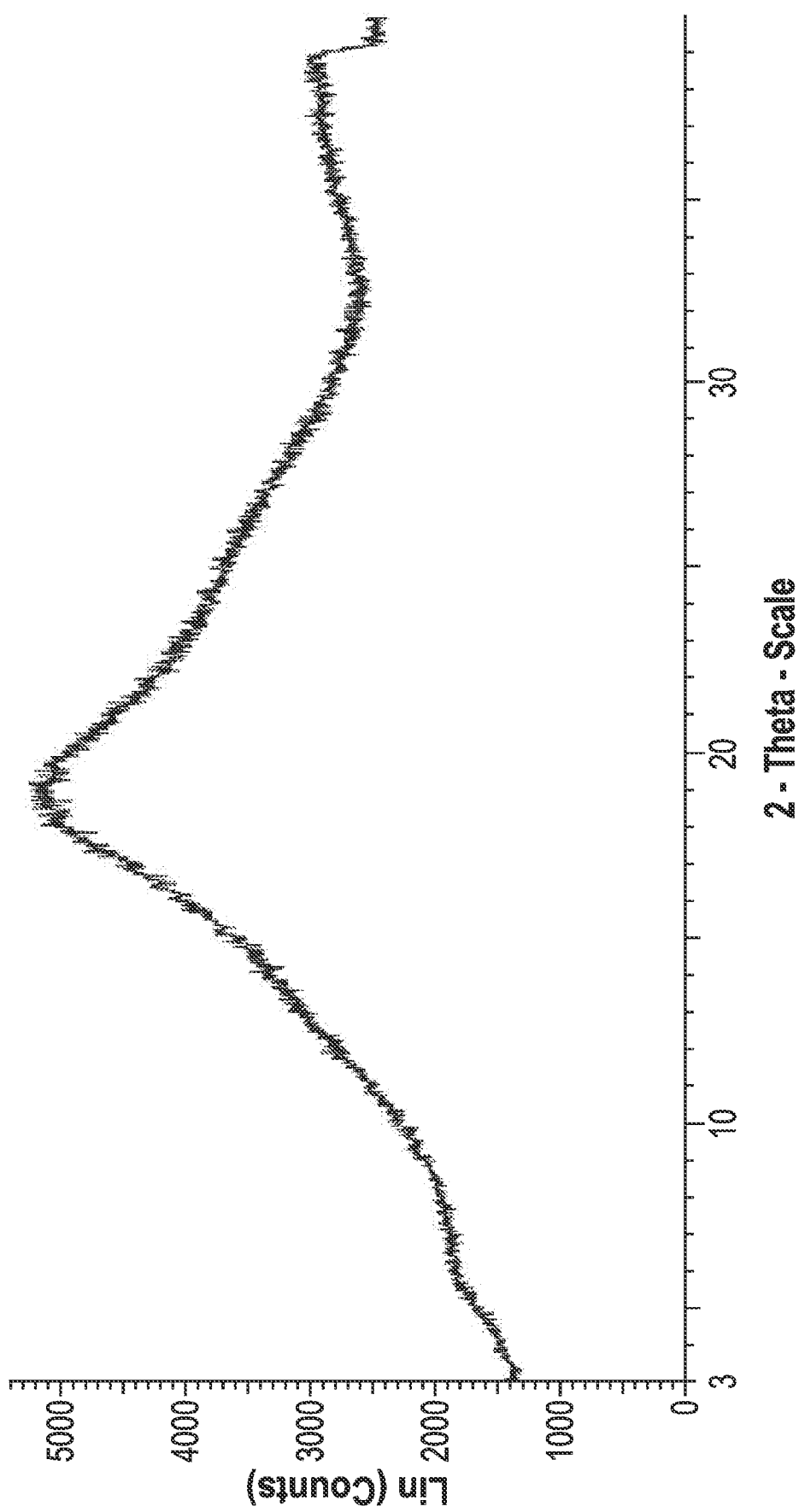
FIG. 1 is an XRPD pattern for the neat spray dried dispersion substantially free of polymer of the present invention formulated with a 1:1 ratio, by weight, of Compound 1 and Compound 2.

The present invention provides pharmaceutical formulations and compositions that are useful for treating cystic fibrosis.

I. Definitions

As used herein, "CFTR" stands for cystic fibrosis transmembrane conductance regulator.

As used herein, "mutations" can refer to mutations in the CFTR gene or the CFTR protein. A "CFTR mutation" refers to a mutation in the CFTR gene, and a "CFTR mutation" refers to a mutation in the CFTR protein. A genetic defect or mutation, or a change in the nucleotides in a gene in general results in a mutation in the CFTR protein translated from that gene.

As used herein, a "ΔF508 mutation" or "F508-del mutation" is a specific mutation within the CFTR protein. The mutation is a deletion of the three nucleotides that comprise the codon for amino acid phenylalanine at position 508, resulting in CFTR protein that lacks this phenylalanine residue.

The term "CFTR gating mutation" as used herein means a CFTR mutation that results in the production of a CFTR protein for which the predominant defect is a low channel open probability compared to normal CFTR (Van Goor, F., Hadida S. and Grootenhuis P., "Pharmacological Rescue of Mutant CFTR function for the Treatment of Cystic Fibrosis", Top. Med. Chem. 3: 91-120 (2008)). Gating mutations include, but are not limited to, G551D, G178R, S549N, S549R, G551S, G970R, G1244E, S1251N, S1255P, and G1349D.

As used herein, a patient who is "homozygous" for a particular mutation, e.g., ΔF508, has the same mutation on each allele.

As used herein, a patient who is "heterozygous" for a particular mutation, e.g., ΔF508, has this mutation on one allele, and a different mutation on the other allele.

As used herein, the term "CFTR corrector" refers to a compound that increases the amount of functional CFTR protein to the cell surface, resulting in enhanced ion transport.

As used herein, the term "CFTR potentiator" refers to a compound that increases the channel activity of CFTR protein located at the cell surface, resulting in enhanced ion transport.

As used herein, the term "inducing", as in inducing CFTR activity, refers to increasing CFTR activity, whether by the corrector, potentiator, or other mechanism.

As used herein, the terms "active pharmaceutical ingredient", "API", and "therapeutic agent" are used interchangeably to refer to a biologically active compound.

A "patient", "subject", or "individual" are used interchangeably and refer to either a human or non-human animal. The term includes mammals such as humans.

As used herein, the term "solvent system" refers to a system comprising an organic solvent capable of dissolving Compound 1 and Compound 2.

As used herein, the term "biological medium" refers to a real or simulated gastrointestinal fluid. A simulated gastrointestinal fluid would be an in vitro gastrointestinal fluid such as, for example, fed state simulated intestinal fluid (FedSIF). A real gastrointestinal fluid would be an in vivo gastrointestinal fluid such as what exists within a patient.

The terms "effective dose" or "effective amount" are used interchangeably herein and refer to that amount that produces the desired effect for which it is administered (e.g., improvement in CF or a symptom of CF or lessening the severity of CF or a symptom of CF). The exact amount will depend on the purpose of the treatment, and will be ascertainable by one skilled in the art using known techniques (see, e.g., Lloyd (1999) The Art, Science and Technology of Pharmaceutical Compounding).

As used herein, the terms "treatment", "treating", and the like generally refer to the improvement of CF or its symptoms or lessening the severity of CF or its symptoms in a subject. "Treatment", as used herein, includes, but is not limited to, the following: increased growth of the subject, increased weight gain, reduction of mucus in the lungs, improved pancreatic and/or liver function, reduced cases of chest infections, and/or reduced instances of coughing or shortness of breath. Improvements in or lessening the severity of any of these conditions can be readily assessed according to standard methods and techniques known in the art.

As used herein, the term "in combination with", when referring to two or more compounds or agents, means that the order of administration includes the compounds or agents being administered prior to, concurrent with, or subsequent to each other to the patient.

The terms "about" and "approximately", when used in connection with doses, amounts, or weight percent of ingredients of a composition or a dosage form, mean a dose, amount, or weight percent that is recognized by one of ordinary skill in the art to provide a pharmacological effect equivalent to that obtained from the specified dose, amount, or weight percent. Specifically the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range.

As used herein, "Compound 1" and "Cmpd 1" are used interchangeably to refer to the compound (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide. This compound has the structure:

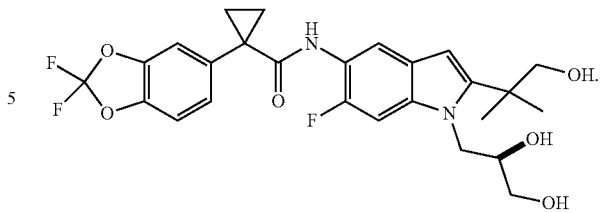

As used herein, "Compound 2" and "Cmpd 2" are used interchangeably to refer to the compound N-[2,4-bis(1,1-dimethylethyl)-5-hydroxyphenyl]-1,4-dihydro-4-oxoquinoline-3-carboxamide. This compound has the structure:

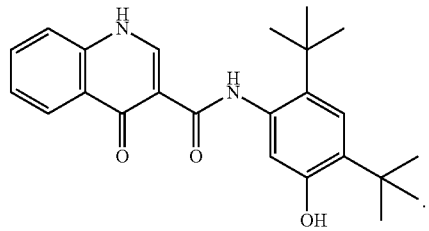 [SMILES: CC(C)(C)c1cc(C(C)(C)C)c(NC(=O)c2c[nH]c3ccccc3c2=O)cc1O]

As used herein, the terms "substantially free" and "neat" are used interchangeably to refer to a mixture or material that has a concentration of less than about 1 wt % (e.g., less than about 0.5 wt %, less than about 0.1 wt %, less than about 1000 ppm, or less than about 500 ppm) of another dopant, compound, impurity, or material (e.g., polymer). A dopant, compound, impurity, or material (e.g., polymer) is absent from a mixture or material when that mixture or material is substantially free of the compound, impurity, or material (e.g., polymer). For example, a mixture or dispersion that is substantially free of a polymer has a concentration of less than about 1 wt % (e.g., less than about 0.5 wt %, less than about 0.1 wt %, less than about 1000 ppm, or less than about 500 ppm) of polymer.

As used herein, "glass transition temperature" or "Tg" refer to the temperature below which the physical properties of amorphous materials vary in a manner similar to those of a solid phase (glassy state), and above which amorphous materials behave like liquids (rubbery state).

As used herein, the term "amorphous" refers to a solid material having no long range order in the position of its molecules. Amorphous solids are generally supercooled liquids in which the molecules are arranged in a random manner so that there is no well-defined arrangement, e.g., molecular packing, and no long range order. Amorphous solids are generally isotropic, i.e. exhibit similar properties in all directions and do not have definite melting points. For example, an amorphous material is a solid material having no sharp characteristic crystalline peak(s) in its X-ray power diffraction (XRPD) pattern (i.e., is not crystalline as determined by XRPD). Instead, one or several broad peaks (e.g., halos) appear in its XRPD pattern. Broad peaks are characteristic of an amorphous solid. See, US 2004/0006237 for a comparison of XRPDs of an amorphous material and crystalline material.

As used herein, the term "substantially amorphous" refers to a solid material having little or no long range order in the position of its molecules. For example, substantially amorphous materials have less than about 15% crystallinity (e.g., less than about 10% crystallinity or less than about 5% crystallinity). It is also noted that the term 'substantially amorphous' includes the descriptor, 'amorphous', which refers to materials having no (0%) crystallinity.

As used herein, the term "dispersion" refers to a disperse system in which one substance, the dispersed phase, is distributed, in discrete units, throughout a second substance (the continuous phase or vehicle). The size of the dispersed phase can vary considerably (e.g. colloidal particles of nanometer dimension, to multiple microns in size). In general, the dispersed phases can be solids, liquids, or gases. In the case of a solid dispersion, the dispersed and continuous phases are both solids. In pharmaceutical applications, a solid dispersion can include a crystalline drug (dispersed phase) in an amorphous polymer (continuous phase); or alternatively, an amorphous drug (dispersed phase) in an amorphous polymer (continuous phase). In some embodiments, a solid dispersion includes the polymer constituting the dispersed phase, and the drug constitute the continuous phase. Or, a solid dispersion includes the drug constituting the dispersed phase, and the polymer constituting the continuous phase.

As used herein, an "excipient" is an inactive ingredient in a pharmaceutical composition. Examples of excipients include fillers or diluents, wetting agents (e.g., surfactants), binders, glidants, lubricants, disintegrants, or the like.

As used herein, a "disintegrant" is an excipient that hydrates a pharmaceutical composition and aids in tablet dispersion. Examples of disintegrants include sodium croscarmellose and/or sodium starch glycolate.

As used herein, a "diluent" or "filler" is an excipient that adds bulkiness to a pharmaceutical composition. Examples of fillers include lactose, sorbitol, celluloses, calcium phosphates, starches, sugars (e.g., mannitol, sucrose, or the like) or any combination thereof.

As used herein, a "lubricant" is an excipient that is added to pharmaceutical compositions that are pressed into tablets. The lubricant aids in compaction of granules into tablets and ejection of a tablet of a pharmaceutical composition from a die press. Example of a lubricant includes magnesium stearate.

As used herein, a "wetting agent" or a "surfactant" is an excipient that imparts pharmaceutical compositions with enhanced solubility and/or wetability. Examples of wetting agents include sodium lauryl sulfate (SLS), sodium stearyl fumarate (SSF), polyoxyethylene 20 sorbitan mono-oleate (e.g., Tween™), or any combination thereof.

As used herein, a "binder" is an excipient that imparts a pharmaceutical composition with enhanced cohesion or tensile strength (e.g., hardness). Examples of binders include dibasic calcium phosphate, sucrose, corn (maize) starch, microcrystalline cellulose, and modified cellulose (e.g., hydroxymethyl cellulose).

As used herein, a "glidant" is an excipient that imparts a pharmaceutical compositions with enhanced flow properties. Examples of glidants include colloidal silica and/or talc.

II. Spray Dried Dispersions Substantially Free of Polymer

A. Spray Dried Dispersions

The present invention provides a spray dried dispersion comprising a plurality of therapeutic agents, wherein the dispersion is substantially free of a polymer.

In some embodiments, the plurality of therapeutic agents consists of a first therapeutic agent and a second therapeutic agent.

In some embodiments, the first agent is a CFTR corrector. For example, the first agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide.

In some embodiments, the second agent is a CFTR potentiator. For example, the second agent is N-[2,4-bis(1,1-dimethylethyl)-5-hydroxyphenyl]-1,4-dihydro-4-oxoquinoline-3-carboxamide.

And, in some embodiments, the first agent is a CFTR corrector and the second agent is a CFTR potentiator. For example, the first agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, and the second agent is N-[2,4-bis(1,1-dimethylethyl)-5-hydroxyphenyl]-1,4-dihydro-4-oxoquinoline-3-carboxamide.

In some embodiments, the ratio of the first agent to the second agent is from about 1:10 to about 10:1 by weight. For example, the ratio of the first agent to the second agent is about 1:1 by weight. In other examples, the ratio of the first agent to the second agent is about 1:3 by weight. In some examples, the ratio of the first agent to the second agent is about 1:6 by weight. In some examples, the ratio of the first agent to the second agent is about 2:3 by weight.

In some embodiments, the spray dried dispersion has a glass transition temperature (Tg) of from about 80° C. to about 180° C.

In some embodiments, the spray dried dispersion comprises a plurality of particles having a mean particle diameter of about 5 to about 100 microns. In some embodiments, the spray dried dispersion comprises a plurality of particles having a mean particle diameter of about to about 30 microns. In some embodiments, the spray dried dispersion comprises a plurality of particles having a mean particle diameter of about 15 microns.

In some embodiments, the spray dried dispersion is substantially amorphous.

Another aspect of the present invention provides a spray dried dispersion consisting of a plurality of therapeutic agents.

In some embodiments, the spray dried dispersion consists of two therapeutic agents, a first therapeutic agent and a second therapeutic agent.

In some embodiments, the first agent is a CFTR corrector. For example, the first agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide.

In some embodiments, the second agent is a CFTR potentiator. For example, the second agent is N-[2,4-bis(1,1-dimethylethyl)-5-hydroxyphenyl]-1,4-dihydro-4-oxoquinoline-3-carboxamide.

And, in some embodiments, the first agent is a CFTR corrector and the second agent is a CFTR potentiator. For example, the first agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, and the second agent is N-[2,4-bis(1,1-dimethylethyl)-5-hydroxyphenyl]-1,4-dihydro-4-oxoquinoline-3-carboxamide.

In some embodiments, the ratio of the first agent to the second agent is from about 1:10 to about 10:1 by weight. For example, the ratio of the first agent to the second agent is about 1:1 by weight. In other examples, the ratio of the first agent to the second agent is about 1:3 by weight. In some examples, the ratio of the first agent to the second agent is about 1:6 by weight. In some examples, the ratio of the first agent to the second agent is about 2:3 by weight.

In some embodiments, the spray dried dispersion has a glass transition temperature (Tg) of from about 80° C. to about 180° C.

In some embodiments, the spray dried dispersion comprises a plurality of particles having a mean particle diameter of about 5 to about 100 microns. In some embodiments, the spray dried dispersion comprises a plurality of particles having a mean particle diameter of about 5 to about 30 microns. In some embodiments, the spray dried dispersion comprises a plurality of particles having a mean particle diameter of about 15 microns.

Another aspect of the present invention provides a spray dried dispersion comprising a particle, wherein the particle comprises a plurality of therapeutic agents, and the particle is substantially free of a polymer.

In some embodiments, the particle consists essentially of a first agent and a second agent.

In some embodiments, the first agent is a CFTR corrector. For example, the first agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide.

In some embodiments, the second agent is a CFTR potentiator. For example, the second agent is N-[2,4-bis(1,1-dimethylethyl)-5-hydroxyphenyl]-1,4-dihydro-4-oxoquinoline-3-carboxamide.

And, in some embodiments, the first agent is a CFTR corrector and the second agent is a CFTR potentiator. For example, the first agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, and the second agent is N-[2,4-bis(1,1-dimethylethyl)-5-hydroxyphenyl]-1,4-dihydro-4-oxoquinoline-3-carboxamide.

In some embodiments, the ratio of the first agent to the second agent is from about 1:10 to about 10:1 by weight. For example, the ratio of the first agent to the second agent is about 1:1 by weight. In other examples, the ratio of the first agent to the second agent is about 1:3 by weight. In some examples, the ratio of the first agent to the second agent is about 1:6 by weight. In some examples, the ratio of the first agent to the second agent is about 2:3 by weight.

In some embodiments, the spray dried dispersion has a glass transition temperature (Tg) of from about 80° C. to about 180° C.

In some embodiments, the spray dried dispersion comprises a plurality of particles having a mean particle diameter of about 5 to about 100 microns. In some embodiments, the spray dried dispersion comprises a plurality of particles having a mean particle diameter of about 5 to about 30 microns. In some embodiments, the spray dried dispersion comprises a plurality of particles having a mean particle diameter of about 15 microns.

In some embodiments, the spray dried dispersion is substantially amorphous.

Another aspect of the present invention provides a pharmaceutical composition comprising a spray dried dispersion, wherein the spray dried dispersion comprises a first particle consisting essentially of an amorphous first agent and a second particle consisting essentially of an amorphous second agent.

In some embodiments, the first agent is a CFTR corrector. For example, the first agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide.

In some embodiments, the second agent is a CFTR potentiator. For example, the second agent is N-[2,4-bis(1,1-dimethylethyl)-5-hydroxyphenyl]-1,4-dihydro-4-oxoquinoline-3-carboxamide.

And, in some embodiments, the first agent is a CFTR corrector and the second agent is a CFTR potentiator. For example, the first agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, and the second agent is N-[2,4-bis(1,1-dimethylethyl)-5-hydroxyphenyl]-1,4-dihydro-4-oxoquinoline-3-carboxamide.

In some embodiments, the ratio of the first particle to the second particle is from about 1:10 to about 10:1 by weight. For example, the ratio of the first particle to the second particle is about 1:1 by weight. In other examples, the ratio of the first particle to the second particle is about 1:3 by weight. In some examples, the ratio of the first particle to the second particle is about 1:6 by weight. In some examples, the ratio of the first particle to the second particle is about 2:3 by weight.

In some embodiments, the spray dried dispersion comprises a plurality of particles having a mean particle diameter of about 5 to about 100 microns. In some embodiments, the first particle, the second particle, or both particles have a mean particle diameter of about 5 to about 30 microns. In some embodiments, the first particle, the second particle, or both particles have a mean particle diameter of about 15 microns.

B. Methods of Preparing a Spray Dried Dispersion Substantially Free of Polymer

Starting from Compound 1 or Compound 2, the amorphous form of Compound 1 or Compound 2 may be prepared by spray drying methods. Spray drying is a process that converts a liquid feed to a dried particulate form. Optionally, a secondary drying process such as fluidized bed drying or vacuum drying may be used to reduce residual solvents to pharmaceutically acceptable levels. Typically, spray drying involves contacting a highly dispersed liquid suspension or solution, and a sufficient volume of hot air to produce evaporation and drying of the liquid droplets. The preparation to be spray dried can be any solution, coarse suspension, slurry, colloidal dispersion, or paste that may be atomized using the selected spray drying apparatus. In one procedure, the preparation is sprayed into a current of warm filtered gas that evaporates the solvent and conveys the dried product to a collector (e.g. a cyclone). The spent gas is then exhausted with the solvent, or alternatively the spent air is sent to a condenser to capture and potentially recycle the solvent. Commercially available types of apparatus may be used to conduct the spray drying. For example, commercial spray dryers are manufactured by Buchi Ltd. And Niro (e.g., the PSD line of spray driers manufactured by Niro) (see, US 2004/0105820; US 2003/0144257).

Techniques and methods for spray drying may be found in Perry's Chemical Engineering Handbook, 6th Ed., R. H. Perry, D. W. Green & J. O. Maloney, eds.), McGraw-Hill book co. (1984); and Marshall "Atomization and Spray-Drying" 50, Chem. Eng. Prog. Monogr. Series 2 (1954). All three references are incorporated herein in their entirety by reference.

Removal of the solvent may require a subsequent drying step, such as tray drying, fluid bed drying (e.g., from about room temperature to about 100° C.), vacuum drying, microwave drying, rotary drum drying or biconical vacuum drying (e.g., from about room temperature to about 200° C.).

In one embodiment, the solid dispersion is fluid bed dried.

In one process, the solvent includes a volatile solvent, for example a solvent having a boiling point of less than about 100° C. In some embodiments, the solvent includes a mixture of solvents, for example a mixture of volatile solvents or a mixture of volatile and non-volatile solvents. Where mixtures of solvents are used, the mixture can include one or more non-volatile solvents, for example, where the non-volatile solvent is present in the mixture at less than about 15%, e.g., less than about 12%, less than about 10%, less than about 8%, less than about 5%, less than about 3%, or less than about 2%.

In some processes, solvents are those solvents where Compound 1 and Compound 2 have solubilities of at least about 10 mg/ml, (e.g., at least about 15 mg/ml, 20 mg/ml, 25 mg/ml, mg/ml, 35 mg/ml, 40 mg/ml, 45 mg/ml, 50 mg/ml, or greater). In other processes, solvents include those solvents where Compound 1 has a solubility of at least about 20 mg/ml.

Exemplary solvents that could be tested include acetone, cyclohexane, dichloromethane, N,N-dimethylacetamide (DMA), N,N-dimethylformamide (DMF), 1,3-dimethyl-2-imidazolidinone (DMI), dimethyl sulfoxide (DMSO), dioxane, ethyl acetate, ethyl ether, glacial acetic acid (HAc), methyl ethyl ketone (MEK), N-methyl-2-pyrrolidinone (NMP), methyl tert-butyl ether (MTBE), tetrahydrofuran (THF), pentane, acetonitrile, methanol, ethanol, isopropyl alcohol, isopropyl acetate, DCM, and toluene. Exemplary co-solvents include acetone/DMSO, acetone/DMF, acetone/water, MEK/water, THF/water, dioxane/water. In a two solvent system, the solvents can be present in of from about 0.1% to about 99.9%. In some preferred embodiments, water is a co-solvent with acetone where water is present from about to about 15%, for example about 9% to about 11%, e.g., about 10%. In some preferred embodiments, water is a co-solvent with MEK where water is present from about 0.1% to about 15%, for example about 9% to about 11%, e.g., about 10%. In some embodiments the solvent system includes three solvents. In instances where amorphous Compound 1 is a component of a solid amorphous dispersion, preferred solvents dissolve both Compound 1 and the polymer. Suitable solvents include those described above, for example, MEK, DCM, water, methanol, IPA, and mixtures thereof.

The particle size and the temperature drying range may be modified to prepare an optimal solid dispersion. As would be appreciated by skilled practitioners, a small particle size would lead to improved solvent removal. Applicants have found however, that smaller particles can lead to fluffy particles that, under some circumstances do not provide optimal solid dispersions for downstream processing such as tableting. At higher temperatures, crystallization or chemical degradation of Compound 1 or Compound 2 may occur. At lower temperatures, a sufficient amount of the solvent may not be removed. The methods herein provide an optimal particle size and an optimal drying temperature.

A spray dried dispersion substantially free of polymer of the present embodiment may optionally include a surfactant. A surfactant or surfactant mixture would generally decrease the interfacial tension between the solid dispersion and an aqueous medium. An appropriate surfactant or surfactant mixture may also enhance aqueous solubility and bioavailability of Compound 1 or Compound 2 from a solid dispersion. The surfactants for use in connection with the present invention include, but are not limited to, sorbitan fatty acid esters (e.g., Spans®), polyoxyethylene sorbitan fatty acid esters (e.g., Tweens®), sodium lauryl sulfate (SLS), sodium dodecylbenzene sulfonate (SDBS) dioctyl sodium sulfosuccinate (Docusate), dioxycholic acid sodium salt (DOSS), sorbitan monostearate, sorbitan tristearate, hexadecyltrimethyl ammonium bromide (HTAB), sodium N-lauroylsarcosine, sodium oleate, sodium myristate, sodium stearate, sodium palmitate, gelucire 44/14, ethylenediamine tetraacetic acid (EDTA), vitamin E d-alpha tocopheryl polyethylene glycol 1000 succinate (TPGS), lecithin, MW 677-692, glutanic acid monosodium monohydrate, labrasol, PEG 8 caprylic/capric glycerides, transcutol, diethylene glycol monoethyl ether, solutol HS-15, polyethylene glycol/hydroxystearate, taurocholic acid, pluronic F68, pluronic F108, and pluronic F127 (or any other polyoxyethylene-polyoxypropylene co-polymers (Pluronics®) or saturated polyglycolized glycerides (Gelucirs®)). Specific example of such surfactants that may be used in connection with this invention include, but are not limited to, Span 65, Span 25, Tween 20, Capryol 90, Pluronic F108, sodium lauryl sulfate (SLS), vitamin E TPGS, pluronics and copolymers. SLS is generally preferred.

The amount of the surfactant (e.g., SLS) relative to the total weight of the solid dispersion may be between 0.1-15%. Preferably, it is from about 0.5% to about 10%, more preferably from about 0.5 to about 5%, e.g., about 0.5 to 4%, about 0.5 to 3%, about 0.5 to 2%, about 0.5 to 1%, or about 0.5%.

In certain embodiments, the amount of the surfactant relative to the total weight of the solid dispersion is at least about 0.1%, preferably at least about 0.5%. In these embodiments, the surfactant would be present in an amount of no more than about 15%, and preferably no more than about 12%, about 11%, about 10%, about 9%, about 8%, about 7%, about 6%, about 5%, about 4%, about 3%, about 2% or about 1%. An embodiment wherein the surfactant is in an amount of about 0.5% by weight is preferred.

Candidate surfactants (or other components) can be tested for suitability for use in the invention in a manner similar to that described for testing polymers.

One aspect of the present invention provides a method of generating a spray dried dispersion comprising (i) providing a mixture of a plurality of therapeutic agents and a solvent, wherein the mixture is substantially free of polymer; and (ii) forcing the mixture through a nozzle under spray drying conditions to generate the spray dried dispersion.

In some implementations, the plurality of therapeutic agents consists of a first agent and a second agent.

In some implementations, the ratio of the first agent to the second agent in the mixture is from about 1:10 to about 10:1 by weight. For example, the ratio of the first agent to the second agent in the mixture is about 1:1 by weight. In other examples, the ratio of the first agent to the second agent is about 1:3 by weight. In some examples, the ratio of the first agent to the second agent is about 1:6 by weight. In some examples, the ratio of the first agent to the second agent is about 2:3 by weight.

In some implementations, the first agent is a CFTR corrector. For example, the first agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide.

In some implementations, the second agent is a CFTR potentiator. For example, the second agent is N-[2,4-bis(1,1-dimethylethyl)-5-hydroxyphenyl]-1,4-dihydro-4-oxoquinoline-3-carboxamide.

In some implementations, the first agent is a CFTR corrector and the second agent is a CFTR potentiator. For example, the first agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, and the second agent is N-[2,4-bis(1,1-dimethylethyl)-5-hydroxyphenyl]-1,4-dihydro-4-oxoquinoline-3-carboxamide.

Some implementations further comprise filtering the mixture before it is forced through the nozzle. Such filtering can be accomplished using any suitable filter media having a suitable pore size (e.g., 20 µm or less).

Some implementations further comprise applying heat to the mixture as it enters the nozzle. This heating can be accomplished using any suitable heating element.

In some implementations, the nozzle comprises an inlet and an outlet, and the inlet is heated to a temperature that is less than the boiling point of the solvent. For example, the inlet is heated to a temperature of from about 90° C. to about 150° C.

In some implementations, the mixture is forced through the nozzle by a pressurized gas. Examples of suitable pressurized gases include those pressurized gas that are inert to the first agent, the second agent, and the solvent. In one example, the pressurized gas comprises elemental nitrogen.

In some implementations, the pressurized gas has a positive pressure of from about 90 psi to about 150 psi.

Some implementations further comprise drying the spray dried dispersion. For example, the spray dried dispersion is dried under reduced pressure. In other examples, the spray dried dispersion is dried at a temperature of from about 50° C. to about 100° C.

In some implementations, the solvent comprises a polar organic solvent. Examples of polar organic solvents include methylethyl ketone, THF, DCM, methanol, or IPA, or any combination thereof, such as, for example DCM/methanol. In other examples, the solvent further comprises water. In other examples, the solvent further comprises water. For instance, the solvent could be methylethyl ketone/water, THF/water, or methylethyl ketone/water/IPA. For example, the ratio of the polar organic solvent to water is from about 70:30 to about 95:5 by volume. In other instances, the ratio of the polar organic solvent to water is about 90:10 by volume.

Another aspect of the present invention provides a method of generating a spray dried dispersion comprising: (i) providing a mixture consisting of a solvent and a plurality of therapeutic agents; and (ii) forcing the mixture out of a nozzle under spray dry drying conditions to generate a spray dried dispersion.

In some implementations, the plurality of therapeutic agents consists of a first agent and a second agent.

In some implementations, the ratio of the first agent to the second agent in the mixture is from about 1:10 to about 10:1 by weight. For example, the ratio of the first agent to the second agent in the mixture is about 1:1 by weight. In other examples, the ratio of the first agent to the second agent is about 1:3 by weight. In some examples, the ratio of the first agent to the second agent is about 1:6 by weight. In some examples, the ratio of the first agent to the second agent is about 2:3 by weight.

In some implementations, the first agent is a CFTR corrector. For example, the first agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide.

In some implementations, the second agent is a CFTR potentiator. For example, the second agent is N-[2,4-bis(1,1-dimethylethyl)-5-hydroxyphenyl]-1,4-dihydro-4-oxoquinoline-3-carboxamide.

In some implementations, the first agent is a CFTR corrector and the second agent is a CFTR potentiator. For example, the first agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, and the second agent is N-[2,4-bis(1,1-dimethylethyl)-5-hydroxyphenyl]-1,4-dihydro-4-oxoquinoline-3-carboxamide.

Some implementations further comprise filtering the mixture before it is forced through the nozzle. Such filtering can be accomplished using any suitable filter media having a suitable pore size (e.g., 20 µm or less).

Some implementations further comprise applying heat to the mixture as it enters the nozzle. This heating can be accomplished using any suitable heating element.

In some implementations, the nozzle comprises an inlet and an outlet, and the inlet is heated to a temperature that is less than the boiling point of the solvent. For example, the inlet is heated to a temperature of from about 90° C. to about 150° C.

In some implementations, the mixture is forced through the nozzle by a pressurized gas. Examples of suitable pressurized gases include those pressurized gas that are inert to the first agent, the second agent, and the solvent. In one example, the pressurized gas comprises elemental nitrogen.

In some implementations, the pressurized gas has a positive pressure of from about 90 psi to about 150 psi.

Some implementations further comprise drying the spray dried dispersion. For example, the spray dried dispersion is dried under reduced pressure. In other examples, the spray dried dispersion is dried at a temperature of from about 50° C. to about 100° C.

In some implementations, the solvent comprises a polar organic solvent. Examples of polar organic solvents include methylethyl ketone, THF, DCM, methanol, or IPA, or any combination thereof. In other examples, the solvent further comprises water. In other examples, the solvent further comprises water. For instance, the solvent could be methylethyl ketone/water, THF/water, or methylethyl ketone/water/IPA. For example, the ratio of the polar organic solvent to water is from about 70:30 to about 95:5 by volume. In other instances, the ratio of the polar organic solvent to water is about 90:10 by volume.

Another aspect of the present invention provides a method of generating a spray dried dispersion comprising (i) spraying a mixture through a nozzle, wherein the mixture comprises a plurality of therapeutic agents and a solvent; and (ii) forcing the mixture through a nozzle under spray drying conditions to generate a particle that comprises the plurality of therapeutic agents.

In some implementations, the plurality of therapeutic agents comprises a first agent and a second agent. In other implementations, the plurality of therapeutic agents consists of a first agent and a second agent.

In some implementations, the ratio of the first agent to the second agent in the mixture is from about 1:10 to about 10:1 by weight. For example, the ratio of the first agent to the second agent in the mixture is about 1:1 by weight. In other examples, the ratio of the first agent to the second agent is about 1:3 by weight. In some examples, the ratio of the first agent to the second agent is about 1:6 by weight. In some examples, the ratio of the first agent to the second agent is about 2:3 by weight.

In some implementations, the first agent is a CFTR corrector. For example, the first agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide.

In some implementations, the second agent is a CFTR potentiator. For example, the second agent is N-[2,4-bis(1,1-dimethylethyl)-5-hydroxyphenyl]-1,4-dihydro-4-oxoquinoline-3-carboxamide.

In some implementations, the first agent is a CFTR corrector and the second agent is a CFTR potentiator. For example, the first agent is (R)-1-(2,2-difluorobenzo[d][1,3]dioxol-5-yl)-N-(1-(2,3-dihydroxypropyl)-6-fluoro-2-(1-hydroxy-2-methylprop an-2-yl)-1H-indol-5-yl)cyclopropanecarboxamide, and the second agent is N-[2,4-bis(1,1-dimethylethyl)-5-hydroxyphenyl]-1,4-dihydro-4-oxoquinoline-3-carboxamide.

Some implementations further comprise filtering the mixture before it is forced through the nozzle. Such filtering can be accomplished using any suitable filter media having a suitable pore size (e.g., 20 μm or less).

Some implementations further comprise applying heat to the mixture as it enters the nozzle. This heating can be accomplished using any suitable heating element.

In some implementations, the nozzle comprises an inlet and an outlet, and the inlet is heated to a temperature that is less than the boiling point of the solvent. For example, the inlet is heated to a temperature of from about 90° C. to about 150° C.

In some implementations, the mixture is forced through the nozzle by a pressurized gas. Examples of suitable pressurized gases include those pressurized gas that are inert to the first agent, the second agent, and the solvent. In one example, the pressurized gas comprises elemental nitrogen.

In some implementations, the pressurized gas has a positive pressure of from about 90 psi to about 150 psi.

Some implementations further comprise drying the spray dried dispersion. For example, the spray dried dispersion is dried under reduced pressure. In other examples, the spray dried dispersion is dried at a temperature of from about 50° C. to about 100° C.

In some implementations, the solvent comprises a polar organic solvent. Examples of polar organic solvents include methylethyl ketone, THF, DCM, methanol, or IPA, or any combination thereof, such as for example DCM/methanol. In other examples, the solvent further comprises water. In other examples, the solvent further comprises water. For instance, the solvent could be methylethyl ketone/water, THF/water, or methylethyl ketone/water/IPA. For example, the ratio of the polar organic solvent to water is from about 70:30 to about 95:5 by volume. In other instances, the ratio of the polar organic solvent to water is about 90:10 by volume.

Another aspect of the present invention provides a spray dried dispersion comprising a plurality of therapeutic agents, wherein the dispersion is substantially free of a polymer, and wherein the spray dried dispersion is generated by (i) providing a mixture that consists essentially of the plurality of therapeutic agents and a solvent; and (ii) forcing the mixture through a nozzle under spray drying conditions to generate the spray dried dispersion.

In some embodiments, the plurality of therapeutic agents comprises a first agent and a second agent. In some embodiments, the plurality of therapeutic agents consists of a first agent and a second agent.

In some embodiments, the ratio of the first agent to the second agent in the mixture is from about 1:10 to about 10:1 by weight. For example, the ratio of the first agent to the second agent in the mixture is about 1:1 by weight. In other examples, the ratio of the first agent to the second agent is about 1:3 by weight. In some examples, the ratio of the first agent to the second agent is about 1:6 by weight. In some examples, the ratio of the first agent to the second agent is about 2:3 by weight.

In some embodiments, the first agent is a CFTR corrector. For example, the first agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide.

In some embodiments, the second agent is a CFTR potentiator. For example, the second agent is N-[2,4-bis(1,1-dimethylethyl)-5-hydroxyphenyl]-1,4-dihydro-4-oxoquinoline-3-carboxamide.

In some embodiments, the first agent is a CFTR corrector and the second agent is a CFTR potentiator. For example, the first agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, and the second agent is N-[2,4-bis(1,1-dimethylethyl)-5-hydroxyphenyl]-1,4-dihydro-4-oxoquinoline-3-carboxamide.

Some embodiments further comprise filtering the mixture before it is forced through the nozzle. Such filtering can be accomplished using any suitable filter media having a suitable pore size (e.g., 20 μm or less).

Some embodiments further comprise applying heat to the mixture as it enters the nozzle. This heating can be accomplished using any suitable heating element.

In some embodiments, the nozzle comprises an inlet and an outlet, and the inlet is heated to a temperature that is less than the boiling point of the solvent. For example, the inlet is heated to a temperature of from about 90° C. to about 150° C.

In some embodiments, the mixture is forced through the nozzle by a pressurized gas. Examples of suitable pressurized gases include those pressurized gas that are inert to the first agent, the second agent, and the solvent. In one example, the pressurized gas comprises elemental nitrogen.

In some embodiments, the pressurized gas has a positive pressure of from about 90 psi to about 150 psi.

Some embodiments further comprise drying the spray dried dispersion. For example, the spray dried dispersion is dried under reduced pressure. In other examples, the spray dried dispersion is dried at a temperature of from about 50° C. to about 100° C.

In some implementations, the solvent comprises a polar organic solvent. Examples of polar organic solvents include methylethyl ketone, THF, DCM, methanol, or IPA, or any combination thereof, such as for example, DCM/methanol. In other examples, the solvent further comprises water. In other examples, the solvent further comprises water. For instance, the solvent could be methylethyl ketone/water, THF/water, or methylethyl ketone/water/IPA. For example, the ratio of the polar organic solvent to water is from about 70:30 to about 95:5 by volume. In other instances, the ratio of the polar organic solvent to water is about 90:10 by volume.

Another aspect of the present invention provides a spray dried dispersion consisting of a plurality of therapeutic agents, wherein the dispersion is generated by (i) providing a mixture that consists of a plurality of therapeutic agents and a solvent; and (ii) forcing the mixture through a nozzle under spray drying conditions to generate the spray dried dispersion.

In some embodiments, the plurality of therapeutic agents consists of a first agent and a second agent.

In some embodiments, the ratio of the first agent to the second agent in the mixture is from about 1:10 to about 10:1 by weight. For example, the ratio of the first agent to the second agent in the mixture is about 1:1 by weight. In other examples, the ratio of the first agent to the second agent is about 1:3 by weight. In some examples, the ratio of the first agent to the second agent is about 1:6 by weight. In some examples, the ratio of the first agent to the second agent is about 2:3 by weight.

In some embodiments, the first agent is a CFTR corrector. For example, the first agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide.

In some embodiments, the second agent is a CFTR potentiator. For example, the second agent is N-[2,4-bis(1,1-dimethylethyl)-5-hydroxyphenyl]-1,4-dihydro-4-oxoquinoline-3-carboxamide.

In some embodiments, the first agent is a CFTR corrector and the second agent is a CFTR potentiator. For example, the first agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, and the second agent is N-[2,4-bis(1,1-dimethylethyl)-5-hydroxyphenyl]-1,4-dihydro-4-oxoquinoline-3-carboxamide.

Some embodiments further comprise filtering the mixture before it is forced through the nozzle. Such filtering can be accomplished using any suitable filter media having a suitable pore size (e.g., 20 μm or less).

Some embodiments further comprise applying heat to the mixture as it enters the nozzle. This heating can be accomplished using any suitable heating element.

In some embodiments, the nozzle comprises an inlet and an outlet, and the inlet is heated to a temperature that is less than the boiling point of the solvent. For example, the inlet is heated to a temperature of from about 90° C. to about 150° C.

In some embodiments, the mixture is forced through the nozzle by a pressurized gas. Examples of suitable pressurized gases include those pressurized gas that are inert to the first agent, the second agent, and the solvent. In one example, the pressurized gas comprises elemental nitrogen.

In some embodiments, the pressurized gas has a positive pressure of from about 90 psi to about 150 psi.

Some embodiments further comprise drying the spray dried dispersion. For example, the spray dried dispersion is dried under reduced pressure. In other examples, the spray dried dispersion is dried at a temperature of from about 50° C. to about 100° C.

In some implementations, the solvent comprises a polar organic solvent. Examples of polar organic solvents include methylethyl ketone, THF, DCM, methanol, or IPA, or any combination thereof. In other examples, the solvent further comprises water. In other examples, the solvent further comprises water. For instance, the solvent could be methylethyl ketone/water, THF/water, or methylethyl ketone/water/IPA. For example, the ratio of the polar organic solvent to water is from about 70:30 to about 95:5 by volume. In other instances, the ratio of the polar organic solvent to water is about 90:10 by volume.

Another aspect of the present invention provides a spray dried dispersion comprising a particle, wherein the particle comprises a plurality of therapeutic agents, and the particle is substantially free of a polymer, and wherein the spray dried dispersion is generated by (i) spraying a mixture through a nozzle, wherein the mixture comprises a plurality of therapeutic agents and a solvent; and (ii) forcing the mixture through a nozzle under spray drying conditions to generate the spray dried dispersion.

In some embodiments, the plurality of therapeutic agents comprises a first agent and a second agent. In some embodiments, the plurality of therapeutic agents consists of a first agent and a second agent.

In some embodiments, the ratio of the first agent to the second agent in the mixture is from about 1:10 to about 10:1 by weight. For example, the ratio of the first agent to the second agent in the mixture is about 1:1 by weight. In other examples, the ratio of the first agent to the second agent is about 1:3 by weight. In some examples, the ratio of the first agent to the second agent is about 1:6 by weight. In some examples, the ratio of the first agent to the second agent is about 2:3 by weight.

In some embodiments, the first agent is a CFTR corrector. For example, the first agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide.

In some embodiments, the second agent is a CFTR potentiator. For example, the second agent is N-[2,4-bis(1,1-dimethylethyl)-5-hydroxyphenyl]-1,4-dihydro-4-oxoquinoline-3-carboxamide.

In some embodiments, the first agent is a CFTR corrector and the second agent is a CFTR potentiator. For example, the first agent is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, and the second agent is N-[2,4-bis(1,1-dimethylethyl)-5-hydroxyphenyl]-1,4-dihydro-4-oxoquinoline-3-carboxamide.

Some embodiments further comprise filtering the mixture before it is forced through the nozzle. Such filtering can be accomplished using any suitable filter media having a suitable pore size (e.g., 20 μm or less).

Some embodiments further comprise applying heat to the mixture as it enters the nozzle. This heating can be accomplished using any suitable heating element.

In some embodiments, the nozzle comprises an inlet and an outlet, and the inlet is heated to a temperature that is less than the boiling point of the solvent. For example, the inlet is heated to a temperature of from about 90° C. to about 150° C.

In some embodiments, the mixture is forced through the nozzle by a pressurized gas. Examples of suitable pressurized gases include those pressurized gas that are inert to the first agent, the second agent, and the solvent. In one example, the pressurized gas comprises elemental nitrogen.

In some embodiments, the pressurized gas has a positive pressure of from about 90 psi to about 150 psi.

Some embodiments further comprise drying the spray dried dispersion. For example, the spray dried dispersion is dried under reduced pressure. In other examples, the spray dried dispersion is dried at a temperature of from about 50° C. to about 100° C.

In some implementations, the solvent comprises a polar organic solvent. Examples of polar organic solvents include methylethyl ketone, THF, DCM, methanol, or IPA, or any combination thereof. In other examples, the solvent further comprises water. In other examples, the solvent further comprises water. For instance, the solvent could be methylethyl ketone/water, THF/water, or methylethyl ketone/water/IPA. For example, the ratio of the polar organic solvent to water is from about 70:30 to about 95:5 by volume. In other instances, the ratio of the polar organic solvent to water is about 90:10 by volume.

Figure 4:
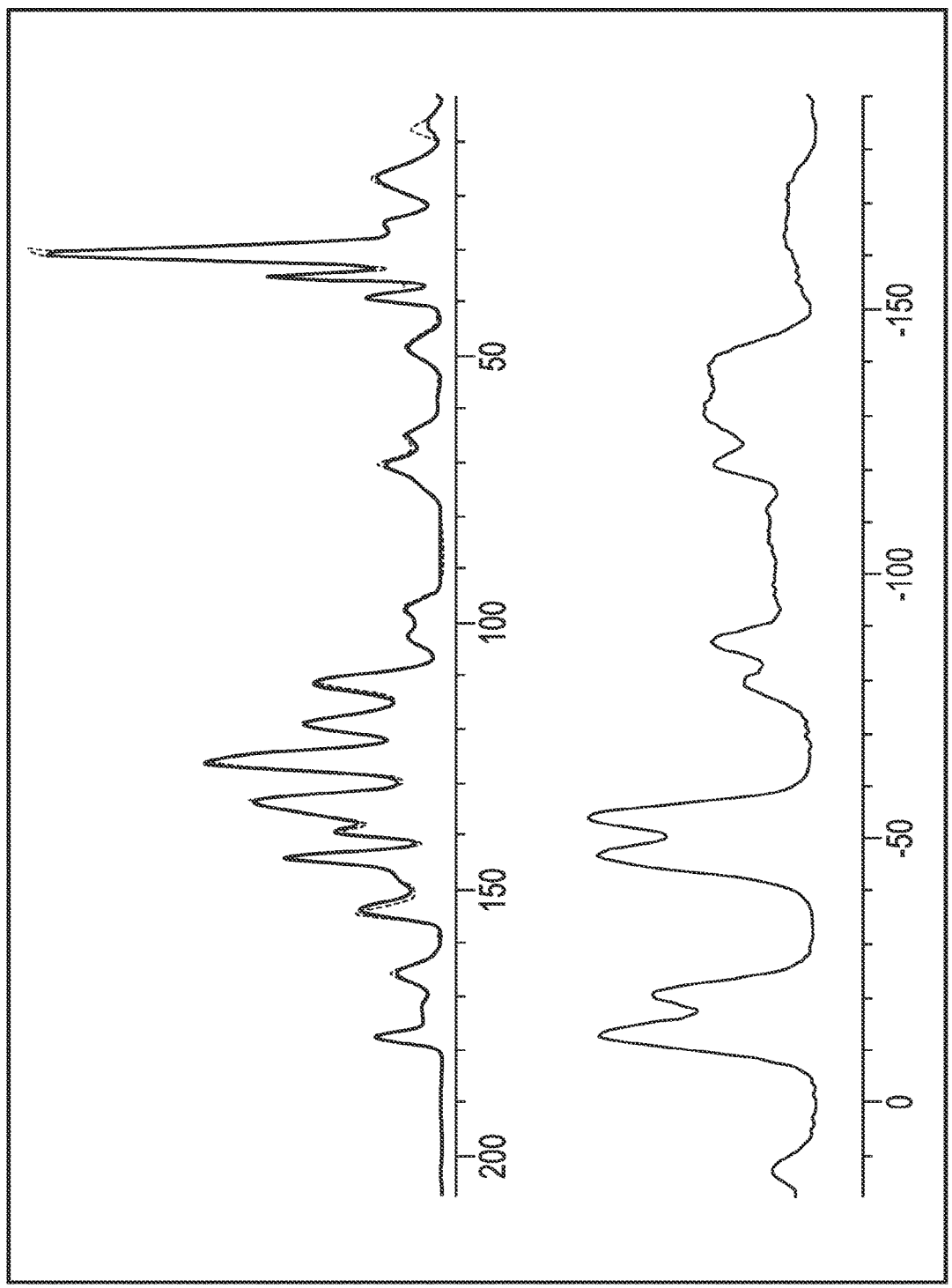
FIG. 4 depicts an overlay of solid state $^{13}$C NMR (top) spectra for the neat spray dried dispersion substantially free of polymer, and cryoground/cryomilled Compound 1 and Compound 2 formulated with a 1:1 ratio, by weight, and $^{19}$F NMR (bottom) spectra for the neat spray dried dispersion substantially free of polymer formulated with a 1:1 ratio, by weight, of Compound 1 and Compound 2.

In some implementations, a composition comprising amorphous Compound 1 and Compound 2, substantially free of polymer may be prepared by non-spray drying techniques, such as, for example, cyrogrounding/cryomilling techniques. FIG. 4 (top) discloses a near identical overlay of $^{13}C$ spectra between amorphous Compound 1 and Compound 2 substantially free of polymer prepared by spray drying techniques described herein and cryogrounding/cryomilling techniques. In the present example, a 1:1 ratio by weight sample of Compound 1 and Compound 2 was cryoground/crymilled at liquid nitrogen temperatures for 100 minutes at 15 cycles/minute. A composition comprising amorphous Compound 1 and Compound 2 may also be prepared by hot melt extrusion techniques.

Figure 9:
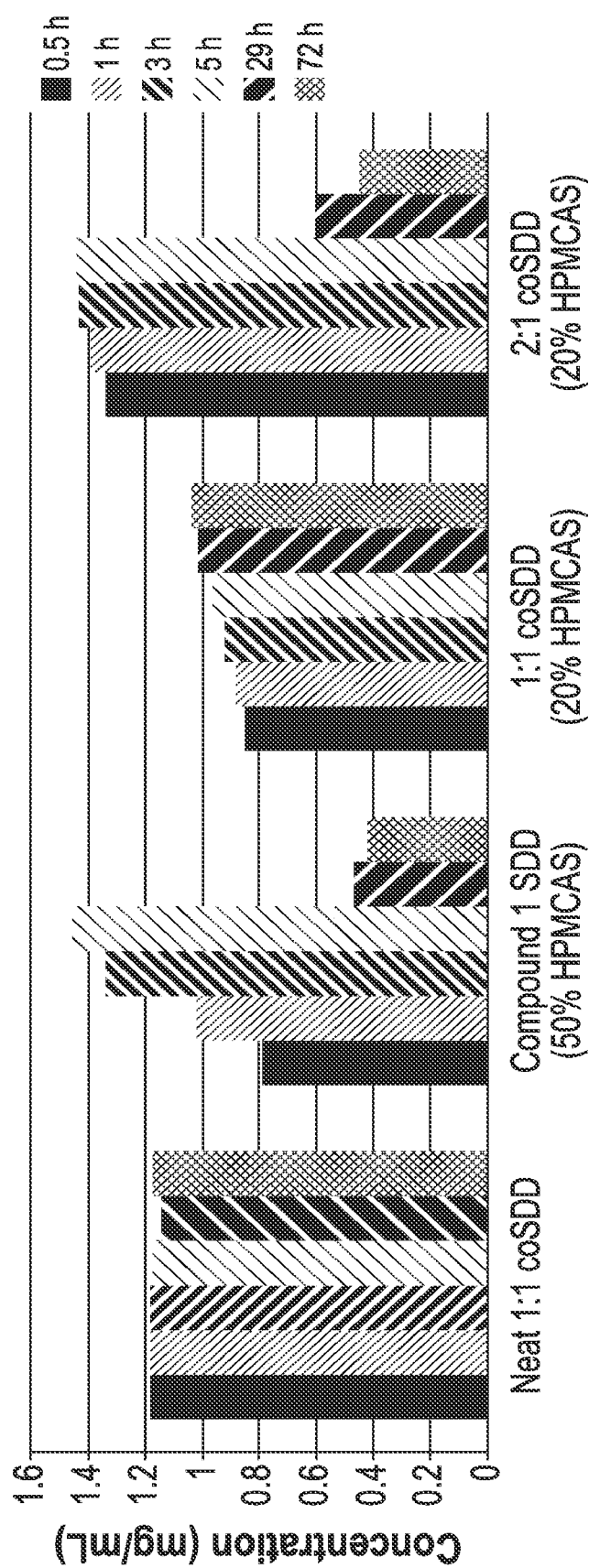
FIG. 9 is a bar graph of kinetic dissolution data for Compound 1 in fed state simulated intestinal fluid (FedSIF) solutions in the presence of Compound 2 in a neat coSDD substantially free of polymer and alone as measured by concentration versus time.

C. Beneficial Properties of Spray Dried Dispersions Substantially Free of Polymer The present invention features compositions where properties such as physical stability and dissolution rates are improved when one therapeutic agent is in the presence of another. For example, Compound 1 and Compound 2 in the presence of each other unexpectedly demonstrate improved properties over individual formulations. FIG. 9 depicts fluid stability of Compound 1 in fed state simulated intestinal fluid (FedSIF). The set of bars labeled Neat 1:1 coSDD is the neat coSDD of Compound 1 and Compound 2 substantially free of polymer featured in the present invention. Along the y axis is concentration of Compound 1 in mg/ml and each bar along the x axis represents time: 0.5h, 1h, 3h, 5h, 29h, and 72h.

The stability of Compound 1 in the neat coSDD of Compound 1 and Compound 2 of the present invention over 72h compared to the set of bar graphs labeled Compound 1 SDD (50% HPMCAS), which is Compound 1 alone in a 50% by weight SDD with the polymer HPMCAS. Achievement of such stability in the absence of a polymer is surprising because a polymer is considered necessary in the art to achieve stable spray dried dispersions. The fact that greater and more consistent stability is achieved is truly unexpected. Such spray dried dispersions would be advantageous for high drug load formulations because more drug could be formulated without the additional volume of a polymer.

Figure 10:
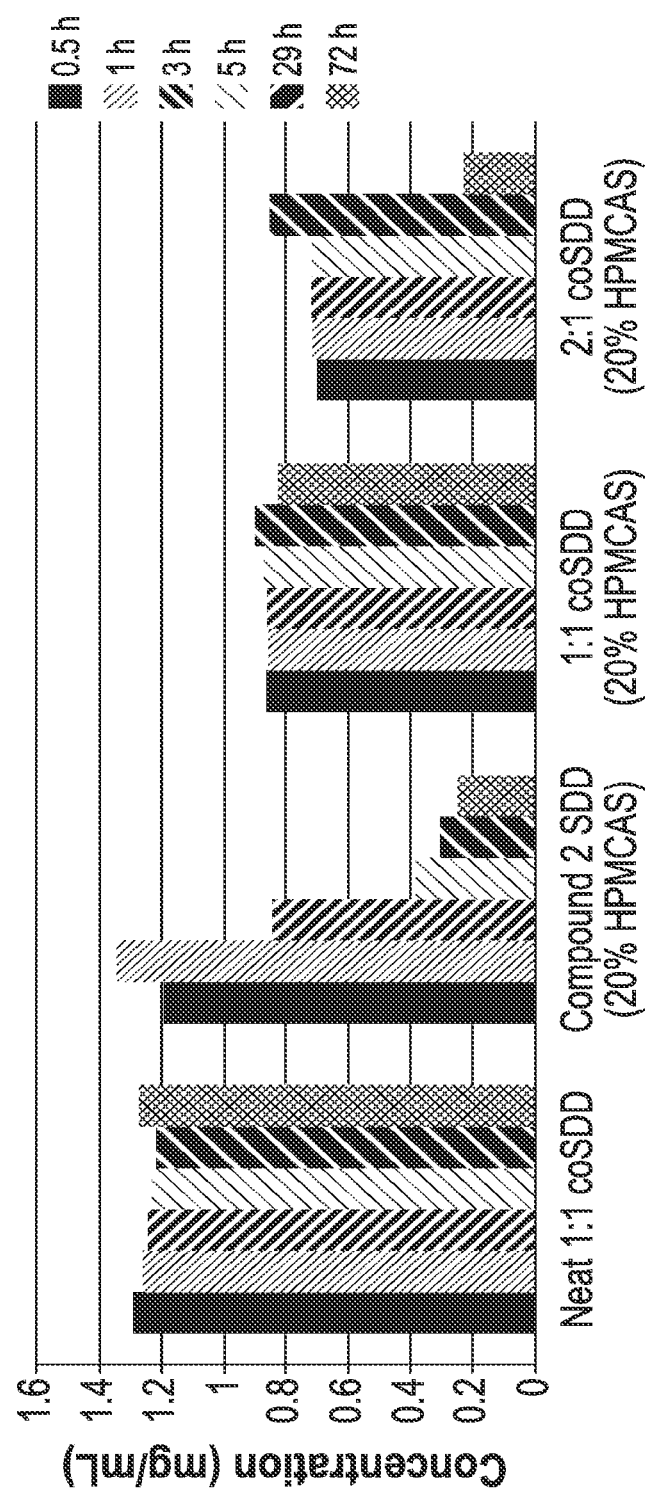
FIG. 10 is a bar graph of kinetic dissolution data for Compound 2 in FedSIF solutions in the presence of Compound 1 in a neat coSDD substantially free of polymer and alone as measured by concentration versus time.

The same unexpected phenomena exist for Compound 2 as can be seen in the analogous set of experiments in FIG. 10. FIG. 10 depicts fluid stability of Compound 2 in compositions of the present invention in FedSIF. The set of bars labeled Neat 1:1 coSDD is the neat coSDD of Compound 1 and Compound 2 substantially free of polymer featured in the present invention.

As with Compound 1 in FIG. 9, one can see the increased stability of Compound 2 in the neat coSDD of Compound 1 and Compound 2 of the present invention over 72 h compared to the set of bar graphs labeled Compound 2 SDD (20% HPMCAS), which is Compound 2 alone in a 20% by weight SDD with the polymer HPMCAS.

Figure 11:
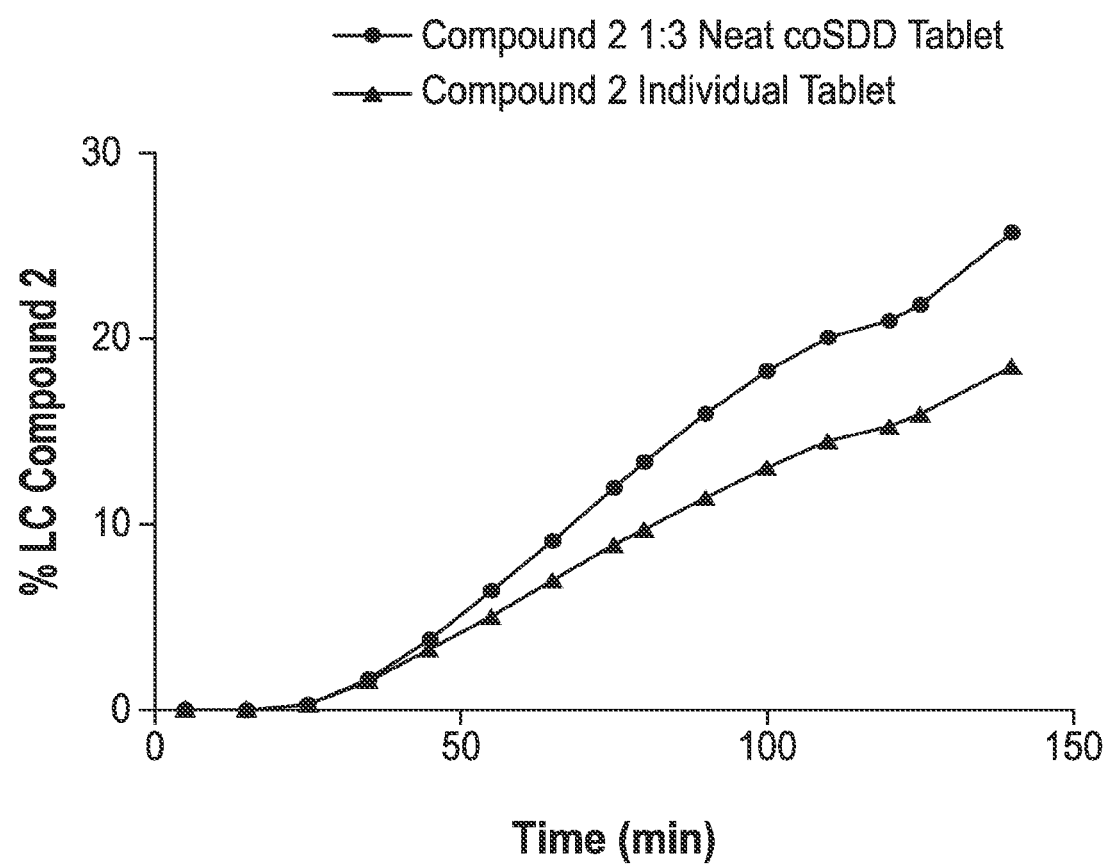
FIG. 11 is a plot of dissolution data for Compound 2 in fasted simulated fluids alone and in the presence of Compound 1 in a neat coSDD substantially free of polymer.

In addition to increased physical stability in solution, Compound 2 in the compositions of the present invention have unexpectedly increased dissolution rates. FIG. 11 depicts the results of dissolution rate experiments for a tablet comprising the neat co-spray dried dispersion of Compound 1 and Compound 2 (circles) and a tablet comprising a spray dried dispersion of Compound 2 alone and polymer (triangles). The neat co-spray dried dispersion of Compound 1 and Compound 2 demonstrates a significant increase in dissolution rates for Compound 2 over those of Compound 2 in the absence of Compound 1. The increased dissolution rate translates into statistically significant increases in exposure in vivo for Compound 2. Table 1 shows dog pK results for Compound 2 in a tablet of the neat coSDD of Compound 1 and Compound 2 of the present invention relative to a tablet of Compound 2 alone.

TABLE 1

| | Relative Comparison (Ratio) | Property | Geometric Mean Ratio | Lower 90% | Upper 90% |
|---|---|---|---|---|---|
| Compound 2 | Neat coSDD/ Individual Tablets | Cmax wt norm | 172.93 | 121.95 | 245.20 |
| | | AUC wt norm | 146.73 | 101.19 | 212.75 |

When Compound 2 is in the presence of Compound 1, the maximum concentration and area under the curve increases by 73% and 47%, respectively, relative to Compound 2 alone.

Figure 2:
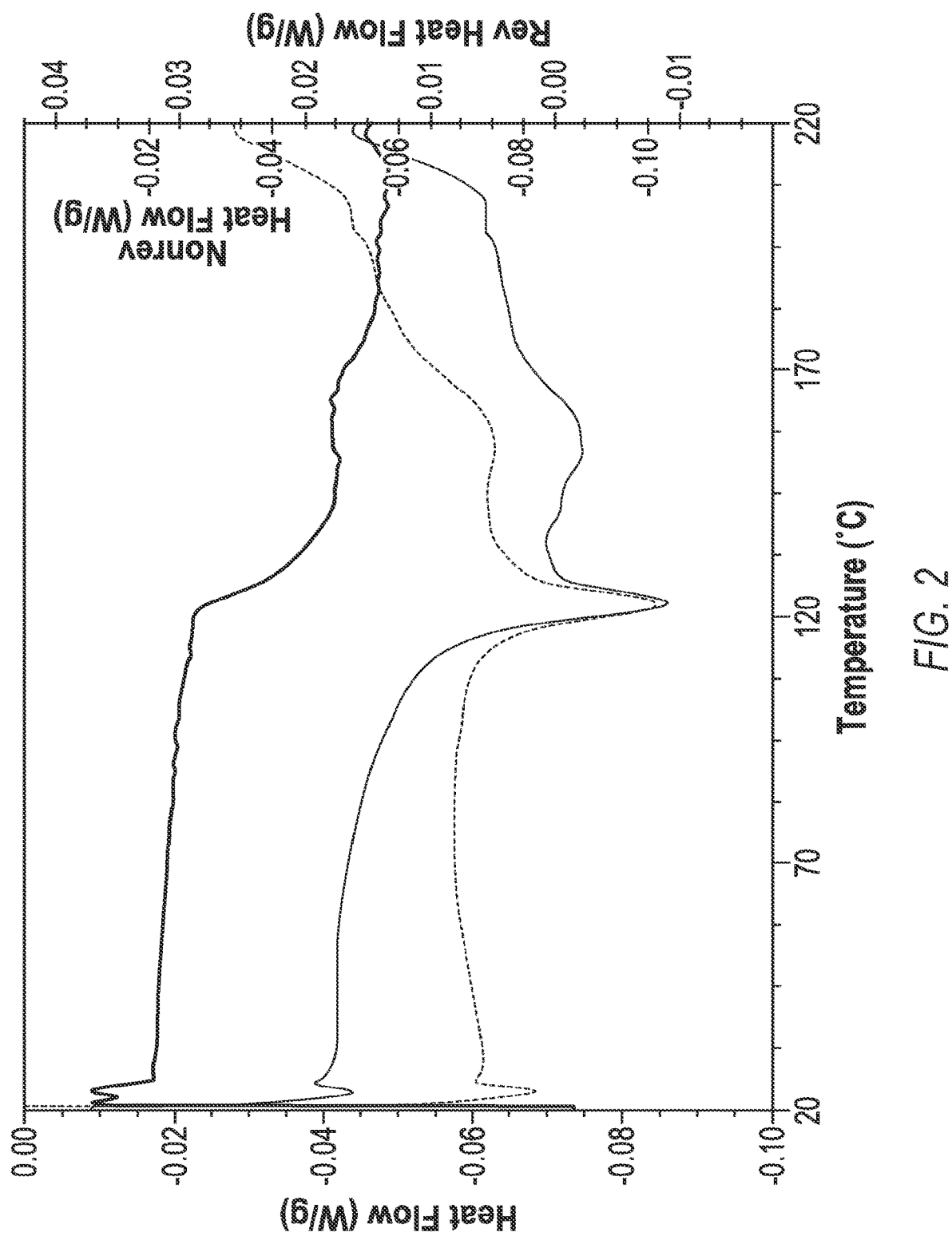
FIG. 2 is a plot of heat flow as a function of temperature generated by differential scanning calorimetry (DSC) analysis of the neat spray dried dispersion substantially free of polymer of the present invention formulated with a 1:1 ratio, by weight, of Compound 1 and Compound 2, showing a glass transition temperature (Tg) of 124° C.
Figure 3A:
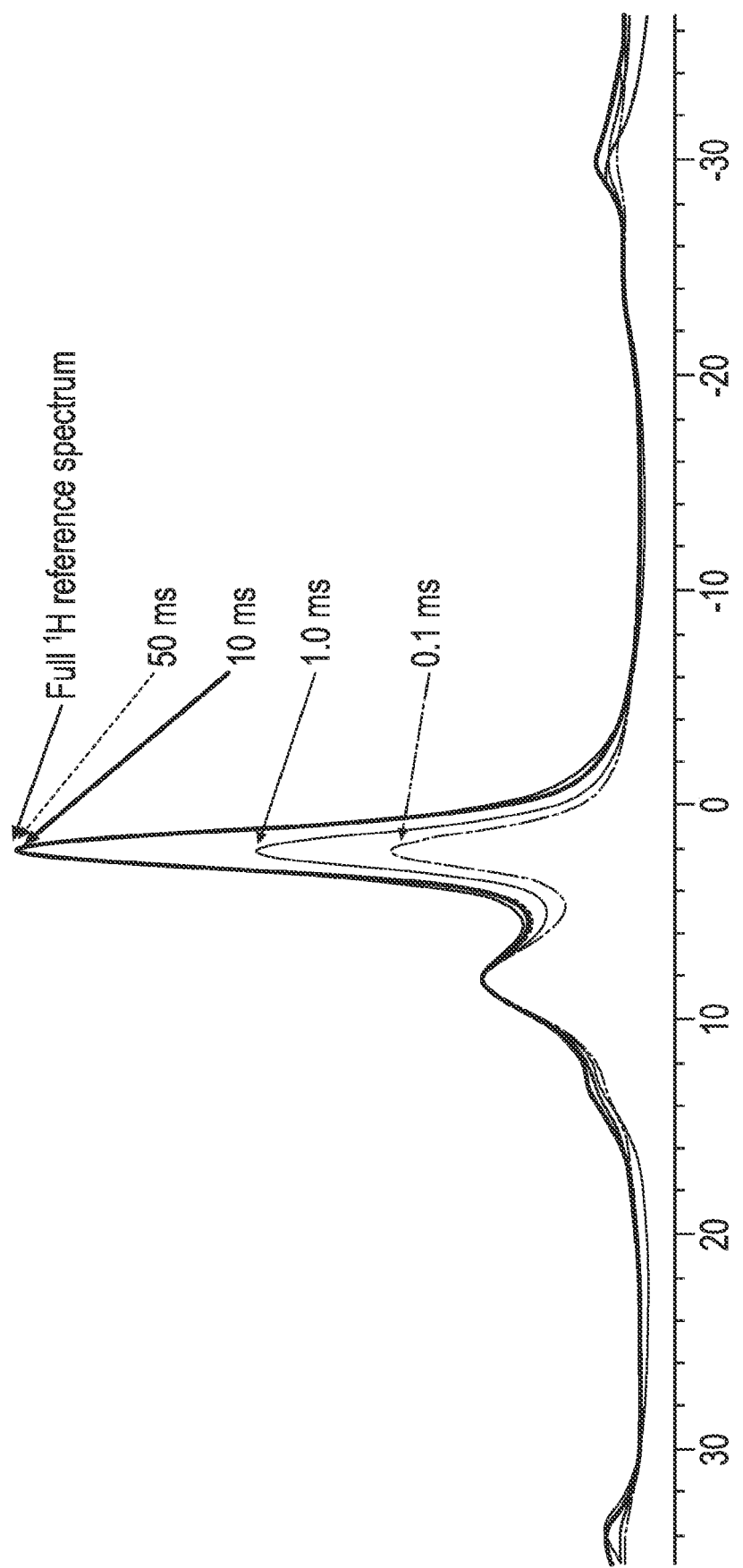
FIG. 3A) depicts solid state $^1$H NMR spectra for the neat spray dried dispersion substantially free of polymer of the present invention formulated with a 1:1 ratio, by weight, of Compound 1 and Compound 2, generated by cross polarization from fluorine atoms to protons on Compound 1.
Figure 3B:
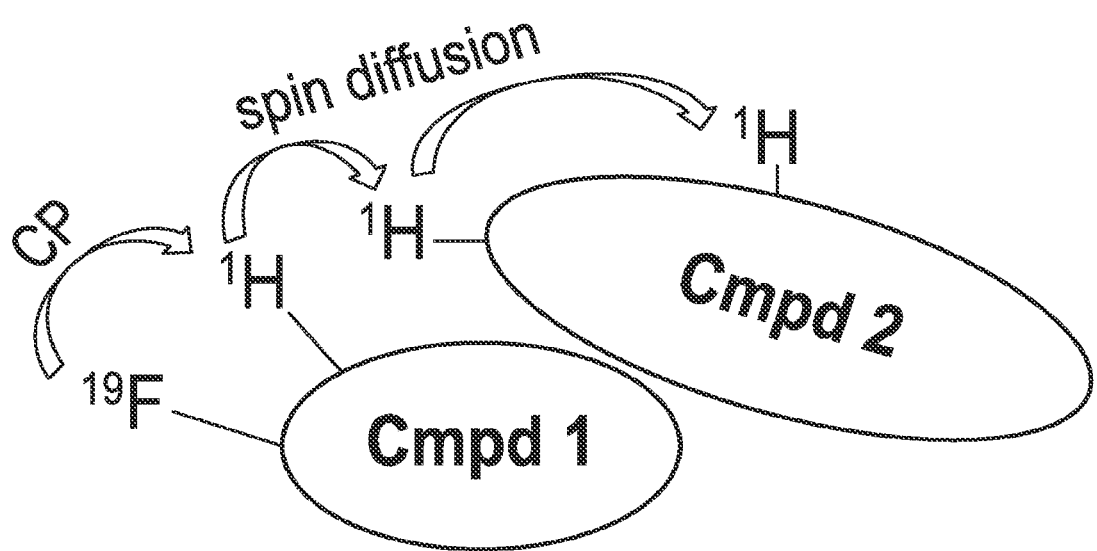
FIG. 3B) illustrates the cross polarization between fluorine atoms and protons on Compound 1 and spin diffusion between protons on Compound 1 and Compound 2.
Figure 6:
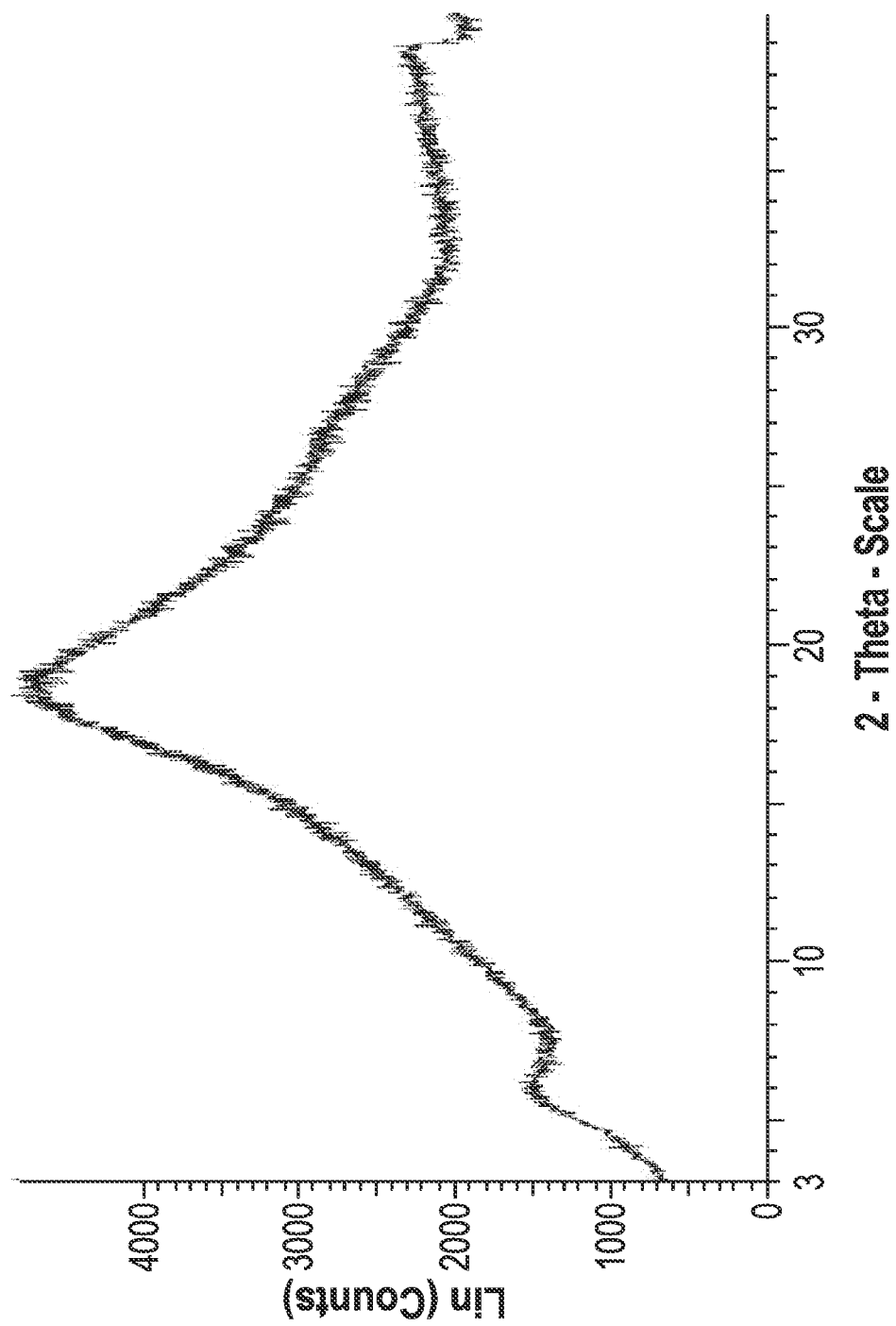
FIG. 6 is an XRPD pattern for the neat spray dried dispersion substantially free of polymer of the present invention formulated with a 1:3 ratio, by weight, of Compound 1 and Compound 2.
Figure 7:
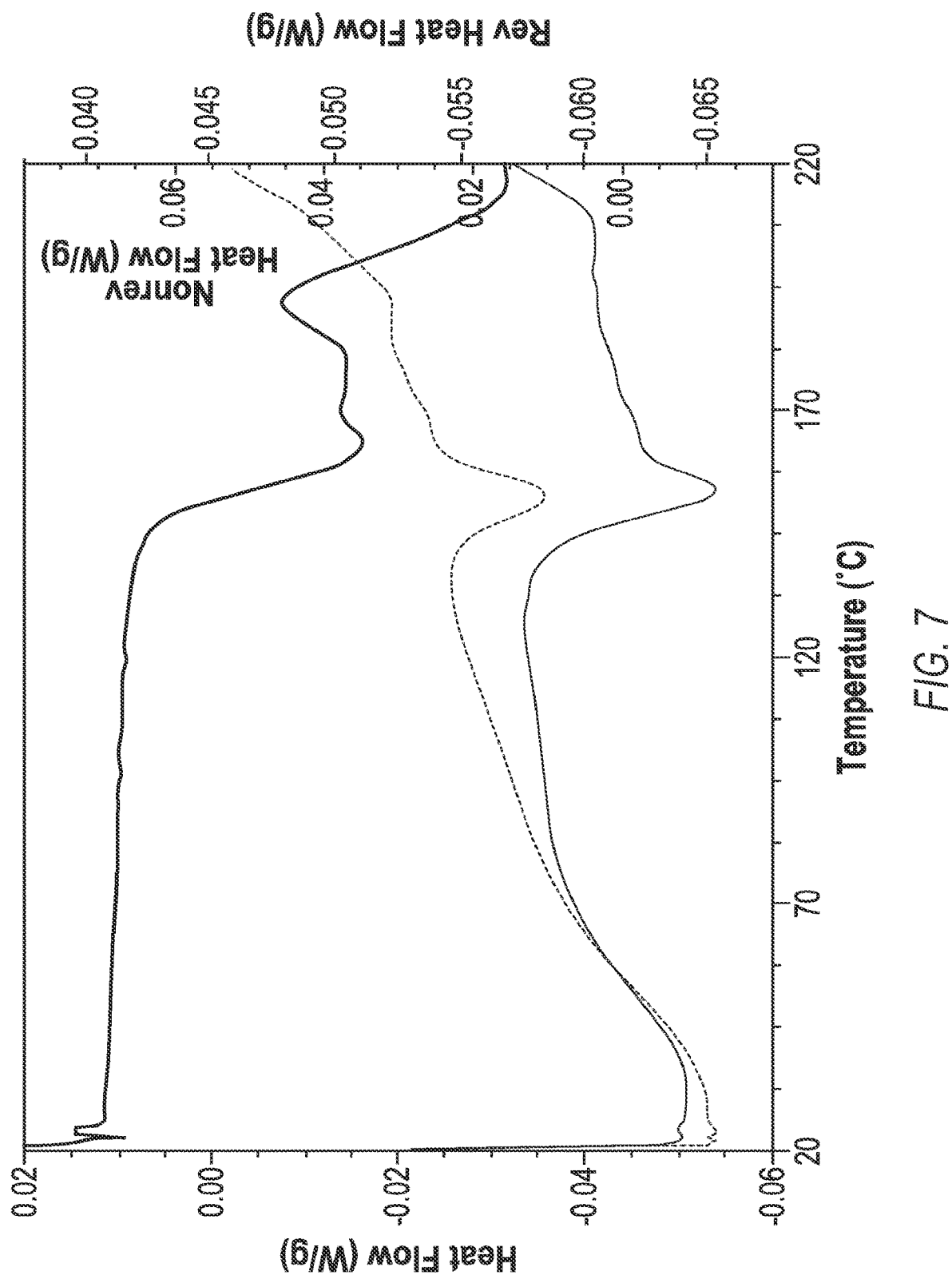
FIG. 7 is a plot of heat flow as a function of temperature generated by differential scanning calorimetry (DSC) analysis of the neat spray dried dispersion substantially free of polymer of the present invention formulated with a 1:3 ratio, by weight, of Compound 1 and Compound 2, showing a Tg of 155° C.

Without being bound by theory, the inventors submit that Compound 1 in the presence of Compound 2 unexpectedly interacts to such an extent that even when in media they do not behave as completely individual species. FIG. 1 depicts an XRPD pattern of a 1:1 neat co-spray dried dispersion of Compound 1 and Compound 2 as an amorphous entity. FIG. 2 depicts a differential scanning calorimetry (DSC) trace of a 1:1 neat coSDD of Compound 1 and Compound 2 showing one transition at a Tg of 124° C. Interestingly, FIG. 3 depicts the solid state NMR spectra of a 1:1 Compound 1 to Compound 2 neat co-spray dried dispersion showing spin diffusion interactions between protons on the different compounds, respectively. FIG. 6 depicts an XRPD pattern of a 1:3 neat coSDD of Compound 1 and Compound 2 as an amorphous entity. FIG. 7 depicts a differential scanning calorimetry (DSC) trace of a 1:3 neat coSDD of Compound 1 and Compound 2 showing one transition at a Tg of 155° C.

III. Spray Dried Dispersions Comprising Amorphous Therapeutic Agents

A. Spray Dried Dispersions

Unlike the previously described embodiments which were substantially free of polymer, the spray dried dispersions of the present embodiment may comprise a polymer. Starting from Compound 1 or Compound 2, the amorphous form of Compound 1 or Compound 2 may be prepared by the spray dry methods described previously except that a polymer may be present.

Solid dispersions including amorphous Compound 1 and Compound 2, and a polymer (or solid state carrier) also are included herein. For example, Compound 1 and Compound 2 are present as amorphous compounds as a component of a solid amorphous dispersion. The solid amorphous dispersion, generally includes Compound 1 and Compound 2 and a polymer. Exemplary polymers include cellulosic polymers such as HPMC, HPMCAS, or pyrrolidone containing polymers such as PVP/VA. In some embodiments, the solid amorphous dispersion includes one or more additional excipients, such as a surfactant.

In one embodiment, a polymer is able to dissolve in aqueous media. The solubility of the polymers may be pH independent or pH dependent. The latter include one or more enteric polymers. The term "enteric polymer" refers to a polymer that is preferentially soluble in the less acidic environment of the intestine relative to the more acid environment of the stomach, for example, a polymer that is insoluble in acidic aqueous media but soluble when the pH is above 5-6. An appropriate polymer should be chemically and biologically inert. In order to improve the physical stability of the solid dispersions, the glass transition temperature (Tg) of the polymer should be as high as possible. For example, polymers have a glass transition temperature at least equal to or greater than the glass transition temperature of the drug (i.e., Compound 1). Other polymers have a glass transition temperature that is within about 10 to about 15° C. of the drug (i.e., Compound 1). Examples of suitable glass transition temperatures of the polymers include at least about 90° C., at least about 95° C., at least about 100° C., at least about 105° C., at least about 110° C., at least about 115° C., at least about 120° C., at least about 125° C., at least about 130° C., at least about 135° C., at least about 140° C., at least about 145° C., at least about 150° C., at least about 155° C., at least about 160° C., at least about 165° C., at least about 170° C., or at least about 175° C. (as measured under dry conditions). Without wishing to be bound by theory, it is believed that the underlying mechanism is that a polymer with a higher Tg generally has lower molecular mobility at room temperature, which can be a crucial factor in stabilizing the physical stability of the amorphous solid dispersion.

Additionally, the hygroscopicity of the polymers should be as low, e.g., less than about 10%. For the purpose of comparison in this application, the hygroscopicity of a polymer or composition is characterized at about 60% relative humidity. In some preferred embodiments, the polymer has less than about 10% water absorption, for example less than about 9%, less than about 8%, less than about 7%, less than about 6%, less than about 5%, less than about 4%, less than about 3%, or less than about 2% water absorption. The hygroscopicity can also affect the physical stability of the solid dispersions. Generally, moisture adsorbed in the polymers can greatly reduce the Tg of the polymers as well as the resulting solid dispersions, which will further reduce the physical stability of the solid dispersions as described above.

In one embodiment, the polymer is one or more water-soluble polymer(s) or partially water-soluble polymer(s). Water-soluble or partially water-soluble polymers include but are not limited to, cellulose derivatives (e.g., hydroxypropylmethylcellulose (HPMC), hydroxypropylcellulose (HPC)) or ethylcellulose; polyvinylpyrrolidones (PVP); polyethylene glycols (PEG); polyvinyl alcohols (PVA); acrylates, such as polymethacrylate (e.g., Eudragit® E); cyclodextrins (e.g., β-cyclodextin) and copolymers and derivatives thereof, including for example PVP-VA (polyvinylpyrollidone-vinyl acetate).

In some embodiments, the polymer is hydroxypropylmethylcellulose (HPMC), such as HPMC E50, HPMC E15, or HPMC E3.

As discussed herein, the polymer can be a pH-dependent enteric polymer. Such pH-dependent enteric polymers include, but are not limited to, cellulose derivatives (e.g., cellulose acetate phthalate (CAP)), hydroxypropyl methyl cellulose phthalates (HPMCP), hydroxypropyl methyl cellulose acetate succinate (HPMCAS), carboxymethylcellulose (CMC) or a salt thereof (e.g., a sodium salt such as (CMC-Na)); cellulose acetate trimellitate (CAT), hydroxypropylcellulose acetate phthalate (HPCAP), hydroxypropylmethyl-cellulose acetate phthalate (HPMCAP), and methylcellulose acetate phthalate (MCAP), or polymethacrylates (e.g., Eudragit® S). In some embodiments, the polymer is hydroxypropyl methyl cellulose acetate succinate (HPMCAS). In some embodiments, the polymer is hydroxypropyl methyl cellulose acetate succinate HG grade (HPMCAS-HG).

In yet another embodiment, the polymer is a polyvinylpyrrolidone co-polymer, for example, a vinylpyrrolidone/vinyl acetate co-polymer (PVP/VA).

In embodiments where Compound 1 forms a solid dispersion with a polymer, for example with an HPMC, HPMCAS, or PVP/VA polymer, the amount of polymer relative to the total weight of the solid dispersion ranges from about 0.1% to 99% by weight. Unless otherwise specified, percentages of drug, polymer and other excipients as described within a dispersion are given in weight percentages. The amount of polymer is typically at least about 20%, and preferably at least about 30%, for example, at least about 35%, at least about 40%, at least about 45%, or about 50% (e.g., 49.5%). The amount is typically about 99% or less, and preferably about 80% or less, for example about 75% or less, about 70% or less, about 65% or less, about 60% or less, or about 55% or less. In one embodiment, the polymer is in an amount of up to about 50% of the total weight of the dispersion (and even more specifically, between about 40% and 50%, such as about 49%, about 49.5%, or about 50%). HPMCAS is available in a number of varieties, including AS-LF, AS-MF, AS-HF, AS-LG, AS-MG, AS-HG. Each of these grades varies with the percent substitution of acetate and succinate.

In some embodiments, Compound 1 or Compound 2, and polymer are present in roughly equal amounts, for example each of the polymer and the drug make up about half of the percentage weight of the dispersion. For example, the polymer is present in about 49.5% and Compound 1 or Compound 2 is present in about 50%. In another embodiment, Compound 1 or Compound 2 are present in an amount greater than half of the percentage weight of the dispersions. For example, the polymer is present in about 20% and Compound 1 or Compound 2 is present in about 80%.

In some embodiments, Compound 1 or Compound 2 and the polymer combined represent 1% to 20% w/w total solid content of the non-solid dispersion prior to spray drying. In some embodiments, Compound 1 or Compound 2 and the polymer combined represent 5% to 15% w/w total solid content of the non-solid dispersion prior to spray drying. In some embodiments, Compound 1 or Compound 2 and the polymer combined represent about 11% w/w total solid content of the non-solid dispersion prior to spray drying.

In some embodiments, the dispersion further includes other minor ingredients, such as a surfactant (e.g., SLS). In some embodiments, the surfactant is present in less than about 10% of the dispersion, for example less than about 9%, less than about 8%, less than about 7%, less than about 6%, less than about 5%, less than about 4%, less than about 3%, less than about 2%, about 1%, or about 0.5%.

In embodiments including a polymer, the polymer should be present in an amount effective for stabilizing the solid dispersion. Stabilizing includes inhibiting or preventing, the crystallization of Compound 1 or Compound 2. Such stabilizing would inhibit the conversion Compound 1 or Compound 2 from amorphous to crystalline form. For example, the polymer would prevent at least a portion (e.g., about 5%, about 10%, about 15%, about 20%, about 25%, about 30%, about 35%, about 40%, about 45%, about 50%, about 55%, about 60%, about 65%, about 70%, about 75%, or greater) of Compound 1 or Compound 2 from converting from an amorphous to a crystalline form. Stabilization can be measured, for example, by measuring the glass transition temperature of the solid dispersion, measuring the rate of relaxation of the amorphous material, or by measuring the solubility or bioavailability of Compound 1 or Compound 2.

Suitable polymers for use in combination with Compound 1 or Compound 2, for example to form a solid dispersion such as an amorphous solid dispersion, should have one or more of the following properties:

The glass transition temperature of the polymer should have a temperature of no less than about 10-15° C. lower than the glass transition temperature of Compound 1 or Compound 2. In some instances, the glass transition temperature of the polymer is greater than the glass transition temperature of Compound 1 or Compound 2, and in general at least 50° C. higher than the desired storage temperature of the drug product. For example, at least about 100° C., at least about 105° C., at least about 105° C., at least about 110° C., at least about 120° C., at least about 130° C., at least about 140° C., at least about 150° C., at least about 160° C., at least about 160° C., or greater.

The polymer should have similar or better solubility in solvents suitable for spray drying processes relative to that of Compound 1 or Compound 2. In some embodiments, the polymer will dissolve in one or more of the same solvents or solvent systems as Compound 1 or Compound 2.

The polymer, when combined with Compound 1 or Compound 2, for example in a solid dispersion or in a liquid suspension, should increase the solubility of Compound 1 in aqueous and physiologically relative media either relative to the solubility of Compound 1 or Compound 2 in the absence of polymer or relative to the solubility of Compound 1 or Compound 2 when combined with a reference polymer. For example, the polymer could increase the solubility of amorphous Compound 1 or Compound 2 by reducing the amount of amorphous Compound 1 or Compound 2 that converts to crystalline Compound 1 or Compound 2, either from a solid amorphous dispersion or from a liquid suspension.

The polymer should decrease the relaxation rate of the amorphous substance.

The polymer should increase the physical and/or chemical stability of Compound 1 or Compound 2.

The polymer should improve the manufacturability of Compound 1 or Compound 2.

The polymer should improve one or more of the handling, administration or storage properties of Compound 1 or Compound 2.

The polymer should not interact unfavorably with other pharmaceutical components, for example excipients.

The suitability of a candidate polymer (or other component) can be tested using the spray drying methods (or other methods) described herein to form an amorphous composition. The candidate composition can be compared in terms of stability, resistance to the formation of crystals, or other properties, and compared to a reference preparation, e.g., a preparation of neat amorphous Compound 1 or Compound 2. For example, a candidate composition could be tested to determine whether it inhibits the time to onset of solvent mediated crystallization, or the percent conversion at a given time under controlled conditions, by at least 50%, 75%, or 100% as well as the reference preparation, or a candidate composition could be tested to determine if it has improved bioavailability or solubility relative to crystalline Compound 1 or Compound 2.

The spray dried dispersion of the present embodiment may include a surfactant as previously described.

Another aspect of the present invention provides a spray dried dispersion comprising a first therapeutic agent and a second therapeutic agent, wherein the first therapeutic agent is an amorphous form of a CFTR corrector and the second therapeutic agent is an amorphous form of a CFTR potentiator.

In some embodiments, the first agent is an amorphous form of (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide.

In some embodiments, the second agent is an amorphous form of N-[2,4-bis(1,1-dimethylethyl)-5-hydroxyphenyl]-1,4-dihydro-4-oxoquinoline-3-carboxamide.

B. Blends of Spray Dried Dispersions

In one aspect, the present invention provides a pharmaceutical composition comprising a mixture of a first spray dried dispersion and a second spray dried dispersion, wherein the first spray dried dispersion comprises amorphous (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, and the second spray dried dispersion comprises amorphous N-[2,4-bis(1,1-dimethylethyl)-5-hydroxyphenyl]-1,4-dihydro-4-oxoquinoline-3-carboxamide.

In some embodiments, the pharmaceutical composition comprises a ratio of amorphous (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide to amorphous N-[2,4-bis(1,1-dimethylethyl)-5-hydroxyphenyl]-1,4-dihydro-4-oxoquinoline-3-carboxamide ranging from about 1:10 to about 10:1 by weight. For example, the ratio of amorphous (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide to amorphous N-[2,4-bis(1,1-dimethylethyl)-5-hydroxyphenyl]-1,4-dihydro-4-oxoquinoline-3-carboxamide is about 1:1 by weight. In other examples, the ratio of amorphous (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide to amorphous N-[2,4-bis(1,1-dimethylethyl)-5-hydroxyphenyl]-1,4-dihydro-4-oxoquinoline-3-carboxamide is about 1:3 by weight. In some examples, the ratio of amorphous (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide to amorphous N-[2,4-bis(1,1-dimethylethyl)-5-hydroxyphenyl]-1,4-dihydro-4-oxoquinoline-3-carboxamide is about 1:6 by weight. In some examples, the ratio of amorphous (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide to amorphous N-[2,4-bis(1,1-dimethylethyl)-5-hydroxyphenyl]-1,4-dihydro-4-oxoquinoline-3-carboxamide is about 2:3 by weight.

In some embodiments, the pharmaceutical composition comprises a ratio of first spray dried dispersion to second spray dried dispersion that is from about 1:10 to about 10:1 by weight. For example, the ratio of first spray dried dispersion to second spray dried dispersion is about 1:1 by weight. In other examples, the ratio of first spray dried dispersion to second spray dried dispersion is about 1:3 by weight. In some examples, the ratio of first spray dried dispersion to second spray dried dispersion is about 1:6 by weight. In some examples, the ratio of first spray dried dispersion to second spray dried dispersion is about 2:3 by weight.

In some embodiments, the first spray dried dispersion further comprises a cellulose polymer. For example, the first spray dried dispersion further comprises hydroxypropyl methylcellulose (HPMC). For example, the first spray dried dispersion comprises a ratio of HPMC to amorphous (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide ranging from about 1:10 to about 1:1. In some instances, the ratio of HPMC to amorphous (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide is from about 1:3 to about 1:5.

In other embodiments, the second spray dried dispersion further comprises a cellulose polymer. For example, the second spray dried dispersion further comprises hydroxypropyl methylcellulose acetate succinate (HPMCAS).

In some embodiments, the spray dried dispersion comprises a plurality of particles having a mean particle diameter of about 5 to about 100 microns. In some embodiments, the first spray dried dispersion comprises a particle having a mean particle diameter of about 5 to about 30 microns. In some embodiments, the first spray dried dispersion comprises a particle having a mean particle diameter of about 15 microns.

In some embodiments, the spray dried dispersion comprises a plurality of particles having a mean particle diameter of about 5 to about 100 microns. In some embodiments, the second spray dried dispersion comprises a particle having a mean particle diameter of about 5 to about 30 microns. In some embodiments, the second spray dried dispersion comprises a particle having a mean particle diameter of about 15 microns.

In some embodiments, the first spray dried dispersion comprises from about 70 wt % to about 95 wt % (e.g., from about 75 wt % to about 85 wt %) of Compound 1.

In some embodiments, the second spray dried dispersion comprises from about 70 wt % to about 95 wt % (e.g., from about 75 wt % to about 85 wt %) of Compound 2.

One aspect of the present invention provides a pharmaceutical composition comprising a mixture of a first spray dried dispersion and a second spray dried dispersion that is generated by combining a first spray dried dispersion and a second spray dried dispersion, wherein the first spray dried dispersion comprises amorphous (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound 1), and the second spray dried dispersion comprises amorphous N-[2,4-bis(1,1-dimethylethyl)-5-hydroxyphenyl]-1,4-dihydro-4-oxoquinoline-3-carboxamide (Compound 2).

In some embodiments, the pharmaceutical composition comprises a ratio of amorphous Compound 1 to amorphous Compound 2 ranging from about 1:10 to about 10:1 by weight. For example, the ratio of amorphous Compound 1 to amorphous Compound 2 is about 1:1 by weight. In other examples, the ratio of amorphous Compound 1 to amorphous Compound 2 is about 1:3 by weight. In some examples, the ratio of amorphous Compound 1 to amorphous Compound 2 is about 1:6 by weight. In some examples, the ratio of amorphous Compound 1 to amorphous Compound 2 is about 2:3 by weight.

In some embodiments, the first spray dried dispersion further comprises a cellulose polymer. For example, the first spray dried dispersion further comprises hydroxypropyl methylcellulose (HPMC).

In other embodiments, the second spray dried dispersion further comprises a cellulose polymer. For example, the second spray dried dispersion further comprises hypromellose acetate succinate (HPMCAS).

One aspect of the present invention provides a method of generating a pharmaceutical composition comprising (i) providing a first mixture comprising Compound 1, a cellulose polymer, and a solvent; (ii) forcing the first mixture through a nozzle under spray drying conditions to generate the first spray dried dispersion comprising amorphous Compound 1; (iii) providing a second mixture comprising Compound 2, a cellulose polymer, and a solvent; (iv) forcing the second mixture through a nozzle under spray drying conditions to generate the second spray dried dispersion comprising amorphous Compound 2; and (v) combining the first spray dried dispersion and the second spray dried dispersion.

In some implementations, the cellulose polymer of the first mixture is HPMC.

In some implementations, the first mixture comprises a ratio of HPMC to Compound 1 ranging from about 1:10 to about 1:1 by weight. For example, the ratio of HPMC to Compound 1 is from about 1:3 to about 1:5 (e.g., about 1:4) by weight.

In some implementations, the first mixture further comprises a solvent, and the solvent comprises a polar organic solvent. Examples of polar organic solvents include methylethyl ketone, THF, methanol, DCM, or IPA, or any combination thereof, such as for example, a DCM/methanol mixture. In other examples, the solvent further comprises water. In other examples, the solvent further comprises water. For instance, the solvent could be methylethyl ketone/water, THF/water, methanol/water, or methylethyl ketone/water/IPA. For example, the ratio of the polar organic solvent to water is from about 70:30 to about 95:5 by volume. In other instances, the ratio of the polar organic solvent to water is about 90:10 by volume.

In other implementations, the cellulose polymer of the second mixture is HPMCAS.

In some implementations, the second mixture comprises a ratio of HPMCAS to Compound 2 ranging from about 1:14 to about 1:2 by weight. For example, the ratio of HPMCAS to Compound 2 is from about 1:4 to about 1:6 (e.g., about 1:5) by weight.

In some implementations, the second mixture further comprises a solvent, and the solvent comprises a polar organic solvent. Examples of polar organic solvents include methylethyl ketone, THF, methanol, DCM, or IPA, or any combination thereof, such as for example, a DCM/methanol mixture. In other examples, the solvent further comprises water. In other examples, the solvent further comprises water. For instance, the solvent could be methylethyl ketone/water, THF/water, methanol/water, or methylethyl ketone/water/IPA. For example, the ratio of the polar organic solvent to water is from about 70:30 to about 95:5 by volume. In other instances, the ratio of the polar organic solvent to water is about 90:10 by volume.

Some implementations further comprise filtering the first mixture before it is forced through the nozzle. Such filtering can be accomplished using any suitable filter media having a suitable pore size (e.g., 20 μm or less). Likewise, the second mixture may also be filtered before it is forced through the nozzle.

Some implementations further comprise drying the first spray dried dispersion, the second spray dried dispersion or both. For example, the spray dried dispersion, i.e., the first spray dried dispersion, the second spray dried dispersion, or both, is dried under reduced pressure. In other examples, the spray dried dispersion is dried at a temperature of from about 30° C. to about 60° C.

Figure 12:
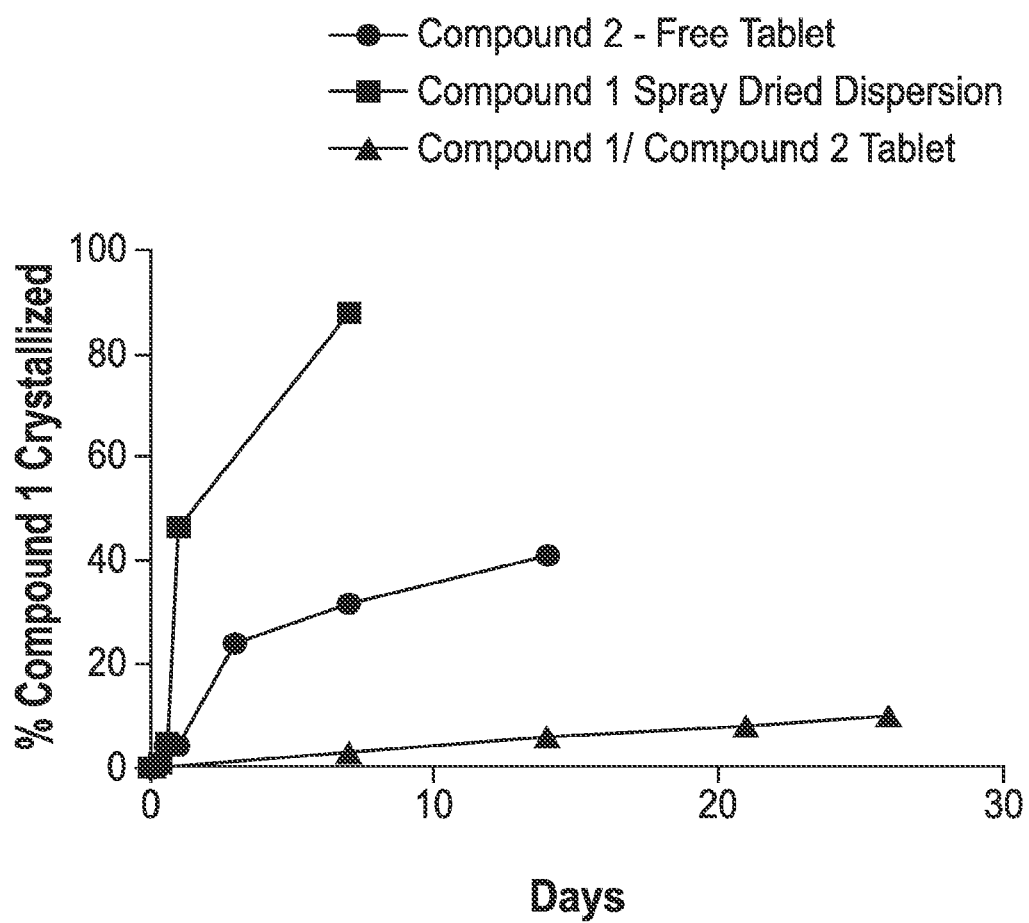
FIG. 12 is a plot of crystallization kinetics data for Compound 1 at 80° C. and 75% relative humidity when in a Compound 2 free tablet (circles), a spray dried dispersion (squares), and a tablet comprising Compound 2 (triangles).
Figure 13:
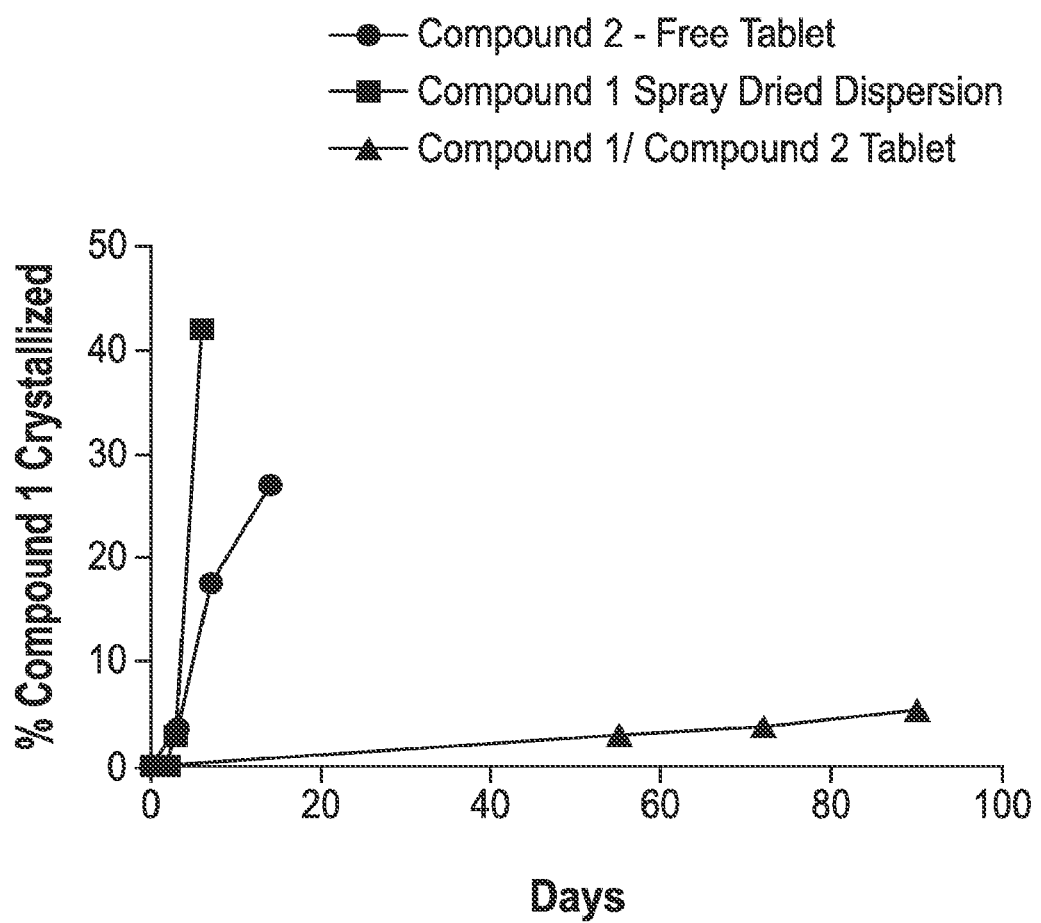
FIG. 13 is a plot of crystallization kinetics data for Compound 1 at 70° C. and 75% relative humidity when in a Compound 2 free tablet (circles), a spray dried dispersion (squares), and a tablet comprising Compound 2 (triangles).

FIGS. 12 and 13 show that the same surprising stability of Compound 1 in the presence of Compound 2 is present even in a blend of two separate spray dried dispersion. FIGS. 12 and 13 depict the Compound 1 crystallization kinetics under 75% relative humidity and 80° C. and 70° C., respectively. Triangles represent a tablet formulation of a blend of the two separate spray dried dispersions of Compound 1 and Compound 2. Circles represent the same tablet formulation just lacking Compound 2. Squares represent the separate spray dried dispersion of Compound 1. Comparing the tablet blend formulation to the Compound 2 free tablet formulation, one can see that Compound 1 is significantly more stable towards crystallization in the presence of Compound 2. Compound 1 is also more stable in the tablet formulation with Compound 2 than in the separate spray dried dispersion of Compound 1.

Figure 14:
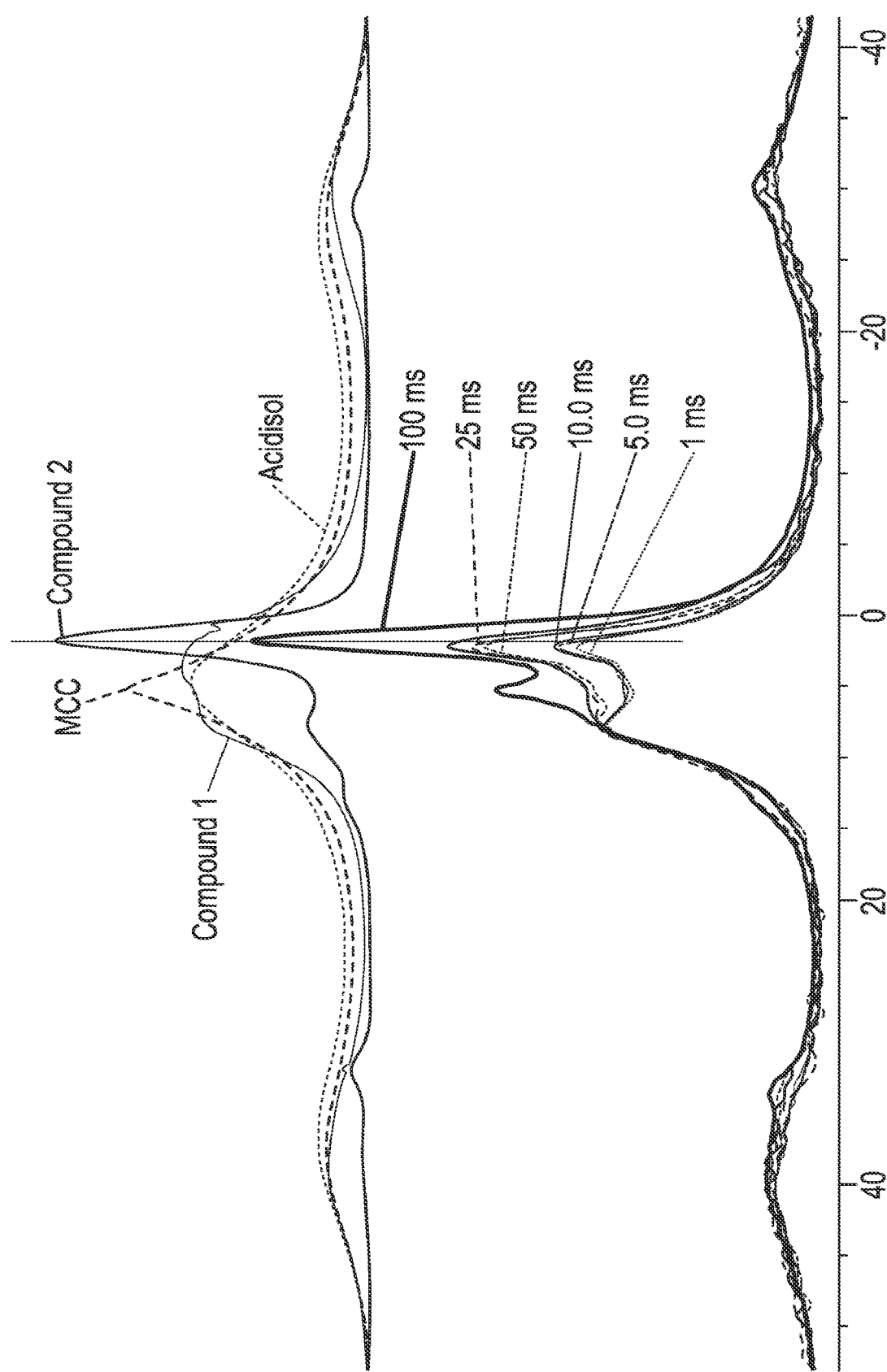
FIG. 14 depicts a solid state $^1$H NMR spectrum of a tablet comprising a blend of a spray dried dispersion of Compound 1 and a spray dried dispersion of Compound 2 at 70° C. and 75% relative humidity. The upper spectrum is the reference $^1$H NMR spectrum identifying the tablet components and the bottom spectrum is generated by cross polarization of the fluorine atom to protons on Compound 1 and spin diffusion between protons on Compound 1 and Compound 2 resulting in the growth of the Compound 2 peak.

One explanation for this phenomenon is shown in FIG. 14. As was seen in the co-spray dried dispersion of Compound 1 and Compound 2 substantially free of polymer (FIG. 3A), a blend of two spray dried dispersions comprising Compound 1 and Compound 2 results in the two compounds interacting on a molecular level. FIG. 14 depicts solid state 1H NMR spectra of a tablet comprising a blend of a spray dried dispersion of Compound 1 and a spray dried dispersion of Compound 2 at 70° C. and 75% relative humidity. The upper spectrum is the reference 1H NMR spectrum identifying the tablet components and the bottom spectrum is generated by cross polarization of the fluorine atom to protons on Compound 1 and spin diffusion between protons on Compound 1 and Compound 2 resulting in the growth of the Compound 2 peak. Surprisingly, molecular interaction between Compound 1 and Compound 2 exists in the blend at temperatures above the Tg as well as the co-spray dried dispersion substantially free of polymer.

C. Co-Spray Dried Dispersions Comprising Multiple APIs

One aspect of the present invention provides a spray dried dispersion comprising amorphous Compound 1 and amorphous Compound 2 prepared by co-spray drying a mixture of Compound 1, Compound 2, a solvent, and a polymer.

In some embodiments, the spray dried dispersion comprises a ratio of amorphous Compound 1 to amorphous Compound 2 ranging from about 1:10 to about 10:1 by weight. For example, the ratio of amorphous Compound 1 to amorphous Compound 2 is about 1:1 by weight. In other examples, the ratio of amorphous Compound 1 to amorphous Compound 2 is about 1:3 by weight. In some examples, the ratio of amorphous Compound 1 to amorphous Compound 2 is about 1:6 by weight. In some examples, the ratio of amorphous Compound 1 to amorphous Compound 2 is about 2:3 by weight.

In some embodiments, the spray dried dispersion further comprises a cellulose polymer. For example, the spray dried dispersion comprises HPMC, HPMCAS, or any combination thereof.

In some embodiments, the spray dried dispersion comprises from about 35 wt % to about 60 wt % of amorphous Compound 1.

In some embodiments, the spray dried dispersion comprises from about 20 wt % to about 45 wt % of amorphous Compound 2.

Another aspect of the present invention provides a pharmaceutical composition comprising a spray dried dispersion and one or more excipients selected from a filler; a disintegrant; a surfactant; a binder; a wetting agent, a lubricant, or any combination thereof, wherein the spray dried dispersion comprises amorphous Compound 1 and amorphous Compound 2.

In some embodiments, the spray dried dispersion has a glass transition temperature (Tg) of from about 80° C. to about 180° C.

In some embodiments, the spray dried dispersion comprises a plurality of particles having a mean particle diameter of about 5 to about 100 microns. In some embodiments, the spray dried dispersion comprises a plurality of particles having a mean particle diameter of about to about 30 microns. In some embodiments, the spray dried dispersion comprises a plurality of particles having a mean particle diameter of about 15 microns.

In some embodiments, the spray dried dispersion is substantially amorphous.

One aspect of the present invention provides a spray dried dispersion comprising amorphous Compound 1 and amorphous Compound 2, wherein the spray dried dispersion is generated by (i) providing a mixture comprising Compound 1, Compound 2, and a solvent; and (ii) forcing the mixture through a nozzle under spray drying conditions to generate the spray dried dispersion.

In some implementations, the second mixture further comprises a solvent, and the solvent comprises a polar organic solvent. Examples of polar organic solvents include methylethyl ketone, THF, DCM, methanol, or IPA, or any combination thereof. In other examples, the solvent further comprises water. In other examples, the solvent further comprises water. For instance, the solvent could be methylethyl ketone/water, THF/water, or methylethyl ketone/water/IPA. For example, the ratio of the polar organic solvent to water is from about to about 95:5 by volume. In other instances, the ratio of the polar organic solvent to water is about 90:10 by volume.

Some embodiments further comprise filtering the mixture before it is forced through the nozzle. Such filtering can be accomplished using any suitable filter media having a suitable pore size (e.g., 20 µm or less).

Some implementations further comprise drying the spray dried dispersion. For example, the spray dried dispersion is dried under reduced pressure. In other examples, the spray dried dispersion is dried at a temperature of from about 30° C. to about 60° C.

D. Beneficial Properties of Spray Dried Dispersions of Amorphous APIs

The phenomena of one therapeutic agent having improved properties in the presence of another therapeutic agent is not limited to the neat co-spray dried dispersions substantially free of polymer previously described. This phenomena is demonstrated in the present embodiment of a blend of two individual spray dried dispersions. For example, Compound 1 has increased physical stability in a blend of a Compound 1 spray dried dispersion and a Compound 2 spray dried dispersion, as demonstrated in Tables 2 and 3. Table 2 lists the % crystallization of an 80% by weight SDD of Compound 1 over time at 80° C. at 75% relative humidity in the absence of Compound 2. Table 3 lists the % crystallization of Compound 1 in the presence of Compound 2 in a tablet of the present invention comprising a blend of Compound 1 SDD and Compound 2 SDD at 80° C. at 75% relative humidity.

TABLE 2

| Time (Hrs.) | Crystallization (%) |
| --- | --- |
| 0 | 0 |
| 5.2 | 0 |

TABLE 2-continued

| Time (Hrs.) | Crystallization (%) |
| --- | --- |
| 6 | 0 |
| 9 | 0.7 |
| 14.7 | 5 |
| 25 | 46.4 |
| 168 | 88 |

TABLE 3

| Time (Hrs.) | Crystallization (%) |
| --- | --- |
| 0 | 0 |
| 7 | 3 |
| 14 | 6 |
| 21 | 8 |
| 26 | 10 |

At about 25 hours, 46% of Compound 1 crystallized in the absence of Compound 2, when only 10% of Compound 1 crystallized when Compound 2 was present.

This phenomenon of increased stability when one therapeutic agent is in the presence of another therapeutic agent is also demonstrated in the present embodiment where two therapeutic agents are co-spray dried from the same solvent. Referring to FIG. 9, the three sets of bar graphs on the far right demonstrate that the unexpected stability of Compound 1 in the presence of Compound 2 is not limited to the neat co-spray dried dispersion embodiment of Compound 1 and Compound 2, nor a blend of the two individual spray dried dispersions. The first of these sets of bars labeled Compound 1 SDD (50% HPMCAS) is a spray dried dispersion of Compound 1 and HPMCAS, without Compound 2. The remaining two sets of bars represent the concentration of Compound 1 within a co-spray dried dispersion of Compound 1, Compound 2, and a polymer. Comparing concentrations of Compound 1 in the bars labeled 1:1 coSDD (20% HPMCAS), which is a 1:1 ratio of Compound 1 to Compound 2 spray dried dispersion with HPMCAS, to those labeled Compound 1 SDD (50% HPMCAS), which is a spray dried dispersion of Compound 1 alone with HPMCAS, one can see that concentration stability is greater for Compound 1 over the 72 h when Compound 2 is present. Greater stability can also be seen in the 2:1 coSDD (20% HPMCAS) set of bars, which is a 2:1 ratio of Compound 1 to Compound 2 spray dried dispersion with HPMCAS, where the concentration of Compound 1 is more consistent than that in the Compound 1 spray dried dispersion (50% HPMCAS) formulation.

As with the neat co-spray dried dispersion of Compound 1 and Compound 2, the unexpected stability in FedSIF solutions in not limited to Compound 1. In FIG. 10, the first set of bars on the far right labeled Compound 2 SDD (20% HPMCAS) is a spray-dried dispersion Compound 2 and HPMCAS, without Compound 1. The remaining two sets of bars represent the concentration of Compound 2 within a co-spray dried dispersion of Compound 1, Compound 2, and polymer. Comparing concentrations of Compound 2 in the bars labeled 1:1 coSDD (20% HPMCAS), which is a 1:1 ratio of Compound 1 to Compound 2 spray dried dispersion with HPMCAS, to those labeled Compound 2 SDD (20% HPMCAS), which is a spray dried dispersion of Compound 2 alone with HPMCAS, one can see that concentration stability is greater for Compound 2 over the 72 h when Compound 1 is present. Greater stability can also be seen in the 2:1 coSDD (20% HPMCAS) set of bars, which is a 2:1 ratio of Compound 1 to Compound 2 spray dried dispersion with HPMCAS, where the concentration of Compound 2 is more consistent than that in the Compound 2 SDD (20% HPMCAS) formulation.

Without being bound by theory, when it comes to solvent systems, such as in vitro solvent systems as, for example, FedSIF, or in vivo solvent systems such as, for example, within a patient after ingesting Compound 1 prior to, subsequent to, or concurrently with Compound 2, the inventors submit that Compound 1 and Compound 2 act to impede the nucleation of each other. Such phenomena, sometimes referred to as poisoning nucleation, is unpredictable by structure.

IV. Pharmaceutical Compositions

Another aspect of the present invention provides a pharmaceutical composition comprising any of the spray dried dispersions or combinations of spray dried dispersions described above and a pharmaceutically acceptable vehicle, adjuvant, or carrier.

A. Pharmaceutically Acceptable Vehicles, Adjuvants, and Carriers

As described above, the pharmaceutical compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington: *The Science and Practice of Pharmacy*, 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York, the contents of each of which is incorporated by reference herein, disclose various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

In one embodiment, the pharmaceutical compositions of the present invention comprise a filler, a disintegrant, and a lubricant.

Fillers suitable for the invention are compatible with the ingredients of the pharmaceutical composition, i.e., they do not substantially reduce the solubility, the hardness, the chemical stability, the physical stability, or the biological activity of the pharmaceutical composition. Exemplary fillers include: celluloses, modified celluloses, (e.g. sodium carboxymethyl cellulose, ethyl cellulose hydroxymethyl cellulose, hydroxypropylcellulose), cellulose acetate, microcrystalline cellulose, calcium phosphates, dibasic calcium phosphate, starches (e.g. corn starch, potato starch), sugars (e.g., sorbitol) lactose, sucrose, or the like), or any combination thereof. In one embodiment, the filler is microcrystalline cellulose.

Thus, in one embodiment, the pharmaceutical composition comprises at least one filler in an amount of at least 5 wt % (e.g., at least about 20 wt %, at least about 30 wt %, or at least about 40 wt %) by weight of the composition. For example, the pharmaceutical composition comprises from about 10 wt % to about 60 wt % (e.g., from about 20 wt % to about 55 wt %, from about 25 wt % to about 50 wt %, or from about 27 wt % to about 45 wt %) of filler, by weight of the composition. In another example, the pharmaceutical composition comprises at least about wt % (e.g., at least 30 wt % or at least 40 wt %) of microcrystalline cellulose, for example MCC Avicel PH102, by weight of the composition. In yet another example, the pharmaceutical composition comprises from about 10 wt % to about 60 wt % (e.g., from about 20 wt % to about wt % or from about 25 wt % to about 45 wt %) of microcellulose, by weight of the composition.

Disintegrants suitable for the invention enhance the dispersal of the pharmaceutical composition and are compatible with the ingredients of the pharmaceutical composition, i.e., they do not substantially reduce the chemical stability, the physical stability, the hardness, or the biological activity of the pharmaceutical composition. Exemplary disintegrants include croscarmellose sodium, sodium starch glycolate, or a combination thereof. In one embodiment, the disintegrant is croscarmellose sodium.

Thus, in one embodiment, the pharmaceutical composition comprises disintegrant in an amount of about 10 wt % or less (e.g., about 7 wt % or less, about 6 wt % or less, or about 5 wt % or less) by weight of the composition. For example, the pharmaceutical composition comprises from about 1 wt % to about 10 wt % (e.g., from about 1.5 wt % to about 7.5 wt % or from about 2.5 wt % to about 6 wt %) of disintegrant, by weight of the composition. In another example, the pharmaceutical composition comprises about 10 wt % or less (e.g., 7 wt % or less, 6 wt % or less, or 5 wt % or less) of croscarmellose sodium, by weight of the composition. In yet another example, the pharmaceutical composition comprises from about 1 wt % to about 10 wt % (e.g., from about 1.5 wt % to about 7.5 wt % or from about 2.5 wt % to about 6 wt %) of croscarmellose sodium, by weight of the composition. In some examples, the pharmaceutical composition comprises from about 0.1% to about 10 wt % (e.g., from about 0.5 wt % to about 7.5 wt % or from about 1.5 wt % to about 6 wt %) of disintegrant, by weight of the composition. In still other examples, the pharmaceutical composition comprises from about 0.5% to about 10 wt % (e.g., from about 1.5 wt % to about 7.5 wt % or from about 2.5 wt % to about 6 wt %) of disintegrant, by weight of the composition.

In some embodiments, the pharmaceutical composition can include an oral solid pharmaceutical dosage form which can comprise a lubricant that can prevent adhesion of a granulate-bead admixture to a surface (e.g., a surface of a mixing bowl, a compression die and/or punch). A lubricant can also reduce interparticle friction within the granulate and improve the compression and ejection of compressed pharmaceutical compositions from a die press. The lubricant is also compatible with the ingredients of the pharmaceutical composition, i.e., they do not substantially reduce the solubility, the hardness, or the biological activity of the pharmaceutical composition. Exemplary lubricants include magnesium stearate, calcium stearate, zinc stearate, sodium stearate, stearic acid, aluminum stearate, leucine, glyceryl behenate, hydrogenated vegetable oil or any combination thereof. In embodiment, the lubricant is magnesium stearate.

Thus, in one embodiment, the pharmaceutical composition comprises a lubricant in an amount of 5 wt % or less (e.g., 4.75 wt %, 4.0 wt % or less, or 3.00 wt % or less, or 2.0 wt % or less) by weight of the composition. For example, the pharmaceutical composition comprises from about 5 wt % to about 0.10 wt % (e.g., from about 4.5 wt % to about 0.5 wt % or from about 3 wt % to about 1 wt %) of lubricant, by weight of the composition. In another example, the pharmaceutical composition comprises 5 wt % or less (e.g., 4.0 wt % or less, 3.0 wt % or less, or 2.0 wt % or less, or 1.0 wt % or less) of magnesium stearate, by weight of the composition. In yet another example, the pharmaceutical composition comprises from about 5 wt % to about 0.10 wt % (e.g., from about 4.5 wt % to about 0.15 wt % or from about 3.0 wt % to about 0.50 wt %) of magnesium stearate, by weight of the composition.

Pharmaceutical compositions of the invention can optionally comprise one or more colorants, flavors, and/or fragrances to enhance the visual appeal, taste, and/or scent of the composition. Suitable colorants, flavors, or fragrances are compatible with the ingredients of the pharmaceutical composition, i.e., they do not substantially reduce the solubility, the chemical stability, the physical stability, the hardness, or the biological activity of the pharmaceutical composition. In one embodiment, the pharmaceutical composition comprises a colorant, a flavor, and/or a fragrance.

In some embodiments, the pharmaceutical composition includes or can be made into tablets and the tablets can be coated with a colorant and optionally labeled with a logo, other image and/or text using a suitable ink. In still other embodiments, the pharmaceutical composition includes or can be made into tablets and the tablets can be coated with a colorant, waxed, and optionally labeled with a logo, other image and/or text using a suitable ink. Suitable colorants and inks are compatible with the ingredients of the pharmaceutical composition, i.e., they do not substantially reduce the solubility, the chemical stability, the physical stability, the hardness, or the biological activity of the pharmaceutical composition. The suitable colorants and inks can be any color and are water based or solvent based. In one embodiment, tablets made from the pharmaceutical composition are coated with a colorant and then labeled with a logo, other image, and/or text using a suitable ink. For example, tablets comprising pharmaceutical composition as described herein can be coated with about 3 wt % (e.g., less than about 6 wt % or less than about 4 wt %) of film coating comprising a colorant. The colored tablets can be labeled with a logo and text indicating the strength of the active ingredient in the tablet using a suitable ink. In another example, tablets comprising pharmaceutical composition as described herein can be coated with about 3 wt % (e.g., less than about 6 wt % or less than about 4 wt %) of a film coating comprising a colorant.

In another embodiment, tablets made from the pharmaceutical composition are coated with a colorant, waxed, and then labeled with a logo, other image, and/or text using a suitable ink. For example, tablets comprising pharmaceutical composition as described herein can be coated with about 3 wt % (e.g., less than about 6 wt % or less than about 4 wt %) of film coating comprising a colorant. The colored tablets can be waxed with Carnauba wax powder weighed out in the amount of about 0.01% w/w of the starting tablet core weight. The waxed tablets can be labeled with a logo and text indicating the strength of the active ingredient in the tablet using a suitable ink. In another example, tablets comprising pharmaceutical composition as described herein can be coated with about 3 wt % (e.g., less than about 6 wt % or less than about 4 wt %) of a film coating comprising a colorant. The colored tablets can be waxed with Carnauba wax powder weighed out in the amount of about 0.01% w/w of the starting tablet core weight. The waxed tablets can be labeled with a logo and text indicating the strength of the active ingredient in the tablet using a pharmaceutical grade ink such as a black ink (e.g., Opacode® S-1-17823, a solvent based ink, commercially available from Colorcon, Inc. of West Point, PA.).

B. Additional Therapeutic Agent(s)

In another embodiment, the pharmaceutical compositions of the present invention further comprise an additional therapeutic agent. In one embodiment, the additional therapeutic agent is a CFTR modulator. In one embodiment, the additional therapeutic agent is a CFTR corrector. In one embodiment, the additional therapeutic agent is a CFTR potentiator. In another embodiment, the pharmaceutical composition comprises a spray dried dispersion of the present invention and one or more of the following additional therapeutic agent(s).

In another embodiment, the additional therapeutic agent is selected from:

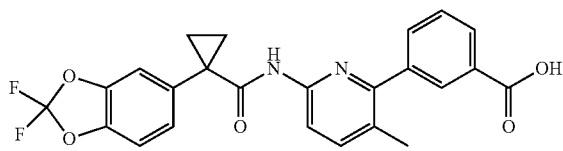 [SMILES: Cc1ccc(NC(=O)C2(c3ccc4c(c3)OC(F)(F)O4)CC2)nc1-c1cccc(C(=O)O)c1]

3-(6-(1-(2,2-difluorobenzo[d][1,3]dioxol-5-yl) cyclopropanecarboxamido)-3-methylpyridin-2-yl)benzoic acid, or pharmaceutically acceptable salt thereof;

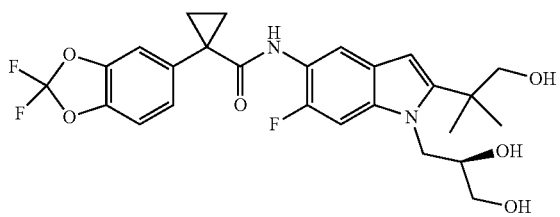 [SMILES: CC(C)(CO)c1cc2cc(NC(=O)C3(c4ccc5c(c4)OC(F)(F)O5)CC3)c(F)cc2n1C[C@@H](O)CO]

(R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or a pharmaceutically acceptable salt thereof; or

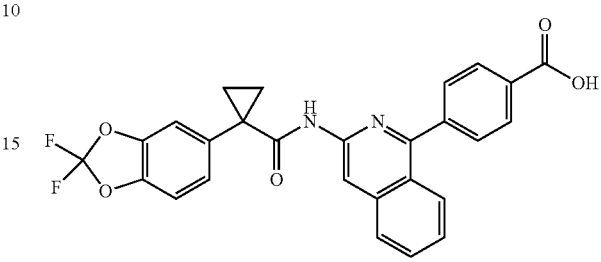

4-(3-(1-(2,2-difluorobenzo[d][1,3]dioxol-5-yl)cyclopropanecarboxamido) isoquinolin-1-yl)benzoic acid, or pharmaceutically acceptable salt thereof.

In another embodiment, the pharmaceutical composition of the present invention comprises a spray dried dispersion of the present invention and 3-(6-(1-(2,2-difluorobenzo[d][1,3]dioxol-5-yl) cyclopropanecarboxamido)-3-methylpyridin-2-yl)benzoic acid, or pharmaceutically acceptable salt thereof.

In another embodiment, the pharmaceutical composition of the present invention comprises a spray dried dispersion of the present invention and (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or pharmaceutically acceptable salt thereof.

In another embodiment, the pharmaceutical composition of the present invention comprises a spray dried dispersion of the present invention and 4-(3-(1-(2,2-difluorobenzo[d][1,3]dioxol-5-yl)cyclopropanecarboxamido) isoquinolin-1-yl)benzoic acid, or pharmaceutically acceptable salt thereof.

In another embodiment, the additional therapeutic agent is selected from Table 4.

Table 4: Additional Agents for Combination Therapies.

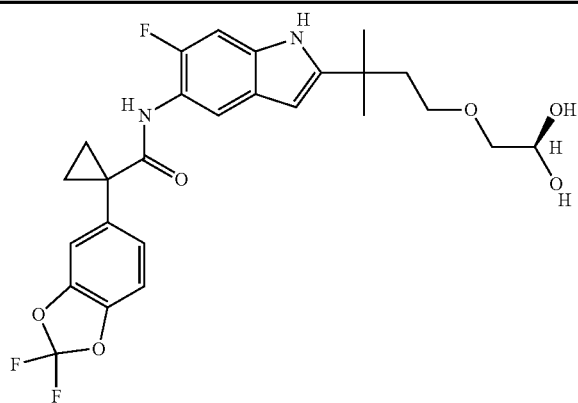

1

-continued
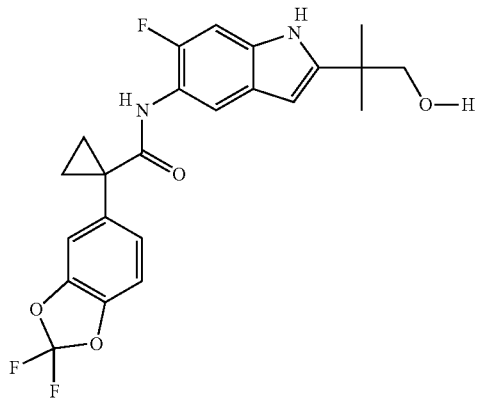
2
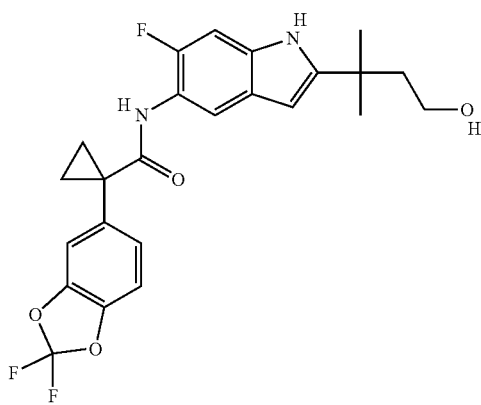
3
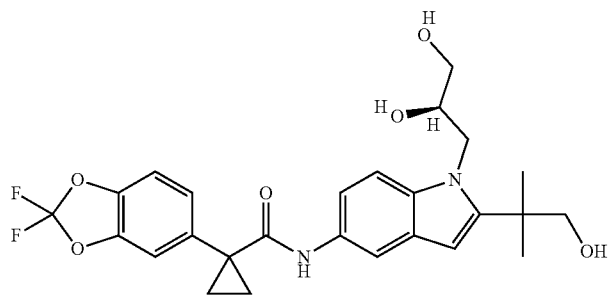
4
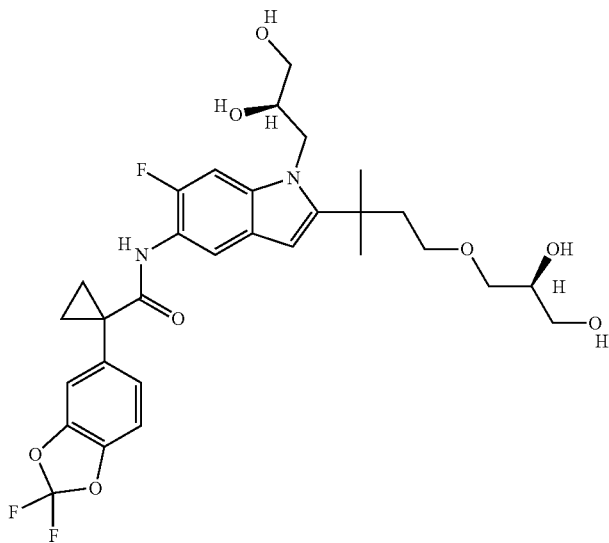
5

-continued
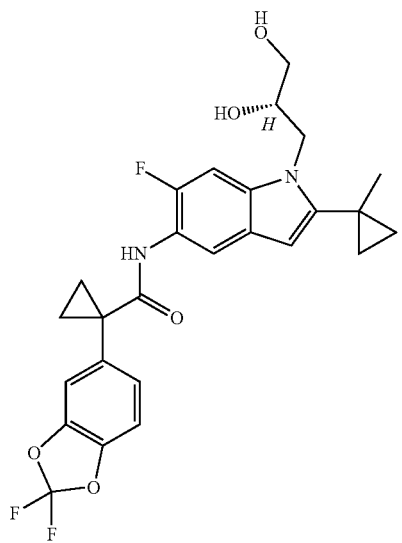
6
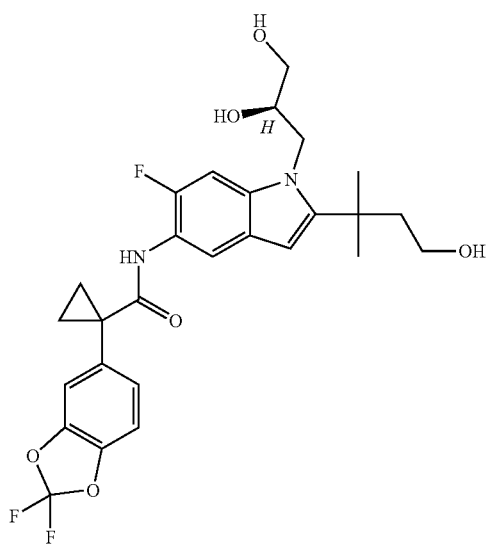
7
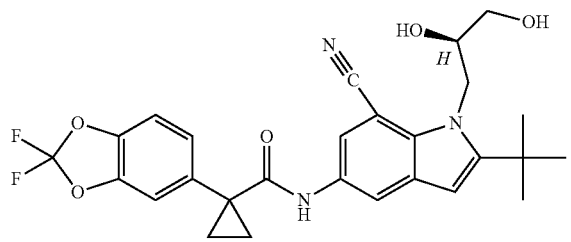
8

-continued
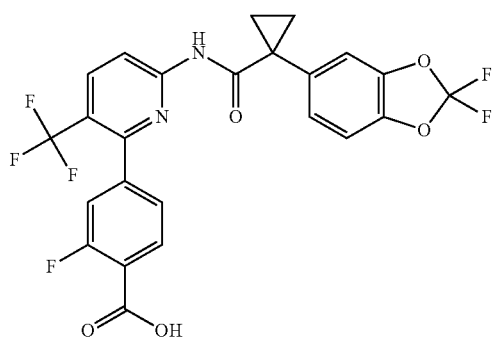 [SMILES: O=C(O)c1ccc(-c2nc(NC(=O)C3(c4ccc5c(c4)OC(F)(F)O5)CC3)ccc2C(F)(F)F)cc1F]
9
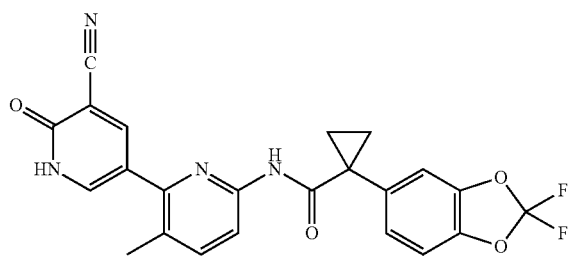 [SMILES: Cc1ccc(NC(=O)C2(c3ccc4c(c3)OC(F)(F)O4)CC2)nc1-c1c[nH]c(=O)c(C#N)c1]
10
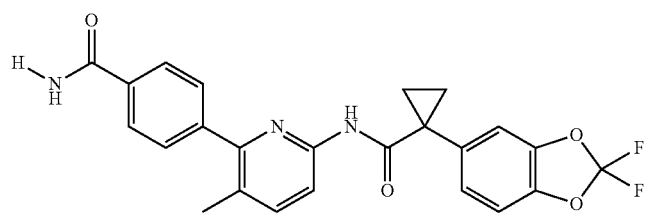 [SMILES: Cc1ccc(NC(=O)C2(c3ccc4c(c3)OC(F)(F)O4)CC2)nc1-c1ccc(C(N)=O)cc1]
11
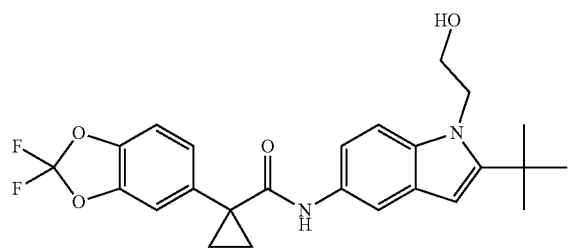 [SMILES: CC(C)(C)c1cc2cc(NC(=O)C3(c4ccc5c(c4)OC(F)(F)O5)CC3)ccc2n1CCO]
12
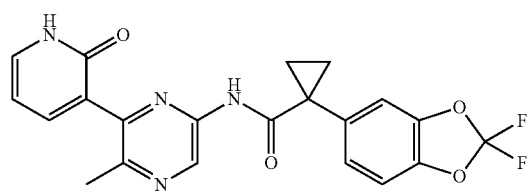 [SMILES: Cc1ncc(NC(=O)C2(c3ccc4c(c3)OC(F)(F)O4)CC2)nc1-c1ccc[nH]c1=O]
13
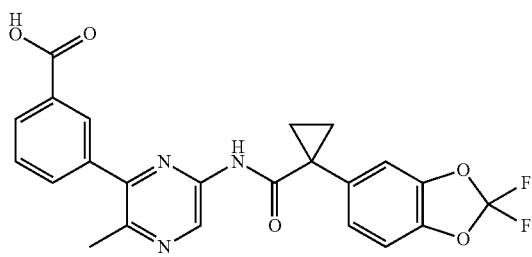 [SMILES: Cc1ncc(NC(=O)C2(c3ccc4c(c3)OC(F)(F)O4)CC2)nc1-c1cccc(C(=O)O)c1]
14

-continued
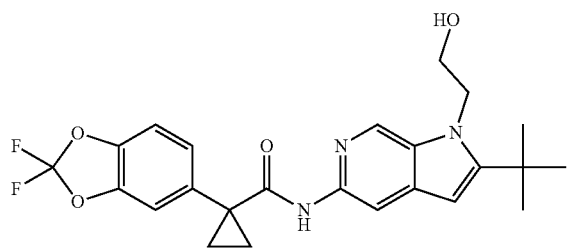 [SMILES: CC(C)(C)c1cc2cc(NC(=O)C3(c4ccc5c(c4)OC(F)(F)O5)CC3)ncc2n1CCO]
15
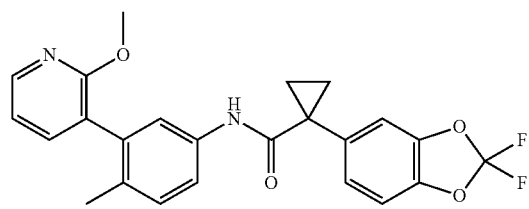 [SMILES: COc1ncccc1-c1cc(NC(=O)C2(c3ccc4c(c3)OC(F)(F)O4)CC2)ccc1C]
16
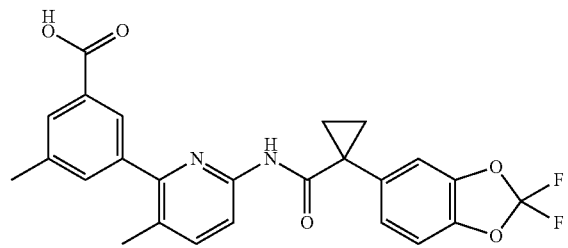 [SMILES: Cc1cc(C(=O)O)cc(-c2nc(NC(=O)C3(c4ccc5c(c4)OC(F)(F)O5)CC3)ccc2C)c1]
17
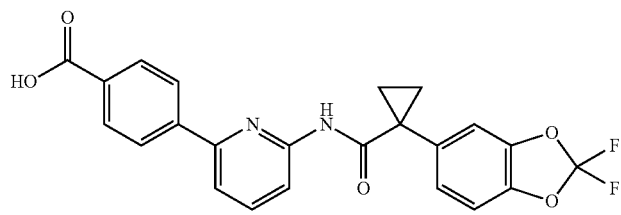 [SMILES: O=C(O)c1ccc(-c2cccc(NC(=O)C3(c4ccc5c(c4)OC(F)(F)O5)CC3)n2)cc1]
18
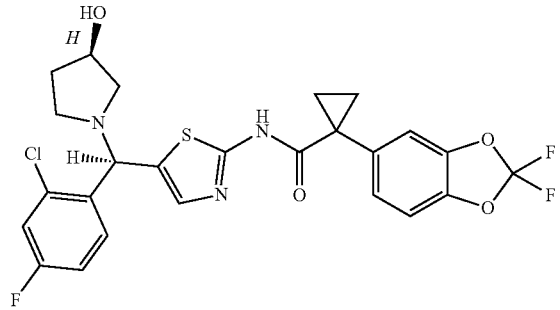
19

-continued

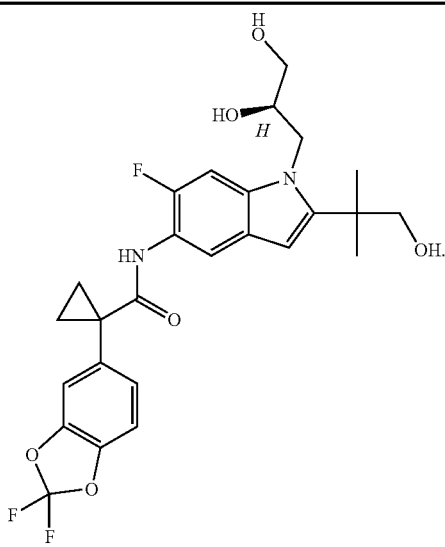

20

In one embodiment, the additional therapeutic agent is selected from Table 5, all US Patents, published US Patent Applications, and published international patent applications are incorporated herein by reference in their entirety.

TABLE 5

Additional agents for combination therapies.

Compounds disclosed in U.S. Pat. No. 7,407,976 (Col 13, ln 35-col 66, ln 67; Compounds 1-100 in Table 1 at col 67, ln 1-col 127, ln 42) incorporated herein by reference,
Compounds disclosed in U.S. Pat. No. 7,645,789 (Col 16, ln 52-col 50, ln 22; Compounds 1-322 in Table 1 at col 50, ln 24-col 167, ln 42) incorporated herein by reference,
Compounds disclosed in U.S. Pat. No. 7,659,268 (Col 16, ln 20-col 70, ln 52; Compounds 1-528 in Table 1 at col 70, ln 53-col 331, ln 34) incorporated herein by reference,
Compounds disclosed in U.S. Pat. No. 7,671,221 (Col 16, ln 12-col 54, ln 48; Compounds 1-1216 in Table 1 at col 54, ln 49-col 699, ln 27) incorporated herein by reference,
Compounds disclosed in U.S. Pat. No. 7,691,902 (Col 16, ln 11-col 54, ln 29; Compounds 1-959 in Table 1 at col 54, ln 29-col 683, ln 44) incorporated herein by reference,
Compounds disclosed in U.S. Pat. No. 7,741,321 (Col 16, ln 25-col 72, ln 17; Compounds 1-422 in Table 1 at col 72, ln 20-col 279, ln 15) incorporated herein by reference,
Compounds disclosed in U.S. Pat. No. 7,754,739 (Col 16, ln 1-col 22, ln 47; Compounds 1-2 in Table 1 at col 18, ln 26-65) incorporated herein by reference,
Compounds disclosed in U.S. Pat. No. 7,776,905 (Col 16, ln 23-col 38, ln 40; Compounds 1-306 in Table 1 at col 38, ln 45-col 96, ln 40) incorporated herein by reference,
Compounds disclosed in U.S. Pat. No. 7,973,169 (Col 9, ln 16-col 40, ln 40; Compounds 1-289 in Table 1 at col. 40, ln 41-col 289, ln 39) incorporated herein by reference,
Compounds disclosed in U.S. Pat. No. 7,977,322 (Col 6, ln 26-col 37, ln 47; Compounds 1-498 in Table 1 at col 37, ln 50-col 141, ln 40) incorporated herein by reference,
Compounds disclosed in U.S. Pat. No. 7,999,113 (Col 6, ln 13-col 10, ln 67; Compounds 1-13 in Table 1 at col 11, ln 5-col 13, ln 65) incorporated herein by reference,
Compounds disclosed in U.S. Pat. No. 8,227,615 (Col 6, ln 10-col 29, ln 66; Compounds 1-78 in Table 1 at col 30, ln 1-col 46, ln 48) incorporated herein by reference
Compounds disclosed in U.S. Pat. No. 8,299,099 (Col 6, ln 10-col 34, ln 18; Compounds 1-47 in Table 1 at col 34, ln 20-col 42, ln 35) incorporated herein by reference,
Compounds disclosed in U.S. Published application No. 2006-0052358 (Paragraphs [0034]-[0056]; [0077]-[0240]; Compounds 1-320 in Table 1 at paragraph [0241]) incorporated herein by reference,
Compounds disclosed in U.S. Published application No. 2009-0143381 (Paragraphs [0102]-[0263]; Compounds 1-28 in Table 1 at paragraph [0264]) incorporated herein by reference,
Compounds disclosed in U.S. Published application No. 2009-0170905 (Paragraphs [0012]-[0013]; [0030]-[0051]) incorporated herein by reference,
Compounds disclosed in U.S. Published application No. 2009-0253736 (Paragraphs [0031]-[0162]; Compounds 1-15 in Table 1 at paragraph [0163]) incorporated herein by reference
Compounds disclosed in U.S. Published application No. 2011-0263654 (Paragraphs [0012]-[0013]; [0066]-[0141]) incorporated herein by reference,
Compounds disclosed in U.S. Published application No. 2011-0251253 (Paragraphs [0012]-[0013]; [0054]-[0079]) incorporated herein by reference,

TABLE 5-continued

Additional agents for combination therapies.

Compounds disclosed in PCT application WO2008141119 (Paragraphs [0100]-[0339];
Compounds 1-117 in Table 1 at paragraph [0340]) incorporated herein by reference,
Compounds disclosed in U.S. application Ser. No. 11/047,361 incorporated herein by reference,
Compounds disclosed in U.S. Published application No. 2013-0116238 (Paragraphs [0028]-[0044]; [0117]-[0128]) incorporated herein by reference, or combinations thereof.

In another embodiment, the additional therapeutic agent is selected from

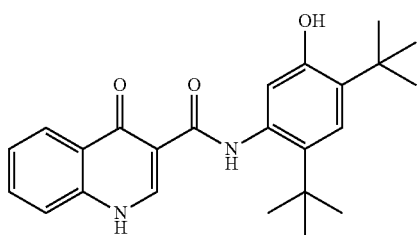 [SMILES: CC(C)(C)c1cc(C(C)(C)C)c(NC(=O)c2c[nH]c3ccccc3c2=O)cc1O]

N-(5-hydroxy-2,4-ditert-butyl-phenyl)-4-oxo-1H-quinoline-3-carboxamide, or pharmaceutically acceptable salt thereof or

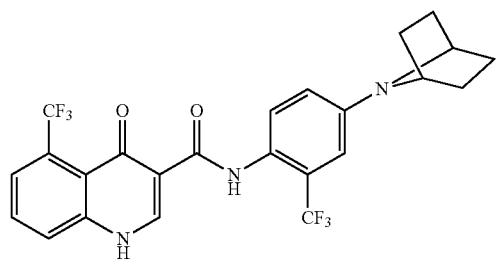 [SMILES: O=C(Nc1ccc(N2C3CCC2CC3)cc1C(F)(F)F)c1c[nH]c2cccc(C(F)(F)F)c2c1=O]

N-(4-(7-azabicyclo[2.21]heptan-7-yl)-2-(trifluoromethyl)phenyl)-4-oxo-5-(trifluoromethyl)-1,4-dihydroquinoline-3-carboxamide, or pharmaceutically acceptable salt thereof.

In another embodiment, the invention features a pharmaceutical composition comprising a) a spray dried dispersion of the present invention; b) a compound selected from 3-(6-(1-(2,2-difluorobenzo[d][1,3]dioxol-5-yl) cyclopropanecarboxamido)-3-methylpyridin-2-yl)benzoic acid, (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, or 4-(3-(1-(2,2-difluorobenzo[d][1,3]dioxol-5-yl) cyclopropanecarboxamido) isoquinolin-1-yl)benzoic acid; and c) a compound selected from N-(5-hydroxy-2,4-ditert-butyl-phenyl)-4-oxo-1H-quinoline-3-carboxamide or N-(4-(7-azabicyclo[2.21]heptan-7-yl)-2-(trifluoromethyl)phenyl)-4-oxo-5-(trifluoromethyl)-1,4-dihydroquinoline-3-carboxamide.

In another embodiment, the invention features a pharmaceutical composition comprising a) a spray dried dispersion of the present invention; b) 3-(6-(1-(2,2-difluorobenzo[d][1,3]dioxol-5-yl) cyclopropanecarboxamido)-3-methylpyridin-2-yl)benzoic acid; and c) N-(5-hydroxy-2,4-ditert-butyl-phenyl)-4-oxo-1H-quinoline-3-carboxamide.

In another embodiment, the invention features a pharmaceutical composition comprising a) a spray dried dispersion of the present invention; b) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide; and c) N-(5-hydroxy-2,4-ditert-butyl-phenyl)-4-oxo-1H-quinoline-3-carboxamide.

In another embodiment, the invention features a pharmaceutical composition comprising a) a spray dried dispersion of the present invention; b) 4-(3-(1-(2,2-difluorobenzo[d][1,3]dioxol-5-yl)cyclopropanecarboxamido) isoquinolin-1-yl) benzoic acid; and c) N-(5-hydroxy-2,4-ditert-butyl-phenyl)-4-oxo-1H-quinoline-3-carboxamide.

In another embodiment, the additional therapeutic agent is selected from Table 6. All US Patents, published US Patent Applications, and published international patent applications are incorporated herein by reference in their entirety.

TABLE 6

Additional agents for combination therapies.

Compounds disclosed in U.S. Published application No. 2005-0113423 (Paragraph [00146]; Compounds IA-1-IA-136 and Compounds I-1-I-21 in Tables 1 and 2 at paragraphs [0391]-[0392]) incorporated herein by reference,
Compounds disclosed in U.S. Published application No. 2005-0059687 (Paragraphs [00100]-[00101]; Compounds 1-405 in Table 1 at paragraph [0169]) incorporated herein by reference,
Compounds 1-108 disclosed in U.S. Pat. No. 7,598,412 (Col 22, ln 14-col 79, ln 20; Table 1) incorporated herein by reference,
Compounds 1-485 disclosed in U.S. Pat. No. 7,495,103 (Col 51, ln 1-col 63, ln 43; Table 1) incorporated herein by reference,
Compounds 1-718 disclosed in U.S. Pat. No. 8,354,427 (Col 51, ln 3-col 71, ln 46; Table 1) incorporated herein by reference,
Compounds 1-233 disclosed in U.S. Published application No. 2007-0105833 (Paragraph [00145]; Table 1) incorporated herein by reference,
Compounds 1-26 disclosed in U.S. Pat. No. 8,242,149 (Col 46, ln 47-col 57, ln 37; Table 1) incorporated herein by reference,

TABLE 6-continued

Additional agents for combination therapies.

Compounds 1-18 disclosed in U.S. Pat. No. 8,314,256 (Col 21, ln 1-col 26, ln 19) incorporated herein by reference,
Compounds 1-14 disclosed in U.S. Pat. No. 8,399,479 (Col 36, ln 20-col 38, ln 40; Table 1) incorporated herein by reference,
Compounds 1-18 disclosed in U.S. Pat. No. 8,188,283 (Col 38, ln 43-col 43, ln 36; Table 1) incorporated herein by reference,
Compounds 1-16 disclosed in U.S. Published application No. 2010-0249180 (Paragraph [0173]; Table 1) incorporated herein by reference,
Compounds 1-19 disclosed in U.S. Published application No. 2011-0008259 (Paragraph [0172]; Table 1) incorporated herein by reference,
Compounds 1-129 disclosed in U.S. Pat. No. 8,367,660 (Col 57, ln 31-col 81, ln 24; Table1) incorporated herein by reference, or combinations thereof.

In one embodiment, the additional therapeutic agent is selected from a mucolytic agent, bronchodialator, an antibiotic, an anti-infective agent, a CFTR modulator, or an anti-inflammatory agent.

In one embodiment, the additional therapeutic agent is an antibiotic. Exemplary antibiotics useful herein include tobramycin, including tobramycin inhaled powder (TIP), azithromycin, cayston, aztreonam, including the aerosolized form of aztreonam, amikacin, including liposomal formulations thereof, ciprofloxacin, including formulations thereof suitable for administration by inhalation, levoflaxacin, including aerosolized formulations thereof, and combinations of two antibiotics, e.g., fosfomycin and tobramycin.

In another embodiment, the additional therapeutic agent is a mucolyte. Exemplary mucolytes useful herein includes Pulmozyme®.

In another embodiment, the additional therapeutic agent is a bronchodilator. Exemplary bronchodilators include albuterol, metaprotenerol sulfate, pirbuterol acetate, salmeterol, or tetrabuline sulfate.

In another embodiment, the additional therapeutic agent is effective in restoring lung airway surface liquid. Such agents improve the movement of salt in and out of cells, allowing mucus in the lung airway to be more hydrated and, therefore, cleared more easily. Exemplary such agents include hypertonic saline, denufosol tetrasodium ([[(3S,5R)-5-(4-amino-2-oxopyrimidin-1-yl)-3-hydroxyoxolan-2-yl]methoxy-hydroxyphosphoryl] [[[(2R,3 S,4R,5R)-5-(2,4-dioxopyrimidin-1-yl)-3,4-dihydroxyoxolan-2-yl]methoxy-hydroxyphosphoryl]oxy-hydroxyphosphoryl] hydrogen phosphate), or bronchitol (inhaled formulation of mannitol).

In another embodiment, the additional therapeutic agent is an anti-inflammatory agent, i.e., an agent that can reduce the inflammation in the lungs. Exemplary such agents useful herein include ibuprofen, docosahexanoic acid (DHA), sildenafil, inhaled glutathione, pioglitazone, hydroxychloroquine, or simavastatin.

In another embodiment, the additional therapeutic agent is a compound that induces CFTR activity other than a compound of formula I. Exemplary such agents include ataluren ("PTC124®"; 3-[5-(2-fluorophenyl)-1,2,4-oxadiazol-3-yl] benzoic acid), sinapultide, lancovutide, depelestat (a human recombinant neutrophil elastase inhibitor), and cobiprostone (7-{(2R,4aR, 7aR)-2-[(3 S)-1,1-difluoro-3-methylpentyl]-2-hydroxy-6-oxooctahydrocyclopenta[b]pyran-5-yl}heptanoic acid).

In another embodiment, the additional therapeutic agent is a nutritional agent. Exemplary nutritional agents include pancrelipase (pancreating enzyme replacement), including Pancrease®, Pancreacarb®, Ultrase®, or Creon®, Liprotamase® (formerly Trizytek®), Aquadeks®, or glutathione inhalation. In one embodiment, the additional nutritional agent is pancrelipase.

In another embodiment, the additional therapeutic agent is a compound selected from gentamicin, curcumin, cyclophosphamide, 4-phenylbutyrate, miglustat, felodipine, nimodipine, philoxin B, geniestein, apigenin, cAMP/cGMP augmenters or inducers such as rolipram, sildenafil, milrinone, tadalafil, amrinone, isoproterenol, albuterol, and almeterol, deoxyspergualin, HSP 90 inhibitors, HSP 70 inhibitors, proteosome inhibitors such as epoxomicin, lactacystin, or the like.

In other embodiments, the additional therapeutic agent is a compound disclosed in WO 2004028480, WO 2004110352, WO 2005094374, WO 2005120497, or WO 2006101740, incorporated herein in their entirety by reference. In another embodiment, the additional agent is a benzo[c]quinolizinium derivative that exhibits CFTR inducing or augmenting activity or a benzopyran derivative that exhibits CFTR inducing or augmenting activity. In another embodiment, the additional agent is a compound disclosed in U.S. Pat. Nos. 7,202,262, 6,992,096, US20060148864, US20060148863, US20060035943, US20050164973, WO2006110483, WO2006044456, WO2006044682, WO2006044505, WO2006044503, WO2006044502, or WO2004091502, incorporated herein by reference in their entireties. In another embodiment, the additional agent is a compound disclosed in WO2004080972, WO2004111014, WO2005035514, WO2005049018, WO2006099256, WO2006127588, or WO2007044560, incorporated herein by reference in their entireties.

In another embodiment, the additional therapeutic agent is selected from the categories ENaC inhibitors, betamimetics, anticholinergics, corticosteroids, PDE4-inhibitors, LTD4-antagonists, EGFR-inhibitors, dopamine agonists, H1-antihistamines, PAF-antagonists, MAP-kinase inhibitors, MPR4-inhibitors, iNOS-inhibitors, or SYK-inhibitors, or double or triple combinations thereof.

In another embodiment, the additional therapeutic agent is an ENaC inhibitor selected from 3-(3-{2-[(E)-3,5-diamino-6-chloro-pyrazine-2-carbonylimino]-1,3,8-triaza-spiro[4.5] decane-8-carbonyl}-benzenesulfonylamino)-propionic acid dipropylcarbamoylmethyl ester; [4-(3-{2-[(Z)-3,5-diamino-6-chloro-pyrazine-2-carbonylimino]-1,3,8-triaza-spiro[4.5] dec-8-yl}-3-oxo-propyl)-phenoxy]-acetic acid [(2-hydroxyethyl)-methyl-carbamoyl]-methyl ester; [4-(3-{2-[(E)-3,5-diamino-6-chloro-pyrazine-2-carbonylimino]-1,3,8-triaza-spiro[4.5]dec-8-yl}-3-oxo-propyl)-phenoxy]-acetic acid cyclohexyloxycarbonylmethyl ester; 3-(3-{2-[(E)-3,5-diamino-6-chloro-pyrazine-2-carbonylimino]-1,3,8-triaza-spiro[4.5]decane-8-carbonyl}-benzene sulfonylamino)-propionic acid cyclohexyloxycarbonylmethyl ester; [4-(3-{2-[(E)-3,5-diamino-6-chloro-pyrazine-2-carbonylimino]-1,3,8-triaza-spiro[4.5]dec-8-yl}-3-oxo-propyl)-phenoxy]-acetic acid dimethylcarbamoylmethyl ester; [4-(3-{2-[(E)-3,5-diamino-6-chloro-pyrazine-2-carbonylimino]-1,3,8-triaza-spiro[4.5]dec-8-yl}-3-oxo-propyl)-phenoxy]-acetic acid dipropylcarbamoylmethyl ester; [4-(3-{2-[(E)-3,5-diamino-6-chloro-pyrazine-2-carbonylimino]-1,3,8-triaza-1-spiro[4.5]dec-8-yl}-3-oxo-propyl)-phenoxy]-acetic acid tert-butoxycarbonylmethyl ester; [4-(3-{2-[(E)-3,5-diamino-6-chloro-pyrazine-2-carbonylimino]-1,3,8-triaza-spiro[4.5]dec-8-yl}-3-oxo-propyl)-phenoxy]-acetic acid benzyloxycarbonylmethyl ester; [4-(3-{2-[(E)-3,5-diamino-6-chloro-pyrazine-2-carbonylimino]-1,3,8-triaza-spiro[4.5]dec-8-yl}-3-oxo-propyl)-phenoxy]-acetic acid diethylcarbamoylmethyl ester; [4-(3-{2-[(E)-3,5-diamino-6-chloro-pyrazine-2-carbonylimino]-1,3,8-triaza-spiro[4.5]dec-8-yl}-3-oxo-propyl)-phenoxy]-acetic acid 2-oxo-2-piperidin-1-yl-ethyl ester; [2-chloro-4-(3-{2-[(E)-3,5-diamino-6-chloro-pyrazine-2-carbonylimino]-1,3-,8-triaza-spiro[4.5]dec-8-yl}-3-oxo-propyl)-phenoxy]-acetic acid dipropylcarbamoylmethyl ester; 3-(3-{2-[(E)-3,5-diamino-6-chloro-pyrazine-2-carbonylimino]-1,3,8-triaza-spiro[4.5]decane-8-carbonyl}-benzenesulfonylamino)-propionic acid 2-oxo-2-(2-trifluoromethyl-pyrrolidin-1-yl)-ethyl ester; [2-chloro-4-(3-{2-[(E)-3,5-diamino-6-chloro-pyrazine-2-carbonylimino]-1,3-,8-triaza-spiro[4.5]dec-8-yl}-3-oxo-propyl)-phenoxy]-acetic acid 2-(2-oxo-piperidin-1-yl)-ethyl ester; [4-(3-{2-[(E)-3,5-diamino-6-chloro-pyrazine-2-carbonylimino]-1,3,8-triaza-spiro[4.5]dec-8-yl}-3-oxo-propyl)-phenoxy]-acetic acid 2-morpholin-4-yl-2-oxo-ethyl ester; 1-[(3-{2-[(E)-3,5-diamino-6-chloro-pyrazine-2-carbonylimino]-1,3,8-triaza-spiro[4.5]decane-8-carbonyl}-benzenesulfonylamino)-methyl]-cyclobutanecarboxylic acid dipropylcarbamoylmethyl ester; 3-[3-(3-{2-[(E)-3,5-diamino-6-chloro-pyrazine-2-carbonylimino]-1,3,8-triaza-spiro[4.5]decane-8-carbonyl}-phenyl)-ureido]-propionic acid dipropylcarbamoylmethyl ester; and 1-[(3-{2-[(E)-3,5-diamino-6-chloro-pyrazine-2-carbonylimino]-1,3,8-triaza-spiro[4.5]decane-8-carbonyl}-benzenesulfonylamino)-methyl]-cyclobutanecar-boxylic acid 2-oxo-2-(2-trifluoromethyl-pyrrolidin-1-yl)-ethyl ester; or a pharmaceutically acceptable salt or solvate thereof. In another embodiment, the additional therapeutic agent is 3-(3-{2-[(E)-3,5-diamino-6-chloro-pyrazine-2-carbonylimino]1,3,8-triaza-spiro[4.5]decane-8-carbonyl}-benzenesulfonylamino)-propionic acid dipropylcarbamoylmethyl ester. In another embodiment, the additional agent is a compound disclosed in U.S. Pat. No. 8,247,436 and International PCT Publication WO 2011113894, incorporated herein by reference in their entireties. In another embodiment, the additional agent is a compound disclosed in United States Publication No. 20130316981, incorporated herein in its entirety by reference.

In another embodiment, the additional therapeutic agent is a betamimetic selected from Albuterole, Arformoterole, Bambuterole, Bitolterole, Broxaterole, Carbuterole, Clenbuterole, Fenoterole, Formoterole, Hexoprenaline, Ibuterole, Isoetharine, Isoprenaline, Levosalbutamole, Mabuterole, Meluadrine, Metaproterenole, Milveterol, Orciprenaline, Pirbuterole, Procaterole, Reproterole, Rimiterole, Ritodrine, Salmefamole, Salmeterole, Soterenole, Sulphonterole, Terbutaline, Tiaramide, Tolubuterole, Zinterole, Nolomirole, and 1-(2-chloro-4-hydroxyphenyl)-t-butylaminoethanole; (−)-2-[7(S)-[2(R)-hydroxy-2-(4-hydroxyphenyl)-ethylamino]-5,6,7,8-tetrahydro-2-naphthyloxy]-N,N-dimethylacetamide hydrochloride monohydrate; 3-(4-{6-[2-[2-hydroxy-2-(4-hydroxy-3-hydroxymethyl-phenyl)-ethylamino]-hexyl-oxy}-butyl)-benzyl-sulfonamide; 5-[2-(5,6-diethyl-indan-2-ylamino)-1-hydroxy-ethyl]-8-hydroxy-1H-quinoline-2-one; 4-hydroxy-7[2-{[2-{[3-(2-phenylethoxy)propyl]sulphonyl}ethyl]-amino}ethy-l]-2(3H)-benzothiazolone; 1-(2-fluoro-4-hydroxyphenyl)-2-[4-(1-benzimidazolyl)-2-methyl-2-butylamino]ethanol; 1-[3-(4-methoxybenzyl-amino)-4-hydroxyphenyl]-2-[4-(1-benzimidazolyl)-2-m-ethyl-2-butylamino]ethanol; 1-[2H-5-hydroxy-3-oxo-4H-1,4-benzoxazin-8-yl]-2-[3-(4-N,N-dimethylaminoph-enyl)-2-methyl-2-propylamino]ethanol; 1-[2H-5-hydroxy-3-oxo-4H-1,4-benzoxazin-8-yl]-2-[3-(4-methoxyphenyl)-2-methyl-2-propylamino]ethanol; 1-[2H-5-hydroxy-3-oxo-4H-1,4-benzoxazin-8-yl]-2-[3-(4-n-butyloxyphenyl)-2-methyl-2-propylamino]ethanol; 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol; 5-hydroxy-8-(1-hydroxy-2-isopropylaminobutyl)-2H-1,4-benzoxazin-3-(4H)-one; 1-(4-amino-3-chloro-5-trifluormethylphenyl)-2-tert-butylamino)ethanol; 6-hydroxy-8-{1-hydroxy-2-[2-(4-methoxyphenyl)-1,1-dimethyl-ethylamino]-ethyl}-4H-benzo[1,4]oxazin-3-one; 6-hydroxy-8-{1-hydroxy-2-[2-(4-phenoxyacetic acid ethylester)-1,1-dimethyl-ethylamino]-ethyl}-4H-benzo[1,4]oxazin-3-one; 6-Hydroxy-8-{1-hydroxy-2-[2-(4-phenoxy-acetic acid)-1,1-dimethyl-ethylamino]-ethyl}-4H-benzo[1,4]oxazin-3-one; 8-{2-[1,1-Dimethyl-2-(2,4,6-trimethylphenyl)-ethylamino]-1-hydroxy-ethyl}-6-hydroxy-4H-benzo[1,4]oxazin-3-one; 6-hydroxy-8-{1-hydroxy-2-[2-(4-hydroxy-phenyl)-1,1-dimethyl-ethylamino]-e-thyl}-4H-benzo[1,4]oxazin-3-one; 6-hydroxy-8-{1-hydroxy-2-[2-(4-isopropyl-phenyl)-1,1-dimethyl-ethylamino]-ethyl}-4H-benzo[1,4]oxazin-3-one; 8-{2-[2-(4-Ethyl-phenyl)-1,1-dimethyl-ethylamino]-1-hydroxy-ethyl}-6-hydroxy-4H-benzo[1,4]oxazin-3-one; 8-{2-[2-(4-Ethoxy-phenyl)-1,1-dimethyl-ethylamino]-1-hydroxy-ethyl}-6-hydroxy-4H-benzo[1,4]oxazin-3-one; 4-(4-{2-[2-Hydroxy-2-(6-hydroxy-3-oxo-3,4-dihydro-2H-benzo[1,4]oxazin-8-yl)-ethylamino]-2-methyl-propyl}-phenoxy)-butyric acid; 8-{2-[2-(3,4-difluor-phenyl)-1,1-dimethyl-ethylamino]-1-hydroxy-ethyl}-6-hydroxy-4H-benzo[1,4]oxazin-3-one; 1-(4-ethoxy-carbonylamino-3-cyano-5-fluorophenyl)-2-(tert-butylamino)ethanol; N-[2-hydroxy-5-(1-hydroxy-2-{2-[4-(2-hydroxy-2-phenyl-ethylamino)-phenyl]-ethylamino}-ethyl)-phenyl]-formamide; 8-hydroxy-5-(1-hydroxy-2-{2-[4-(6-methoxy-biphenyl-3-yl amino)-phenyl]-ethylamino}-ethyl)-1H-quinolin-2-one; 8-Hydroxy-5-[1-hydroxy-2-(6-phenethylamino-hexylamino)-ethyl]-1H-quinolin-2-one; 5-[2-(2-{4-[4-(2-Amino-2-methyl-propoxy)-phenyl amino]-phenyl}-ethylamino)-1-hydroxy-ethyl]-8-hydroxy-1H-quinolin-2-one; [3-(4-{6-[2-hydroxy-2-(4-hydroxy-3-hydroxymethyl-phenyl)-ethylamino]hexyl-oxy}-butyl)-5-methyl-phenyl]-urea; 4-(2-{6-[2-(2,6-dichloro-benzyloxy)-ethoxy-hexylamino}-1-hydroxy-ethyl)-2-hydroxymethyl-phenole; 3-(4-{6-[2-hydroxy-2-(4-hydroxy-3-hydroxymethyl-phenyl)-ethylamino]-hexyl-oxy}-butyl)-benzenesulfonamide; 3-(3-{7-[2-hydroxy-2-(4-hydroxy-3-hydroxymethyl-phenyl)-ethylamino]-hepty-loxy}-propyl)-benzenesulfonamide; 4-(2-{6-[4-(3-cyclopentanesulfonyl-phenyl)-butoxy]-hexylamino}-1-hydroxy-ethyl)-2-hydroxymethyl-phenole; N-adamantan-2-yl-2-(3-{2-[2-hydroxy-2-(4-hydroxy-3-hydroxymethyl-phenyl)-ethylamino]-propyl}-phenyl)-acetamide; (R,S)-4-(2-{[6-(2,2-difluoro-4-phenylbutoxy)hexyl]amino}-1-hydroxy-ethyl)-2-(hydroxymethyl)phenol; (R,S)-4-(2-{[6-(2,2-difluoro-2-phenylethoxy)hexyl]amino}-1-hydroxy-ethyl)-2-(hydroxymethyl)phenol; (R,S)-4-(2-{[4, 4-difluoro-6-(4-phenylbutoxy)hexyl]amino}-1-hydroxy-ethyl)-2-(hydroxy-methyl)phenol; (R,S)-4-(2-{[6-(4,4-difluoro-4-phenylbutoxy)hexyl]amino}-1-hydroxy-ethyl)-2-(hydroxymethyl)phenol; (R,S)-5-(2-{[6-(2,2-difluoro-2-phenylethoxy)hexyl]amino}-1-hydroxy-ethyl)-8-hydroxyquinolin-2(1H)-one; (R,S)-[2-({6-[2,2-difluoro-2-(3-methylphenyl)ethoxy]hexyl}amino)-1-hydroxyethyl]-2-(hydroxymethyl)phenol; 4-(1R)-2-{[6-(2,2-difluoro-2-phenylethoxy)hexyl]amino}-1-hydroxyethyl)-2-(hydroxymethyl)phenol; (R,S)-2-(hydroxymethyl)-4-(1-hydroxy-2-{[4,4,515-tetrafluoro-6-(3-phenylpropoxy)-hexyl]amino}ethyl)phenol; (R,S)-[5-(2-{[6-(2,2-difluoro-2-phenylethoxy)hexyl]amino}-1-hydroxy-ethyl-)-2-hydroxy-phenyl]formamide; (R,S)-4-[2-({6-[2-(3-bromophenyl)-2,2-difluoroethoxy]hexyl}amino)-1-hydro-xyethyl]-2-(hydroxymethyl)phenol; (R,S)—N-[3-(1,1-difluoro-2-{[6-({2-hydroxy-2-[4-hydroxy-3-(hydroxymethyl)-phenyl]-ethyl}amino)hexyl]oxy}ethyl)phenyl]urea; 3-[3-(1,1-difluoro-2-{[6-({2-hydroxy-2-[4-hydroxy-3-(hydroxymethyl)phenyl]ethyl}-amino)hexyl]oxy}ethyl)phenyl]imidazolidine-2,4-dione; (R,S)-4-[2-({6-[2,2-difluoro-2-(3-methoxyphenyl)ethoxy]hexyl}amino)-1-hydroxyethyl]-2-(hydroxymethyl)phenol; 5-((1R)-2-{[6-(2,2-difluoro-2-phenylethoxy)hexyl]amino}-1-hydroxyethyl)-8-hydroxyquinolin-2(1H)-one; 4-((1R)-2-{[4,4-difluoro-6-(4-phenylbutoxy)hexyl]amino}-1-hydroxy-ethyl)-2-(hydroxymethyl)phenol; (R,S)-4-(2-{[6-(3,3-difluoro-3-phenylpropoxy)hexyl]amino}-1-hydroxy-ethyl-)-2-(hydroxymethyl)phenol; (R,S)-(2-{[6-(2,2-difluoro-2-phenylethoxy)-4,4-difluorohexyl]amino}-1-hydroxyethyl)-2-(hydroxymethyl)phenol; (R,S)-4-(2-{[6-(2,2-difluoro-3-phenylpropoxy)hexyl]amino}-1-hydroxyethyl)-2-(hydroxymethyl)phenol; 3-[2-(3-chloro-phenyl)-ethoxy]-N-(2-diethylamino-ethyl)-N-{2-[2-(4-hydroxy-2-oxo-2,3-dihydro-benzothiazol-7-yl)-ethylamino]-ethyl}propionamide; N-(2-diethylamino-ethyl)-N-{2-[2-(4-hydroxy-2-oxo-2,3-dihydro-benzothiazol-7-yl)-ethylamino]-ethyl}-3-(2-naphthalen-1-yl-ethoxy)-propionamide; 7-[2-(2-{3-[2-(2-chloro-phenyl)-ethylamino]-propylsulfanyl}-ethylamino)-1-hydroxy-ethyl]-4-hydroxy-3H-benzothiazol-2-one; or 7-[(1R)-2-(2-{3-[2-(2-Chloro-phenyl)-ethylamino]-propylsulfanyl}ethylamino)-1-hydroxyethyl]-4-hydroxy-3H-benzothiazol-2-one; optionally in racemic form, as enantiomers, diastereomers, or as pharmaceutically acceptable salts, solvates or hydrates. Preferred salts are selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate, and hydro-p-toluenesulfonate.

In one embodiment, the additional therapeutic agent is an anticholinergic selected from Tiotropium salts, preferably the bromide salt, Oxitropium salts, preferably the bromide salt, Flutropium salts, preferably the bromide salt, Ipratropium salts, preferably the bromide salt, Aclidinium salts, preferably the bromide salt, Glycopyrronium salts, preferably the bromide salt, Trospium salts, preferably the chloride salt, Tolterodin. From the above mentioned salts, the pharmaceutically active part is the cation, possible anions are chloride, bromide, iodide, sulfate, phosphate, methansulfonate, nitrate, maleate, acetate, citrate, fumarate, tartrate, oxalate, succinate, benzoate, or p-toluenesulfonate. Further examples of preferred anticholinergics are selected from among 2,2-diphenylpropionic acid tropenole ester-methobromide; 2,2-diphenylpropionic acid scopine ester-methobromide; 2-fluor-2,2-diphenylacetic acid scopine ester-methobromide; 2-fluor-2,2-diphenylacetic acid tropenole ester-methobromide; 3,3',4,4'-tetrafluorbenzil acid tropenole ester-methobromide; 3,3',4,4'-tetrafluorbenzil acid scopine ester-methobromide; 4,4'-difluorbenzil acid tropenole ester-methobromide; 4,4'-difluorbenzil acid scopine ester-methobromide; 3,3'-difluorbenzil acid tropenole ester-methobromide; 3,3'-difluorbenzil acid scopine ester-methobromide; 9-hydroxy-fluorene-9-carbon acid tropenole ester-methobromide; 9-fluor-fluorene-9-carbon acid tropenole ester-methobromide; 9-hydroxy-fluorene-9-carbon acid scopine ester-methobromide; 9-fluor-fluorene-9-carbon acid scopine ester methobromide; 9-methyl-fluorene-9-carbon acid tropenole estermethobromide; 9-methyl-fluorene-9-carbon acid scopine estermethobromide; benzil acid cyclopropyl tropine ester-methobromide; 2,2-diphenylpropionic acid cyclopropyl tropine ester-methobromide; 9-hydroxy-xanthene-9-carbon acid cyclopropyl tropine ester-methobromide; 9-methyl-fluorene-9-carbon acid cyclopropyl tropine ester-methobromide; 9-methyl-xanthene-9-carbon acid cyclopropyl tropine ester-methobromide; 9-hydroxy-fluorene-9-carbon acid cyclopropyl tropine ester-methobromide; 4,4'-difluorbenzil acid methylester cyclopropyl tropine ester-methobromide; 9-hydroxy-xanthene-9-carbon acid tropenole ester-methobromide; 9-hydroxy-xanthene-9-carbon acid scopine ester methobromide; 9-methyl-xanthene-9-carbon acid tropenole ester-methobromide; 9-methyl-xanthene-9-carbon acid scopine estermethobromide; 9-ethyl-xanthene-9-carbon acid tropenole ester methobromide; 9-difluoromethyl-xanthene-9-carbon acid tropenole ester-methobromide; or 9-hydroxymethyl-xanthene-9-carbon acid scopine ester methobromide.

In one embodiment, the additional therapeutic agent is a corticosteroid selected from Beclomethasone, Betamethasone, Budesonide, Butixocorte, Ciclesonide, Deflazacorte, Dexamethasone, Etiprednole, Flunisolide, Fluticasone, Loteprednole, Mometasone, Prednisolone, Prednisone, Rofleponide, Triamcinolone, Tipredane, {20R-16alpha,17alpha-[butylidenebis(oxy)]-6alpha,9alpha-difluoro-11beta-hydroxy-17beta-(methylthio)androsta-4-en-3-one}; 9-fluoro-11beta,17,21-trihydroxy-16alpha-methylpregna-1,4-diene-3,20-dione 21-cyclohexanecarboxylate 17-cyclopropanecarboxylate; 16,17-butylidenedioxy-6,9-difluoro-11-hydroxy-17-(methylthio)androst-4-en-3-one; flunisolide-21-[4'-(nitrooxymethyl)benzoate]; 6,9-difluoro-17-[(2-furanylcarbonyl)oxy]-11-hydroxy-16-methyl-3-oxo-androsta-1,4-di en-17-carbothion acid (S)-fluoromethyl-ester; 6,9-difluoro-11-hydroxy-16-methyl-3-oxo-17-propionyloxy-androsta-1,4-dien-17-carbothion acid (S)-(2-oxo-tetrahydro-furan-3S-yl)ester; or 6alpha,9alpha-difluoro-11beta-hydroxy-16alpha-methyl-3-oxo-17alpha-(2,2,3,3-tertamethylcyclopropylcarbonyl)oxy-androsta-1,4-diene-17beta-carboxylic acid cyanomethyl ester; optionally in racemic form, as enantiomers, diastereomers, or as pharmaceutically acceptable salts, solvates, or hydrates. Examples of preferred salts and derivatives are alkali salts, i.e., sodium or potassium salts, sulfobenzoates, phosphates, isonicotinates, acetates, dichloroacetates, propionates, dihydrogenphosphates, palmitates, pivalates, or furoates.

In one embodiment, the additional therapeutic agent is a PDE4-inhibitor selected from Enprofylline, Theophylline, Roflumilaste, Ariflo (Cilomilaste), Tofimilaste, Pumafentrine, Lirimilaste, Apremilaste, Arofylline, Atizorame, Oglemilastum, Tetomilaste; 5-[(N-(2,5-dichloro-3-pyridinyl)-carboxamide]-8-methoxy-quinoline; 5-[N-(3,5-dichloro-1-oxido-4-pyridinyl)-carboxamide]-8-methoxy-2-(trifluo-romethyl)-quinoline; N-(3,5-dichloropyrid-4-yl)-[1-

(4-fluorobenzyl)-5-hydroxy-indole-3-yl]glyoxyl acid amide); 9-[(2-fluorophenyl)methyl]-N-methyl-2-(trifluoromethyl)-9H-purine-6-amine; 4-[(2R)-2-[3-(cyclopentyloxy)-4-methoxyphenyl]-2-phenylethyl]-pyridine; N-[(3R)-3,4,6,7-tetrahydro-9-methyl-4-oxo-1-phenylpyrrolo[3,2,1-jk-][1,4]benzodiazepin-3-yl]-4-pyridinecarboxamide; 4-[6,7-diethoxy-2,3-bis(hydroxymethyl)-1-naphthalenyl]-1-(2-methoxyethyl)-2(1H)-pyridinone; 2-[4-[6,7-diethoxy-2,3-bis(hydroxymethyl)-1-naphthalenyl]-2-pyridinyl]-4-(3-pyridinyl)-1 (2H)-phthalazinone; (3-(3-cyclopenyloxy-4-methoxybenzyl)-6-ethylamino-8-isopropyl-3H-purine; beta-[3-(cyclopentyloxy)-4-methoxyphenyl]-1,3-dihydro-1,3-dioxo-2H-isoindole-2-propanamide; 9-ethyl-2-methoxy-7-methyl-5-propyl-imidazo[1,5-a]pyrido[3,2-e]pyrazin-6(-5H)-one; 5-[3-(cyclopentyloxy)-4-methoxyphenyl]-3-[(3-methylphenyl)methyl](3 S,5 S)-2-piperidinone; 4-[1-[3,4-bis(difluoromethoxy)phenyl]-2-(3-methyl-1-oxido-4-pyridinyl)ethyl]-alpha,alpha-bis(trifluoromethyl)-benzenemethanol; N-(3,5-dichloro-1-oxo-pyridine-4-yl)-4-difluoromethoxy-3-cyclopropylmethoxy-benzamide; (−)p-[(4aR*,10b S*)-9-ethoxy-1,2,3,4,4a,10b-hexahydro-8-methoxy-2-methyl-benzo[s][1,6]naphthyridin-6-yl]-N,N-diisopropylbenzamide; (R)-(+)-1-(4-bromobenzyl)-4-[(3-cyclopentyloxy)-4-methoxyphenyl]-2-pyrrolidone; 3-(cyclopentyloxy-4-methoxyphenyl)-1-(4-N'-[N-2-cyano-S-methyl-isothioureido]-benzyl)-2-pyrrolidone; cis[4-cyano-4-(3-cyclopentyloxy-4-methoxyphenyl)cyclohexan-1-carbon acid]; 2-Carbomethoxy-4-cyano-4-(3-cyclopropylmethoxy-4-difluoromethoxyphenyl)-cyclohexan-1-one; cis[4-cyano-4-(3-cyclopropylmethoxy-4-difluoromethoxyphenyl)cyclohexan-1-ol]; (R)-(+)-ethyl [4-(3-cyclopentyloxy-4-methoxyphenyl)pyrrolidine-2-yliden]acetate; (S)-(−)-ethyl[4-(3-cyclopentyloxy-4-methoxyphenyl)pyrrolidine-2-yliden]acetate; 9-cyclopentyl-5,6-dihydro-7-ethyl-3-(2-thienyl)-9H-pyrazolo[3,4-c]-1,2,4-triazolo[4,3-a]pyridine; or 9-cyclopentyl-5,6-dihydro-7-ethyl-3-(tert-butyl)-9H-pyrazolo[3,4-c]-1,2,4-triazolo[4,3-a]pyridine; optionally in racemic form, as enantiomers, diastereomers, or as pharmaceutically acceptable salts, solvates or hydrates. Preferred salts are selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate, and hydro-p-toluenesulfonate.

In one embodiment, the additional therapeutic agent is a LTD4-antagonist selected from Montelukast, Pranlukast, Zafirlukast, Masikulast, L-733321 (see compound 2ab of D. Guay et al, Bioorg. Med. Chem. Lett. 8 (1998) 453-458); (E)-8-[2-[4-[4-(4-fluorophenyl)butoxy]phenyl]ethenyl]-2-(1H-tetrazole-5-yl)-4H-1-benzopyran-4-one; 4-[6-acetyl-3-[3-(4-acetyl-3-hydroxy-2-propylphenylthio)propoxy]-2-propyl-phenoxy]-butyric acid; 1-(((R)-3-(2-(6,7-difluoro-2-quinolinyl)ethenyl)phenyl)-3-(2-(2-hydroxy-2-propyl)phenyl)thio)methylcyclopropane-acetic acid; 1-(((1(R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropane acetic acid; or [2-[[2-(4-tert-butyl-2-thiazolyl)-5-benzofuranyl]oxymethyl]phenyl]acetic acid; optionally in racemic form, as enantiomers, diastereomers, or as pharmaceutically acceptable salts, solvates or hydrates. Preferred salts are selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate, and hydro-p-toluenesulfonate. Further examples for optionally preferred salts and derivatives are alkali salts, i.e. sodium or potassium salts, sulfobenzoates, phosphates, isonicotinates, acetates, propionates, dihydrogenphosphates, palmitates, pivalates, or furoates.

In one embodiment, the additional therapeutic agent is an EGFR-inhibitor selected from Cetuximab; Trastuzumab; Panitumumab; Gefitinib; Canertinib; Erlotinib; Mab ICR-62; 4-[(3-chlor-4-fluorophenyl)amino]-6-{[4-(morpholine-4-yl)-1-oxo-2-butene-1-yl]amino}-7-cyclopropylmethoxy-quinazoline; 4-[(3-chlor-4-fluorophenyl)amino]-6-{[4-(N,N-diethylamino)-1-oxo-2-butene-1-yl]amino}-7-cyclopropylmethoxy-quinazoline; 4-[(3-chlor-4-fluorophenyl)amino]-6-{[4-(N,N-dimethylamino)-1-oxo-2-butene-1-yl]amino}-7-cyclopropylmethoxy-quinazoline; 4-[(R)-(1-phenyl-ethyl)amino]-6-{[4-(morpholine-4-yl)-1-oxo-2-butene-1-yl-]amino}-7-cyclopentyloxy-quinazoline; 4-[(3-chlor-4-fluorophenyl)amino]-6-{[4-((R)-6-methyl-2-oxo-morpholine-4-yl)-1-oxo-2-butene-1-yl]amino}-7-cyclopropylmethoxy-quinazoline; 4-[(3-chlor-4-fluorophenyl)amino]-6-{[4-((R)-6-methyl-2-oxo-morpholine-4-yl)-1-oxo-2-butene-1-yl]amino}-7-[(S)-(tetrahydrofuran-3-yl)oxy]-quinazoline; 4-[(3-chlor-4-fluorophenyl)amino]-6-{[4-((R)-2-methoxymethyl-6-oxo-morpholine-4-yl)-1-oxo-2-butene-1-yl]amino}-7-cyclopropylmethoxy-quinazoline; 4-[(3-chlor-4-fluorophenyl)amino]-6-[2-((S)-6-methyl-2-oxo-morpholine-4-yl)-ethoxy]-7-methoxy-quinazoline; 4-[(3-chlor-4-fluorophenyl)amino]-6-({4-[N-(2-methoxy-ethyl)-N-methyl-amino]-1-oxo-2-butene-1-yl}amino)-7-cyclopropylmethoxy-quinazoline; 4-[(3-chlor-4-fluorophenyl)amino]-6-{[4-(N,N-dimethylamino)-1-oxo-2-butene-1-yl]amino}-7-cyclopentyloxy-quinazoline; 4-[(R)-(1-phenyl-ethyl)amino]-6-{[4-(N,N-bis-(2-methoxy-ethyl)-amino)-1-oxo-2-butene-1-yl]amino}-7-cyclopropylmethoxy-quinazoline; 4-[(R)-(1-phenyl-ethyl)amino]-6-({4-[N-(2-methoxy-ethyl)-N-ethyl-amino]-1-oxo-2-butene-1-yl}amino)-7-cyclopropylmethoxy-quinazoline; 4-[(R)-(1-phenyl-ethyl)amino]-6-({4-[N-(2-methoxy-ethyl)-N-methyl-amino]-1-oxo-2-butene-1-yl}amino)-7-cyclopropylmethoxy-quinazoline; 4-[(R)-(1-phenyl-ethyl)amino]-6-({4-[N-(tetrahydropyran-4-yl)-N-methyl-amino]-1-oxo-2-butene-1-yl}amino)-7-cyclopropylmethoxy-quinazoline; 4-[(3-chlor-4-fluorophenyl)amino]-6-{[4-(N,N-dimethylamino)-1-oxo-2-butene-1-yl]amino}-7-((R)-tetrahydrofuran-3-yloxy)-quinazoline; 4-[(3-chlor-4-fluorophenyl)amino]-6-{[4-(N,N-dimethylamino)-1-oxo-2-butene-1-yl]amino}-7-((S)-tetrahydrofuran-3-yloxy)-quinazoline; 4-[(3-chlor-4-fluorophenyl)amino]-6-({4-[N-(2-methoxy-ethyl)-N-methyl-amino]-1-oxo-2-butene-1-yl}amino)-7-cyclopentyloxy-quinazoline; 4-[(3-chlor-4-fluorophenyl)amino]-6-{[4-(N-cyclopropyl-N-methyl-amino)-1-oxo-2-butene-1-yl]amino}-7-cyclopentyloxy-quinazoline; 4-[(3-chlor-4-fluorophenyl)amino]-6-{[4-(N,N-dimethylamino)-1-oxo-2-butene-1-yl]amino}-7-[(R)-(tetrahydrofuran-2-yl)methoxy]-quinazoline; 4-[(3-chlor-4-fluorophenyl)amino]-6-{[4-(N,N-dimethylamino)-1-oxo-2-butene-1-yl]amino}-7-[(S)-(tetrahydrofuran-2-yl)methoxy]-quinazoline; 4-[(3-ethinyl-phenyl)amino]-6,7-bis-(2-methoxy-ethoxy)-quinazoline; 4-[(3-Chlor-4-fluorophenyl)amino]-7-[3-(morpholine-4-yl)-propyloxy]-6-[(vinylcarbonyl)amino]-quinazoline; 4-[(R)-(1-phenyl-ethyl)amino]-6-(4-hydroxy-phenyl)-7H-pyrrolo[2,3-d]pyrimidine; 3-cyano-4-[(3-chlor-4-fluorophenyl)amino]-6-{[4-(N,N-dimethylamino)-1-oxo-2-butene-1-yl]amino}-7-ethoxy-quinoline; 4-{[3-chlor-4-(3-fluor-benzyloxy)-phenyl]amino}-6-(5-{[(2-methansulfonyl-ethyl)amino]methyl}-furan-2-yl)quinazoline; 4-[(R)-(1-phenyl-ethyl)

amino]-6-{[4-((R)-6-methyl-2-oxo-morpholine-4-yl)-1-oxo-2-butene-1-yl]amino}-7-methoxy-quinazoline; 4-[(3-chlor-4-fluorophenyl)amino]-6-{[4-(morpholine-4-yl)-1-oxo-2-butene-1-yl]amino}-7-[(tetrahydrofuran-2-yl)methoxy]-quinazoline; 4-[(3-chlor-4-fluorophenyl)amino]-6-({4-[N,N-bis-(2-methoxy-ethyl)-amino]-1-oxo-2-butene-1-yl}amino)-7-[(tetrahydrofuran-2-yl)methoxy]-quinazoline; 4-[(3-ethinyl-phenyl)amino]-6-{[4-(5,5-dimethyl-2-oxo-morpholine-4-yl)-1-oxo-2-butene-1-yl]amino}-quinazoline; 4-[(3-chlor-4-fluorophenyl)amino]-6-[2-(2,2-dimethyl-6-oxo-morpholine-4-yl)-ethoxy]-7-methoxy-quinazoline; 4-[(3-chlor-4-fluorophenyl)amino]-6-[2-(2,2-dimethyl-6-oxo-morpholine-4-yl)-ethoxy]-7-[(R)-(tetrahydrofuran-2-yl)methoxy]-quinazoline; 4-[(3-chlor-4-fluorophenyl)amino]-7-[2-(2,2-dimethyl-6-oxo-morpholine-4-yl)-ethoxy]-6-[(S)-(tetrahydrofuran-2-yl)methoxy]-quinazoline; 4-[(3-chlor-4-fluorophenyl)amino]-6-{2-[4-(2-oxo-morpholine-4-yl)-piperidin-1-yl]-ethoxy}-7-methoxy-quinazoline; 4-[(3-chlor-4-fluorophenyl)amino]-6-[1-(tert-butyloxycarbonyl)-piperidine-4-yloxy]-7-methoxy-quinazoline; 4-[(3-chlor-4-fluorophenyl)amino]-6-(trans-4-amino-cyclohexane-1-yloxy)-7-methoxy-quinazoline; 4-[(3-chlor-4-fluorophenyl)amino]-6-(trans-4-methansulfonylamino-cyclohexane-1-yloxy)-7-methoxy-quinazoline; 4-[(3-chlor-4-fluorophenyl)amino]-6-(tetrahydropyran-3-yloxy)-7-methoxy-quinazoline; 4-[(3-chlor-4-fluorophenyl)amino]-6-(1-methyl-piperidine-4-yloxy)-7-methoxy-quinazoline; 4-[(3-chlor-4-fluorophenyl)amino]-6-{1-[(morpholine-4-yl)carbonyl]-piperidine-4-yloxy}-7-methoxy-quinazoline; 4-[(3-chlor-4-fluorophenyl)amino]-6-{1-[(methoxymethyl)carbonyl]-piperidine-4-yloxy}-7-methoxy-quinazoline; 4-[(3-chlor-4-fluorophenyl)amino]-6-(piperidine-3-yloxy)-7-methoxy-quinazoline; 4-[(3-chlor-4-fluorophenyl)amino]-6-[1-(2-acetylamino-ethyl)-piperidine-4-yloxy]-7-methoxy-quinazoline; 4-[(3-chlor-4-fluorophenyl)amino]-6-(tetrahydropyran-4-yloxy)-7-ethoxy-quinazoline; 4-[(3-chlor-4-fluorophenyl)amino]-6-((S)-tetrahydrofuran-3-yloxy)-7-hydroxy-quinazoline; 4-[(3-chlor-4-fluorophenyl)amino]-6-(tetrahydropyran-4-yloxy)-7-(2-methoxy-ethoxy)-quinazoline; 4-[(3-chlor-4-fluorophenyl)amino]-6-{trans-4-[(dimethylamino)sulfonylamino]-cyclohexane-1-yloxy}-7-methoxy-quinazoline; 4-[(3-chlor-4-fluorophenyl)amino]-6-{trans-4-[(morpholine-4-yl)carbonylamino]-cyclohexane-1-yloxy}-7-methoxy-quinazoline; 4-[(3-chlor-4-fluorophenyl)amino]-6-{trans-4-[(morpholine-4-yl)sulfonylamino]-cyclohexane-1-yloxy}-7-methoxy-quinazoline; 4-[(3-chlor-4-fluorophenyl)amino]-6-(tetrahydropyran-4-yloxy)-7-(2-acetyl-amino-ethoxy)-quinazoline; 4-[(3-chlor-4-fluorophenyl)amino]-6-(tetrahydropyran-4-yloxy)-7-(2-methane-sulfonylamino-ethoxy)-quinazoline; 4-[(3-chlor-4-fluorophenyl)amino]-6-{1-[(piperidine-1-yl)carbonyl]-piperidine-4-yloxy}-7-methoxy-quinazoline; 4-[(3-chlor-4-fluorophenyl)amino]-6-(1-aminocarbonylmethyl-piperidine-4-yloxy)-7-methoxy-quinazoline; 4-[(3-chlor-4-fluorophenyl)amino]-6-(cis-4-{N-[(tetrahydropyran-4-yl)carbonyl]-N-methyl-amino}-cyclohexane-1-yloxy)-7-methoxy-quinazoline; 4-[(3-chlor-4-fluorophenyl)amino]-6-(cis-4-{N-[(morpholine-4-yl)carbonyl]-N-methyl-amino}-cyclohexane-1-yloxy)-7-methoxy-quinazoline; 4-[(3-chlor-4-fluorophenyl)amino]-6-(cis-4-{N-[(morpholine-4-yl)sulfonyl]-N-methyl-amino}-cyclohexane-1-yloxy)-7-methoxy-quinazoline; 4-[(3-chlor-4-fluorophenyl)amino]-6-(trans-4-ethansulfonylamino-cyclohexane-1-yloxy)-7-methoxy-quinazoline; 4-[(3-chlor-4-fluorophenyl)amino]-6-(1-methansulfonyl-piperidine-4-yloxy)-7-ethoxy-quinazoline; 4-[(3-chlor-4-fluorophenyl)amino]-6-(1-methansulfonyl-piperidine-4-yloxy)-7-(2-methoxy-ethoxy)-quinazoline; 4-[(3-chlor-4-fluorophenyl)amino]-6-[1-(2-methoxy-acetyl)-piperidine-4-yl-oxy]-7-(2-methoxy-ethoxy)-quinazoline; 4-[(3-chlor-4-fluorophenyl)amino]-6-(cis-4-acetylamino-cyclohexane-1-yloxy)-7-methoxy-quinazoline; 4-[(3-ethinyl-phenyl)amino]-6-[1-(tert-butyloxycarbonyl)-piperidine-4-yloxy]-7-methoxy-quinazoline; 4-[(3-ethinyl-phenyl)amino]-6-(tetrahydropyran-4-yloxy]-7-methoxy-quinazoline; 4-[(3-chlor-4-fluorophenyl)amino]-6-(cis-4-{N-[(piperidine-1-yl)carbonyl]-N-methyl-amino)-cyclohexane-1-yloxy)-7-methoxy-quinazoline; 4-[(3-chlor-4-fluorophenyl)amino]-6-(cis-4-{N-[(4-methyl-piperazine-1-yl)-carbonyl]-N-methyl-amino}-cyclohexane-1-yloxy)-7-methoxy-quinazoline; 4-[(3-chlor-4-fluorophenyl)amino]-6-{cis-4-[(morpholine-4-yl)carbonylamino]-cyclohexane-1-yloxy}-7-methoxy-quinazoline; 4-[(3-chlor-4-fluorophenyl)amino]-6-{1-[2-(2-oxopyrrolidine-1-yl)ethyl]-piperidine-4-yloxy}-7-methoxy-quinazoline; 4-[(3-chlor-4-fluorophenyl)amino]-6-{1-[(morpholine-4-yl)carbonyl]-piperidine-4-yloxy}-7-(2-methoxy-ethoxy)-quinazoline; 4-[(3-ethinyl-phenyl)amino]-6-(1-acetyl-piperidine-4-yloxy)-7-methoxy-quinazoline; 4-[(3-ethinyl-phenyl)amino]-6-(1-methyl-piperidine-4-yloxy)-7-methoxy-quinazoline; 4-[(3-ethinyl-phenyl)amino]-6-(1-methansulfonyl-piperidine-4-yloxy)-7-methoxy-quinazoline; 4-[(3-chlor-4-fluorophenyl)amino]-6-(1-methyl-piperidine-4-yloxy)-7-(2-methoxy-ethoxy)-quinazoline; 4-[(3-chlor-4-fluorophenyl)amino]-6-(1-isopropyloxycarbonyl-piperidine-4-yloxy)-7-methoxy-quinazoline; 4-[(3-chlor-4-fluorophenyl)amino]-6-(cis-4-methylamino-cyclohexane-1-yloxy)-7-methoxy-chinazoline; 4-[(3-chlor-4-fluorophenyl)amino]-6-{cis-4-[N-(2-methoxy-acetyl)-N-methyl-amino]-cyclohexane-1-yloxy}-7-methoxy-quinazoline; 4-[(3-ethinyl-phenyl)amino]-6-(piperidine-4-yloxy)-7-methoxy-quinazoline; 4-[(3-ethinyl-phenyl)amino]-6-[1-(2-methoxy-acetyl)-piperidine-4-yloxy]-7-methoxy-quinazoline; 4-[(3-ethinyl-phenyl)amino]-6-{1-[(morpholine-4-yl)carbonyl]-piperidine-4-yloxy}-7-methoxy-quinazoline; 4-[(3-chlor-4-fluorophenyl)amino]-6-{1-[cis-2,6-dimethyl-morpholine-4-yl)-carbonyl]-piperidine-4-yloxy}-7-methoxy-quinazoline; 4-[(3-chlor-4-fluorophenyl)amino]-6-{1-[(2-methyl-morpholine-4-yl)carbony-l]-piperidine-4-yloxy}-7-methoxy-quinazoline; 4-[(3-chlor-4-fluorophenyl)amino]-6-{1-[(S,S)-(2-oxa-5-aza-bicyclo[2.2.1]-hept-5-yl)carbonyl]-piperidine-4-yloxy}-7-methoxy-quinazoline; 4-[(3-chlor-4-fluorophenyl)amino]-6-{1-[(N-methyl-N-2-methoxyethyl-amino)-carbonyl]-piperidine-4-yloxy}-7-methoxy-quinazoline; 4-[(3-chlor-4-fluorophenyl)amino]-6-(1-ethyl-piperidine-4-yloxy)-7-methoxy-quinazoline; 4-[(3-chlor-4-fluorophenyl)amino]-6-{1-[(2-methoxyethyl)carbonyl]-piperidine-4-yloxy}-7-methoxy-quinazoline; 4-[(3-chlor-4-fluorophenyl)amino]-6-{1-[(3-methoxypropyl-amino)-carbonyl]-piperidine-4-yloxy}-7-methoxy-quinazoline; 4-[(3-chlor-4-fluorophenyl)amino]-6-[cis-4-(N-methansulfonyl-N-methyl-amino)-cyclohexane-1-yloxy]-7-methoxy-quinazoline; 4-[(3-chlor-4-fluorophenyl)amino]-6-[cis-4-(N-acetyl-N-methyl-amino)-cyclohexane-1-yloxy]-7-methoxy-quinazoline; 4-[(3-chlor-4-fluorophenyl)amino]-6-(trans-4-methylamino-cyclohexane-1-yloxy)-7-methoxy-quinazoline; 4-[(3-chlor-4-fluorophenyl)amino]-6-[trans-4-(N-methansulfonyl-N-methyl-amino)-cyclohexane-1-yloxy]-7-methoxy-quinazoline; 4-[(3-chlor-4-fluorophenyl)amino]-6-(trans-4-dimethylamino-cyclohexane-1-yloxy)-7-methoxy-quinazoline; 4-[(3-chlor-4-fluorophenyl)amino]-6-(trans-4-{N-[(morpholine-4-yl)carbony-l]-N-methyl-amino}-cyclohexane-1-yloxy)-7-methoxy-quinazoline; 4-[(3-chlor-4-fluorophenyl)amino]-6-[2-(2,2-dimethyl-6- oxo-morpholine-4-yl)-ethoxy]-7-[(S)-(tetrahydrofuran-2-yl) methoxy]-quinazoline; 4-[(3-chlor-4-fluorophenyl)amino]-6-(1-methansulfonyl-piperidine-4-yloxy)-7-methoxy-quinazoline; or 4-[(3-chlor-4-fluorophenyl)amino]-6-(1-cyano-piperidine-4-yloxy)-7-methoxy-quinazoline; optionally in racemic form, as enantiomers, diastereomers, or as pharmaceutically acceptable salts, solvates or hydrates. Preferred salts are selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate, and hydro-p-toluenesulfonate.

In another embodiment, the additional therapeutic agent is a dopamine antagonist selected from Bromocriptine, Cabergoline, Alpha-dihydroergocryptine, Lisuride, Pergolide, Pramipexole, Roxindole, Ropinirole, Talipexole, Terguride, and Viozane, optionally in racemic form, as enantiomers, diastereomers, or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate, and hydro-p-toluenesulfonate.

In another embodiment, the additional therapeutic agent is an antiallergic agent selected from Epinastine, Cetirizine, Azelastine, Fexofenadine, Levocabastine, Loratadine, Mizolastine, Ketotifene, Emedastine, Dimetindene, Clemastine, Bamipine, Cexchlorpheniramine, Pheniramine, Doxylamine, Chlorphenoxamine, Dimenhydrinate, Diphenhydramine, Promethazine, Ebastine, Olopatadine, Desloratidine, and Meclozine, optionally in racemic form, as enantiomers, diastereomers, or as pharmaceutically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate, and hydro-p-toluenesulfonate.

In one embodiment, the additional therapeutic agent is an MAP kinase inhibitor selected from Bentamapimod, Doramapimod, 5-Carbamoylindole, 6-[(aminocarbonyl)(2,6-difluorophenyl)amino]-2-(2,4-difluorophenyl)-3-pyridine carboxamide, alpha-[2-[[2-(3-pyridinyl)ethyl]amino]-4-pyrimidinyl]-2-benzothiazole acetonitrile, 9,12-epoxy-1H-diindolo[1,2,3-fg:3',2',1'-kl]pyrrolo[3,4-i][1,6]benzodiazocine-10-carboxylic acid, or 4-[3-(4-chlorophenyl)-5-(1-methyl-4-piperidinyl)-1H-pyrazole-4-yl]-pyrimidine, optionally in racemic form, as enantiomers, diastereomers, or as pharmaceutically acceptable salts, solvates, or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate, and hydro-p-toluenesulfonate.

In one embodiment, the additional therapeutic agent is an MRP4-inhibitor selected from N-acetyl-dinitrophenyl-cysteine, cGMP, cholate, diclofenac, dehydroepiandrosterone-3-glucuronide, dehydroepiandrosterone-3-sulphate, dilazep, dinitrophenyl-S-glutathione, estradiol-17-beta-glucuronide, estradiol-3,17-disulphate, estradiol-3-glucuronide, estradiol-3-sulphate, estrone-3-sulphate, flurbiprofen, folate, N5-formyl-tetrahydrofolate, glycocholate, glycolithocholic acid sulphate, ibuprofen, indomethacin, indoprofen, ketoprofen, lithocholic acid sulphate, methotrexate, (E)-3-[[[3-[2-(7-chloro-2-quinolinyl)ethenyl]phenyl]-[3-dimethyl-amino)-3-oxopropyl]thio]methyl]thio]-propanoic acid, alpha-naphthyl-beta-D-glucuronide, nitrobenzyl mercaptopurine riboside, probenecid, valspodar, sildenafil, sulfinpyrazone, taurochenodeoxycholate, taurocholate, taurodeoxycholate, taurolithocholate, taurolithocholic acid sulphate, topotecan, trequinsin, zaprinast or dipyridamol, optionally in racemic form, as enantiomers, diastereomers, or as pharmaceutically acceptable salts, solvates, or hydrates. Preferred salts are selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate, and hydro-p-toluenesulfonate.

In one embodiment, the additional therapeutic is an iNOS-inhibitor selected from S-(2-aminoethyl)isothio-urea, aminoguanidine, 2-aminomethylpyridine, 5,6-dihydro-6-methyl-4H-1,3-thiazine-2-amine (AMT), L-canavanin, 2-iminopiperidine, S-isopropylisothiourea, S-methylisothiourea, S-ethylisothiourea, S-methylthiocitrulline, S-ethylthiocitrulline, L-NA ($N^{\omega}$-nitro-L-arginin), L-NAME ($N^{\omega}$-nitro-L-argininmethylester), L-NMMA ($N^{\omega}$-monomethyl-L-arginin), L-NIO ($N^{\omega}$-iminoethyl-L-ornithin), L-NIL ($N^{\omega}$-iminoethyl-lysin), (S)-6-acetimidoylamino-2-amino-hexanoic acid (1H-tetrazole-5-yl)-amide; N-[[3-(aminomethyl)phenyl]methyl]-ethanimidamide; (S)-4-(2-acetimidoylamino-ethylsulfanyl)-2-amino-buturic acid; 2-[2-(4-methoxy-pyridine-2-yl)-ethyl]-3H-imidazo[4,5-b] pyridine; 2-((R)-3-amino-1-phenyl-propoxy)-4-chlor-5-fluorbenzonitrile; 2-((1R,3S)-3-amino-4-hydroxy-1-thiazole-5-yl-butylsulfanyl)-6-trifluoromethyl-nicotinonitrile; 2-((1R,3S)-3-amino-4-hydroxy-1-thiazole-5-yl-butylsulfanyl)-4-chlor-benzonitrile; 2-((1R,3S)-3-amino-4-hydroxy-1-thiazole-5-yl-butylsulfanyl)-5-chlor-benzonitrile; (2S,4R)-2-amino-4-(2-chlor-5-trifluoromethyl-phenyl sulfanyl)-4-thiazole-5-yl-butane-1-ol; 2-((1R,3S)-3-amino-4-hydroxy-1-thiazole-5-yl-butylsulfanyl)-5-chlor-nicotinonitrile; 4-((S)-3-amino-4-hydroxy-1-phenyl-butylsulfanyl)-6-methoxy-nicotinonitrile; or substituted 3-phenyl-3,4-dihydro-1-isoquinolinamine as for instance 1S,5S,6R)-7-chlor-5-methyl-2-aza-bicyclo[4.1.0]hept-2-ene-3-ylamin(4R,5R)-5-ethyl-4-methyl-thiazolidine-2-ylideneamine, (1S,5S,6R)-7-chlor-5-methyl-2-aza-bicyclo [4.1.0]hept-2-ene-3-ylamin, (4R,5R)-5-ethyl-4-methyl-thiazolidine-2-ylideneamine, (4R,5R)-5-ethyl-4-methyl-selenazolidine-2-ylideneamine, 4-aminotetrahydrobiopterine, (E)-3-(4-chlor-phenyl)-N-(1-{2-oxo-2-[4-(6-trifluormethyl-pyrimidine-4-yloxy)-piperidine-1-yl]-ethylcarbamoyl}-2-pyridine-2-yl-ethyl)-acrylamide, 3-(2,4-difluor-phenyl)-6-[2-(4-imidazole-1-ylmethyl-phenoxy)-ethoxy]-2-phenyl-pyridine, 3-{[(benzo[1,3]dioxol-5-ylmethyl)-carbamoyl]-methyl}-4-(2-imidazole-1-yl-pyrimidine-4-yl)-piperazine-1-carbon acid methylester, or (R)-1-(2-imidazole-1-yl-6-methyl-pyrimidine-4-yl)-pyrrolidine-2-carbon acid (2-benzo[1,3]dioxol-5-yl-ethyl)-amide, optionally in racemic form, as enantiomers, diastereomers, or as pharmaceutically acceptable salts, solvates, or hydrates. Preferred salts are selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate, and hydro-p-toluenesulfonate. Further examples of preferred iNOS-inhibitors which may be mentioned include antisense-oligonucleotide, especially those antisense-oligonucleotide binding iNOS-coding nucleic acids, examples therefore are disclosed in WO 01/52902, incorporated herein by reference in its entirety.

In another embodiment, the additional therapeutic agent is a SYK-inhibitor selected from 2-[(2-aminoethyl)amino]-4-[(3-bromophenyl)amino]-5-pyrimidinecarboxamide; 2-[[7-(3,4-dimethoxyphenyl)imidazo[1,2-c]pyrimidine-5-yl]amino]-3-pyridinecarboxamide; 6-[[5-fluoro-2-[3,4,5-trimethoxyphenyl)amino]-4-pyrimidinyl]amino]-2,2-dimethyl-2H-pyrido[3,2-b]-1,4-oxazin-3(4H)-one; N-[3-bromo-7-(4-methoxyphenyl)-1,6-naphthyridine-5-yl]-1,3-propanediamine; 7-(4-methoxyphenyl)-N-methyl-1,6-naphthyridine-5-amine; N-[7-(4-methoxyphenyl)-1,6-naphthyridine-5-yl]-1,3-propanediamine; N-[7-(2-thienyl)-1,6-naphthyridine-5-yl-1,3-propanediamine; N-[7-[4-(dimethylamino)phenyl]-1,6-naphthyridine-5-yl]-1,2-ethanediamine; N-[7-(4-methoxyphenyl)-2-(trifluoromethyl)-1,6-naphthyridine-5-yl]-1,3-propanediamine; N-[7-(4-methoxyphenyl)-3-phenyl-1,6-naphthyridine-5-yl]-1,3-propanediamine; N-(7-phenyl-1,6-naphthyridine-5-yl)-1,3-propanediamine; N-[7-(3-fluorophenyl)-1,6-naphthyridine-5-yl]-1,3-propanediamine; N-[7-(3-chlorophenyl)-1,6-naphthyridine-5-yl]-1,3-propanediamine; N-[7-(4-(trifluoromethoxy)phenyl]-1,6-naphthyridine-N-[7-(4-fluorophenyl)-1,6-naphthyridine-5-yl]-1,3-propanediamine; N-[7-(4-fluorophenyl)-1,6-naphthyridine-5-yl]-1,3-propanediamine; N-[7-(4-chlorophenyl)-1,6-naphthyridine-5-yl]-1,3-propanediamine; N-[7-(4'-methyl[1,1'-biphenyl]-4-yl)-1,6-naphthyridine-1,3-propanediamine; N-[7-[4-(dimethylamino)phenyl]-1,6-naphthyridine-5-yl]-1,3-propanediamine; N-[7-[4-(diethylamino)phenyl]-1,6-naphthyridine-5-yl]-1,3-propanediamine; N-[7-[4-(4-morpholinyl)phenyl]-1,6-naphthyridine-5-yl]-1,3-propanediamine; N-[7-[4-[[2-(dimethylamino)ethyl]methylamino]phenyl]-1,6-naphthyridine-5-yl]-1,3-propanediamine; N-[7-(4-bromophenyl)-1,6-naphthyridine-5-yl]-1,3-propanediamine; N-[7-(4-methylphenyl)-1,6-naphthyridine-5-yl]-1,3-propanediamine; N-[7-[4-(methylthio)phenyl]-1,6-naphthyridine-5-yl]-1,3-propanediamine; N-[7-[4-(1-methylethyl)phenyl]-1,6-naphthyridine-5-yl]-1,3-propanediamine; 7-[4-(dimethylamino)phenyl]-N-methyl-1,6-naphthyridine-5-amine; 7-[4-(dimethylamino)phenyl]-N,N-dimethyl-1,6-naphthyridine-5-amine; N-[7-[4-(dimethylamino)phenyl]-1,6-naphthyridine-5-yl]-1,4-butanediamine; N-[7-[4-(dimethylamino)phenyl]-1,6-naphthyridine-5-yl]-1,5-pentanediamine; 3-[[7-[4-(dimethylamino)phenyl]-1,6-naphthyridine-5-yl]oxy]-1-propanole; 4-[5-(4-aminobutoxy)-1,6-naphthyridine-7-yl]-N,N-dimethyl-benzenamine; 4-[[7-[4-(dimethylamino)phenyl]-1,6-naphthyridine-5-yl]amino]-1-butanole; N-[7-[4-(dimethylamino)phenyl]-1,6-naphthyridine-5-yl]-N-methyl-1,3-propanediamine; N-[7-[4-(dimethylamino)phenyl]-1,6-naphthyridine-5-yl]-N'-methyl-1,3-propanediamine; N-[7-[4-(dimethylamino)phenyl]-1,6-naphthyridine-5-yl]-N,N'-dimethyl-1,3-propanediamine; 1-amino-3-[[7-[4-(dimethylamino)phenyl]-1,6-naphthyridine-5-yl]amino]-2-propanole; N-[7-[4-(dimethylamino)phenyl]-1,6-naphthyridine-5-yl]-2,2-dimethyl-1,3-propanediamine; 7-[4-(dimethylamino)phenyl]-N-(3-pyridinylmethyl)-1,6-naphthyridine-5-amine; N-[(2-aminophenyl)methyl]-7-[4-(dimethylamino)phenyl]-1,6-naphthyridine-5-amine; N-[7-[6-(dimethylamino)[1,1'-biphenyl]-3-yl)-1,6-naphthyridine-5-yl]-1,3-propanediamine; N-[7-[3-chloro-4-(diethylamino)phenyl]-1,6-naphthyridine-5-yl]-1,3-propanediamine; N-[7-[4-(dimethylamino)-3-methoxyphenyl]-1,6-naphthyridine-5-yl]-1,3-propanediamine; N-[7-[4-(diethylamino)phenyl]-3-methyl-1,6-naphthyridine-5-yl]-1,3-propanediamine; N-[7-(3'-fluoro[1,1'-biphenyl]-3-yl)-1,6-naphthyridine-5-yl]-1,2-ethanediamine; N-[7-(4-methoxyphenyl)-1,6-naphthyridine-5-yl]-1,6-naphthyridine-1,3-propanediamine; N,N'-bis(3-aminopropyl)-7-(4-methoxyphenyl)-2,5-diamine; N-[7-(4-methoxyphenyl)-2-(phenylmethoxy)-1,6-naphthyridine-5-yl]-1,6-naphthyridine-1,3-propanediamine; N5-(3-aminopropyl)-7-(4-methoxyphenyl)-N2-(phenylmethyl)-2,5-diamine; N-[7-(2-naphthalenyl)-1,6-naphthyridine-5-yl]-1,3-propanediamine; N-[7-(2'-fluoro[1,1'-biphenyl]-4-yl)-1,6-naphthyridine-5-yl]-1,3-propanediamine; N-[7-(3,4,5-trimethoxyphenyl)-1,6-naphthyridine-5-yl]-1,3-propanediamine; N-[7-(3,4-dimethylphenyl)-1,6-naphthyridine-5-yl]-1,3-propanediamine; 1-amino-3-[[7-(2-naphthalenyl)-1,6-naphthyridine-5-yl]amino]-2-propanole; 1-amino-3-[[7-(2'-fluoro[1,1'-biphenyl]-4-yl)-1,6-naphthyridine-5-yl]amino]-2-propanole; 1-amino-3-[[7-(4'-methoxy[1,1'-biphenyl]-4-yl)-1,6-naphthyridine-5-yl]amino]-2-propanole; 1-amino-3-[[7-(3,4,5-trimethoxyphenyl)-1,6-naphthyridine-5-yl]amino]-2-propanole; 1-amino-3-[[7-(4-bromophenyl)-1,6-naphthyridine-5-yl]amino]-2-propanole; N-[7-(4'-methoxy[1,1'-biphenyl]-4-yl)-1,6-naphthyridine-5-yl]-2,2-dimethyl-1,3-propanediamine; 1-[[7-[4-(dimethylamino)phenyl]-1,6-naphthyridine-5-yl]amino]-2-propanole; 2-[[2-[[7-[4-(dimethylamino)phenyl]-1,6-naphthyridine-5-yl]amino]-ethyl]thio]-ethanole; 7-[4-(dimethylamino)phenyl]-N-(3-methyl-5-isoxazolyl)-1,6-naphthyridine-5-amine; 7-[4-(dimethylamino)phenyl]-N-4-pyrimidinyl-1,6-naphthyridine-5-amine; N-[7-[4-(dimethylamino)phenyl]-1,6-naphthyridine-5-yl]-1,3-cyclohexane diamine; N,N-dimethyl-4-[5-(1-piperazinyl)-1,6-naphthyridine-7-yl]-benzenamine; 4-[5-(2-methoxyethoxy)-1,6-naphthyridine-7-yl]-N,N-dimethyl-benzeneamine; 1-[7-[4-(dimethylamino)phenyl]-1,6-naphthyridine-5-yl]-4-piperidinole; 1-[7-[4-(dimethylamino)phenyl]-1,6-naphthyridine-5-yl]-3-pyrrolidinole; 7-[4-(dimethylamino)phenyl]-N-(2-furanylmethyl)-1,6-naphthyridine-5-amine; 7-[4-(dimethylamino)phenyl]-N-[3-(1H-imidazole-1-yl)propyl]-1,6-naphthyridine-5-amine; 1-[7-[4-(dimethylamino)phenyl]-1,6-naphthyridine-5-yl]-4-piperidine carboxamide; 1-[3-[[7-[4-(dimethylamino)phenyl]-1,6-naphthyridine-5-yl]amino]propyl]-2-pyrrolidinone; N-[3'-[5-[(3-aminopropyl)amino]-1,6-naphthyridine-7-yl][1,1'-biphenyl]-3-yl]-acetamide; N-[7-(4'-fluoro[1,1'-biphenyl]-4-yl)-1,6-naphthyridine-5-yl]-1,3-propanediamine; N-[4'-[5-[(3-aminopropyl)amino]-1,6-naphthyridine-7-yl][1,1'-biphenyl]-3-yl]-acetamide; N-[7-[4-(1,3-benzodioxol-5-yl)phenyl]-1,6-naphthyridine-5-yl]-1,3-propanediamine; N-[7-[4-(2-thienyl)phenyl]-1,6-naphthyridine-5-yl]-1,3-propanediamine; N-[7-[4-fluoro-3-(trifluoromethyl)phenyl]-1,6-naphthyridine-5-yl]-1,3-propanediamine; N-[7-[4-(3-pyridinyl)phenyl]-1,6-naphthyridine-5-yl]-1,3-propanediamine; N-[7-(1,3-benzodioxol-5-yl)-1,6-naphthyridine-5-yl]-1,3-propanediamine; N-[7-(6-methoxy-2-naphthalenyl)-1,6-naphthyridine-5-yl]-1,3-propanediamine; 7-[4-(dimethylamino)phenyl]-N-(4-pyridinylmethyl)-1,6-naphthyridine-5-amine; 3-[[7-[4-(dimethylamino)phenyl]-1,6-naphthyridine-5-yl]methylamino]-propanenitrile; 7-[4-(dimethylamino)phenyl]-N-[1-(phenylmethyl)-4-piperidinyl]-1,6-naphthyridine-5-amine; N-[7-[4-(dimethylamino)phenyl]-1,6-naphthyridine-5-yl]-1,2-cyclohexanediamine; N-[7-[4-(dimethylamino)phenyl]-1,6-naphthyridine-5-yl]-1,2-cyclohexanediamine, (1R,2S)-rel-; N-[7-[4-(dimethylamino)phenyl]-1,6-naphthyridine-5-yl]-1,2-benzene dimethanamine; N-[7-[4-(diethylamino)phenyl]-1, 6-naphthyridine-5-yl]-1,4-butanediamine; N-[7-[3',5'-bis(trifluoromethyl)[1,1'-biphenyl]-4-yl]-1,6-naphthyr-idine-5-yl]-,3-propanediamine; N-[7-(3'-methoxy[1,1'-biphenyl]-4-yl)-1,6-naphthyridine-5-yl]-1,3-propane-diamine; N-[7-(3'-fluoro[1,1'-biphenyl]-4-yl)-1,6-naphthyridine-5-yl]-1,3-propanediamine; 4-[[7-[4-(dimethylamino)phenyl]-1,6-naphthyridine-5-yl]oxy]-1-butanole; N-[7-[4-(dimethylamino)phenyl]-1,6-naphthyridine-5-yl]-1,4-cyclohexanediamine; 7-[4-(dimethylamino)phenyl]-N-(2,2,6,6-tetramethyl-4-piperidinyl)-1,6-nap-hthyridine-5-amine; N-[7-[3-bromo-4-(dimethylamino)phenyl]-1,6-naphthyridine-5-yl]-1,3-propan-ediamine; N-[7-(1-methyl-1H-indole-5-yl)-1,6-naphthyridine-5-yl]-1,3-propanediamine; N-[7-[3-(trifluoromethyl)phenyl]-1,6-naphthyridine-5-yl]-1,3-propanediamine; N-[7-[4-(trifluoromethyl)phenyl]-1,6-naphthyridine-5-yl]-1,3-propanediamine; N-[7-(3-bromo-4-methoxyphenyl)-1,6-naphthyridine-5-yl]-1,3-propanediamine; N-[7-[4-[[3-(dimethylamino)propyl]methylamino]phenyl]-1,6-naphthyridine-5-yl]-1,4-cyclohexanediamine; N-[7-[4-[[2-(dimethylamino)ethyl]methylamino]phenyl]-1,6-naphthyridine-5-yl]-1,4-cyclohexanediamine; N-[7-[4-(dimethylamino)-3-methoxyphenyl]-1,6-naphthyridine-5-yl]-1,4-cyclohexanediamine; N-[7-[4-(4-morpholinyl)phenyl]-1,6-naphthyridine-5-yl]-1,4-cyclohexanediamine; N-[7-[3-bromo-4-(4-morpholinyl)phenyl]-1,6-naphthyridine-5-yl]-1,4-cyclohexane-diamine; 4-[[7-[4-[[2-(dimethylamino)ethyl]methylamino]phenyl]-1,6-naphthyridine-5-yl]oxy]-cyclohexanole; N-[7-[3-bromo-4-(4-morpholinyl)phenyl]-1,6-naphthyridine-5-yl]-1,3-propane-diamine; N,N-dimethyl-4-[5-(4-methyl-1-piperazinyl)-1,6-naphthyridine-7-yl]-benzenamine; 4-[[7-[4-[[3-(dimethylamino)propyl]methylamino]phenyl]-1,6-naphthyridine-5-yl]oxy]-cyclohexanole; N-[7-[4-[[2-(dimethylamino)ethyl]methylamino]phenyl]-1,6-naphthyridine-5-yl]-1,4-butanediamine; or [3-[[5-[(3-aminopropyl)amino]-7-(4-methoxyphenyl)-1,6-naphthyridine-2-yl]-amino]propyl]-carbamic acid-1,1-dimethylethyl ester, optionally in racemic form, as enantiomers, diastereomers, or as pharmaceutically acceptable salts, solvates or hydrates. Preferred salts are selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate, and hydro-p-toluenesulfonate.

These pharmaceutical compositions are administered as oral formulations containing about 25 mg, 50 mg, 100 mg, 125 mg, 150 mg, 200 mg, 250 mg, 300 mg, or 400 mg of a compound of Compound 1, Compound 2, or both. In this aspect, the pharmaceutical compositions further comprise a filler; a disintegrant; or a lubricant, or combinations thereof.

It will also be appreciated that the pharmaceutical compositions of the invention can be employed in combination therapies; that is, the compositions can be administered concurrently with, prior to, or subsequent to, one or more other desired therapeutic agents or medical procedures.

One aspect of the present invention provides a pharmaceutical composition comprising a tablet, wherein the tablet comprises a spray dried dispersion of Compound 1 and Compound 2 and one or more excipients selected from a filler; a disintegrant; a surfactant; a binder; a wetting agent, and a lubricant.

In some embodiments, the tablet comprises from about 25 mg to about 75 mg of Compound 1.

In some embodiments, the tablet comprises from about 100 mg to about 200 mg of Compound 2.

And, in some embodiments, the tablet comprises one or more excipients selected from a bulking agent, a disintegrant, a lubricant, a binder, or any combination thereof. For example, the tablet comprises from about 100 mg to about 300 mg of a bulking agent. In some instances, the bulking agent comprises microcrystalline cellulose. In other examples, the tablet comprises from about 12 mg to about 36 mg of a disintegrant. In some instances, the disintegrant comprises croscarmellose sodium. In some examples, the tablet comprises from about 1 mg to about 5 mg of a lubricant. In some instances, the lubricant comprises magnesium stearate. And, in some examples, the tablet comprises from about 25 mg to about 75 mg of a binder. In some instances, the binder comprises hydroxypropyl methylcellulose.

One aspect of the present invention provides a pharmaceutical composition comprising a first agent and a second agent, wherein the first agent comprises an amorphous form of Compound 1, and the second agent comprises an amorphous form of Compound 2.

In some embodiments, the first agent further comprises a first spray dried dispersion comprising Compound 1 and binder. For example, the first spray dried dispersion comprises from about 70 wt % to about 90 wt % of Compound 1 and from about 10 wt % to about 30 wt % of the binder. In some examples, the binder comprises hydroxypropyl methylcellulose.

In some embodiments, the second agent further comprises a second spray dried dispersion comprising Compound 2 and a binder. For example, the second spray dried dispersion comprises from about 70 wt % to about 90 wt % of Compound 2 and from about 10 wt % to about 30 wt % of the binder.

In some embodiments, the pharmaceutical composition further comprises from about 5 wt % to about 20 wt % of the first agent.

In some embodiments, the pharmaceutical composition further comprises from about wt % to about 60 wt % of the second agent.

In some embodiments, the pharmaceutical composition further comprises one or more excipients selected from a bulking agent, a disintegrant, a lubricant, a binder, or any combination thereof. For example, the pharmaceutical composition further comprises from about 30 wt % to about 50 wt % of a bulking agent. In some instances, the bulking agent comprises microcrystalline cellulose.

In some embodiments, the pharmaceutical composition further comprises from about 1 wt % to about 10 wt % of a disintegrant. In some examples, the disintegrant comprises croscarmellose sodium.

In some embodiments, the pharmaceutical composition further comprises less than about 1 wt % of a lubricant. In some examples, the lubricant comprises magnesium stearate.

In some embodiments, the pharmaceutical composition comprises a tablet.

In some embodiments, the tablet comprises from about 30 mg to about 85 mg of the first agent.

In some embodiments, the tablet comprises from about 150 mg to about 250 mg of the second agent.

In some embodiments, the tablet comprises one or more excipients selected from a bulking agent, a disintegrant, a lubricant, a binder, or any combination thereof. For example, the tablet comprises from about 100 mg to about 300 mg of a bulking agent. In some instances, the bulking agent comprises microcrystalline cellulose. In other examples, the tablet comprises from about 12 mg to about 36 mg of a disintegrant. In some instances, the disintegrant comprises croscarmellose sodium. In some examples, the tablet comprises from about 1 mg to about 5 mg of a lubricant. For instance, the lubricant comprises magnesium stearate.

In some embodiments, the pharmaceutical composition further comprises an additional therapeutic agent (e.g., any of the additional APIs described herein). In some examples, the additional therapeutic agent is another CFTR corrector (e.g., any of the CFTR correctors described herein) different from Compound 1. In other examples, the additional therapeutic agent is another CFTR potentiator (e.g., any of the CFTR potentiators described herein) different from the Compound 2.

The tablets of the present invention can be produced by compacting or compressing an admixture or composition, for example, powder or granules, under pressure to form a stable three-dimensional shape (e.g., a tablet). As used herein, "tablet" includes compressed pharmaceutical dosage unit forms of all shapes and sizes, whether coated or uncoated.

Granulation and Compression

In some embodiments, solid forms, including powders comprising the active agents amorphous Compound 1 and amorphous Compound 2 and the included pharmaceutically acceptable excipients (e.g. filler, diluent, disintegrant, surfactant, glidant, binder, lubricant, or any combination thereof) can be subjected to a dry granulation process. The dry granulation process causes the powder to agglomerate into larger particles having a size suitable for further processing. Dry granulation can improve the flowability of a mixture to produce tablets that comply with the demand of mass variation or content uniformity.

Formulations as described herein may be produced using one or more mixing and dry granulations steps. The order and the number of the mixing and granulation steps do not seem to be critical. However, at least one of the excipients and amorphous Compound land amorphous Compound 2 can be subject to dry granulation or wet high shear granulation before compression into tablets. Dry granulation of amorphous Compound 1 and amorphous Compound 2 and the excipients made together prior to tablet compression seem, surprisingly, to be a simple, inexpensive and efficient way of providing close physical contact between the ingredients of the present compositions and formulations and thus results in a tablet formulation with good stability properties. Dry granulation can be carried out by a mechanical process, which transfers energy to the mixture without any use of any liquid substances (neither in the form of aqueous solutions, solutions based on organic solutes, or mixtures thereof) in contrast to wet granulation processes, also contemplated herein. Generally, the mechanical process requires compaction such as the one provided by roller compaction. An example of an alternative method for dry granulation is slugging.

In some embodiments, roller compaction is a granulation process comprising highly intensive mechanical compacting of one or more substances. In some embodiments, a pharmaceutical composition comprising an admixture of powders is pressed, that is roller compacted, between two counter rotating rollers to make a solid sheet that is subsequently crushed in a sieve to form a particulate matter. In this particulate matter, a close mechanical contact between the ingredients can be obtained. An example of roller compaction equipment is Minipactor® a Gerteis 3W-Polygran from Gerteis Maschinen+Processengineering AG.

In some embodiments, tablet compression according to the invention can occur without any use of any liquid substances (neither in the form of aqueous solutions, solutions based on organic solutes, or mixtures thereof), i.e., a dry granulation process. In a typical embodiment the resulting core or tablet has a compressive strength in the range of from about 1 kp to about 15 kP; such as 1.5 to 12.5 kP, preferably in the range of 2 to 10 kP.

Brief Manufacturing Procedure

In some embodiments, the ingredients are weighed according to the formula set herein. Next, all of the intragranular ingredients are sifted and mixed well. The ingredients can be lubricated with a suitable lubricant, for example, magnesium stearate. The next step can comprise compaction/slugging of the powder admixture and sized ingredients. Next, the compacted or slugged blends are milled into granules and sifted to obtain the desired size. Next, the granules can be further lubricated with, for example, magnesium stearate. Next, the granular composition of the invention can be compressed on suitable punches into various pharmaceutical formulations in accordance with the invention. Optionally the tablets can be coated with a film, colorant or other coating.

Another aspect of the invention provides a method for producing a pharmaceutical composition comprising an admixture of a composition comprising amorphous Compound 1 and amorphous Compound 2 and one or more excipients selected from: a filler, a diluent, a binder, a glidant, a surfactant, a lubricant, a disintegrant, and compressing the composition into a tablet having a dissolution of at least about 50% in about 30 minutes.

In another embodiment, a wet granulation process is performed to yield the pharmaceutical formulation of the invention from an admixture of powdered and liquid ingredients. For example, a pharmaceutical composition comprising an admixture of a composition comprising amorphous Compound 1 and amorphous Compound 2 and one or more excipients selected from: a filler, a diluent, a binder, a glidant, a surfactant, a lubricant, a disintegrant, are weighed as per the formula set herein. Next, all of the intragranular ingredients are sifted and mixed in a high shear or low shear granulator using water or water with a surfactant or water with a binder or water with a surfactant and a binder to granulate the powder blend. A fluid other than water can also be used with or without surfactant and/or binder to granulate the powder blend. Next, the wet granules can optionally be milled using a suitable mill. Next, water may optionally be removed from the admixture by drying the ingredients in any suitable manner. Next, the dried granules can optionally be milled to the required size. Next, extra granular excipients can be added by blending (for example a filler, a diluent, and a disintegrant). Next, the sized granules can be further lubricated with magnesium stearate and a disintegrant, for example, croscarmellose sodium. Next, the granular composition of the invention can be sifted for sufficient time to obtain the correct size and then compressed on suitable punches into various pharmaceutical formulations in accordance with the invention. Optionally, the tablets can be coated with a film, colorant or other coating.

Each of the ingredients of this exemplary admixture is described above and in the Examples below. Furthermore, the admixture can comprise optional additives, such as, one or more colorants, one or more flavors, and/or one or more fragrances as described above and in the Examples below. In some embodiments, the relative concentrations (e.g., wt %) of each of these ingredients (and any optional additives) in the admixture are also presented above and in the Examples below. The ingredients constituting the admixture can be provided sequentially or in any combination of additions;

and, the ingredients or combination of ingredients can be provided in any order. In one embodiment, the lubricant is the last component added to the admixture.

In another embodiment, the admixture comprises a composition of amorphous Compound 1 and amorphous Compound 2, and any one or more of the excipients; a binder, a glidant, a surfactant, a diluent, a lubricant, a disintegrant, and a filler, wherein each of these ingredients is provided in a powder form (e.g., provided as particles having a mean or average diameter, measured by light scattering, of 250 µm or less (e.g., 150 µm or less, 100 µm or less, 50 µm or less, 45 µm or less, 40 µm or less, or 35 µm or less)). For instance, the admixture comprises a composition of amorphous Compound 1 and amorphous Compound 2, a diluent, a glidant, a surfactant, a lubricant, a disintegrant, and a filler, wherein each of these ingredients is provided in a powder form (e.g., provided as particles having a mean diameter, measured by light scattering, of 250 µm or less (e.g., 150 µm or less, 100 µm or less, 50 µm or less, 45 µm or less, 40 µm or less, or 35 µm or less)). In another example, the admixture comprises a composition of amorphous Compound 1, amorphous Compound 2, a diluent, a binder, a surfactant, a lubricant, a disintegrant, and a filler, wherein each of these ingredients is provided in a powder form (e.g., provided as particles having a mean diameter, measured by light scattering, of 250 µm or less (e.g., 150 µm or less, 100 µm or less, 50 µm or less, 45 µm or less, 40 µm or less, or 35 µm or less)).

In another embodiment, the admixture comprises a composition of amorphous Compound 1, amorphous Compound 2 and any combination of: a binder, a glidant, a diluent, a surfactant, a lubricant, a disintegrant, and a filler, wherein each of these ingredients is substantially free of water. Each of the ingredients comprises less than 5 wt % (e.g., less than 2 wt %, less than 1 wt %, less than 0.75 wt %, less than 0.5 wt %, or less than 0.25 wt %) of water by weight of the ingredient. For instance, the admixture comprises a composition of amorphous Compound 1, amorphous Compound 2, a diluent, a glidant, a surfactant, a lubricant, a disintegrant, and a filler, wherein each of these ingredients is substantially free of water. In some embodiments, each of the ingredients comprises less than 5 wt % (e.g., less than 2 wt %, less than 1 wt %, less than 0.75 wt %, less than 0.5 wt %, or less than 0.25 wt %) of water by weight of the ingredient.

In another embodiment, compressing the admixture into a tablet is accomplished by filling a form (e.g., a mold) with the admixture and applying pressure to admixture. This can be accomplished using a die press or other similar apparatus. In some embodiments, the admixture of amorphous Compound 1, amorphous Compound 2, and excipients can be first processed into granular form. The granules can then be sized and compressed into tablets or formulated for encapsulation according to known methods in the pharmaceutical art. It is also noted that the application of pressure to the admixture in the form can be repeated using the same pressure during each compression or using different pressures during the compressions. In another example, the admixture of powdered ingredients or granules can be compressed using a die press that applies sufficient pressure to form a tablet having a dissolution of about 50% or more at about 30 minutes (e.g., about 55% or more at about 30 minutes or about 60% or more at about 30 minutes). For instance, the admixture is compressed using a die press to produce a tablet hardness of at least about 5 kP (at least about 5.5 kP, at least about 6 kP, at least about 7 kP, at least about 10 kP, or at least 15 kP). In some instances, the admixture is compressed to produce a tablet hardness of between about 5 and 20 kP.

In some embodiments, tablets comprising a pharmaceutical composition as described herein can be coated with about 3.0 wt % of a film coating comprising a colorant by weight of the tablet. In certain instances, the colorant suspension or solution used to coat the tablets comprises about 20% w/w of solids by weight of the colorant suspension or solution. In still further instances, the coated tablets can be labeled with a logo, other image or text.

In another embodiment, the method for producing a pharmaceutical composition comprises providing an admixture of a solid forms, e.g. an admixture of powdered and/or liquid ingredients, the admixture comprising amorphous Compound 1, amorphous Compound 2, and one or more excipients selected from: a binder, a glidant, a diluent, a surfactant, a lubricant, a disintegrant, and a filler; mixing the admixture until the admixture is substantially homogenous, and compressing or compacting the admixture into a granular form. Then the granular composition comprising amorphous Compound 1 and amorphous Compound 2 can be compressed into tablets as described above or in the Examples below. Alternatively, methods for producing a pharmaceutical composition comprise providing an admixture of amorphous Compound 1, amorphous Compound 2, and one or more excipients, e.g. a binder, a glidant, a diluent, a surfactant, a lubricant, a disintegrant, and a filler; mixing the admixture until the admixture is substantially homogenous, and compressing/compacting the admixture into a granular form using a roller compactor using a dry granulation composition as set forth in the Examples below or alternatively, compressed/compacted into granules using a high shear wet granule compaction process as set forth in the Examples below. Pharmaceutical formulations, for example a tablet as described herein, can be made using the granules prepared incorporating amorphous Compound 1 and amorphous Compound 2 in addition to the selected excipients described herein.

In some embodiments, the admixture is mixed by stirring, blending, shaking, or the like using hand mixing, a mixer, a blender, any combination thereof, or the like. When ingredients or combinations of ingredients are added sequentially, mixing can occur between successive additions, continuously throughout the ingredient addition, after the addition of all of the ingredients or combinations of ingredients, or any combination thereof. The admixture is mixed until it has a substantially homogenous composition.

In another embodiment, the present invention comprises jet milling amorphous Compound 1 and amorphous Compound 2 in a suitable, conventional milling apparatus using air pressure suitable to produce particles having a significant particle size fraction between 0.1 microns and 50 microns. In another embodiment, the particle size is between 0.1 microns and 20 microns. In another embodiment, the particles size is between 0.1 microns and 10 microns. In another embodiment, the particle size is between 1.0 microns and 5 microns. In still another embodiment, amorphous Compound 1 and amorphous Compound 2 have a particle size D50 of about 5 to about 100 microns. In still another embodiment, amorphous Compound 1 and amorphous Compound 2 have a particle size D50 of about 5 to about 30 microns. In still another embodiment amorphous Compound 1 and amorphous Compound 2 have a particle size D50 of 15 microns.

In various embodiments, an additional therapeutic agent(s) can be formulated together with amorphous Compound 1 and amorphous Compound 2 to form a unitary or single dose form, for example, a tablet.

Tablets prepared as above can be subjected to in vitro dissolution evaluations according to Test 711 "Dissolution" in United States Pharmacopoeia 29, United States Pharmacopeial Convention, Inc., Rockville, Md., 2005 ("USP"), to determine the rate at which the active substance is released from the dosage forms. The content of active substance and the impurity levels are conveniently measured by techniques such as high performance liquid chromatography (HPLC).

In some embodiments, the invention includes use of packaging materials such as containers and closures of high-density polyethylene (HDPE), low-density polyethylene (LDPE) and or polypropylene and/or glass, glassine foil, aluminum pouches, and blisters or strips composed of aluminum or high-density polyvinyl chloride (PVC), optionally including a desiccant, polyethylene (PE), polyvinylidene dichloride (PVDC), PVC/PE/PVDC, and the like. These package materials can be used to store the various pharmaceutical compositions and formulations in a sterile fashion after appropriate sterilization of the package and its contents using chemical or physical sterilization techniques commonly employed in the pharmaceutical arts.

V. Methods of Treating Cystic Fibrosis

The spray dried dispersions and pharmaceutical compositions described above are useful for treating cystic fibrosis. Accordingly, one aspect of the present invention provides a method of treating cystic fibrosis in a patient comprising administering to the patient any of the spray dried dispersions or the pharmaceutical compositions described above.

In some implementations, the patient is orally administered the spray dried dispersion or pharmaceutical composition.

And, some implementations further comprise administering to the patient an additional therapeutic agent that is absent from the spray dried dispersion or the pharmaceutical composition described above.

In some implementations, the additional therapeutic agent is administered before, after, or concurrently with the spray dried dispersion or the pharmaceutical composition described above.

A. Mutations

In one aspect, the invention provides a method of treating a CFTR-mediated disease in a patient comprising administering to the patient any of the spray dried dispersions or the pharmaceutical compositions described above wherein the patient possesses a human CFTR mutation selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C, and 621+3A→G.

In one aspect, the invention provides a method of treating a CFTR-mediated disease in a patient comprising administering to the patient any of the spray dried dispersions or the pharmaceutical compositions described above wherein the patient possesses a human CFTR mutation selected from G178R, G551S, G970R, G1244E, S1255P, G1349D, S549N, S549R, S1251N, E193K, F1052V, and G1069R. In one implementation of this aspect, the invention provides a method of treating a CFTR-mediated disease wherein the patient possesses a human CFTR mutation selected from G178R, G551S, G970R, G1244E, S1255P, G1349D, S549N, S549R, and S1251N. In another implementation of this aspect, the invention provides a method of treating a CFTR-mediated disease wherein the patient possesses a human CFTR mutation selected from E193K, F1052V, and G1069R. In some implementations of this aspect, the method produces a greater than 10-fold increase in chloride transport relative to baseline chloride transport.

In one aspect, the invention provides a method of treating a CFTR-mediated disease in a patient comprising administering to the patient any of the spray dried dispersions or the pharmaceutical compositions described above wherein the patient possesses a human CFTR mutation selected from R117C, D110H, R347H, R352Q, E56K, P67L, L206W, A455E, D579G, S1235R, S945L, R1070W, F1074L, D110E, D1270N, and D1152H. In one implementation of this aspect, the method produces an increase in chloride transport which is greater or equal to 10% above the baseline chloride transport.

In one aspect, the invention provides a method of treating a CFTR-mediated disease in a patient comprising administering to the patient any of the spray dried dispersions or the pharmaceutical compositions described above wherein the patient possesses a human CFTR mutation selected from 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C, and 621+3A→G. In one implementation of this aspect, the patient possesses a human CFTR mutation selected from 1717-1G→A, 1811+1.6kbA→G, 2789+5G→A, 3272-26A→G, and 3849+10kbC→T. In still another implementation of this aspect, the patient possesses a human CFTR mutation selected from 2789+5G→A and 3272-26A→G.

In one aspect, the invention provides a method of treating a CFTR-mediated disease in a patient comprising administering to the patient any of the spray dried dispersions or the pharmaceutical compositions described above wherein the patient possesses a human CFTR mutation selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C, and 621+3A→G, and a human CFTR mutation selected from ΔF508, R117H, and G551D.

In one aspect, the invention provides a method of treating a CFTR-mediated disease in a patient comprising administering to the patient any of the spray dried dispersions or the pharmaceutical compositions described above wherein the patient possesses a human CFTR mutation selected from G178R, G551S, G970R, G1244E, S1255P, G1349D, S549N, S549R, S1251N, E193K, F1052V, and G1069R, and a human CFTR mutation selected from ΔF508, R117H, and G551D. In one implementation of this aspect, the invention provides a method of treating a CFTR-mediated disease wherein the patient possesses a human CFTR mutation selected from G178R, G551S, G970R, G1244E, S1255P, G1349D, S549N, S549R, and S1251N, and a human CFTR mutation selected from ΔF508, R117H, and G551D. In another implementation of this aspect, the invention provides a method of treating a CFTR mediated disease wherein the patient possesses a human CFTR mutation selected from E193K, F1052V and G1069R, and a human CFTR mutation selected from ΔF508, R117H, and G551D. In some implementations of this aspect, the method produces a greater than 10-fold increase in chloride transport relative to baseline chloride transport.

In one aspect, the invention provides a method of treating a CFTR-mediated disease in a patient comprising administering to the patient any of the spray dried dispersions or the pharmaceutical compositions described above wherein the patient possesses a human CFTR mutation selected from R117C, D110H, R347H, R352Q, E56K, P67L, L206W, A455E, D579G, S1235R, S945L, R1070W, F1074L, D110E, D1270N, and D1152H, and a human CFTR mutation selected from ΔF508, R117H, and G551D. In one implementation of this aspect, the method produces an increase in chloride transport which is greater or equal to 10% above the baseline chloride transport.

In one aspect, the invention provides a method of treating a CFTR-mediated disease in a patient comprising administering to the patient any of the spray dried dispersions or the pharmaceutical compositions described above wherein the patient possesses a human CFTR mutation selected from 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C, and 621+3A→G, and a human CFTR mutation selected from ΔF508, R117H, and G551D. In one implementation of this aspect, the patient possesses a human CFTR mutation selected from 1717-1G→A, 1811+1.6kbA→G, 2789+5G→A, 3272-26A→G, and 3849+10kbC→T, and a human CFTR mutation selected from ΔF508, R117H, and G551D. In still another implementation of this aspect, the patient possesses a human CFTR mutation selected from 2789+5G→A and 3272-26A→G, and a human CFTR mutation selected from ΔF508, R117H.

In one aspect, the invention provides a method of treating a CFTR-mediated disease in a patient comprising administering to the patient any of the spray dried dispersions or the pharmaceutical compositions described above wherein the patient possesses one or more human CFTR mutation selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C, and 621+3A→G, and a human CFTR mutation selected from ΔF508, R117H, and G551D.

In one aspect, the invention provides a method of treating a CFTR-mediated disease in a patient comprising administering to the patient any of the spray dried dispersions or the pharmaceutical compositions described above wherein the patient possesses one or more human CFTR mutations selected from G178R, G551S, G970R, G1244E, S1255P, G1349D, S549N, S549R, S1251N, E193K, F1052V, and G1069R. In one implementation of this aspect, the patient possesses one or more human CFTR mutations selected from G178R, G551S, G970R, G1244E, S1255P, G1349D, S549N, S549R, and S1251N. In another implementation of this aspect, the patient possesses one or more human CFTR mutations selected from E193K, F1052V, and G1069R. In some implementations of this aspect, the method produces a greater than 10-fold increase in chloride transport relative to baseline chloride transport.

In one aspect, the invention provides a method of treating a CFTR-mediated disease in a patient comprising administering to the patient any of the spray dried dispersions or the pharmaceutical compositions described above wherein the patient possesses one or more human CFTR mutations selected from R117C, D110H, R347H, R352Q, E56K, P67L, L206W, A455E, D579G, S1235R, S945L, R1070W, F1074L, D110E, D1270N, and D1152H. In one implementation of this aspect, the method produces an increase in chloride transport which is greater or equal to 10% above the baseline chloride transport.

In one aspect, the invention provides a method of treating a CFTR-mediated disease in a patient comprising administering to the patient any of the spray dried dispersions or the pharmaceutical compositions described above wherein the patient possesses one or more human CFTR mutations selected from 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C, and 621+3A→G. In one implementation of this aspect, the patient possesses one or more human CFTR mutations selected from 1717-1G→A, 1811+1.6kbA→G, 2789+5G→A, 3272-26A→G, and 3849+10kbC→T. In still another implementation of this aspect, the patient possesses one or more human CFTR mutations selected from 2789+5G→A and 3272-26A→G.

In one aspect, the invention provides a method of treating a CFTR-mediated disease in a patient comprising administering to the patient any of the spray dried dispersions or the pharmaceutical compositions described above wherein the patient possesses one or more human CFTR mutation selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+

1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C, and 621+3A→G, and a human CFTR mutation selected from ΔF508, R117H, and G551D, and one or more human CFTR mutations selected from ΔF508, R117H, and G551D.

In one aspect, the invention provides a method of treating a CFTR-mediated disease in a patient comprising administering to the patient any of the spray dried dispersions or the pharmaceutical compositions described above wherein the patient possesses one or more human CFTR mutations selected from G178R, G551S, G970R, G1244E, S1255P, G1349D, S549N, S549R, S1251N, E193K, F1052V, and G1069R, and one or more human CFTR mutations selected from ΔF508, R117H, and G551D. In one implementation of this aspect, the patient possesses one or more human CFTR mutations selected from G178R, G551S, G970R, G1244E, S1255P, G1349D, S549N, S549R, and S1251N, and one or more human CFTR mutations selected from ΔF508, R117H, and G551D. In another implementation of this aspect, the patient possesses one or more human CFTR mutations selected from E193K, F1052V, and G1069R, and one or more human CFTR mutations selected from ΔF508, R117H, and G551D. In some implementations of this aspect, the method produces a greater than 10-fold increase in chloride transport relative to baseline chloride transport.

In one aspect, the invention provides a method of treating a CFTR-mediated disease in a patient comprising administering to the patient any of the spray dried dispersions or the pharmaceutical compositions described above wherein the patient possesses one or more human CFTR mutations selected from R117C, D110H, R347H, R352Q, E56K, P67L, L206W, A455E, D579G, S1235R, S945L, R1070W, F1074L, D110E, D1270N, and D1152H, and one or more human CFTR mutations selected from ΔF508, R117H, and G551D. In one implementation of this aspect, the method produces an increase in chloride transport which is greater or equal to 10% above the baseline chloride transport.

In one aspect, the invention provides a method of treating a CFTR-mediated disease in a patient comprising administering to the patient any of the spray dried dispersions or the pharmaceutical compositions described above wherein the patient possesses one or more human CFTR mutations selected from 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C, and 621+3A→G, and one or more human CFTR mutations selected from ΔF508, R117H, and G551D. In one implementation of this aspect, the patient possesses one or more human CFTR mutations selected from 1717-1G→A, 1811+1.6kbA→G, 2789+5G→A, 3272-26A→G, and 3849+10kbC→T, and one or more human CFTR mutations selected from ΔF508, R117H, and G551D. In still another implementation of this aspect, the patient possesses one or more human CFTR mutations selected from 2789+5G→A and 3272-26A→G, and one or more human CFTR mutations selected from ΔF508, R117H, and G551D.

In another aspect, the invention provides a method of treating a CFTR-mediated disease in a patient comprising administering to the patient any of the spray dried dispersions or the pharmaceutical compositions described above wherein the patient possesses a human CFTR mutation selected from R74W, R668C, S977F, L997F, K1060T, A1067T, R1070Q, R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, and S341P.

In one implementation, the human CFTR mutation is selected from R74W, R668C, S977F, L997F, K1060T, A1067T, and R1070Q.

In one implementation, the human CFTR mutation is selected from R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, and S341P.

In a further implementation, the human CFTR mutation is selected from R1066H, T338I, R334W, I336K, H1054D, M1V, E92K, and L927P. In another aspect, the patient possesses a human CFTR mutation selected from R74W, R668C, S977F, L997F, K1060T, A1067T, R1070Q, R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, and S341P, and a human CFTR mutation selected from ΔF508, R117H, and G551D.

In one implementation, the patient possesses a human CFTR mutation selected from R74W, R668C, S977F, L997F, K1060T, A1067T, and R1070Q, and a human CFTR mutation selected from ΔF508, R117H, and G551D.

In one implementation, the patient possesses a human CFTR mutation selected from R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, and S341P, and a human CFTR mutation selected from ΔF508, R117H, and G551D.

In a further implementation, the patient possesses a human CFTR mutation selected from R1066H, T338I, R334W, I336K, H1054D, M1V, E92K, and L927P, and a human CFTR mutation selected from ΔF508, R117H, and G551D.

In another aspect, the invention includes a method of treating a CFTR-mediated disease in a patient comprising administering to a patient any of the spray dried dispersions or the pharmaceutical compositions described above wherein the patient possesses possessing one or more human CFTR mutations selected from R74W, R668C, S977F, L997F, K1060T, A1067T, R1070Q, R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, and S341P.

In one implementation, the patient possesses one or more human CFTR mutations selected from R74W, R668C, S977F, L997F, K1060T, A1067T, and R1070Q.

In one implementation, the patient possesses one or more human CFTR mutations selected from R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, and S341P.

In a further implementation, the patient possesses one or more human CFTR mutations selected from R1066H, T338I, R334W, I336K, H1054D, M1V, E92K, and L927P.

In another aspect, the invention includes a method of treating a CFTR-mediated disease in a patient comprising administering to the patient any of the spray dried dispersions or the pharmaceutical compositions described above wherein the patient possesses one or more human CFTR mutations selected from R74W, R668C, S977F, L997F, K1060T, A1067T, R1070Q, R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, and S341P, and one or more human CFTR mutations selected from ΔF508, R117H, and G551D.

In one implementation, the patient possesses one or more human CFTR mutations selected from R74W, R668C, S977F, L997F, K1060T, A1067T, and R1070Q, and one or more human CFTR mutations selected from ΔF508, R117H, and G551D.

In one implementation, the patient possesses one or more human CFTR mutations selected from R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, and S341P, and one or more human CFTR mutations selected from ΔF508, R117H, and G551D.

In a further implementation, the patient possesses one or more human CFTR mutations selected from R1066H, T338I, R334W, I336K, H1054D, M1V, E92K, and L927P, and one or more human CFTR mutations selected from ΔF508, R117H, and G551D.

In one aspect, the invention includes a method of treating a CFTR-mediated disease in a patient comprising administering to the patient any of the spray dried dispersions or the pharmaceutical compositions described above wherein the patient possesses a human CFTR mutation selected from R74W, R668C, S977F, L997F, K1060T, A1067T, R1070Q, R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, and S341P.

In one implementation, the human CFTR mutation is selected from R74W, R668C, S977F, L997F, K1060T, A1067T, and R1070Q.

In one implementation, the human CFTR mutation is selected from R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, and S341P.

In a further implementation, the human CFTR mutation is selected from R1066H, T338I, R334W, I336K, H1054D, M1V, E92K, and L927P.

In another aspect, the invention includes a method of treating a CFTR-mediated disease in a patient comprising administering to the patient any of the spray dried dispersions or the pharmaceutical compositions described above wherein the patient possesses a human CFTR mutation selected from R74W, R668C, S977F, L997F, K1060T, A1067T, R1070Q, R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, and S341P, and a human CFTR mutation selected from ΔF508, R117H, and G551D.

In one implementation, the patient possesses a human CFTR mutation selected from R74W, R668C, S977F, L997F, K1060T, A1067T, and R1070Q, and a human CFTR mutation selected from ΔF508, R117H, and G551D.

In one implementation, the patient possesses a human CFTR mutation selected from R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, and S341P, and a human CFTR mutation selected from ΔF508, R117H, and G551D.

In a further implementation, the patient possesses a human CFTR mutation selected from R1066H, T338I, R334W, I336K, H1054D, M1V, E92K, and L927P, and a human CFTR mutation selected from ΔF508, R117H, and G551D.

In another aspect, the invention includes a method of treating a CFTR-mediated disease in a patient comprising administering to the patient any of the spray dried dispersions or the pharmaceutical compositions described above wherein the patient possesses one or more human CFTR mutations selected from R74W, R668C, S977F, L997F, K1060T, A1067T, R1070Q, R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, and S341P.

In one implementation, the patient possesses one or more human CFTR mutations selected from R74W, R668C, S977F, L997F, K1060T, A1067T, and R1070Q.

In one implementation, the patient possesses one or more human CFTR mutations selected from R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, and S341P.

In another implementation, the patient possesses one or more human CFTR mutations selected from R1066H, T338I, R334W, I336K, H1054D, M1V, E92K, and L927P.

In another aspect, the invention includes a method of treating a CFTR-mediated disease in a patient comprising administering to the patient any of the spray dried dispersions or the pharmaceutical compositions described above wherein the patient possesses one or more human CFTR mutations selected from R74W, R668C, S977F, L997F, K1060T, A1067T, R1070Q, R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, and S341P, and one or more human CFTR mutations selected from ΔF508, R117H, and G551D.

In one implementation, the patient possesses one or more human CFTR mutations selected from R74W, R668C, S977F, L997F, K1060T, A1067T, and R1070Q, and one or more human CFTR mutations selected from ΔF508, R117H, and G551D.

In one implementation, the patient possesses one or more human CFTR mutations selected from R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, and S341P, and one or more human CFTR mutations selected from ΔF508, R117H, and G551D.

In a further implementation, the patient possesses one or more human CFTR mutations selected from R1066H, T338I, R334W, I336K, H1054D, M1V, E92K, and L927P, and one or more human CFTR mutations selected from ΔF508, R117H, and G551D.

In one aspect, the invention includes a method of treating a CFTR-mediated disease in a patient comprising administering to the patient any of the spray dried dispersions or the pharmaceutical compositions described above wherein the patient possesses a human CFTR mutation selected from R74W, R668C, S977F, L997F, K1060T, A1067T, R1070Q, R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, and S341P.

In one implementation, the human CFTR mutation is selected from R74W, R668C, S977F, L997F, K1060T, A1067T, and R1070Q.

In one implementation, the human CFTR mutation is selected from R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, and S341P.

In a further implementation, the human CFTR mutation is selected from R1066H, T338I, R334W, I336K, H1054D, M1V, E92K, and L927P.

In another aspect, the invention includes a method of treating a CFTR-mediated disease in a patient comprising administering to the patient any of the spray dried dispersions or the pharmaceutical compositions described above wherein the patient possesses a human CFTR mutation selected from R74W, R668C, S977F, L997F, K1060T, A1067T, R1070Q, R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, and S341P, and a human CFTR mutation selected from ΔF508, R117H, and G551D.

In one implementation, the patient possesses a human CFTR mutation selected from R74W, R668C, S977F, L997F, K1060T, A1067T, and R1070Q, and a human CFTR mutation selected from ΔF508, R117H, and G551D.

In one implementation, the patient possesses a human CFTR mutation selected from R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, and S341P, and a human CFTR mutation selected from ΔF508, R117H, and G551D.

In another implementation, the patient possesses a human CFTR mutation selected from R1066H, T338I, R334W, I336K, H1054D, M1V, E92K, and L927P, and a human CFTR mutation selected from ΔF508, R117H, and G551D.

In another aspect, the invention includes a method of treating a CFTR-mediated disease in a patient administering to the patient any of the spray dried dispersions or the pharmaceutical compositions described above wherein the patient possesses one or more human CFTR mutations selected from R74W, R668C, S977F, L997F, K1060T, A1067T, R1070Q, R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, and S341P.

In one implementation, the patient possesses one or more human CFTR mutations selected from R74W, R668C, S977F, L997F, K1060T, A1067T, and R1070Q.

In one implementation, the patient possesses one or more human CFTR mutations selected from R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, and S341P.

In a further implementation, the patient possesses one or more human CFTR mutations selected from R1066H, T338I, R334W, I336K, H1054D, M1V, E92K, and L927P.

In another aspect, the invention includes a method of treating a CFTR-mediated disease in a patient comprising administering to the patient any of the spray dried dispersions or the pharmaceutical compositions described above wherein the patient possesses one or more human CFTR mutations selected from R74W, R668C, S977F, L997F, K1060T, A1067T, R1070Q, R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, and S341P, and one or more human CFTR mutations selected from ΔF508, R117H, and G551D.

In one implementation, the patient possesses one or more human CFTR mutations selected from R74W, R668C, S977F, L997F, K1060T, A1067T, and R1070Q, and one or more human CFTR mutations selected from ΔF508, R117H, and G551D.

In one implementation, the patient possesses one or more human CFTR mutations selected from R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, and S341P, and one or more human CFTR mutations selected from ΔF508, R117H, and G551D.

In a further implementation, the patient possesses one or more human CFTR mutations selected from R1066H, T338I, R334W, I336K, H1054D, M1V, E92K, and L927P, and one or more human CFTR mutations selected from ΔF508, R117H, and G551D.

In one aspect, the invention includes a method of treating a CFTR-mediated disease in a patient comprising administering to the patient any of the spray dried dispersions or the pharmaceutical compositions described above wherein the patient possesses a human CFTR mutation selected from R74W, R668C, S977F, L997F, K1060T, A1067T, R1070Q, R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, S341P, I507del, G1061R, G542X, W1282X, and 2184InsA.

In one implementation of this aspect, the human CFTR mutation is selected from R74W, R668C, S977F, L997F, K1060T, A1067T, R1070Q, I507del, G1061R, G542X, W1282X, and 2184InsA.

In another implementation of this aspect, the human CFTR mutation is selected from R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, S341P, I507del, G1061R, G542X, W1282X, and 2184InsA.

In still another implementation of this aspect, the human CFTR mutation is selected from R1066H, T338I, R334W, I336K, H1054D, M1V, E92K, L927P, I507del, G1061R, G542X, W1282X, and 2184InsA.

In one aspect, the invention includes a method of treating a CFTR-mediated disease in a patient comprising administering to the patient any of the spray dried dispersions or the pharmaceutical compositions described above wherein the patient possesses a human CFTR mutation selected from R74W, R668C, S977F, L997F, K1060T, A1067T, R1070Q, R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, S341P, I507del, G1061R, G542X, W1282X, and 2184InsA, and a human CFTR mutation selected from ΔF508, R117H, and G551D.

In one implementation of this aspect, the patient possesses a human CFTR mutation selected from R74W, R668C, S977F, L997F, K1060T, A1067T, R1070Q, I507del, G1061R, G542X, W1282X, and 2184InsA, and a human CFTR mutation selected from ΔF508, R117H, and G551D.

In another implementation of this aspect, the patient possesses a human CFTR mutation selected from R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, S341P, I507del, G1061R, G542X, W1282X, and 2184InsA, and a human CFTR mutation selected from ΔF508, R117H, and G551D.

In still another implementation of this aspect, the patient possesses a human CFTR mutation selected from R1066H, T338I, R334W, I336K, H1054D, M1V, E92K, L927P, I507del, G1061R, G542X, W1282X, and 2184InsA, and a human CFTR mutation selected from ΔF508, R117H, and G551D.

In one aspect, the invention includes a method of treating a CFTR-mediated disease in a patient comprising administering to the patient any of the spray dried dispersions or the pharmaceutical compositions described above wherein the patient possesses one or more human CFTR mutations selected from R74W, R668C, S977F, L997F, K1060T, A1067T, R1070Q, R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, S341P, I507del, G1061R, G542X, W1282X, and 2184InsA.

In one implementation of this aspect, the patient possesses one or more human CFTR mutations selected from R74W, R668C, S977F, L997F, K1060T, A1067T, R1070Q, I507del, G1061R, G542X, W1282X, and 2184InsA.

In another implementation of this aspect, the patient possesses one or more human CFTR mutations selected from R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, S341P, I507del, G1061R, G542X, W1282X, and 2184InsA.

In still another implementation of this aspect, the patient possesses one or more human CFTR mutations selected from R1066H, T338I, R334W, I336K, H1054D, M1V, E92K, L927P, I507del, G1061R, G542X, W1282X, and 2184InsA.

In one aspect, the invention includes a method of treating a CFTR-mediated disease in a patient comprising administering to the patient any of the spray dried dispersions or the pharmaceutical compositions described above wherein the patient possesses one or more human CFTR mutations selected from R74W, R668C, S977F, L997F, K1060T, A1067T, R1070Q, R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, S341P, I507del, G1061R, G542X, W1282X, and 2184InsA, and one or more human CFTR mutations selected from ΔF508, R117H, and G551D.

In one implementation of this aspect, the patient possesses one or more human CFTR mutations selected from R74W, R668C, S977F, L997F, K1060T, A1067T, R1070Q, I507del, G1061R, G542X, W1282X, and 2184InsA, and one or more human CFTR mutations selected from ΔF508, R117H, and G551D.

In another implementation of this aspect, the patient possesses one or more human CFTR mutations selected from R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, S341P, I507del, G1061R, G542X, W1282X, and 2184InsA, and one or more human CFTR mutations selected from ΔF508, R117H, and G551D.

In still another implementation of this aspect, the patient possesses one or more human CFTR mutations selected from R1066H, T338I, R334W, I336K, H1054D, M1V, E92K, L927P, I507del, G1061R, G542X, W1282X, and 2184InsA, and one or more human CFTR mutations selected from ΔF508, R117H, and G551D.

In one aspect, the invention includes a method of treating a CFTR-mediated disease in a patient comprising administering to the patient any of the spray dried dispersions or the pharmaceutical compositions described above wherein the patient possesses a human CFTR mutation selected from R74W, R668C, S977F, L997F, K1060T, A1067T, R1070Q, R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, S341P, I507del, G1061R, G542X, W1282X, and 2184InsA.

In one implementation of this aspect, the human CFTR mutation is selected from R74W, R668C, S977F, L997F, K1060T, A1067T, R1070Q, I507del, G1061R, G542X, W1282X, and 2184InsA.

In another implementation of this aspect, the human CFTR mutation is selected from R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, S341P, I507del, G1061R, G542X, W1282X, and 2184InsA.

In still another implementation of this aspect, the human CFTR mutation is selected from R1066H, T338I, R334W, I336K, H1054D, M1V, E92K, L927P, I507del, G1061R, G542X, W1282X, and 2184InsA.

In one aspect, the invention includes a method of treating a CFTR-mediated disease in a patient comprising administering to the patient any of the spray dried dispersions or the pharmaceutical compositions described above wherein the patient possesses a human CFTR mutation selected from R74W, R668C, S977F, L997F, K1060T, A1067T, R1070Q, R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, S341P, I507del, G1061R, G542X, W1282X, and 2184InsA, and a human CFTR mutation selected from ΔF508, R117H, and G551D.

In one implementation of this aspect, the patient possesses a human CFTR mutation selected from R74W, R668C, S977F, L997F, K1060T, A1067T, R1070Q, I507del, G1061R, G542X, W1282X, and 2184InsA, and a human CFTR mutation selected from ΔF508, R117H, and G551D.

In another implementation of this aspect, the patient possesses a human CFTR mutation selected from R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, S341P, I507del, G1061R, G542X, W1282X, and 2184InsA, and a human CFTR mutation selected from ΔF508, R117H, and G551D.

In still another implementation of this aspect, the patient possesses a human CFTR mutation selected from R1066H, T338I, R334W, I336K, H1054D, M1V, E92K, L927P, I507del, G1061R, G542X, W1282X, and 2184InsA, and a human CFTR mutation selected from ΔF508, R117H, and G551D.

In one aspect, the invention includes a method of treating a CFTR-mediated disease in a patient comprising administering to the patient any of the spray dried dispersions or the pharmaceutical compositions described above wherein the patient possesses one or more human CFTR mutations selected from R74W, R668C, S977F, L997F, K1060T, A1067T, R1070Q, R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, S341P, I507del, G1061R, G542X, W1282X, and 2184InsA.

In one implementation of this aspect, the patient possesses one or more human CFTR mutations selected from R74W, R668C, S977F, L997F, K1060T, A1067T, R1070Q, I507del, G1061R, G542X, W1282X, and 2184InsA.

In another implementation of this aspect, the patient possesses one or more human CFTR mutations selected from R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, S341P, I507del, G1061R, G542X, W1282X, and 2184InsA.

In still another implementation of this aspect, wherein the patient possesses one or more human CFTR mutations selected from R1066H, T338I, R334W, I336K, H1054D, M1V, E92K, L927P, I507del, G1061R, G542X, W1282X, and 2184InsA.

In one aspect, the invention includes a method of treating a CFTR-mediated disease in a patient comprising administering to the patient any of the spray dried dispersions or the pharmaceutical compositions described above wherein the patient possesses one or more human CFTR mutations selected from R74W, R668C, S977F, L997F, K1060T, A1067T, R1070Q, R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, S341P, I507del, G1061R, G542X, W1282X, and 2184InsA, and one or more human CFTR mutations selected from ΔF508, R117H, and G551D.

In one implementation of this aspect, the patient possesses one or more human CFTR mutations selected from R74W, R668C, S977F, L997F, K1060T, A1067T, R1070Q, I507del, G1061R, G542X, W1282X, and 2184InsA, and one or more human CFTR mutations selected from ΔF508, R117H, and G551D.

In another implementation of this aspect, the patient possesses one or more human CFTR mutations selected from R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, S341P, I507del, G1061R, G542X, W1282X, and 2184InsA, and one or more human CFTR mutations selected from ΔF508, R117H, and G551D.

In still another implementation of this aspect, the patient possesses one or more human CFTR mutations selected from R1066H, T338I, R334W, I336K, H1054D, M1V, E92K, L927P, I507del, G1061R, G542X, W1282X, and 2184InsA, and one or more human CFTR mutations selected from ΔF508, R117H, and G551D.

In one aspect, the invention includes a method of treating a CFTR-mediated disease in a patient comprising administering to the patient any of the spray dried dispersions or the pharmaceutical compositions described above wherein the patient possesses a human CFTR mutation selected from R74W, R668C, S977F, L997F, K1060T, A1067T, R1070Q, R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, S341P, I507del, G1061R, G542X, W1282X, and 2184InsA.

In one implementation of this aspect, the human CFTR mutation is selected from R74W, R668C, S977F, L997F, K1060T, A1067T, R1070Q, I507del, G1061R, G542X, W1282X, and 2184InsA.

In another implementation of this aspect, the human CFTR mutation is selected from R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, S341P, I507del, G1061R, G542X, W1282X, and 2184InsA.

In still another implementation of this aspect, the human CFTR mutation is selected from R1066H, T338I, R334W, I336K, H1054D, M1V, E92K, L927P, I507del, G1061R, G542X, W1282X, and 2184InsA.

In one aspect, the invention includes a method of treating a CFTR-mediated disease in a patient comprising administering to the patient any of the spray dried dispersions or the pharmaceutical compositions described above wherein the patient possesses a human CFTR mutation selected from R74W, R668C, S977F, L997F, K1060T, A1067T, R1070Q, R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, S341P, I507del, G1061R, G542X, W1282X, and 2184InsA, and a human CFTR mutation selected from ΔF508, R117H, and G551D.

In one implementation of this aspect, the patient possesses a human CFTR mutation selected from R74W, R668C, S977F, L997F, K1060T, A1067T, R1070Q, I507del, G1061R, G542X, W1282X, and 2184InsA, and a human CFTR mutation selected from ΔF508, R117H, and G551D.

In another implementation of this aspect, the patient possesses a human CFTR mutation selected from R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, S341P, I507del, G1061R, G542X, W1282X, and 2184InsA, and a human CFTR mutation selected from ΔF508, R117H, and G551D.

In still another implementation of this aspect, the patient possesses a human CFTR mutation selected from R1066H, T338I, R334W, I336K, H1054D, M1V, E92K, L927P, I507del, G1061R, G542X, W1282X, and 2184InsA, and a human CFTR mutation selected from ΔF508, R117H, and G551D.

In one aspect, the invention includes a method of treating a CFTR-mediated disease in a patient comprising administering to the patient any of the spray dried dispersions or the pharmaceutical compositions described above wherein the patient possesses one or more human CFTR mutations selected from R74W, R668C, S977F, L997F, K1060T, A1067T, R1070Q, R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, S341P, I507del, G1061R, G542X, W1282X, and 2184InsA.

In one implementation of this aspect, the patient possesses one or more human CFTR mutations selected from R74W, R668C, S977F, L997F, K1060T, A1067T, R1070Q, I507del, G1061R, G542X, W1282X, and 2184InsA.

In another implementation of this aspect, the patient possesses one or more human CFTR mutations selected from R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, S341P, I507del, G1061R, G542X, W1282X, and 2184InsA.

In still another implementation of this aspect, the patient possesses one or more human CFTR mutations selected from R1066H, T338I, R334W, I336K, H1054D, M1V, E92K, L927P, I507del, G1061R, G542X, W1282X, and 2184InsA.

In one aspect, the invention includes a method of treating a CFTR-mediated disease in a patient comprising administering to the patient any of the spray dried dispersions or the pharmaceutical compositions described above wherein the patient possesses one or more human CFTR mutations selected from R74W, R668C, S977F, L997F, K1060T, A1067T, R1070Q, R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, S341P, I507del, G1061R, G542X, W1282X, and 2184InsA, and one or more human CFTR mutations selected from ΔF508, R117H, and G551D.

In one implementation of this aspect, the patient possesses one or more human CFTR mutations selected from R74W, R668C, S977F, L997F, K1060T, A1067T, R1070Q, I507del, G1061R, G542X, W1282X, and 2184InsA, and one or more human CFTR mutations selected from ΔF508, R117H, and G551D.

In another implementation of this aspect, the patient possesses one or more human CFTR mutations selected from R1066H, T338I, R334W, G85E, A46D, I336K, H1054D, M1V, E92K, V520F, H1085R, R560T, L927P, R560S, N1303K, M1101K, L1077P, R1066M, R1066C, L1065P, Y569D, A561E, A559T, S492F, L467P, R347P, S341P, I507del, G1061R, G542X, W1282X, and 2184InsA, and one or more human CFTR mutations selected from ΔF508, R117H, and G551D.

In still another implementation of this aspect, the patient possesses one or more human CFTR mutations selected from R1066H, T338I, R334W, I336K, H1054D, M1V, E92K, L927P, I507del, G1061R, G542X, W1282X, and 2184InsA, and one or more human CFTR mutations selected from ΔF508, R117H, and G551D.

In one aspect, the invention also provides a method of treating, lessening the severity of, or symptomatically treating a disease in a patient, the method comprising administering an effective amount of the spray dried dispersion or pharmaceutical composition of the invention to the patient, preferably a mammal, wherein the disease is selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington's, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease, osteoporosis, osteopenia, bone healing and bone growth (including bone repair, bone regeneration, reducing bone resorption and increasing bone deposition), Gorham's Syndrome, chloride channelopathies such as myotonia congenita (Thomson and Becker forms), Bartter's syndrome type III, Dent's disease, hyperekplexia, epilepsy, lysosomal storage disease, Angelman syndrome, and Primary Ciliary Dyskinesia (PCD), a term for inherited disorders of the structure and/or function of cilia, including PCD with situs inversus (also known as Kartagener syndrome), PCD without situs inversus and ciliary aplasia.

In one aspect, the invention also provides a method of treating, lessening the severity of, or symptomatically treating a disease in a patient comprising administering an effective amount of the spray dried dispersion or pharmaceutical composition of the invention to the patient, preferably a mammal, wherein the disease is selected from generalized epilepsy with ferbrile seizures plus (GEFS+), general epilepsy with ferbile and aferbrile seizures, myotonia, paramyotonia congenital, potassium-aggravated myotonia, hyperkalemic periodic paralysis, LQTS, LQTS/Brugada syndrome, autosomal-dominant LQTS with deafness, autosomal-recessive LQTS, LQTS with dysmorphic features, congenital and acquired LQTS, Timothy syndrome, persistent hyperinsulinemic hypolglycemia of infancy, dilated cardiomyopathy, autosomal-dominant LQTS, Dent disease, Osteopetrosis, Bartter syndrome type III, central core disease, malignant hyperthermia, and catecholaminergic polymorphic tachycardia.

In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation N1303K, ΔI507, or R560T.

In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation G551D. In another implementation, the patient is homozygous in G551D. In another implementation, the patient is heterozygous in G551D wherein the other CFTR genetic mutation is any one of ΔF508, G542X, N1303K, W1282X, R117H, R553X, 1717-1G→A, 621+1G→T, 2789+5G→A, 3849+10kbC→T, R1162X, G85E, 3120+1G→A, ΔI507, 1898+1G→A, 3659delC, R347P, R560T, R334W, A455E, 2184delA, or 711+1G→T.

In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation ΔF508. In another implementation, the patient is homozygous in ΔF508. In another implementation, the patient is heterozygous in ΔF508 wherein the other CFTR genetic mutation is any one of G551D, G542X, N1303K, W1282X, R117H, R553X, 1717-1G→A, 621+1G→T, 2789+5G→A, 3849+10kbC→T, R1162X, G85E, 3120+1G→A, 41507, 1898+1G→A, 3659delC, R347P, R560T, R334W, A455E, 2184delA, or 711+1G→T.

In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C, and 621+3A→G.

In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation selected from G178R, G551S, G970R, G1244E, S1255P, G1349D, S549N, S549R, S1251N, E193K, F1052V, and G1069R. In one implementation of this aspect, the invention provides a method of treating a CFTR mediated disease comprising administering a spray dried dispersion, as described above, to a patient possessing a human CFTR mutation selected from G178R, G551S, G970R, G1244E, S1255P, G1349D, S549N, S549R, and S1251N. In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation selected from E193K, F1052V, and G1069R. In some implementations of this aspect, the method produces a greater than 10-fold increase in chloride transport relative to baseline chloride transport.

In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation selected from R117C, D110H, R347H, R352Q, E56K, P67L, L206W, A455E, D579G, S1235R, S945L, R1070W, F1074L, D110E, D1270N, and D1152H. In one embodiment of this aspect, the method produces an increase in chloride transport which is greater or equal to 10% above the baseline chloride transport.

In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation selected from 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C, and 621+3A→G. In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation selected from 1717-1G→A, 1811+1.6kbA→G, 2789+5G→A, 3272-26A→G, and 3849+10kbC→T. In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation selected from 2789+5G→A and 3272-26A→G.

In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C, and 621+3A→G, and a human CFTR mutation selected from ΔF508, R117H, and G551D.

In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation selected from G178R, G551S, G970R, G1244E, S1255P, G1349D, S549N, S549R, S1251N, E193K, F1052V, and G1069R, and a human CFTR mutation selected from ΔF508, R117H, and G551D. In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation selected from G178R, G551S, G970R, G1244E, S1255P, G1349D, S549N, S549R, and S1251N, and a human CFTR mutation selected from ΔF508, R117H, and G551D. In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation selected from E193K, F1052V, and G1069R, and a human CFTR mutation selected from ΔF508, R117H, and G551D. In some embodiments of this aspect, the method produces a greater than 10-fold increase in chloride transport relative to baseline chloride transport.

In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation selected from R117C, D110H, R347H, R352Q, E56K, P67L, L206W, A455E, D579G, S1235R, S945L, R1070W, F1074L, D110E, D1270N, and D1152H, and a human CFTR mutation selected from ΔF508, R117H, and G551D. In one embodiment of this aspect, the method produces an increase in chloride transport which is greater or equal to 10% above the baseline chloride transport.

In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation selected from 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C, and 621+3A→G, and a human CFTR mutation selected from ΔF508, R117H, and G551D. In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation selected from 1717-1G→A, 1811+1.6kbA→G, 2789+5G→A, 3272-26A→G, and 3849+10kbC→T, and a human CFTR mutation selected from ΔF508, R117H, and G551D. In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation selected from 2789+5G→A and 3272-26A→G, and a human CFTR mutation selected from ΔF508, R117H.

In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C, and 621+3A→G, and a human CFTR mutation selected from ΔF508, R117H, and G551D.

In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation selected from G178R, G551S, G970R, G1244E, S1255P, G1349D, S549N, S549R, S1251N, E193K, F1052V, and G1069R. In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation selected from G178R, G551S, G970R, G1244E, S1255P, G1349D, S549N, S549R, and S1251N. In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation selected from E193K, F1052V, and G1069R. In some embodiments of this aspect, the method produces a greater than 10-fold increase in chloride transport relative to baseline chloride transport.

In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation selected from R117C, D110H, R347H, R352Q, E56K, P67L, L206W, A455E, D579G, S1235R, S945L, R1070W, F1074L, D110E, D1270N, and D1152H. In one embodiment of this aspect, the method produces an increase in chloride transport which is greater or equal to 10% above the baseline chloride transport.

In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation selected from 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C, and 621+3A→G. In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation selected from 1717-1G→A, 1811+1.6kbA→G, 2789+5G→A, 3272-26A→G, and 3849+10kbC→T. In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation selected from 2789+5G→A and 3272-26A→G.

In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C, and 621+3A→G, and a human CFTR mutation selected from ΔF508, R117H, and G551D, and one or more human CFTR mutations selected from ΔF508, R117H, and G551D.

In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation selected from G178R, G551S, G970R, G1244E, S1255P, G1349D, S549N, S549R, S1251N, E193K, F1052V, and G1069R, and one or more human CFTR mutations selected from ΔF508, R117H, and G551D. In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation selected from G178R, G551S, G970R, G1244E, S1255P, G1349D, S549N, S549R, and S1251N, and one or more human CFTR mutations selected from ΔF508, R117H, and G551D. In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation selected from E193K, F1052V, and G1069R, and one or more human CFTR mutations selected from ΔF508, R117H, and G551D. In some embodiments of this aspect, the method produces a greater than 10-fold increase in chloride transport relative to baseline chloride transport.

In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation selected from R117C, D110H, R347H, R352Q, E56K, P67L, L206W, A455E, D579G, S1235R, S945L, R1070W, F1074L, D110E, D1270N, and D1152H, and one or more human CFTR mutations selected from ΔF508, R117H, and G551D. In one embodiment of this aspect, the method produces an increase in chloride transport which is greater or equal to 10% above the baseline chloride transport.

In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation selected from 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+

5G→A, 3120G→A, 1811+1.6kbA→G, 711+3A→G, 1898+ 3A→G, 1717-8G→A, 1342-2A→C, 405+3A→C, 1716G/ A, 1811+1G→C, 1898+5G→T, 3850-3T→G, IVS14b+ 5G→A, 1898+1G→T, 4005+2T→C, and 621+3A→G, and one or more human CFTR mutations selected from ΔF508, R117H, and G551D. In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation selected from 1717-1G→A, 1811+1.6kbA→G, 2789+5G→A, 3272-26A→G, and 3849+10kbC→T, and one or more human CFTR mutations selected from ΔF508, R117H, and G551D. In one aspect, the present invention is directed to a method of treating, lessening the severity of, or symptomatically treating cystic fibrosis in a patient comprising administering an effective amount of the spray dried dispersion or pharmaceutical composition of the invention to the patient, preferably a mammal, wherein the patient possesses the CFTR genetic mutation selected from 2789+5G→A and 3272-26A→G, and one or more human CFTR mutations selected from ΔF508, R117H, and G551D.

1. Homozygous Mutations

In some implementations, the patient is homozygous in any of the mutations recited above.

In some implementations, the patient is homozygous in the ΔF508 human CFTR mutation.

In some implementations, the patient is homozygous in a human mutation other than the ΔF508 CFTR mutation.

2. Heterozygous Mutations

In some implementations, the patient is heterozygous in any of the mutations recited above.

In some implementations, the patient is heterozygous in the ΔF508 human CFTR mutation. For example, the patient is heterozygous in the ΔF508 human CFTR mutation and a gating mutation selected from G551D, G178R, S549N, S549R, G551S, G970R, G1244E, S1251N, S1255P, and G1349D.

In some implementations, the patient is heterozygous in the ΔF508 human CFTR mutation and a residual function mutation selected from R117H, A455E, D1152H, L206W, R347H, P67L, R117C, S945L, S1235R, I1027T, R668C, R352Q, G576A, M470V, D110H, D1270N, L997F, R75Q, R74W, D579G, R1070Q, F1052V, R1070W, R31C, D614G, S977F, G1069R, R1162L, E56K, F1074L, D110E, F1074L, E56K, D110E, A1067T, E193K, or K1060T.

In some implementations, the patient is heterozygous in the human CFTR mutation ΔF508 and residual mutation R117H.

In some implementations, the patient is heterozygous in the human CFTR mutation ΔF508 and a splice mutation selected from 2789+5G→A, 3120G→A, 5T, 711+3A→G, 711+5G→A, 7T, 1717-8G→A, 1898+3A→G, 1811+ 1.6kbA→G, 3272-26A→G, and 3849+10kbC→T.

In some implementations, the patient is heterozygous in a mutation other than ΔF508 and a gating mutation selected from G551D, G178R, S549N, S549R, G551S, G970R, G1244E, S1251N, S1255P, and G1349D.

In some implementations, the patient is heterozygous in a mutation other than ΔF508 and a residual function mutation selected from R117H, A455E, D1152H, L206W, R347H, P67L, R117C, S945L, S1235R, I1027T, R668C, R352Q, G576A, M470V, D110H, D1270N, L997F, R75Q, R74W, D579G, R1070Q, F1052V, R1070W, R31C, D614G, S977F, G1069R, R1162L, E56K, F1074L, D110E, F1074L, E56K, D110E, A1067T, E193K, or K1060T. For example, the patient is heterozygous in a mutation other than ΔF508 and residual mutation R117H.

In some implementations, the patient is heterozygous in a mutation other than ΔF508 and a splice mutation selected from 2789+5G→A, 3120G→A, 5T, 711+3A→G, 711+5G→A, 7T, 1717-8G→A, 1898+3A→G, 1811+1.6kbA→G, 3272-26A→G, or 3849+10kbC→T.

B. Dosage Regime

In one embodiment, 50 mg of substantially amorphous Compound 1 and 150 mg of substantially amorphous Compound 2 may be administered to a subject in need thereof. In these embodiments, the dosage amounts may be achieved by administration of one or more tablets of the invention. For example, administration of 50 mg of substantially amorphous Compound 1 and 150 mg of substantially amorphous Compound 2 may be achieved by administering one tablet containing 50 mg of substantially amorphous Compound 1, and 150 mg of substantially amorphous Compound 2. The duration of administration may continue until amelioration of the disease is achieved or until a subject's physician advises, e.g. duration of administration may be less than a week, 1 week, 2 weeks, 3 weeks, four weeks (28 days), or a month or longer. In one embodiment, two tablets each comprising 50 mg of substantially amorphous Compound 1, and 150 mg of substantially amorphous Compound 2 may be administered to the patient per day. In a further embodiment, the two tablets may be administered at the same time or at different times during the day. In a further embodiment, one tablet is administered daily (qd). In a further embodiment, one tablet is administered twice per day (bid). In a further embodiment, one tablet is administered every 12 hours (q12h). In a further embodiment, two tablets are administered daily (qd). In a further embodiment, two tablets are administered twice per day (bid). In a further embodiment, two tablets are administered every 12 hours (q12h).

In another embodiment, administration of a pharmaceutical composition of the present invention, such as, for example, a tablet, may be supplemented by addition of either Compound 1 or Compound 2 prior, subsequent, or concurrent with the pharmaceutical composition. For example, a tablet of the present invention may be administered followed by the administration of Compound 1 or Compound 2 alone. In one embodiment, a tablet of the present invention is administered once daily (qd) followed by the administration of 150 mg of Compound 2 once daily (qd). In one embodiment, a tablet of the present invention is administered once daily (qd) followed by the administration of a tablet of Kalydeco™ once daily (qd).

In another embodiment, an effective amount of the compositions of the present invention may be administered to a patient wherein the patient is 1 to 5 years old. In another embodiment, the patient is 6 to 11 years old. In another embodiment, the patient is 12 to 18 years old. In another embodiment, the patient is 18 years old or older. In another embodiment, the patient in the previous embodiments is taking an effective amount of the compositions of the present invention for the treatment of cystic fibrosis.

VI. Kits

Another aspect of the present invention provides a kit comprising a pharmaceutical composition of the present invention and instructions for use thereof.

In some embodiments, the kit further comprises an additional therapeutic agent that is absent from the spray dried dispersion or the pharmaceutical composition described above.

In some embodiments, the additional therapeutic agent is selected from any of the additional therapeutic agents described above.

In some embodiments, the additional therapeutic agent is another CFTR corrector different from the first agent.

In some embodiments, the additional therapeutic agent is another CFTR potentiator different from the second agent.

And, in some embodiments, the additional therapeutic agent is selected from

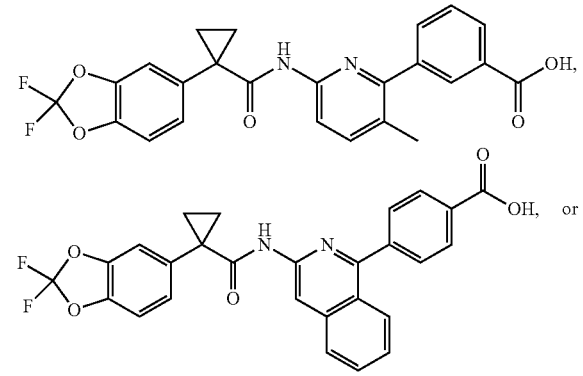

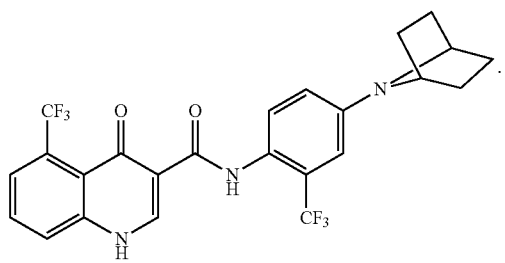

In some embodiments, the additional therapeutic agent and the pharmaceutical composition of the present invention are stored in the same container. In some examples, the pharmaceutical composition of the present invention and the additional therapeutic agent are stored in the same container, and the container is a bottle, vial, or blister pack.

In other embodiments, the additional therapeutic agent and the pharmaceutical composition of the present invention are stored in separate containers. For example, the pharmaceutical composition of the present invention is stored in a bottle, vial, or blister pack, and the additional therapeutic agent is stored in a separate bottle, vial, or blister pack.

VII. General Synthetic Schemes

Compound 1 may be prepared by coupling the acid halide moiety 1-1 with the amine moiety 1-2 to form compound 1-3 followed by deprotection according to Scheme 1.

Scheme 1: Preparation of Compound 1.

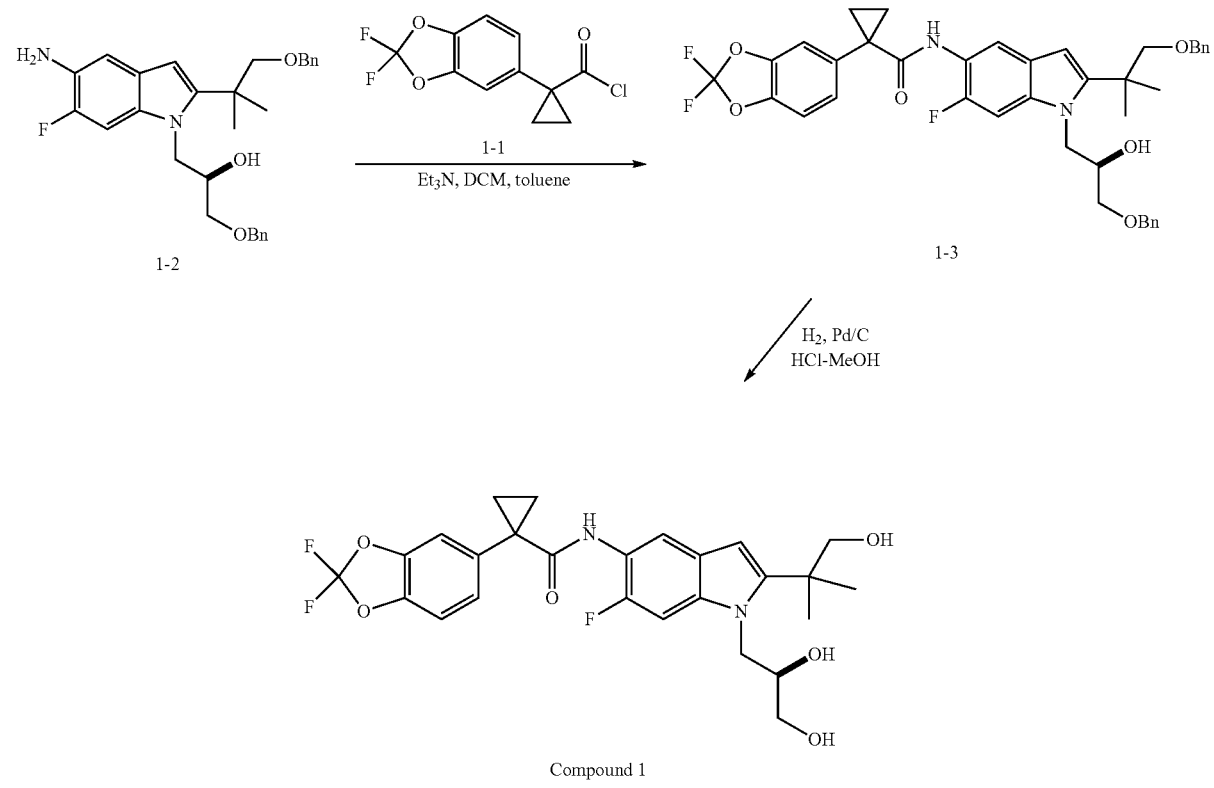

Compound 1-1 is prepared according to Scheme 2.
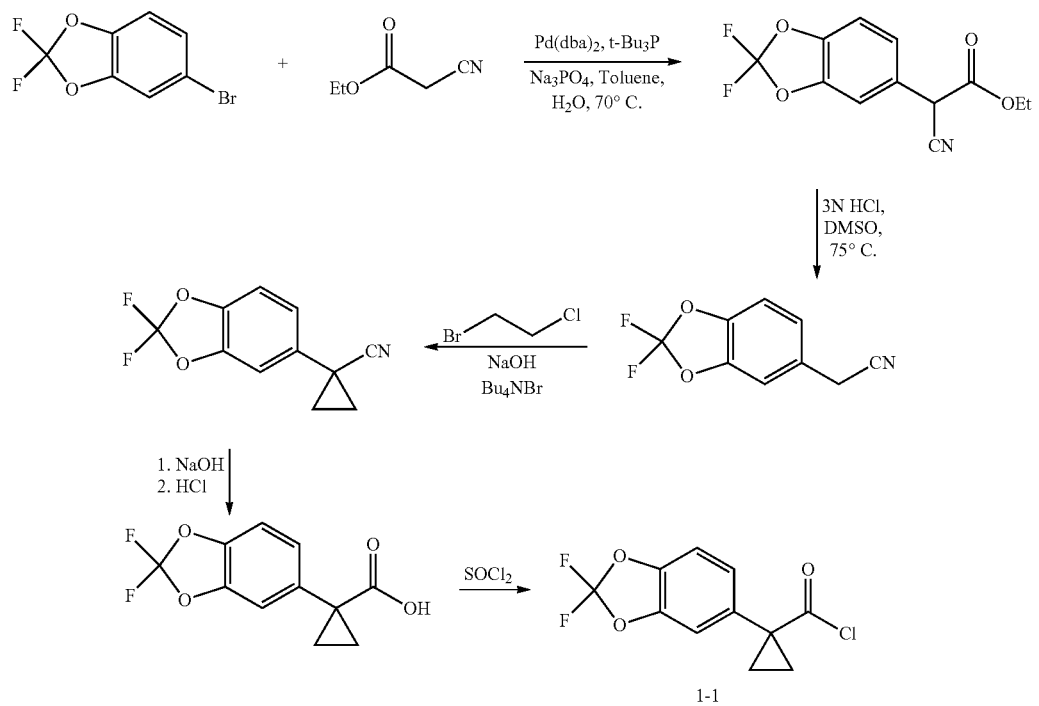
Compound 1-2 is prepared according to Scheme 3.
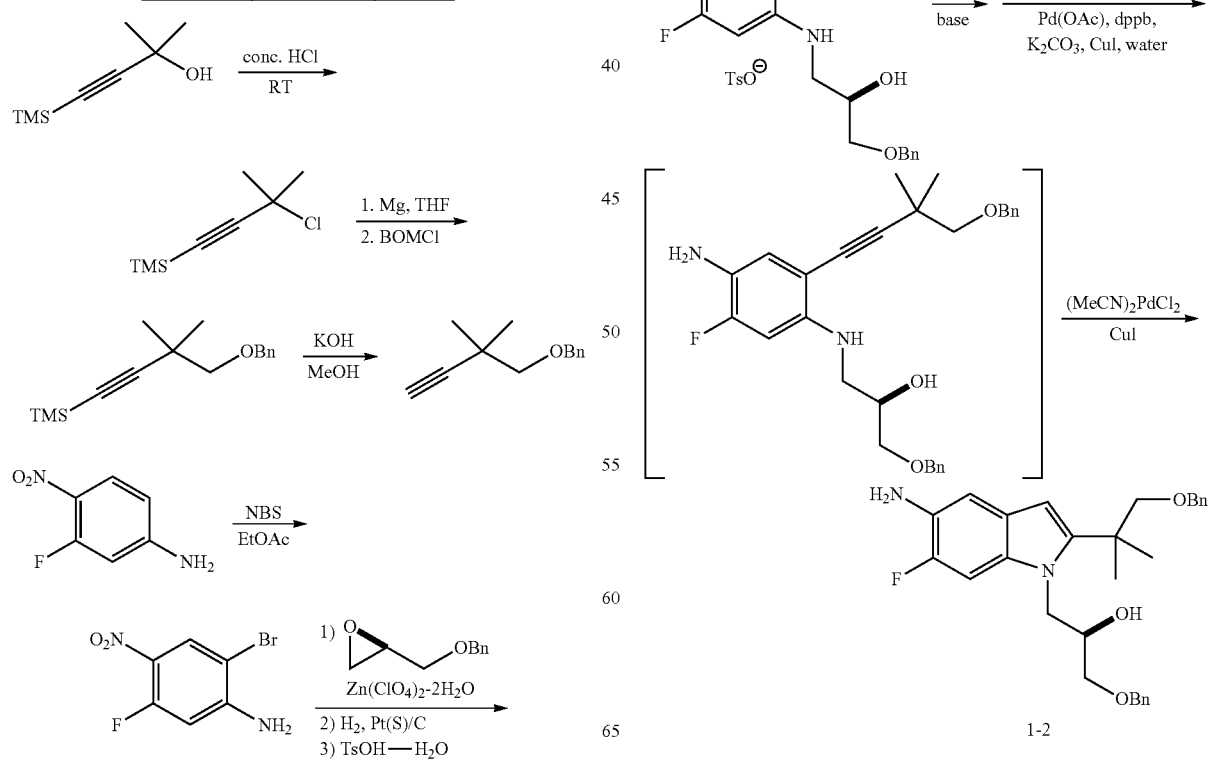

Compound 2 can be prepared by coupling a 4-oxo-dihydroquinoline carboxylic acid moiety with an amine moiety according to Schemes 4-6.
Scheme 4: Synthesis of the 4-oxo-dihydroquinoline carboxylic acid moiety.
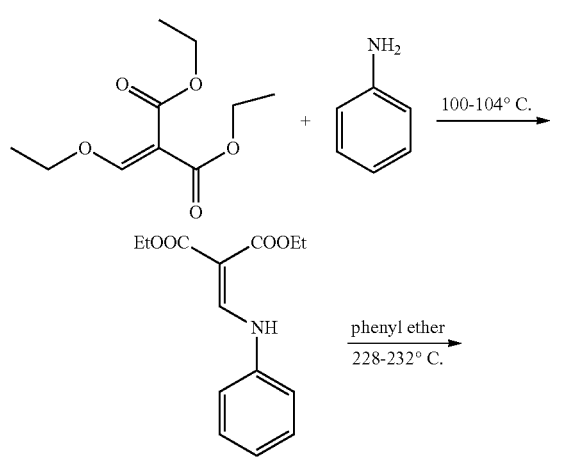
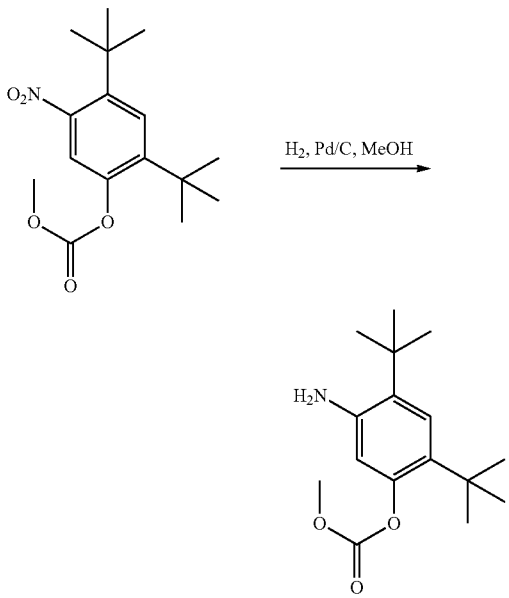
Scheme 6:
Coupling of the 4-oxo-dihydroquinoline carboxylic acid moiety with the amine moiety.
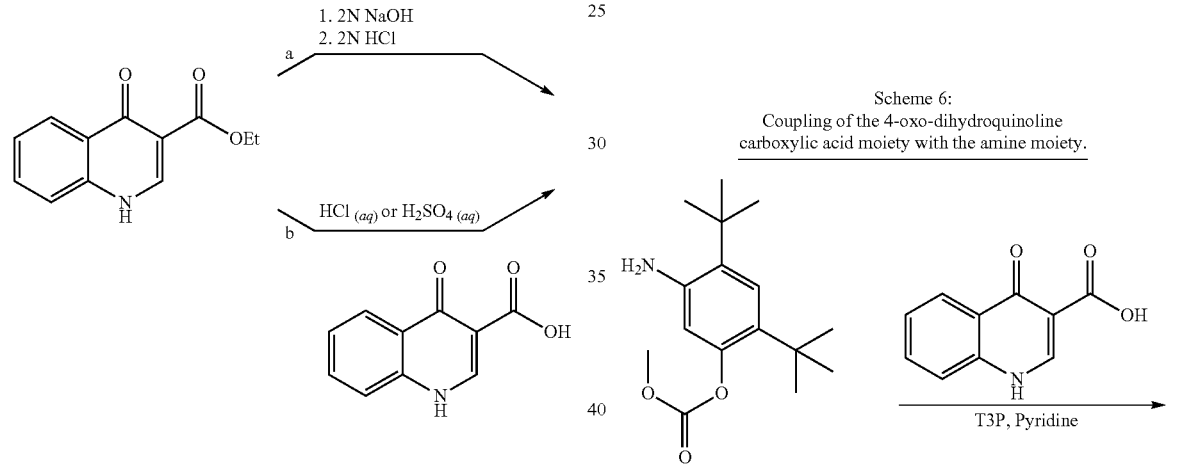
Scheme 5:
Synthesis of the amine moiety.
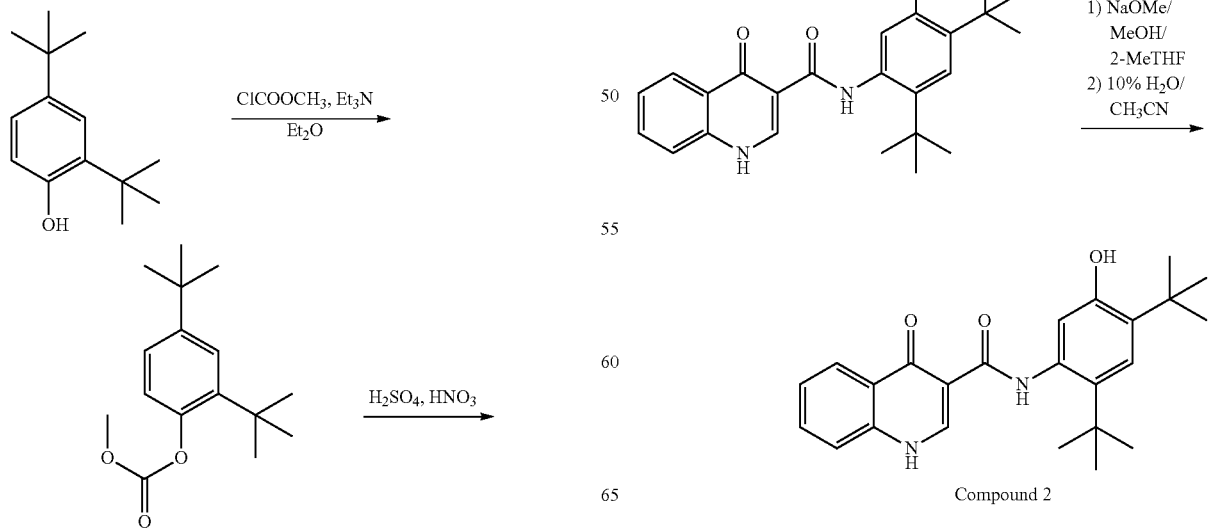
Compound 2

VIII. EXAMPLES

Analytical Methods

1. Differential Scanning calorimetry (DSC)

Referring to FIGS. 2 and 7, the differential scanning calorimetry (DSC) data of spray dried dispersions of the present invention were collected using a DSC Q2000 (TA Instruments, New Castle, DE). Temperature was calibrated with indium and heat capacity was calibrated with sapphire. Samples of 8-15 mg were weighed into T-zero aluminum pans that were crimped using lids with 1 pin hole. The samples were scanned from 20° C. to 250° C. at a heating rate of 2° C./min and with a nitrogen gas purge of 50 ml/min. The reported numbers represent single analyses.

2. Thermogravimetric Analysis (TGA)

Thermal gravimetric analysis (TGA) was performed with a TGA Q500 V6.3 Build 189 (TA Instruments, New Castle, DE). Temperature was equilibrated by Curie point with nickel. Samples of 10-20 mg were scanned from 25° C. to 350° C. at a heating rate of 10° C./min. A nitrogen gas balance purge of 10 ml/min and a sample purge of 90 ml/min were used. Data were collected by Thermal Advantage Q Series™ software version 2.2.0.248 and analyzed by Universal Analysis software version 4.1D (TA Instruments, New Castle, DE). The reported numbers represent single analyses.

3. XRPD (X-Ray Powder Diffraction)

Referring to FIGS. 1 and 6, the X-Ray diffraction (XRD) data of spray dried dispersions of the present invention were collected on a Bruker Advance with Vantec-1 detector. Cu sealed tube with Kα radiation was used at 40 kV, 40 mA. The samples were placed on zero-background silicon wafers at 25° C. For each sample, the 2θ angles ranged from: 3° to 40° for a total of 12 minute scan times.

Example 1: Synthesis of Compound 1: (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide Acid Moiety Synthesis of (2,2-difluoro-1,3-benzodioxol-5-yl)-1-ethylacetate-acetonitrile

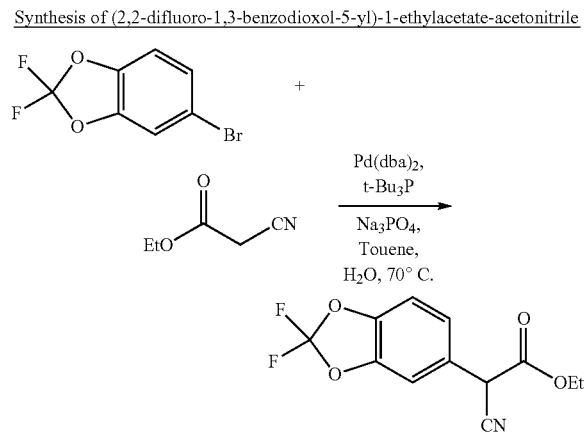

A reactor was purged with nitrogen and charged with 900 mL of toluene. The solvent was degassed via nitrogen sparge for no less than 16 h. To the reactor was then charged Na₃PO₄ (155.7 g, 949.5 mmol), followed by bis(dibenzylideneacetone) palladium (0) (7.28 g, 12.66 mmol). A 10% w/w solution of tert-butylphosphine in hexanes (51.23 g, 25.32 mmol) was charged over 10 min at 23° C. from a nitrogen purged addition funnel. The mixture was allowed to stir for 50 min, at which time 5-bromo-2,2-difluoro-1,3-benzodioxole (75 g, 316.5 mmol) was added over 1 min. After stirring for an additional 50 min, the mixture was charged with ethyl cyanoacetate (71.6 g, 633.0 mmol) over 5 min followed by water (4.5 mL) in one portion. The mixture was heated to 70° C. over 40 min and analyzed by HPLC every 1-2 h for the percent conversion of the reactant to the product. After complete conversion was observed (typically 100% conversion after 5-8 h), the mixture was cooled to 20-25° C. and filtered through a celite pad. The celite pad was rinsed with toluene (2×450 mL) and the combined organics were concentrated to 300 mL under vacuum at 60-65° C. The concentrate was charged with 225 mL DMSO and concentrated under vacuum at 70-80° C. until active distillation of the solvent ceased. The solution was cooled to 20-25° C. and diluted to 900 mL with DMSO in preparation for Step 2. $^1$H NMR (500 MHz, CDCl₃) δ 7.16-7.10 (m, 2H), 7.03 (d, J=8.2 Hz, 1H), 4.63 (s, 1H), 4.19 (m, 2H), 1.23 (t, J=7.1 Hz, 3H).

Synthesis of (2,2-difluoro-1,3-benzodioxol-5-yl)-acetonitrile.

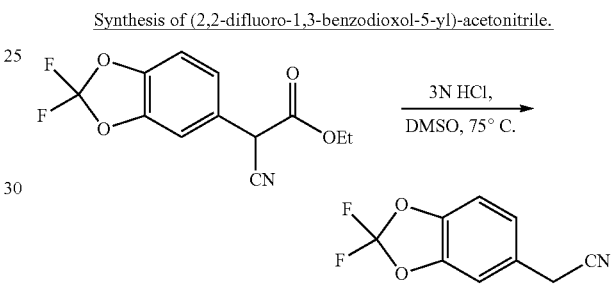

The DMSO solution of (2,2-difluoro-1,3-benzodioxol-5-yl)-1-ethylacetate-acetonitrile from above was charged with 3 N HCl (617.3 mL, 1.85 mol) over 20 min while maintaining an internal temperature<40° C. The mixture was then heated to 75° C. over 1 h and analyzed by HPLC every 1-2 h for percent conversion. When a conversion of >99% was observed (typically after 5-6 h), the reaction was cooled to 20-25° C. and extracted with MTBE (2×525 mL), with sufficient time to allow for complete phase separation during the extractions. The combined organic extracts were washed with 5% NaCl (2×375 mL). The solution was then transferred to equipment appropriate for a 1.5-2.5 Torr vacuum distillation that was equipped with a cooled receiver flask. The solution was concentrated under vacuum at <60° C. to remove the solvents. (2,2-Difluoro-1,3-benzodioxol-5-yl)-acetonitrile was then distilled from the resulting oil at 125-130° C. (oven temperature) and 1.5-2.0 Torr. (2,2-Difluoro-1,3-benzodioxol-5-yl)-acetonitrile was isolated as a clear oil in 66% yield from 5-bromo-2,2-difluoro-1,3-benzodioxole (2 steps) and with an HPLC purity of 91.5% AUC (corresponds to a w/w assay of 95%). $^1$H NMR (500 MHz, DMSO) δ 7.44 (br s, 1H), 7.43 (d, J=8.4 Hz, 1H), 7.22 (dd, J=8.2, 1.8 Hz, 1H), 4.07 (s, 2H).

Synthesis of (2,2-difluoro-1,3-benzodioxol-5-yl)-cyclopropanecarbonitrile.

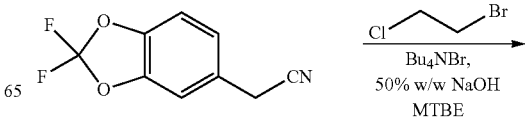

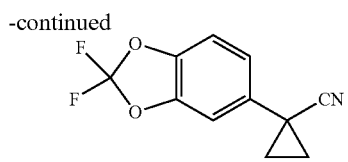

A stock solution of 50% w/w NaOH was degassed via nitrogen sparge for no less than 16 h. An appropriate amount of MTBE was similarly degassed for several hours. To a reactor purged with nitrogen was charged degassed MTBE (143 mL) followed by (2,2-difluoro-1,3-benzodioxol-5-yl)-acetonitrile (40.95 g, 207.7 mmol) and tetrabutylammonium bromide (2.25 g, 10.38 mmol). The volume of the mixture was noted and the mixture was degassed via nitrogen sparge for 30 min. Enough degassed MTBE is charged to return the mixture to the original volume prior to degassing. To the stirring mixture at 23° C. was charged degassed 50% w/w NaOH (143 mL) over 10 min followed by 1-bromo-2-chloroethane (44.7 g, 311.6 mmol) over 30 min. The reaction was analyzed by HPLC in 1 h intervals for percent conversion. Before sampling, stirring was stopped and the phases allowed to separate. The top organic phase was sampled for analysis. When a percent conversion of >99% was observed (typically after 2.5-3 h), the reaction mixture was cooled to 10° C. and was charged with water (461 mL) at such a rate as to maintain a temperature<25° C. The temperature was adjusted to 20-25° C. and the phases separated. Note: sufficient time should be allowed for complete phase separation. The aqueous phase was extracted with MTBE (123 mL), and the combined organic phase was washed with 1 N HCl (163 mL) and 5% NaCl (163 mL). The solution of (2,2-difluoro-1,3-benzodioxol-5-yl)-cyclopropanecarbonitrile in MTBE was concentrated to 164 mL under vacuum at 40-50° C. The solution was charged with ethanol (256 mL) and again concentrated to 164 mL under vacuum at 50-60° C. Ethanol (256 mL) was charged and the mixture concentrated to 164 mL under vacuum at 50-60° C. The resulting mixture was cooled to 20-25° C. and diluted with ethanol to 266 mL in preparation for the next step. ¹H NMR (500 MHz, DMSO) δ 7.43 (d, J=8.4 Hz, 1H), 7.40 (d, J=1.9 Hz, 1H), 7.30 (dd, J=8.4, 1.9 Hz, 1H), 1.75 (m, 2H), 1.53 (m, 2H).

Synthesis of 1-(2,2-difluoro-1,3-benzodioxol-5-yl)-cyclopropanecarboxylic acid.

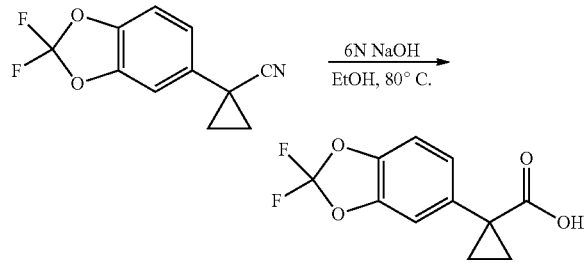

The solution of (2,2-difluoro-1,3-benzodioxol-5-yl)-cyclopropanecarbonitrile in ethanol from the previous step was charged with 6 N NaOH (277 mL) over 20 min and heated to an internal temperature of 77-78° C. over 45 min. The reaction progress was monitored by HPLC after 16 h. Note: the consumption of both (2,2-difluoro-1,3-benzodioxol-5-yl)-cyclopropanecarbonitrile and the primary amide resulting from partial hydrolysis of (2,2-difluoro-1,3-benzodioxol-5-yl)-cyclopropanecarbonitrile were monitored. When a percent conversion of >99% was observed (typically 100% conversion after 16 h), the reaction mixture was cooled to 25° C. and charged with ethanol (41 mL) and DCM (164 mL). The solution was cooled to 10° C. and charged with 6 N HCl (290 mL) at such a rate as to maintain a temperature<25° C. After warming to 20-25° C., the phases were allowed to separate. The bottom organic phase was collected and the top aqueous phase was back extracted with DCM (164 mL). Note: the aqueous phase was somewhat cloudy before and after the extraction due to a high concentration of inorganic salts. The organics were combined and concentrated under vacuum to 164 mL. Toluene (328 mL) was charged and the mixture condensed to 164 mL at 70-75° C. The mixture was cooled to 45° C., charged with MTBE (364 mL) and stirred at 60° C. for 20 min. The solution was cooled to 25° C. and polish filtered to remove residual inorganic salts. MTBE (123 mL) was used to rinse the reactor and the collected solids. The combined organics were transferred to a clean reactor in preparation for the next step.

Isolation of 1-(2,2-difluoro-1,3-benzodioxol-5-yl)-cyclopropanecarboxylic acid.

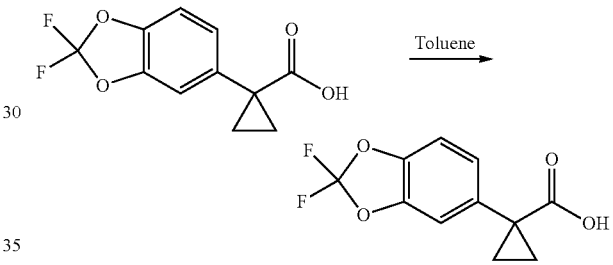

The solution of 1-(2,2-difluoro-1,3-benzodioxol-5-yl)-cyclopropanecarboxylic acid from the previous step is concentrated under vacuum to 164 mL, charged with toluene (328 mL) and concentrated to 164 mL at 70-75° C. The mixture was then heated to 100-105° C. to give a homogeneous solution. After stirring at that temperature for 30 min, the solution was cooled to ° C. over 2 hours and maintained at 5° C. for 3 hours. The mixture was then filtered and the reactor and collected solid washed with cold 1:1 toluene/n-heptane (2×123 mL). The material was dried under vacuum at 55° C. for 17 hours to provide 1-(2,2-difluoro-1,3-benzodioxol-5-yl)-cyclopropanecarboxylic acid as an off-white crystalline solid. 1-(2,2-difluoro-1,3-benzodioxol-acid was isolated in 79% yield from (2,2-difluoro-1,3-benzodioxol-5-yl)-acetonitrile (3 steps including isolation) and with an HPLC purity of 99.0% AUC. ESI-MS m/z calc. 242.04, found 241.58 (M+1)⁺; ¹H NMR (500 MHz, DMSO) δ 12.40 (s, 1H), 7.40 (d, J=1.6 Hz, 1H), 7.30 (d, J=8.3 Hz, 1H), 7.17 (dd, J=8.3, 1.7 Hz, 1H), 1.46 (m, 2H), 1.17 (m, 2H).

Alternative Synthesis of the Acid Moiety

Synthesis of (2,2-difluoro-1,3-benzodioxol-5-yl)-methanol.

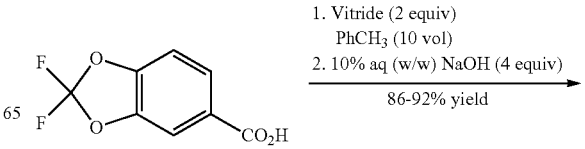

-continued

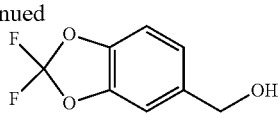

Commercially available 2,2-difluoro-1,3-benzodioxole-5-carboxylic acid (1.0 eq) is slurried in toluene (10 vol). Vitride® (2 eq) is added via addition funnel at a rate to maintain the temperature at 15-25° C. At the end of addition the temperature is increased to 40° C. for 2 h then 10% (w/w) aq. NaOH (4.0 eq) is carefully added via addition funnel maintaining the temperature at 40-50° C. After stirring for an additional 30 minutes, the layers are allowed to separate at ° C. The organic phase is cooled to 20° C. then washed with water (2×1.5 vol), dried (Na$_2$SO$_4$), filtered, and concentrated to afford crude (2,2-difluoro-1,3-benzodioxol-5-yl)-methanol that is used directly in the next step.

Synthesis of 5-chloromethyl-2,2-difluoro-1,3-benzodioxole.

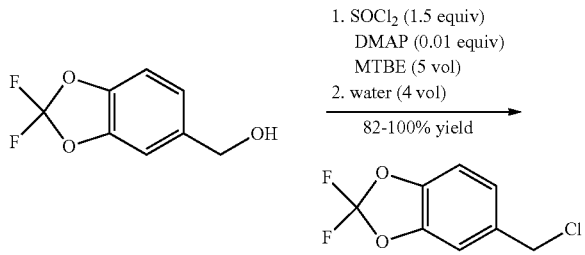

1. SOCl$_2$ (1.5 equiv)
   DMAP (0.01 equiv)
   MTBE (5 vol)
2. water (4 vol)

82-100% yield (2,2-difluoro-1,3-benzodioxol-5-yl)-methanol (1.0 eq) is dissolved in MTBE (5 vol). A catalytic amount of DMAP (1 mol %) is added and SOCl$_2$ (1.2 eq) is added via addition funnel. The SOCl$_2$ is added at a rate to maintain the temperature in the reactor at 15-25° C. The temperature is increased to 30° C. for 1 hour then cooled to 20° C. then water (4 vol) is added via addition funnel maintaining the temperature at less than 30° C. After stirring for an additional 30 minutes, the layers are allowed to separate. The organic layer is stirred and 10% (w/v) aq. NaOH (4.4 vol) is added. After stirring for 15 to 20 minutes, the layers are allowed to separate. The organic phase is then dried (Na$_2$SO$_4$), filtered, and concentrated to afford crude 5-chloromethyl-2,2-difluoro-1,3-benzodioxole that is used directly in the next step.

Synthesis of (2,2-difluoro-1,3-benzodioxol-5-yl)-acetonitrile.

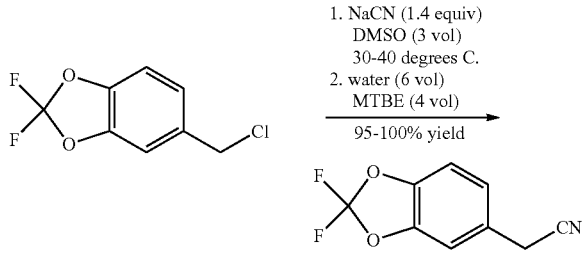

1. NaCN (1.4 equiv)
   DMSO (3 vol)
   30-40 degrees C.
2. water (6 vol)
   MTBE (4 vol)

95-100% yield

A solution of 5-chloromethyl-2,2-difluoro-1,3-benzodioxole (1 eq) in DMSO (1.25 vol) is added to a slurry of NaCN (1.4 eq) in DMSO (3 vol) maintaining the temperature between 30-40° C. The mixture is stirred for 1 hour then water (6 vol) is added followed by MTBE (4 vol). After stirring for 30 min, the layers are separated. The aqueous layer is extracted with MTBE (1.8 vol). The combined organic layers are washed with water (1.8 vol), dried (Na$_2$SO$_4$), filtered, and concentrated to afford crude (2,2-difluoro-1,3-benzodioxol-5-yl)-acetonitrile (95%) that is used directly in the next step.

The remaining steps are the same as described above for the synthesis of the acid moiety.

Amine Moiety

Synthesis of 2-bromo-5-fluoro-4-nitroaniline.

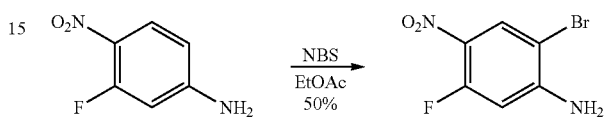

A flask was charged with 3-fluoro-4-nitroaniline (1.0 equiv) followed by ethyl acetate (10 vol) and stirred to dissolve all solids. N-Bromosuccinimide (1.0 equiv) was added as a portion-wise as to maintain internal temperature of 22° C. At the end of the reaction, the reaction mixture was concentrated in vacuo on a rotavap. The residue was slurried in distilled water (5 vol) to dissolve and remove succinimide. (The succinimide can also be removed by water workup procedure.) The water was decanted and the solid was slurried in 2-propanol (5 vol) overnight. The resulting slurry was filtered and the wetcake was washed with 2-propanol, dried in vacuum oven at 50° C. overnight with N$_2$ bleed until constant weight was achieved. A yellowish tan solid was isolated (50% yield, 97.5% AUC). Other impurities were a bromo-regioisomer (1.4% AUC) and a di-bromo adduct (1.1% AUC). $^1$H NMR (500 MHz, DMSO) δ 8.19 (1H, d, J=8.1 Hz), 7.06 (br. s, 2H), 6.64 (d, 1H, J=14.3 Hz).

Synthesis of p-toluenesulfonic acid salt of (R)-1-((4-amino-2-bromo-5-fluorophenyl)amino)-3-(benzyloxy)propan-2-ol.

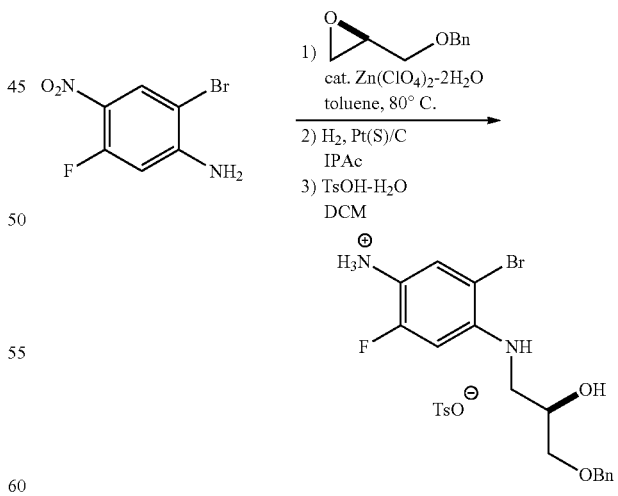

A thoroughly dried flask under N$_2$ was charged with the following: Activated powdered 4A molecular sieves (50 wt % based on 2-bromo-5-fluoro-4-nitroaniline), 2-Bromo-5-fluoro-4-nitroaniline (1.0 equiv), zinc perchlorate dihydrate (20 mol %), and toluene (8 vol). The mixture was stirred at room temperature for NMT 30 min. Lastly, (R)-benzyl glycidyl ether (2.0 equiv) in toluene (2 vol) was added in a steady stream. The reaction was heated to 80° C. (internal temperature) and stirred for approximately 7 hours or until 2-bromo-5-fluoro-4-nitroaniline was <5% AUC.

The reaction was cooled to room temperature and celite (50 wt %) was added, followed by ethyl acetate (10 vol). The resulting mixture was filtered to remove celite and sieves and washed with ethyl acetate (2 vol). The filtrate was washed with ammonium chloride solution (4 vol, 20% w/v). The organic layer was washed with sodium bicarbonate solution (4 vol×2.5% w/v). The organic layer was concentrated in vacuo on a rotovap. The resulting slurry was dissolved in isopropyl acetate (10 vol) and this solution was transferred to a Buchi hydrogenator.

The hydrogenator was charged with 5 wt % Pt(S)/C (1.5 mol %) and the mixture was stirred under N₂ at 30° C. (internal temperature). The reaction was flushed with N₂ followed by hydrogen. The hydrogenator pressure was adjusted to 1 bar of hydrogen and the mixture was stirred rapidly (>1200 rpm). At the end of the reaction, the catalyst was filtered through a pad of Celite and washed with dichloromethane (10 vol). The filtrate was concentrated in vacuo. Any remaining isopropyl acetate was chased with dichloromethane (2 vol) and concentrated on a rotavap to dryness.

The resulting residue was dissolved in dichloromethane (10 vol). p-Toluenesulfonic acid monohydrate (1.2 equiv) was added and stirred overnight. The product was filtered and washed with dichloromethane (2 vol) and suction dried. The wetcake was transferred to drying trays and into a vacuum oven and dried at 45° C. with N₂ bleed until constant weight was achieved. p-Toluenesulfonic acid salt of (R)-1-((4-amino-2-bromo-5-fluorophenyl)amino)-3-(benzyloxy)propan-2-ol was isolated as an off-white solid.

Chiral purity was determined to be >97% ee.

Synthesis of (3-Chloro-3-methylbut-1-ynyl)trimethylsilane.

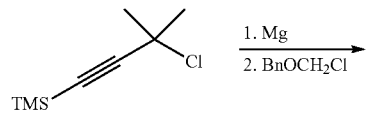

Propargyl alcohol (1.0 equiv) was charged to a vessel. Aqueous hydrochloric acid (37%, 3.75 vol) was added and stirring begun. During dissolution of the solid alcohol, a modest endotherm (5-6° C.) is observed. The resulting mixture was stirred overnight (16 h), slowly becoming dark red. A 30 L jacketed vessel is charged with water (5 vol) which is then cooled to 10° C. The reaction mixture is transferred slowly into the water by vacuum, maintaining the internal temperature of the mixture below 25° C. Hexanes (3 vol) is added and the resulting mixture is stirred for 0.5 h. The phases were settled and the aqueous phase (pH<1) was drained off and discarded. The organic phase was concentrated in vacuo using a rotary evaporator, furnishing the product as red oil.

Synthesis of (4-(Benzyloxy)-3,3-dimethylbut-1-ynyl)trimethylsilane.

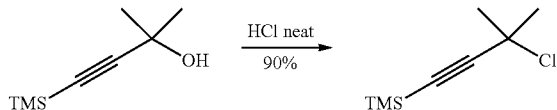

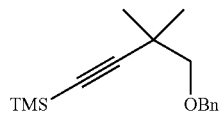

Method 1A.

All equivalent and volume descriptors in this part are based on a 250 g reaction. Magnesium turnings (69.5 g, 2.86 mol, 2.0 equiv) were charged to a 3 L 4-neck reactor and stirred with a magnetic stirrer under nitrogen for 0.5 h. The reactor was immersed in an ice-water bath. A solution of the propargyl chloride (250 g, 1.43 mol, 1.0 equiv) in THF (1.8 L, 7.2 vol) was added slowly to the reactor, with stirring, until an initial exotherm (~10° C.) was observed. The Grignard reagent formation was confirmed by IPC using ¹H-NMR spectroscopy. Once the exotherm subsided, the remainder of the solution was added slowly, maintaining the batch temperature<15° C. The addition required ~3.5 h. The resulting dark green mixture was decanted into a 2 L capped bottle.

All equivalent and volume descriptors in this part are based on a 500 g reaction. A 22 L reactor was charged with a solution of benzyl chloromethyl ether (95%, 375 g, 2.31 mol, 0.8 equiv) in THF (1.5 L, 3 vol). The reactor was cooled in an ice-water bath. Two Grignard reagent batches prepared as described above were combined and then added slowly to the benzyl chloromethyl ether solution via an addition funnel, maintaining the batch temperature below 25° C. The addition required 1.5 h. The reaction mixture was stirred overnight (16 h).

All equivalent and volume descriptors in this part are based on a 1 kg reaction. A solution of 15% ammonium chloride was prepared in a 30 L jacketed reactor (1.5 kg in 8.5 kg of water, 10 vol). The solution was cooled to 5° C. Two Grignard reaction mixtures prepared as described above were combined and then transferred into the ammonium chloride solution via a header vessel. An exotherm was observed in this quench, which was carried out at a rate such as to keep the internal temperature below 25° C. Once the transfer was complete, the vessel jacket temperature was set to 25° C. Hexanes (8 L, 8 vol) was added and the mixture was stirred for 0.5 h. After settling the phases, the aqueous phase (pH 9) was drained off and discarded. The remaining organic phase was washed with water (2 L, 2 vol). The organic phase was concentrated in vacuo using a 22 L rotary evaporator, providing the crude product as an orange oil.

Method 1B.

Magnesium turnings (106 g, 4.35 mol, 1.0 eq) were charged to a 22 L reactor and then suspended in THF (760 mL, 1 vol). The vessel was cooled in an ice-water bath such that the batch temperature reached 2° C. A solution of the propargyl chloride (760 g, 4.35 mol, 1.0 equiv) in THF (4.5 L, 6 vol) was added slowly to the reactor. After 100 mL was added, the addition was stopped and the mixture stirred until a 13° C. exotherm was observed, indicating the Grignard reagent initiation. Once the exotherm subsided, another 500 mL of the propargyl chloride solution was added slowly, maintaining the batch temperature<20° C. The Grignard reagent formation was confirmed by IPC using ¹H-NMR spectroscopy. The remainder of the propargyl chloride solution was added slowly, maintaining the batch temperature<20° C. The addition required ~1.5 h. The resulting dark green solution was stirred for 0.5 h. The Grignard reagent formation was confirmed by IPC using ¹H-NMR spectroscopy. Neat benzyl chloromethyl ether was charged to the reactor addition funnel and then added dropwise into the reactor, maintaining the batch temperature below 25° C. The addition required 1.0 h. The reaction mixture was stirred overnight. The aqueous work-up and concentration was carried out using the same procedure and relative amounts of materials as in Method A to give the product as an orange oil.

Syntheisis of 4-Benzyloxy-3,3-dimethylbut-1-yne.

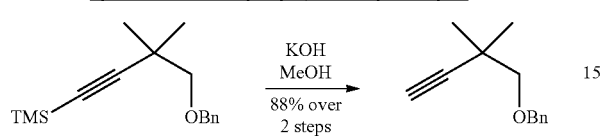

A 30 L jacketed reactor was charged with methanol (6 vol) which was then cooled to 5° C. Potassium hydroxide (85%, 1.3 equiv) was added to the reactor. A 15-20° C. exotherm was observed as the potassium hydroxide dissolved. The jacket temperature was set to 25° C. A solution of 4-benzyloxy-3,3-dimethyl-1-trimethylsilylbut-1-yne (1.0 equiv) in methanol (2 vol) was added and the resulting mixture was stirred until reaction completion, as monitored by HPLC. Typical reaction time at 25° C. is 3-4 h. The reaction mixture is diluted with water (8 vol) and then stirred for 0.5 h. Hexanes (6 vol) was added and the resulting mixture was stirred for 0.5 h. The phases were allowed to settle and then the aqueous phase (pH 10-11) was drained off and discarded. The organic phase was washed with a solution of KOH (85%, 0.4 equiv) in water (8 vol) followed by water (8 vol). The organic phase was then concentrated down using a rotary evaporator, yielding the title material as a yellow-orange oil. Typical purity of this material is in the 80% range with primarily a single impurity present. $^1$H NMR (400 MHz, $C_6D_6$) δ 7.28 (d, 2H, J=7.4 Hz), 7.18 (t, 2H, J=7.2 Hz), 7.10 (d, 1H, J=7.2 Hz), 4.35 (s, 2H), 3.24 (s, 2H), 1.91 (s, 1H), 1.25 (s, 6H).

Synthesis of N-benzylglycolated-5-amino-2-(2-benzyloxy-1,1-dimethylethyl)-6-fluoroindole Method 1C.

Synthesis of (R)-1-((4-amino-2-(4-(benzyloxy)-3,3-dimethylbut-1-yn-1-yl)-5-fluorophenyl)amino)-3-(benzyloxy)propan-2-ol.

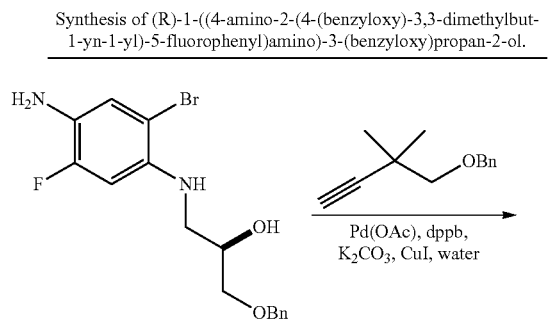

-continued

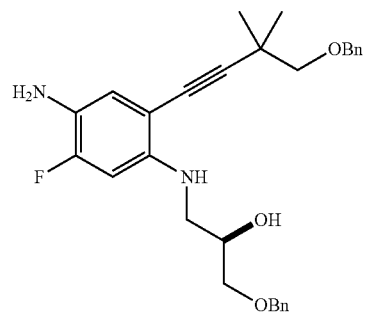

p-Toluenesulfonic acid salt of (R)-1-((4-amino-2-bromo-5-fluorophenyl)amino)-3-(benzyloxy)propan-2-ol was free-based by stirring the solid in dichloromethane (5 vol) and saturated $NaHCO_3$ solution (5 vol) until clear organic layer was achieved. The resulting layers were separated and the organic layer was washed with saturated $NaHCO_3$ solution (5 vol) followed by brine and concentrated in vacuo to obtain (R)-1-((4-amino-2-bromo-5-fluorophenyl)amino)-3-(benzyloxy)propan-2-ol free base as an oil.

Palladium acetate (0.01 eq), dppb (0.015 eq), CuI (0.015 eq) and potassium carbonate (3 eq) are suspended in acetonitrile (1.2 vol). After stirring for 15 minutes, a solution of 4-benzyloxy-3,3-dimethylbut-1-yne (1.1 eq) in acetonitrile (0.2 vol) is added. The mixture is sparged with nitrogen gas for 1 h and then a solution of (R)-1-((4-amino-2-bromo-5-fluorophenyl)amino)-3-(benzyloxy)propan-2-ol free base (1 eq) in acetonitrile (4.1 vol) is added. The mixture is sparged with nitrogen gas for another hour and then is heated to 80° C. Reaction progress is monitored by HPLC and the reaction is usually complete within 3-5 h. The mixture is cooled to room temperature and then filtered through Celite. The cake is washed with acetonitrile (4 vol). The combined filtrates are azeotroped to dryness and then the mixture is polish filtered into the next reactor. The acetonitrile solution of (R)-1-((4-amino-2-(4-(benzyloxy)-3,3-dimethylbut-1-yn-1-yl)-5-fluorophenyl)amino)-3-(benzyloxy)propan-2-ol thus obtained is used directly in the next procedure (cyclization) without further manipulation.

Synthesis of N-benzylglycolated-5-amino-2-(2-benzyloxy-1,1-dimethylethyl)-6-fluoroindole.

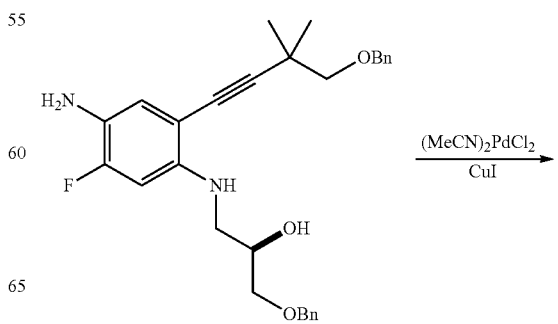

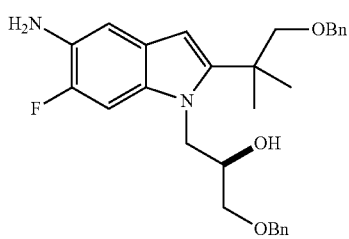

Bis-acetonitriledichloropalladium (0.1 eq) and CuI (0.1 eq) are charged to the reactor and then suspended in a solution of (R)-1-((4-amino-2-(4-(benzyloxy)-3,3-dimethyl-but-1-yn-1-yl)-5-fluorophenyl)amino)-3-(benzyloxy)propan-2-ol obtained above (1 eq) in acetonitrile (9.5 vol total). The mixture is sparged with nitrogen gas for 1 h and then is heated to 80° C. The reaction progress is monitored by HPLC and the reaction is typically complete within 1-3 h. The mixture is filtered through celite and the cake is washed with acetonitrile. A solvent swap into ethyl acetate (7.5 vol) is performed. The ethyl acetate solution is washed with aqueous $NH_3$—$NH_4Cl$ solution (2×2.5 vol) followed by 10% brine (2.5 vol). The ethyl acetate solution is then stirred with silica gel (1.8 wt eq) and Si-TMT (0.1 wt eq) for 6 h. After filtration, the resulting solution is concentrated down. The residual oil is dissolved in DCM/heptane (4 vol) and then purified by column chromatography. The oil thus obtained is then crystallized from 25% EtOAc/heptane (4 vol). Crystalline (R)-1-(5-amino-2-(1-(benzyloxy)-2-methylpropan-2-yl)-6-fluoro-1H-indol-1-yl)-3-(benzyloxy)propan-2-ol is typically obtained in 27-38% yield. $^1$H NMR (400 MHz, DMSO) δ 7.38-7.34 (m, 4H), 7.32-7.23 (m, 6H), 7.21 (d, 1H, J=12.8 Hz), 6.77 (d, 1H, J=9.0 Hz), 6.06 (s, 1H), 5.13 (d, 1H, J=4.9 Hz), 4.54 (s, 2H), 4.46 (br. s, 2H), 4.45 (s, 2H), 4.33 (d, 1H, J=12.4 Hz), 4.09-4.04 (m, 2H), 3.63 (d, 1H, J=9.2 Hz), 3.56 (d, 1H, J=9.2 Hz), 3.49 (dd, 1H, J=9.8, 4.4 Hz), 3.43 (dd, 1H, J=9.8, 5.7 Hz), 1.40 (s, 6H).

Synthesis of N-benzylglycolated-5-amino-2-(2-benzyloxy-1,1-dimethylethyl)-6-fluoroindole.
Method 1D.

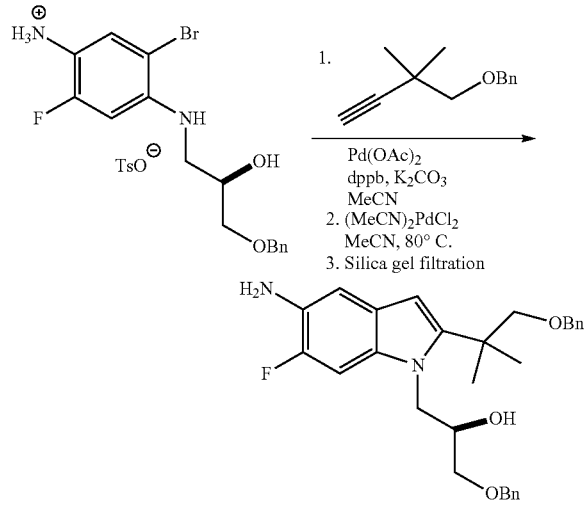

Palladium acetate (33 g, 0.04 eq), dppb (94 g, 0.06 eq), and potassium carbonate (1.5 kg, 3.0 eq) are charged to a reactor. The free based oil benzylglocolated 4-ammonium-2-bromo-5-flouroaniline (1.5 kg, 1.0 eq) was dissolved in acetonitrile (8.2 L, 4.1 vol) and then added to the reactor. The mixture was sparged with nitrogen gas for NLT 1 h. A solution of 4-benzyloxy-3,3-dimethylbut-1-yne (70%, 1.1 kg, 1.05 eq) in acetonitrile was added to the mixture which was then sparged with nitrogen gas for NLT 1 h. The mixture was heated to 80° C. and then stirred overnight. IPC by HPLC is carried out and the reaction is determined to be complete after 16 h. The mixture was cooled to ambient temperature and then filtered through a pad of celite (228 g). The reactor and celite pad were washed with acetonitrile (2×2 L, 2 vol). The combined phases are concentrated on a 22 L rotary evaporator until 8 L of solvent have been collected, leaving the crude product in 7 L (3.5 vol) of acetonitrile.

Bis-acetonitriledichloropalladium (144 g, 0.15 eq) was charged to the reactor. The crude solution was transferred back into the reactor and the roto-vap bulb was washed with acetonitrile (4 L, 2 vol). The combined solutions were sparged with nitrogen gas for NLT 1 h. The reaction mixture was heated to 80° C. for NLT 16 h. In process control by HPLC shows complete consumption of starting material. The reaction mixture was filtered through celite (300 g). The reactor and filter cake were washed with acetonitrile (3 L, 1.5 vol). The combined filtrates were concentrated to an oil by rotary evaporation. The oil was dissolved in ethyl acetate (8.8 L, 4.4 vol). The solution was washed with 20% ammonium chloride (5 L, 2.5 vol) followed by 5% brine (5 L, 2.5 vol). Silica gel (3.5 kg, 1.8 wt. eq.) of silica gel was added to the organic phase, which was stirred overnight. Deloxan THP II metal scavenger (358 g) and heptane (17.6 L) were added and the resulting mixture was stirred for NLT 3 h. The mixture was filtered through a sintered glass funnel. The filter cake was washed with 30% ethyl acetate in heptane (25 L). The combined filtrates were concentrated under reduced pressure to give N-benzylglycolated-5-amino-2-(2-benzyloxy-1,1-dimethylethyl)-6-fluoroindole as a brown paste (1.4 kg).

Synthesis of benzyl protected Compound 1.

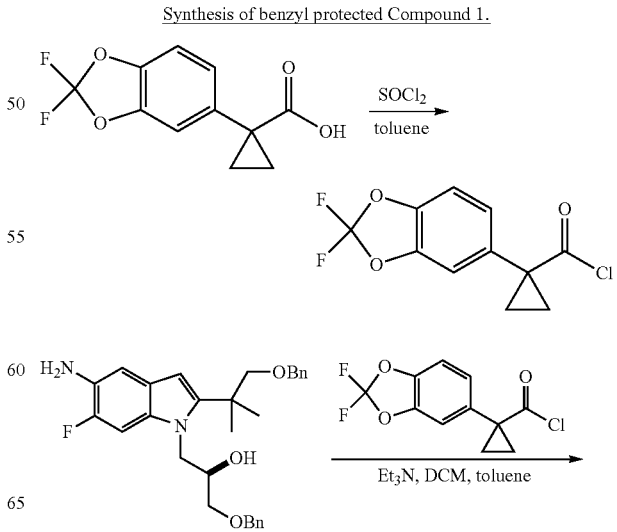

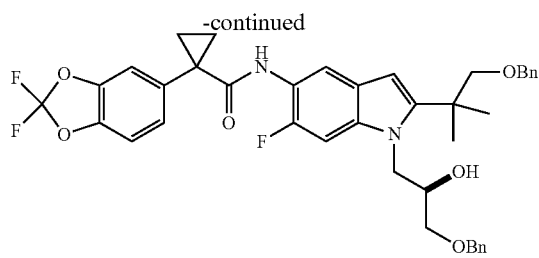

1-(2,2-Difluoro-1,3-benzodioxol-5-yl)-cyclopropanecarboxylic acid (1.3 equiv) was slurried in toluene (2.5 vol, based on 1-(2,2-difluoro-1,3-benzodioxol-5-yl)-cyclopropanecarboxylic acid). Thionyl chloride (SOCl$_2$, 1.7 equiv) was added via addition funnel and the mixture was heated to 60° C. The resulting mixture was stirred for 2 h. The toluene and the excess SOCl$_2$ were distilled off using rotavop. Additional toluene (2.5 vol, based on 1-(2,2-difluoro-1,3-benzodioxol-5-yl)-cyclopropanecarboxylic acid) was added and the mixture was distilled down to 1 vol of toluene. A solution of (R)-1-(5-amino-2-(1-(benzyloxy)-2-methylpropan-2-yl)-6-fluoro-1H-indol-1-yl)-3-(benzyloxy)propan-2-ol (1 eq) and triethylamine (3 eq) in DCM (4 vol) is cooled to 0° C. The acid chloride solution in toluene (1 vol) is added while maintaining the batch temperature below 10° C. The reaction progress is monitored by HPLC, and the reaction is usually complete within minutes. After warming to 25° C., the reaction mixture is washed with 5% NaHCO$_3$ (3.5 vol), 1 M NaOH (3.5 vol) and 1 M HCl (5 vol). A solvent swap to into methanol (2 vol) is performed and the resulting solution of (R)—N-(1-(3-(benzyloxy)-2-hydroxypropyl)-2-(1-(benzyloxy)-2-methylpropan-2-yl)-6-fluoro-1H-indol-5-yl)-1-(2,2-difluorobenzo[d][1,3]dioxol-5-yl)cyclopropanecarboxamide in methanol is used without further manipulation in the next step (hydrogenolysis).

Synthesis of Compound 1.

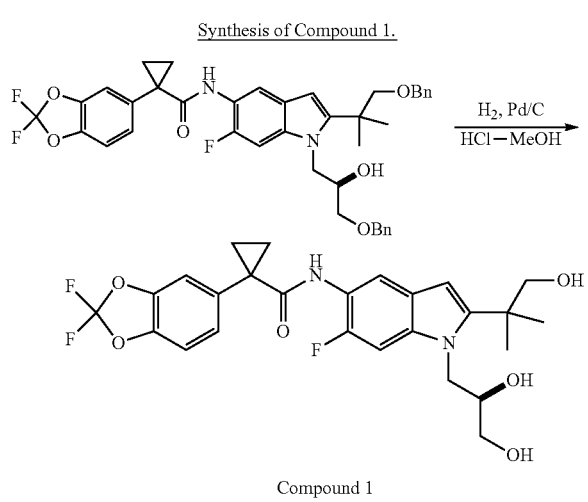

Compound 1

5% palladium on charcoal (~50% wet, 0.01 eq) is charged to an appropriate hydrogenation vessel. The (R)—N-(1-(3-(benzyloxy)-2-hydroxypropyl)-2-(1-(benzyloxy)-2-methylpropan-2-yl)-6-fluoro-1H-indol-5-yl)-1-(2,2-difluorobenzo[d][1,3]dioxol-5-yl)cyclopropanecarboxamide solution in methanol (2 vol) obtained above is added carefully, followed by a 3 M solution of HCl in methanol. The vessel is purged with nitrogen gas and then with hydrogen gas. The mixture is stirred vigorously until the reaction is complete, as determined by HPLC analysis. Typical reaction time is 3-5 h. The reaction mixture is filtered through celite and the cake is washed with methanol (2 vol). A solvent swap into isopropanol (3 vol) is performed. Crude compound 1 is crystallized from 75% IPA-heptane (4 vol, i.e. 1 vol heptane added to the 3 vol of IPA) and the resulting crystals are matured in 50% IPA-heptane (i.e. 2 vol of heptane added to the mixture). Typical yields of compound 4 from the two-step acylation/hydrogenolysis procedure range from 68% to 84%. Compound 4 can be recrystallized from IPA-heptane following the same procedure just described.

Compound 1 may also be prepared by one of several synthetic routes disclosed in US published patent application US20090131492, incorporated herein by reference.

TABLE 7

Physical data for Compound 1.

| Cmpd. No. | LC/ MS M + 1 | LC/ RT min | NMR |
|---|---|---|---|
| 1 | 521.5 | 1.69 | 1H NMR (400.0 MHz, CD$_3$CN) d 7.69 (d, J = 7.7 Hz, 1H), 7.44 (d, J = 1.6 Hz, 1H), 7.39 (dd, J = 1.7, 8.3 Hz, 1H), 7.31 (s, 1H), 7.27 (d, J = 8.3 Hz, 1H), 7.20 (d, J = 12.0 Hz, 1H), 6.34 (s, 1H), 4.32 (d, J = 6.8 Hz, 2H), 4.15-4.09 (m, 1H), 3.89 (dd, J = 6.0, 11.5 Hz, 1H), 3.63-3.52 (m, 3H), 3.42 (d, J = 4.6 Hz, 1H), 3.21 (dd, J = 6.2, 7.2 Hz, 1H), 3.04 (t, J = 5.8 Hz, 1H), 1.59 (dd, J = 3.8, 6.8 Hz, 2H), 1.44 (s, 3H), 1.33 (s, 3H) and 1.18 (dd, J = 3.7, 6.8 Hz, 2H) ppm. |

Example 2: Synthesis of Compound 2: N-[2,4-bis (1,1-dimethylethyl)-5-hydroxyphenyl]-1,4-dihydro-4-oxoquinoline-3-carboxamide Synthesis of 4-oxo-1,4-dihydroquinoline-3-carboxylic acid (26).

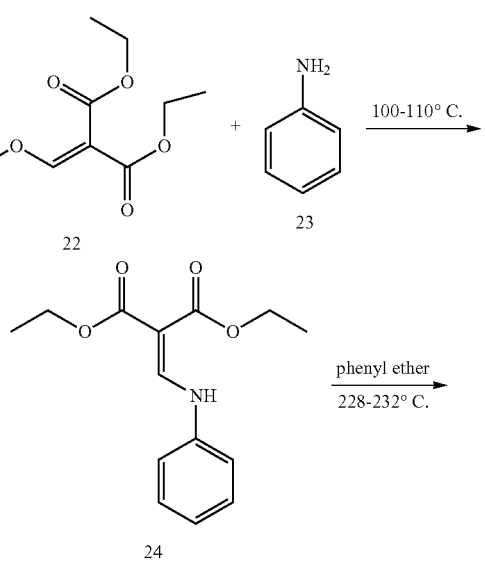

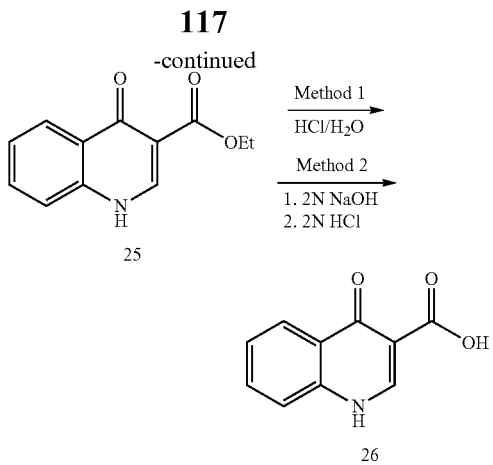

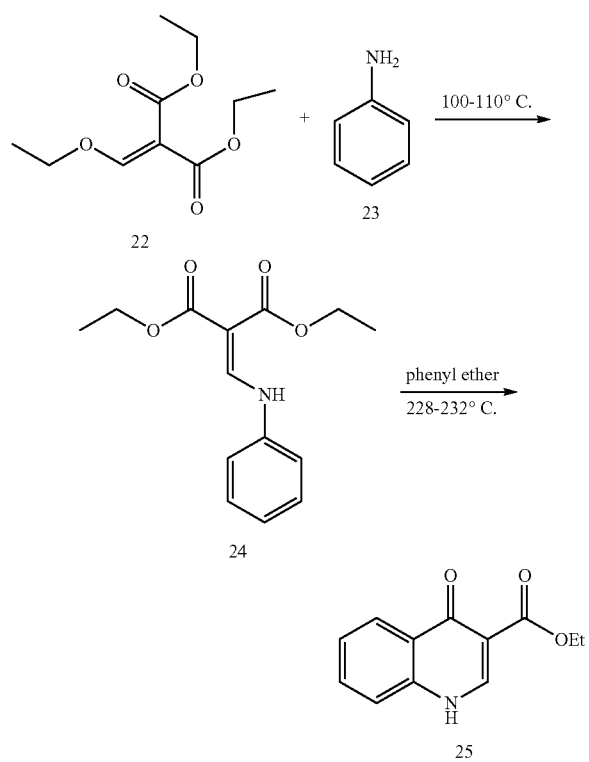

Compound 23 (4.77 g, 47.7 mmol) was added dropwise to compound 22 (10 g, 46.3 mmol) with subsurface Na flow to drive out ethanol below 30° C. for 0.5 hours. The solution was then heated to 100-110° C. and stirred for 2.5 hours. After cooling the mixture to below 60° C., diphenyl ether was added. The resulting solution was added dropwise to diphenyl ether that had been heated to 228-232° C. for 1.5 hours with subsurface Na flow to drive out ethanol. The mixture was stirred at 228-232° C. for another 2 hours, cooled to below 100° C. and then heptane was added to precipitate the product. The resulting slurry was stirred at 30° C. for 0.5 hours. The solids were then filtrated, and the cake was washed with heptane and dried in vacuo to give compound 25 as brown solid. $^1$H NMR (DMSO-d$_6$; 400 MHz) δ 12.25 (s), δ 8.49 (d), δ 8.10 (m), δ 7.64 (m), δ 7.55 (m), δ 7.34 (m), δ 4.16 (q), δ 1.23 (t).

Procedure for the preparation of 4-oxo-1,4-dihydroquinoline-3-carboxylic acid (26).

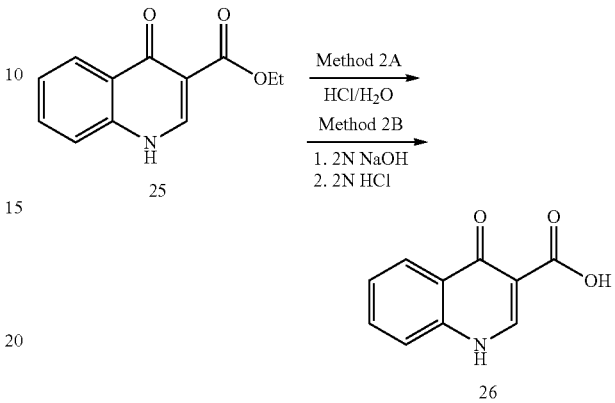

Method 2A.

Compound 25 (1.0 eq) was suspended in a solution of HCl (10.0 eq) and H$_2$O (11.6 vol). The slurry was heated to 85-90° C., although alternative temperatures are also suitable for this hydrolysis step. For example, the hydrolysis can alternatively be performed at a temperature of from about 75 to about 100° C. In some instances, the hydrolysis is performed at a temperature of from about 80 to about 95° C. In others, the hydrolysis step is performed at a temperature of from about 82 to about 93° C. (e.g., from about 82.5 to about 92.5° C. or from about 86 to about 89° C.). After stirring at 85-90° C. for approximately 6.5 hours, the reaction was sampled for reaction completion. Stirring may be performed under any of the temperatures suited for the hydrolysis. The solution was then cooled to 20-25° C. and filtered. The reactor/cake was rinsed with H$_2$O (2 vol×2). The cake was then washed with 2 vol H$_2$O until the pH≥3.0. The cake was then dried under vacuum at 60° C. to give compound 26.

Method 2B.

Compound 25 (11.3 g, 52 mmol) was added to a mixture of 10% NaOH (aq) (10 mL) and ethanol (100 mL). The solution was heated to reflux for 16 hours, cooled to 20-25° C. and then the pH was adjusted to 2-3 with 8% HCl. The mixture was then stirred for 0.5 hours and filtered. The cake was washed with water (50 mL) and then dried in vacuo to give compound 26 as a brown solid. $^1$H NMR (DMSO-d$_6$; 400 MHz) δ 15.33 (s), δ 13.39 (s), δ 8.87 (s), δ 8.26 (m), δ 7.87 (m), δ 7.80 (m), δ 7.56 (m).

Total synthesis of N-(2,4-di-tert-butyl-5-hydroxyphenyl)-4-oxo-1,4-dihydroquinoline-3-carboxamide (Compound 2).

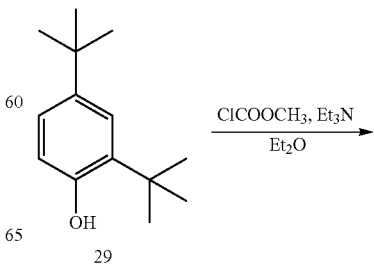

-continued

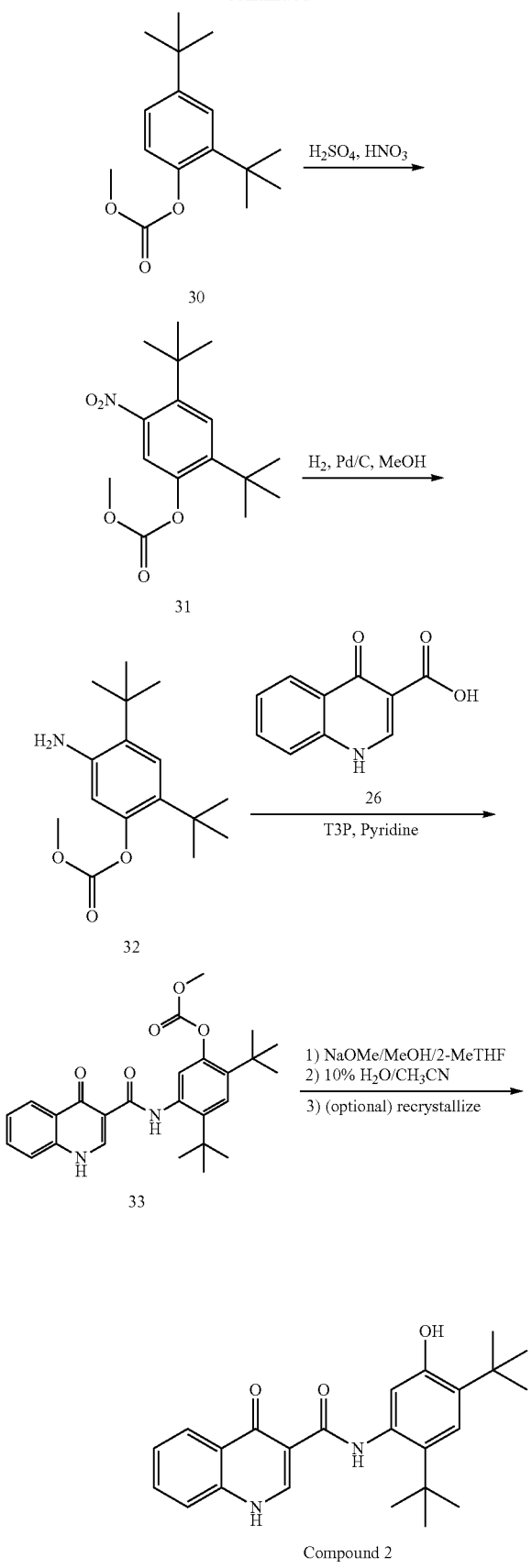

Procedure for the preparation of 2,4-di-tert-butylphenyl methyl carbonate (30).

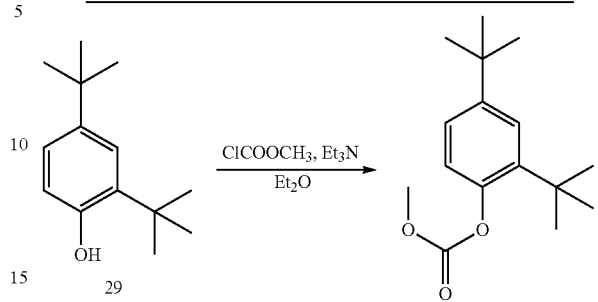

Method 2C.

To a solution of 2,4-di-tert-butyl phenol, 29, (10 g, 48.5 mmol) in diethyl ether (100 mL) and triethylamine (10.1 mL, 72.8 mmol), was added methyl chloroformate (7.46 mL, 97 mmol) dropwise at 0° C. The mixture was then allowed to warm to room temperature and stir for an additional 2 hours. An additional 5 mL triethylamine and 3.7 mL methyl chloroformate was then added and the reaction stirred overnight. The reaction was then filtered, the filtrate was cooled to 0° C., and an additional 5 mL triethylamine and 3.7 mL methyl chloroformate was then added and the reaction was allowed to warm to room temperature and then stir for an addition 1 hours. At this stage, the reaction was almost complete and was worked up by filtering, then washing with water (2×), followed by brine. The solution was then concentrated to produce a yellow oil and purified using column chromatography to give compound 30. $^1$H NMR (400 MHz, DMSO-$d_6$) δ 7.35 (d, J=2.4 Hz, 1H), 7.29 (dd, J=8.4, 2.4 Hz, 1H), 7.06 (d, J=8.4 Hz, 1H), 3.85 (s, 3H), 1.30 (s, 9H), 1.29 (s, 9H).

Method 2D.

To a reactor vessel charged with 4-dimethylaminopyridine (DMAP, 3.16 g, 25.7 mmol) and 2,4-di-tertbutyl phenol (compound 29, 103.5 g, 501.6 mmol) was added methylene chloride (415 g, 313 mL) and the solution was agitated until all solids dissolved. Triethylamine (76 g, 751 mmol) was then added and the solution was cooled to 0-5° C. Methyl chloroformate (52 g, 550.3 mmol) was then added dropwise over 2.5-4 hours, while keeping the solution temperature between 0-5° C. The reaction mixture was then slowly heated to 23-28° C. and stirred for 20 hours. The reaction was then cooled to 10-15° C. and charged with 150 mL water. The mixture was stirred at 15-20° C. for 35-45 minutes and the aqueous layer was then separated and extracted with 150 mL methylene chloride. The organic layers were combined and neutralized with 2.5% HCl (aq) at a temperature of 5-20° C. to give a final pH of 5-6. The organic layer was then washed with water and concentrated in vacuo at a temperature below ° C. to 150 mL to give compound 30 in methylene chloride.

Procedure for the preparation of 5-nitro-2,4-di-tert-butylphenyl methyl carbonate (31).

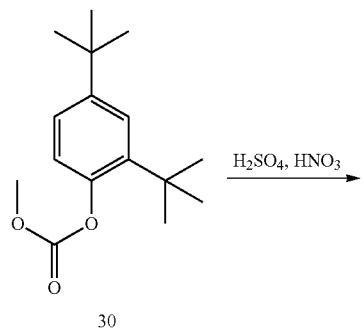

30

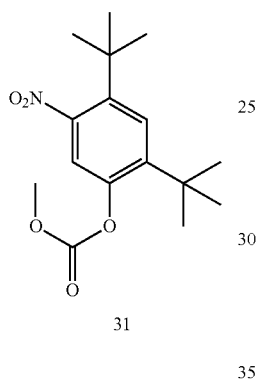

31

Method 2E.

To a stirred solution of compound 30 (6.77 g, 25.6 mmol) was added 6 mL of a 1:1 mixture of sulfuric acid and nitric acid at 0° C. dropwise. The mixture was allowed to warm to room temperature and stirred for 1 hour. The product was purified using liquid chromatography (ISCO, 120 g, 0-7% EtOAc/Hexanes, 38 min) producing about an 8:1-10:1 mixture of regioisomers of compound 31 as a white solid. $^1$H NMR (400 MHz, DMSO-d$_6$) δ 7.63 (s, 1H), 7.56 (s, 1H), 3.87 (s, 3H), 1.36 (s, 9H), 1.32 (s, 9H). HPLC ret. time 3.92 min 10-99% CH$_3$CN, 5 min run; ESI-MS 310 m/z (MH)$^+$.

Method 2F.

To compound 30 (100 g, 378 mmol) was added DCM (540 g, 408 mL). The mixture was stirred until all solids dissolved, and then cooled to −5-0° C. Concentrated sulfuric acid (163 g) was then added dropwise, while maintaining the initial temperature of the reaction, and the mixture was stirred for 4.5 hours. Nitric acid (62 g) was then added dropwise over 2-4 hours while maintaining the initial temperature of the reaction, and was then stirred at this temperature for an additional 4.5 hours. The reaction mixture was then slowly added to cold water, maintaining a temperature below 5° C. The quenched reaction was then heated to 25° C. and the aqueous layer was removed and extracted with methylene chloride. The combined organic layers were washed with water, dried using Na$_2$SO$_4$, and concentrated to 124-155 mL. Hexane (48 g) was added and the resulting mixture was again concentrated to 124-155 mL. More hexane (160 g) was subsequently added to the mixture. The mixture was then stirred at 23-27° C. for 15.5 hours, and was then filtered. To the filter cake was added hexane (115 g), the resulting mixture was heated to reflux and stirred for 2-2.5 hours. The mixture was then cooled to 3-7° C., stirred for an additional 1-1.5 hours, and filtered to give compound 31 as a pale yellow solid.

Procedure for the preparation of 5-amino-2,4-di-tert-butylphenyl methyl carbonate (32).

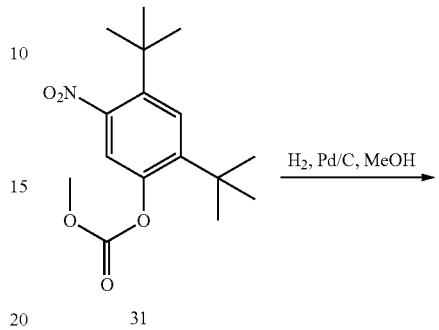

2,4-Di-tert-butyl-5-nitrophenyl methyl carbonate (1.00 eq) was charged to a suitable hydrogenation reactor, followed by 5% Pd/C (2.50 wt % dry basis, Johnson-Matthey Type 37). MeOH (15.0 vol) was charged to the reactor, and the system was closed. The system was purged with N2 (g), and was then pressurized to 2.0 Bar with H$_2$ (g). The reaction was performed at a reaction temperature of 25° C.+/−5° C. When complete, the reaction was filtered, and the reactor/cake was washed with MeOH (4.00 vol). The resulting filtrate was distilled under vacuum at no more than 50° C. to 8.00 vol. Water (2.00 vol) was added at 45° C.+/−5° C. The resultant slurry was cooled to 0° C.+/−5° C. The slurry was held at 0° C.+/−5° C. for no less than 1 hour, and filtered. The cake was washed once with 0° C.+/−5° C. MeOH/H$_2$O (8:2) (2.00 vol). The cake was dried under vacuum (−0.90 bar and −0.86 bar) at 35° C.-40° C. to give compound 32. $^1$H NMR (400 MHz, DMSO-d$_6$) δ 7.05 (s, 1H), 6.39 (s, 1H), 4.80 (s, 2H), 3.82 (s, 3H), 1.33 (s, 9H), 1.23 (s, 9H).

Once the reaction was complete, the resulting mixture was diluted with from about 5 to 10 volumes of MeOH (e.g., from about 6 to about 9 volumes of MeOH, from about 7 to about 8.5 volumes of MeOH, from about 7.5 to about 8 volumes of MeOH, or about 7.7 volumes of MeOH), heated to a temperature of about 35±5° C., filtered, washed, and dried, as described above.

Preparation of N-(2,4-di-tert-butyl-5-hydroxyphenyl)-4-oxo-1,4-dihydroquinoline-3-carboxamide (Compound 2).

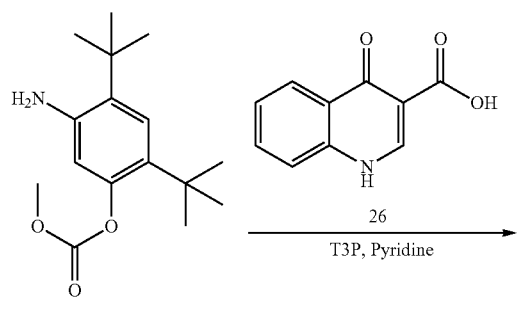

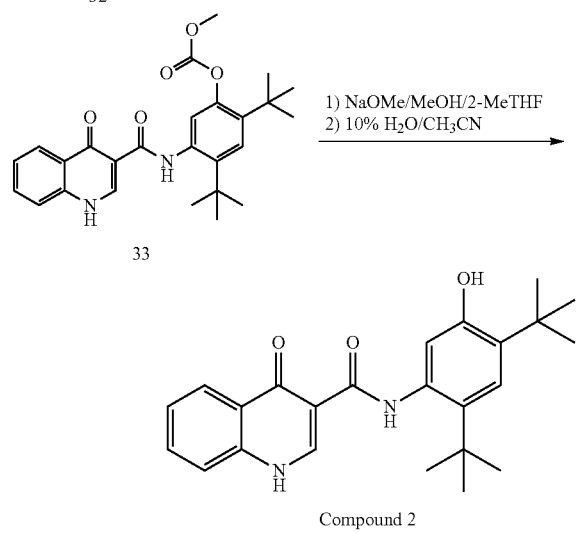

Compound 2

4-Oxo-1,4-dihydroquinoline-3-carboxylic acid, 26, (1.0 eq) and 5-amino-2,4-di-tert-butylphenyl methyl carbonate, 32, (1.1 eq) were charged to a reactor. 2-MeTHF (4.0 vol, relative to the acid) was added followed by T3P° 50% solution in 2-MeTHF (1.7 eq). The T3P charged vessel was washed with 2-MeTHF (0.6 vol). Pyridine (2.0 eq) was then added, and the resulting suspension was heated to 47.5+/−5.0° C. and held at this temperature for 8 hours. A sample was taken and checked for completion by HPLC. Once complete, the resulting mixture was cooled to 25.0° C.+/−2.5° C. 2-MeTHF was added (12.5 vol) to dilute the mixture. The reaction mixture was washed with water (10.0 vol) 2 times. 2-MeTHF was added to bring the total volume of reaction to 40.0 vol (~16.5 vol charged). To this solution was added NaOMe/MeOH (1.7 equiv) to perform the methanolysis. The reaction was stirred for no less than 1.0 hour, and checked for completion by HPLC. Once complete, the reaction was quenched with 1 N HCl (10.0 vol), and washed with 0.1 N HCl (10.0 vol). The organic solution was polish filtered to remove any particulates and placed in a second reactor. The filtered solution was concentrated at no more than 35° C. (jacket temperature) and no less than 8.0° C. (internal reaction temperature) under reduced pressure to 20 vol. CH$_3$CN was added to 40 vol and the solution concentrated at no more than 35° C. (jacket temperature) and no less than 8.0° C. (internal reaction temperature) to 20 vol. The addition of CH$_3$CN and concentration cycle was repeated 2 more times for a total of 3 additions of CH$_3$CN and 4 concentrations to 20 vol. After the final concentration to 20 vol, 16.0 vol of CH$_3$CN was added followed by 4.0 vol of H$_2$O to make a final concentration of 40 vol of 10% H$_2$O/CH$_3$CN relative to the starting acid. This slurry was heated to 78.0° C.+/−5.0° C. (reflux). The slurry was then stirred for no less than 5 hours. The slurry was cooled to 0.0° C.+/−5° C. over 5 hours, and filtered. The cake was washed with 0.0° C.+/−5.0° C. CH$_3$CN (5 vol) 4 times. The resulting solid (Compound 2) was dried in a vacuum oven at 50.0° C.+/−5.0° C. $^1$H NMR (400 MHz, DMSO-d$_6$) δ 12.8 (s, 1H), 11.8 (s, 1H), 9.2 (s, 1H), 8.9 (s, 1H), 8.3 (s, 1H), 7.2 (s, 1H), 7.9 (t, 1H), 7.8 (d, 1H), 7.5 (t, 1H), 7.1 (s, 1H), 1.4 (s, 9H), 1.4 (s, 9H).

Alternative Preparation of N-(2,4-di-tert-butyl-5-hydroxyphenyl)-4-oxo-1,4-dihydroquinoline-3-carboxamide (Coompound 2).

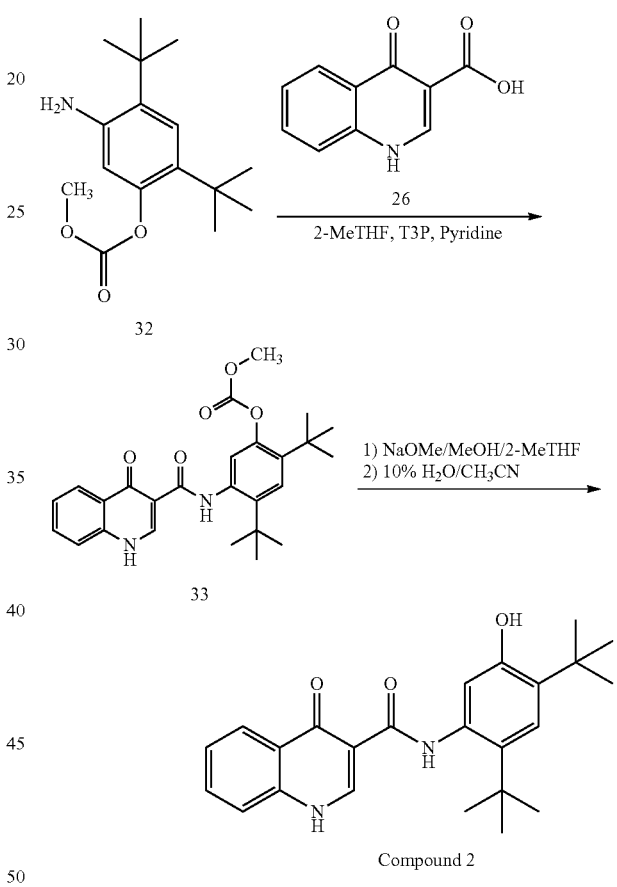

Compound 2

4-Oxo-1,4-dihydroquinoline-3-carboxylic acid, 26, (1.0 eq) and 5-amino-2,4-di-tert-butylphenyl methyl carbonate, 32, (1.1 eq) were charged to a reactor. 2-MeTHF (4.0 vol, relative to the acid) was added followed by T3P® 50% solution in 2-MeTHF (1.7 eq). The T3P charged vessel was washed with 2-MeTHF (0.6 vol). Pyridine (2.0 eq) was then added, and the resulting suspension was heated to 47.5+/−5.0° C. and held at this temperature for 8 hours. A sample was taken and checked for completion by HPLC. Once complete, the resulting mixture was cooled to 20° C.+/−5° C. 2-MeTHF was added (12.5 vol) to dilute the mixture. The reaction mixture was washed with water (10.0 vol) 2 times and 2-MeTHF (16.5 vol) was charged to the reactor. This solution was charged with 30% w/w NaOMe/MeOH (1.7 equiv) to perform the methanolysis. The reaction was stirred at 25.0° C.+/−5.0° C. for no less than 1.0 hour, and checked for completion by HPLC. Once complete, the reaction was quenched with 1.2 N HCl/H$_2$O (10.0 vol), and washed with 0.1 N HCl/H$_2$O (10.0 vol). The organic solution was polish filtered to remove any particulates and placed in a second reactor.

The filtered solution was concentrated at no more than 35° C. (jacket temperature) and no less than 8.0° C. (internal reaction temperature) under reduced pressure to 20 vol. CH$_3$CN was added to 40 vol and the solution concentrated at no more than 35° C. (jacket temperature) and no less than 8.0° C. (internal reaction temperature) to 20 vol. The addition of CH$_3$CN and concentration cycle was repeated 2 more times for a total of 3 additions of CH$_3$CN and 4 concentrations to 20 vol. After the final concentration to 20 vol, 16.0 vol of CH$_3$CN was charged followed by 4.0 vol of H$_2$O to make a final concentration of 40 vol of 10% H$_2$O/CH$_3$CN relative to the starting acid. This slurry was heated to 78.0° C.+/−5.0° C. (reflux). The slurry was then stirred for no less than 5 hours. The slurry was cooled to 20 to 25° C. over 5 hours, and filtered. The cake was washed with CH$_3$CN (5 vol) heated to 20 to 25° C. 4 times. The resulting solid (Compound 2) was dried in a vacuum oven at 50.0° C.+/−5.0° C. $^1$H NMR (400 MHz, DMSO-d$_6$) δ 12.8 (s, 1H), 11.8 (s, 1H), 9.2 (s, 1H), 8.9 (s, 1H), 8.3 (s, 1H), 7.2 (s, 1H), 7.9 (t, 1H), 7.8 (d, 1H), 7.5 (t, 1H), 7.1 (s, 1H), 1.4 (s, 9H), 1.4 (s, 9H).

Procedure for the recrystallization of N-(2,4-di-tert-butyl-5-hydroxyphenyl)-4-oxo-1,4-dihydroquinoline-3-carboxamide (Compound 2)

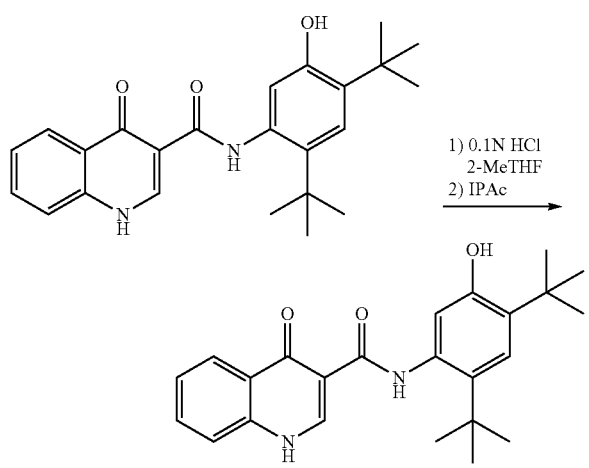

Compound 2 (1.0 eq) was charged to a reactor. 2-MeTHF (20.0 vol) was added followed by 0.1N HCl (5.0 vol). The biphasic solution was stirred and separated and the top organic phase was washed twice more with 0.1N HCl (5.0 vol). The organic solution was polish filtered to remove any particulates and placed in a second reactor. The filtered solution was concentrated at no more than 35° C. (jacket temperature) and no more than 8.0° C. (internal reaction temperature) under reduced pressure to 10 vol. Isopropyl acetate (IPAc) (10 vol) was added and the solution concentrated at no more than 35° C. (jacket temperature) and no more than 8.0° C. (internal reaction temperature) to 10 vol. The addition of IPAc and concentration was repeated 2 more times for a total of 3 additions of IPAc and 4 concentrations to 10 vol. After the final concentration, 10 vol of IPAc was charged and the slurry was heated to reflux and maintained at this temperature for 5 hours. The slurry was cooled to 0.0° C.+/−5° C. over 5 hours and filtered. The cake was washed with IPAc (5 vol) once. The resulting solid was dried in a vacuum oven at 50.0° C.+/−5.0° C.

Example 3: Preparation of Solid Dispersion of Amorphous Compound 1 and Amorphous Compound 2 (1:1) Substantially Free of Polymer 56.5 g of Compound 1 and 56.5 g Compound 2 were added to 895.9 g of 90:10 methyl ethyl ketone (MEK):water in a 2 L amber bottle. The material was stirred until both compounds had dissolved and was spray dried using a Buchi Mini Spray Dryer set to the parameters described below in Table 8:

TABLE 8

50/50 Spray dried dispersion processing parameters.

| Formulation Description: | Compound 1/Compound 2 (50/50) |
|---|---|
| T inlet (setpoint) | 115° C. |
| T outlet (start) | 56° C. |
| T outlet (end) | 42° C. |
| Nitrogen Pressure | 120 psi |
| Aspirator | 100% |
| Pump | 40% |
| Rotometer | 40 mm |
| Filter Pressure | −60 mbar |
| Condenser Temp | −20° C. |
| Run Time | 1 h 17 min |

Figure 5:
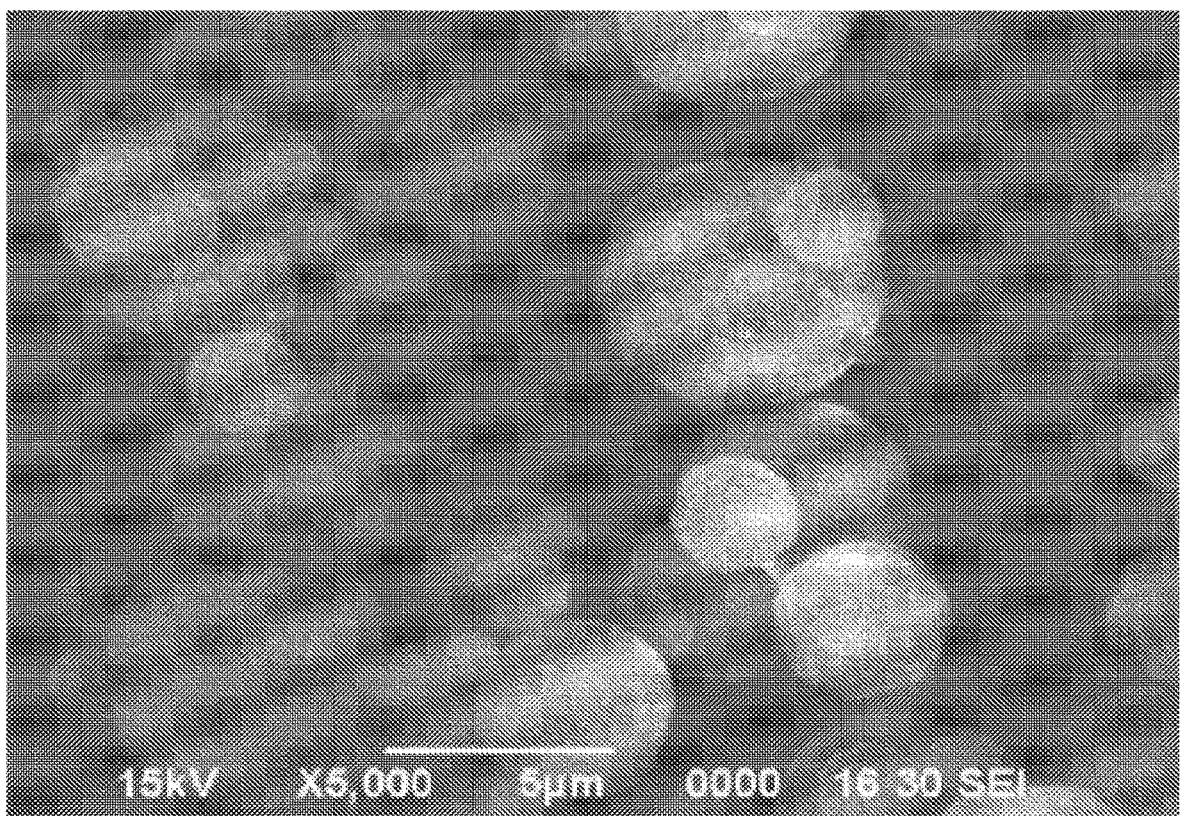
FIG. 5 is an SEM image of the neat spray dried dispersion substantially free of polymer of the present invention formulated with a 1:1 ratio, by weight, of Compound 1 and Compound 2 at 5000×.

The material was secondary dried in a vacuum oven with nitrogen purge for 2 hours at ° C. and overnight at 80° C. FIG. 5 presents an SEM image of this spray dried dispersion. Referring to FIGS. 1 and 2, the amorphous form was confirmed by XRPD and DSC, showing a glass transition temperature of 124° C.

Referring to FIG. 3, the spray dried dispersion underwent solid state NMR analysis for $^1$H-$^1$H spin diffusion on Compound 1 and Compound 2. For the NMR spectrum in FIG. 3, the following solid state NMR parameters were used:

$^{19}$F T$_1$ (spin lattice relaxation time): 7-9 seconds
Spinning: 12.5 kHz
Temp (K): 275
Reference: 29.5 ppm adamantane
D20: 0.1-50 ms As illustrated in the solid state NMR spectrum in FIG. 3, Compound 1 and Compound 2 contact at a molecular level.

Referring to FIG. 4, $^{19}$F and $^{13}$C solid state NMR spectra were recorded for the spray dried dispersion of Compound 1 and Compound 2. FIG. 4 (top) is an overlay of Peak A and Peak B. FIG. 4 (bottom) is peak C.

PEAK A: $^{13}$C CPMAS
Sample Prep: Compound 1 and Compound 2 were cryoground/cryomilled for 100 min.
$^1$H T$_1$: 0.85 s
Spinning: 12.0 kHz
Reference: 29.5 ppm adamantane
Temp (K): 275
PEAK B: $^{13}$C CPMAS
Sample Prep: spray dried dispersion was dried for 72 hr.
$^1$H T$_1$: 0.85 s
Spinning: 12.0 kHz
Reference: 29.5 ppm adamantane
Temp (K): 275
PEAK C: $^{19}$F MAS
Sample Prep: spray dried dispersion was dried for 72 hr.
$^{19}$F T$_1$: 7-9 s Spinning: 12.5 kHz
Reference: 29.5 ppm adamantane
Temp (K): 275
RD: 2 s Thermogravimetric analyses were performed on the spray dried dispersion that underwent the following processing:

Sample A: 3 days at 90° C. under vacuum, followed by N2 purge.

Sample B: 3 days at 40° C.

FIG. 5 presents an SEM image of this spray dried dispersion.

Example 4: Preparation of Solid Dispersion of Amorphous Compound 1 and Amorphous Compound 2 (1:3) Substantially Free of Polymer 29.94 g of Compound 1 and 90.01 g Compound 2 were added to 955.7 g of 90:10 methyl ethyl ketone (MEK):water in a 2 L amber bottle. The material was stirred until both compounds had dissolved and was spray dried using a Buchi mini spray drier set to the parameters described below in Table 9:

TABLE 9

25/75 Spray dried dispersion processing parameters.

| Formulation Description: | Compound 1/Compound 2 (25/75) |
| --- | --- |
| T inlet (setpoint) | 115° C. |
| T outlet (start) | 57° C. |
| T outlet (end) | 47° C. |
| Nitrogen Pressure | 120 psi |
| Aspirator | 100% |
| Pump | 40% |
| Rotometer | 40 mm |
| Filter Pressure | −45 mbar |
| Condenser Temp | 0° C. |
| Run Time | 25 min |

Figure 8:
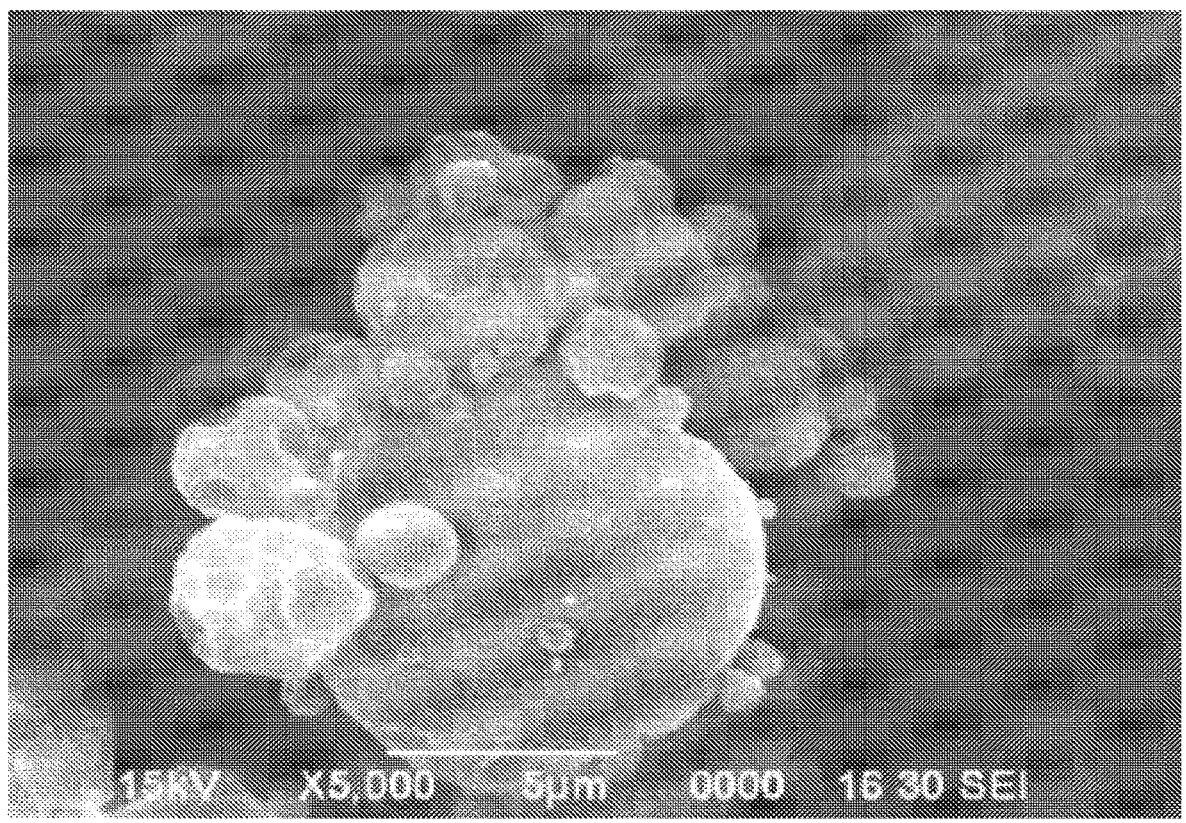
FIG. 8 is an SEM image of the neat spray dried dispersion substantially free of polymer of the present invention formulated with a 1:3 ratio, by weight, of Compound 1 and Compound 2 at 5000×.

700 g of solution was spray dried. The material was secondary dried in a vacuum oven with nitrogen purge overnight at 80° C. Approximately 20 g of amorphous Compound 1 and Compound 2 (26% yield) was recovered. FIG. 8 presents an SEM image of this spray dried dispersion. Referring to FIGS. 6 and 7, the amorphous form was confirmed by XRPD and DSC showing a glass transition temperature of 155° C.

Example 5: Preparation of Solid Dispersion of Amorphous Compound 1 and Amorphous Compound 2 (1:10) Substantially Free of Polymer 2.03 g of Compound 1 and 20.08 g Compound 2 were added to 234.1 g of 90:10 methyl ethyl ketone (MEK):water in a 0.5 L amber bottle. The material was stirred until both compounds had dissolved and was spray dried using a Buchi mini spray dried set to the parameters described below in Table 10:

TABLE 10

9/91 Spray dried dispersion processing parameters.

| Formulation Description: | Compound 1/Compound 2 (9/91) |
| --- | --- |
| T inlet (setpoint) | 120° C. |
| T outlet (start) | 57° C. |
| T outlet (end) | 56° C. |
| Nitrogen Pressure | 120 psi |

TABLE 10-continued

9/91 Spray dried dispersion processing parameters.

| Formulation Description: | Compound 1/Compound 2 (9/91) |
| --- | --- |
| Aspirator | 100% |
| Pump | 35% |
| Rotometer | 40 mm |
| Filter Pressure | −50 mbar |
| Condenser Temp | 2° C. |
| Run Time | 21 min |

Approximately 15 g of amorphous Compound 1 and Compound 2 (68% yield) was recovered. The material was secondary dried in a vacuum oven at 60° C. for 3 days.

Example 6: Preparation of Solid Dispersion of Amorphous Compound 1 and Amorphous Compound 2 (10:1) Substantially Free of Polymer 20.03 g of Compound 1 and 2.04 g Compound 2 were added to 231.1 g of 90:10 methyl ethyl ketone (MEK):water in a 0.5 L amber bottle. The material was stirred until both compounds had dissolved and was spray dried using a Buchi mini spray dried set to the parameters described below in Table 11:

TABLE 11

9/91 Spray drying dispersion processing parameters.

| Formulation Description: | Compound 1/Compound 2 (91/9) |
| --- | --- |
| T inlet (setpoint) | 105° C. |
| T outlet (start) | 48° C. |
| T outlet (end) | 44° C. |
| Nitrogen Pressure | 150 psi |
| Aspirator | 100% |
| Pump | 35% |
| Rotometer | 35 mm |
| Filter Pressure | −50 mbar |
| Condenser Temp | 2° C. |
| Run Time | 20 min |

Approximately 11 g of amorphous Compound 1 and Compound 2 (50% yield) was recovered. The material was secondary dried in a vacuum oven at 60° C. for 3 days. Amorphous form was confirmed by XRPD and DSC.

Example 7: Preparation of Solid Dispersion of Amorphous Compound 1 and Amorphous Compound 2 (1:3) Via Hot Pressure/Hot Temperature Method Compound 1 and compound 2 were spray dried in a 1:3 ratio (25 wt % Compound 1/75 wt % Compound 2) using a solvent system consisting of methanol. The resulting mixture contained 5% solids load. The actual amounts of materials used in this process are listed in Table 12.

TABLE 12

Spray dry materials and amounts.

| Material | Amount (g) |
| --- | --- |
| Compound 1 | 140 |
| Compound 2 | 46.7 |
| Methanol | 3553.0 |

Compound 1 and Compound 2 were added to methanol to form a suspension at room temperature in an appropriately sized vessel. This suspension was delivered to a heat exchanger via a high pressure pump. The solids then dissolve at the target temperature in the heat exchanger before entering the nozzle.

The resulting suspension was spray dried on a PSD1 spray dryer using a Bend research flash atomizer. Spray dryer operating parameters are listed in Table 13.

TABLE 13

Spray dryer operating parameters.

| Function | Parameter Setting |
| --- | --- |
| Atomizer Sheath Gas Pressure (psi) | 50 |
| Feed Pressure (psi) | 283 |
| Feed Rate (g/min) | 129 |
| Inlet Temp (° C.) | 130 |
| Outlet Temp (° C.) | 51 |

Wet SDD was collected and placed in a vacuum tray dryer with a nitrogen sweep gas due to possible oxidation risks. The residual levels of Methanol were tested for over 24 hr until low levels were detected (<10 ppm). Dried material was analyzed for bulk density and particle size resulting in values of 0.24 g/mL and a D50 of 6 μm, respectively.

Example 8: Preparation of a Solid Dispersion Comprising Substantially Amorphous Compound 1 and HPMC Polymer A solvent system of dichloromethane (DCM) and methanol (MeOH), is formulated according to the ratio 80 wt % DCM/20 wt % MeOH, in an appropriately sized container, equipped with a magnetic stirrer and stir plate. Into this solvent system, hypromellose polymer (HPMC, E15 grade) and Compound 1 were added according to the ratio 20 wt % hypromellose/80 wt % Compound 1. The resulting mixture contained 12.5 wt % solids. The actual amounts of ingredients and solvents used to generate this mixture are recited in Table 14, below:

TABLE 14

Solid spray dispersion ingredients for amorphous Compound 1.

|  | Units | Batch |
| --- | --- | --- |
| Compound 1 | g | 2400 |
| HPMC | g | 600 |
| Total Solids | g | 3000 |
| DCM | g | 16800 |
| MeOH | g | 4200 |
| Total Solvents | g | 21000 |
| Total Spray Solution Weight | g | 24000 |

The mixture was mixed until it was substantially homogenous and all components were substantially dissolved.

A spray drier, Anhydro MS-35 Spray Drier, fitted with two fluid 0.8 mm nozzle (Schlick series 970/0 S4), was used under normal spray drying mode, following the dry spray process parameters recited in Table 15, below.

TABLE 15

Spray drying dispersion processing parameters to generate solid spray dispersion of amorphous Compound 1.

| Parameter: | Value: |
| --- | --- |
| Process Gas Flow Rate | 34 Kg/hr |
| Nozzle Gas Flow Rate | 4.2 Kg/hr |
| Feed Flow Rate | 2 Kg/hr |
| Inlet Temperature | 96-108° C. |
| Outlet Temperature | 40° C. |
| Vacuum Dryer Temperature | 45° C. |
| Vacuum Drying Time | 24-72 hours |

A high efficiency cyclone separated the wet product from the spray gas and solvent vapors. The wet product was transferred into trays and placed in vacuum dryer for drying to reduce residual solvents to a level of less than about 3000 ppm for MeOH and less than 600 ppm of DCM and to generate dry spray dry dispersion of amorphous Compound 1, containing <0.02% MeOH and <0.06% DCM.

Example 9: Preparation of a Solid Dispersion Comprising Substantially Amorphous Compound 2 and HPMCAS Polymer A solvent system of MEK and DI water, formulated according to the ratio 90 wt % MEK/10 wt % DI water, was heated to a temperature of 20-30° C. in a reactor, equipped with a magnetic stirrer and thermal circuit. Into this solvent system, hypromellose acetate succinate polymer (HPMCAS)(HG grade), SLS, and Compound 2 were added according to the ratio 19.5 wt % hypromellose acetate succinate/0.5 wt % SLS/80 wt % Compound 2. The resulting mixture contained 10.5 wt % solids. The actual amounts of ingredients and solvents used to generate this mixture are recited in Table 16, below.

TABLE 16

Solid spray dispersion ingredients for amorphous compound 2.

|  | Units | Batch |
| --- | --- | --- |
| Compound 2 | Kg | 70.0 |
| HPMCAS | Kg | 17.1 |
| SLS | Kg | 0.438 |
| Total Solids | Kg | 87.5 |
| MEK | Kg | 671 |
| Water | Kg | 74.6 |
| Total Solvents | Kg | 746 |
| Total Spray Solution Weight | Kg | 833 |

The mixture temperature was adjusted to a range of 20-45° C. and mixed until it was substantially homogenous and all components were substantially dissolved.

A spray drier, Niro PSD4 Commercial Spray Dryer, fitted with pressure nozzle (Spray Systems Maximum Passage series SK-MEP having orifice/core size 54/21) equipped with anti-bearding cap, was used under normal spray drying mode, following the dry spray process parameters recited in Table 17, below.

TABLE 17

Spray drying dispersion processing parameters to generate solid spray dispersion of amorphous Compound 2.

| Parameter: | Value: |
| --- | --- |
| Feed Pressure | 20 bar |
| Feed Flow Rate | 92-100 Kg/hr |
| Inlet Temperature | 93-99° C. |
| Outlet Temperature | 53-57° C. |
| Vacuum Dryer Temperature | 80° C. for 2 hours then 110° C. (+/−5° C.) |
| Vacuum Drying Time | 20-24 hours |

A high efficiency cyclone separated the wet product from the spray gas and solvent vapors. The wet product contained 8.5-9.7% MEK and 0.56-0.83% water and had a mean particle size of 17-19 μm and a bulk density of 0.27-0.33 g/cc. The wet product was transferred to a 4000 L stainless steel double cone vacuum dryer for drying to reduce residual solvents to a level of less than about 5000 ppm and to generate dry spray dry dispersion of amorphous Compound 2, containing <0.03% MEK and 0.3% Water.

Example 10: Preparation of Solid Dispersion of Amorphous Compound 1 and Amorphous Compound 2 (1:1)

Compound 1 and Compound 2 were spray dried in a 1:1 ratio (40 wt % Compound 1/40 wt % Compound 2) along with 20 wt % hypromellose acetate succinate polymer (HPMCAS, HG grade) using a solvent system consisting of 90 wt % methyl ethyl ketone (MEK)/10 wt % DI water. The resulting mixture contained 11% solids load. The actual amounts of materials used in this process are listed in Table 18.

TABLE 18

Spray dry materials and amounts.

| Material | Amount (g) |
| --- | --- |
| Compound 1 | 30.1 |
| Compound 2 | 30 |
| HPMCAS-HG | 15 |
| MEK | 546.1 |
| Water | 60.7 |

MEK and water were mixed at room temperature in an appropriately sized vessel using a magnetic stir bar. Compound 2 was added to the MEK/water mixture and allowed to stir until dissolved. Compound 1 was then added and stirred until dissolved. Lastly, HPMCAS-HG was added and stirred until dissolved.

The resulting mixture was spray dried on a Buchi B-290 spray dryer using a 2 fluid nozzle, 1.5 mm. Spray dryer operating parameters are listed in Table 19.

TABLE 19

Spray dryer operating parameters.

| Function | Parameter Setting |
| --- | --- |
| Inlet Temp (° C.) | 122 |
| Outlet Temp (° C.)* | 52 |
| Rotometer (mm) | 30 |
| Solution Pump (%) | 60 |
| Filter Pressure (psi)* | −10 |
| Nitrogen Pressure (psi) | 120 |

TABLE 19-continued

Spray dryer operating parameters.

| Function | Parameter Setting |
| --- | --- |
| Aspirator (%) | 100 |
| Condenser Temp (° C.) | 2 |

*Observed condition, not a set parameter.

Wet SDD was collected and placed in a vacuum oven at ambient temperature and allowed to dry until residual MEK levels were <5000 ppm. Dried material was analyzed for bulk density and particle size resulting in values of 0.33 g/mL and a D50 of 4.092 μm, respectively.

Example 11: Preparation of Solid Dispersion of Amorphous Compound 1 and Amorphous Compound 2 (2:1)

Compound 1 and Compound 2 were spray dried in a 2:1 ratio (53 wt % Compound 1/27 wt % Compound 2) along with 20 wt % hypromellose acetate succinate polymer (HPMCAS, HG grade) using a solvent system consisting of 90 wt % methyl ethyl ketone (MEK)/10 wt % DI water. The resulting mixture contained 11% solids load. The actual amounts of materials used in this process are listed in Table 20.

TABLE 20

Spray dry materials and amounts.

| Material | Amount (g) |
| --- | --- |
| Compound 1 | 40 |
| Compound 2 | 20 |
| HPMCAS-HG | 15 |
| MEK | 546.1 |
| Water | 60.7 |

MEK and water were mixed at room temperature in an appropriately sized vessel using a magnetic stir bar. Compound 2 was added to the MEK/water mixture and allowed to stir until dissolved. Compound 1 was then added and stirred until dissolved. Lastly, HPMCAS-HG was added and stirred until dissolved.

The resulting mixture was spray dried on a Buchi B-290 spray dryer using a 2 fluid nozzle, 1.5 mm. Spray dryer operating parameters are listed in Table 21.

TABLE 21

Spray Dryer Operating Parameters.

| Function | Parameter Setting |
| --- | --- |
| Inlet Temp (° C.) | 119 |
| Outlet Temp (° C.)* | 54 |
| Rotometer (mm) | 40 |
| Solution Pump (%) | 60 |
| Filter Pressure (psi)* | −10 |
| Nitrogen Pressure (psi) | 120 |
| Aspirator (%) | 100 |
| Condenser Temp (° C.) | 2 |

*Observed condition, not a set parameter.

Wet SDD was collected and placed in a vacuum oven at ambient temperature and allowed to dry until residual MEK levels were <5000 ppm. Dried material was analyzed for bulk density and particle size resulting in values of 0.35 g/mL and a D50 of 4.682 μm, respectively.

Example 12: Preparation of a Tablet Formulation from Dry Granulation Roller Compaction Equipment:

Turbula blender, V-shell blender or a bin blender, Gerteis Roller Compactor, Piccola tablet press Screening/Weighing:

The solid dispersion comprising substantially amorphous Compound 1, the solid dispersion comprising substantially amorphous Compound 2, and excipients may be screened prior to or after weigh-out. Appropriate screen sizes are mesh 30, or mesh 60.

Blending:

The solid dispersion comprising substantially amorphous Compound 1, the solid dispersion comprising substantially amorphous Compound 2, and excipients may be added to the blender in different order. Additional lubing step might be required. The blending and lubing may be performed in a Turbula blender, a v-shell blender, or a bin blender. The components may be blended for 10 or may be lubed for 4 minutes.

Dry Granulation:

The blend may be granulated using a Gerteis roller compactor. The blend may be granulated using combined smooth/smooth rolls and with the integrated 0.8 mm mesh milling screen with pocketed rotor and paddle agitator. The Gerteis roller compactor may be operated with a roll gap of 2 mm, roll pressure of 4 kNcm, roll speed of 2 rpm, agitator speed 15 rpm, granulation speed clockwise/counterclockwise of 80/80 rpm, and oscillation clockwise/counterclockwise of 330/360 degrees. The ribbons produced may be milled with integrated mill equipped with 0.8 mm mesh screen.

Blending:

The roller compacted granules may be blended with extra-granular excipients such as filler, disintegrant and, if needed lubricant using a Turbula blender, V-shell blender or a bin blender. The blending time may be 10 or may be lubed for 4 minutes.

Compression:

The compression blend may be compressed into tablets using a single station or rotary tablet presses, such as the Piccola press, using Tooling Size D Caplet Tooling (0.568"× 0.2885"). The weight of the tablets for a dose of 50 mg of substantially amorphous Compound 1 and 150 mg of substantially amorphous Compound 2 may be about 400 or 600 mg.

TABLE 22

Tablet Comprising 50 mg Compound 1 and 150 mg Compound 2.

|  | Ingredient | Amount per tablet (mg) |
| --- | --- | --- |
| Intra-granular | Compound 1 SDD | 62.5 |
|  | Compound 2 SDD | 187.5 |
|  | Microcrystalline cellulose | 116.35 |
|  | Croscarmellose Sodium | 17.31 |
|  | Magnesium Stearate | 0.96 |
|  | Total | 384.62 |

TABLE 22-continued

Tablet Comprising 50 mg Compound 1 and 150 mg Compound 2.

|  | Ingredient | Amount per tablet (mg) |
| --- | --- | --- |
| Extra-granular | Microcrystalline cellulose | 87.74 |
|  | Croscarmellose Sodium | 7.21 |
|  | Magnesium Stearate | 1.20 |
|  | Total | 96.15 |

Example 13: Preparation of a 100 mg Compound 1 and 150 mg Compound 2 Tablet Formulation from Dry Granulation Roller Compaction Equipment:

Turbula blender, V-shell blender or a bin blender, Gerteis Roller Compactor, MTS Universal Testing System Screening/Weighing:

The solid dispersion comprising substantially amorphous Compound 1, the solid dispersion comprising substantially amorphous Compound 2, and excipients may be screened prior to or after weigh-out. Appropriate screen sizes are mesh 30, or mesh 60.

Blending:

The solid dispersion comprising substantially amorphous Compound 1, the solid dispersion comprising substantially amorphous Compound 2, and excipients may be added to the blender in different order. Additional lubing step might be required. The blending and lubing may be performed in a Turbula blender, a v-shell blender, or a bin blender. The components may be blended for 10 or may be lubed for 4 minutes.

Dry Granulation:

The blend may be granulated using a Gerteis roller compactor. The blend may be granulated using combined smooth/smooth rolls and with the integrated 0.8 mm mesh milling screen with pocketed rotor and paddle agitator. The Gerteis roller compactor may be operated with a roll gap of 2 mm, roll pressure of 4 kNcm, roll speed of 2 rpm, agitator speed 15 rpm, granulation speed clockwise/counterclockwise of 80/80 rpm, and oscillation clockwise/counterclockwise of 330/360 degrees. The ribbons produced may be milled with integrated mill equipped with 0.8 mm mesh screen.

Blending:

The roller compacted granules may be blended with extra-granular excipients such as filler, disintegrant and, if needed lubricant using a Turbula blender, V-shell blender or a bin blender. The blending time may be 10 or may be lubed for 4 minutes.

Compression:

The compression blend may be compressed into tablets using a single station or rotary tablet presses, such as the MTS Universal Testing System, using Tooling Size D Caplet Tooling (0.65"×0.33"). The weight of the tablets for a dose of 100 mg of substantially amorphous Compound 1 and 150 mg of substantially amorphous Compound 2 may be about 500 to 700 mg.

TABLE 23

Tablet comprising 100 mg Compound 1 and 150 mg Compound 2.

| | Ingredient | Amount per tablet (mg) |
|---|---|---|
| Intra-granular | Compound 1 SDD | 125 |
| | Compound 2 SDD | 187.5 |
| | Microcrystalline cellulose | 145.45 |
| | Croscarmellose Sodium | 21.65 |
| | Magnesium Stearate | 1.20 |
| | Total | 480.80 |
| Extra-granular | Microcrystalline cellulose | 109.68 |
| | Croscarmellose Sodium | 9.02 |
| | Magnesium Stearate | 1.50 |
| | Total | 120.20 |

Example 14: Preparation of a 100 mg Compound 1 and 150 mg Compound 2 Tablet Formulation from Dry Granulation Roller Compaction Equipment:

Turbula blender, V-shell blender or a bin blender, Gerteis Roller Compactor, Courtoy tablet press, Omega coating system Screening/Weighing:

The solid dispersion comprising substantially amorphous Compound 1, the solid dispersion comprising substantially amorphous Compound 2, and excipients may be screened prior to or after weigh-out. Appropriate screen sizes are 24R, or mesh 60.

Blending:

The solid dispersion comprising substantially amorphous Compound 1, the solid dispersion comprising substantially amorphous Compound 2, and excipients may be added to the blender in different order. The blending may be performed in a Turbula blender, a v-shell blender, or a bin blender. The components may be blended for 25 minutes.

Dry Granulation:

The blend may be granulated using a Gerteis roller compactor. The blend may be granulated using combined smooth/smooth rolls and with the integrated 0.8 mm mesh milling screen with pocketed rotor and paddle agitator. The Gerteis roller compactor may be operated with a roll gap of 3 mm, roll pressure of 10 kNcm, roll speed of 8 rpm, agitator speed 15 rpm, granulation speed clockwise/counterclockwise of 150/150 rpm, and oscillation clockwise/counterclockwise of 375/375 degrees. The ribbons produced may be milled with integrated mill equipped with 0.8 mm mesh screen.

Blending:

The roller compacted granules may be blended with extra-granular excipients such as filler and, if needed lubricant using a Turbula blender, V-shell blender or a bin blender. The blending time may be 7 or may be lubed for 5 minutes.

Compression:

The compression blend may be compressed into tablets using a single station or rotary tablet presses, such as the Courtoy tablet press, using Tooling Size D Caplet Tooling (0.625"×0.334"). The weight of the tablets for a dose of 100 mg of substantially amorphous Compound 1 and 150 mg of substantially amorphous Compound 2 may be about 500 to 700 mg.

Coating:

The core tablets are film coated using a continuous pan Omega coater. The film coat suspension is prepared by adding the Opadry yellow 20A120010 powder to purified water. The required amount of film coating suspension (3% of the tablet weight) is sprayed onto the tablets to achieve the desired weight gain.

TABLE 24

Tablet Comprising 100 mg Compound 1 and 150 mg Compound 2.

| | Component | Amount per tablet (mg) |
|---|---|---|
| Intra-granular | Compound 1 SDD | 125 |
| | Compound 2 SDD | 187.5 |
| | Microcrystalline cellulose | 131.4 |
| | Croscarmellose Sodium | 29.6 |
| | Total | 473.5 |
| Extra-granular | Microcrystalline cellulose | 112.5 |
| | Magnesium Stearate | 5.9 |
| | Total | 118.4 |
| Total uncoated tablet | | 591.9 |
| Film coat | Opadry | 17.7 |
| Total coated tablet | | 609.6 |

OTHER EMBODIMENTS

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the invention. One skilled in the art will readily recognize from such discussion and from the accompanying drawings and claims, that various changes, modifications and variations can be made therein without departing from the spirit and scope of the invention as defined in the following claims.

What is claimed is:

1. A pharmaceutical composition comprising a blend of a first solid dispersion and a second solid dispersion,
   wherein the first solid dispersion comprises 70 wt % to 90 wt % of amorphous (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound 1) relative to the total weight of the first solid dispersion and 10 wt % to 30 wt % of a polymer relative to the total weight of the first solid dispersion,
   wherein the second solid dispersion comprises 70 wt % to 90 wt % of amorphous N-[2,4-bis(1,1-dimethylethyl)-5-hydroxyphenyl]-1,4-dihydro-4-oxoquinoline-3-carboxamide (Compound 2) relative to the total weight of the second solid dispersion; and wherein the pharmaceutical composition is a tablet that comprises 25 mg to 125 mg of Compound 1 and 100 mg to 200 mg of Compound 2.

2. The pharmaceutical composition of claim 1, wherein the first solid dispersion comprises 80 wt % of amorphous Compound 1 relative to the total weight of the first solid dispersion and 20 wt % of a polymer relative to the total weight of the first solid dispersion.

3. The pharmaceutical composition of claim 1, wherein the polymer is selected from a water-soluble polymer and a partially water-soluble polymer.

4. The pharmaceutical composition of claim 1, wherein the polymer is selected from cellulose derivatives, polyvinylpyrrolidones (PVP), polyethylene glycols (PEG), polyvinyl alcohols (PVA), acrylates, cyclodextrins, copolymers thereof, and derivatives thereof.

5. The pharmaceutical composition of claim 4, wherein the polymer is a cellulose derivative.

6. The pharmaceutical composition of claim 5, wherein the polymer is selected from hydroxypropylmethylcellulose (HPMC), hydroxypropylcellulose (HPC), and ethylcellulose.

7. The pharmaceutical composition of claim 6, wherein the HPMC is selected from HPMC E50, HPMC E15, and HPMC E3.

8. The pharmaceutical composition of claim 2, wherein the polymer is selected from cellulose acetate phthalate (CAP), hydroxypropyl methyl cellulose phthalates (HPMCP), hydroxypropyl methyl cellulose acetate succinate (HPMCAS), carboxymethylcellulose (CMC), cellulose acetate trimellitate (CAT), hydroxypropylmethyl-cellulose acetate phthalate (HPMCAP), methylcellulose acetate phthalate (MCAP), and polymethacrylates.

9. The pharmaceutical composition according to claim 4, wherein the copolymer is a polyvinylpyrrolidone/vinyl acetate copolymer (PVP/VA).

10. The pharmaceutical composition of claim 1, wherein the second solid dispersion further comprises wt % to 30 wt % of a polymer relative to the total weight of the second solid dispersion.

11. The pharmaceutical composition of claim 10, wherein the second solid dispersion comprises 80 wt % of amorphous Compound 2 relative to the total weight of the second solid dispersion, 19.5 wt % of polymer relative to the total weight of the second solid dispersion, and 0.5 wt % of sodium lauryl sulfate relative to the total weight of the second solid dispersion.

12. The pharmaceutical composition of claim 10, wherein the polymer in the second solid dispersion is selected from cellulose derivatives, polyvinylpyrrolidones (PVP), polyethylene glycols (PEG), polyvinyl alcohols (PVA), acrylates, cyclodextrins, copolymers thereof, and derivatives thereof.

13. The pharmaceutical composition of claim 12, wherein the polymer in the second solid dispersion is a cellulose derivative.

14. The pharmaceutical composition of claim 13, wherein the polymer in the second solid dispersion is hydroxypropyl methylcellulose acetate succinate (HPMCAS).

15. The pharmaceutical composition of claim 14, wherein the HPMCAS is hydroxypropyl methyl cellulose acetate succinate HG (HPMCAS-HG).

16. The pharmaceutical composition of claim 1, wherein the tablet comprises 100 mg of Compound 1.

17. The pharmaceutical composition of claim 1, wherein the tablet comprises 150 mg of Compound 2.

18. The pharmaceutical composition of claim 1, wherein the tablet comprises one or more excipients selected from a filler, a disintegrant, and a lubricant, or any combination thereof.

19. The pharmaceutical composition of claim 18, wherein the tablet comprises a filler in an amount of 30 wt % to 50 wt % relative to the total weight of the tablet.

20. The pharmaceutical composition of claim 19, wherein the tablet comprises 100 mg to 300 mg of a filler.

21. The pharmaceutical composition of claim 20, wherein the filler is microcrystalline cellulose.

22. The pharmaceutical composition of claim 18, wherein the tablet comprises a disintegrant in an amount of 1 wt % to 10 wt % relative to the total weight of the tablet.

23. The pharmaceutical composition of claim 22, wherein the tablet comprises 12 mg to 36 mg of a disintegrant.

24. The pharmaceutical composition of claim 23, wherein the disintegrant is croscarmellose sodium.

25. The pharmaceutical composition of claim 18, wherein the tablet comprises a lubricant in an amount of 1 wt % relative to the total weight of the tablet.

26. The pharmaceutical composition of claim 25, wherein the tablet comprises 5.9 mg of a lubricant.

27. The pharmaceutical composition of claim 26, wherein the lubricant is magnesium stearate.

28. The pharmaceutical composition of claim 1, wherein the tablet comprises:
  125 mg of a first solid dispersion which comprises 80 wt % of amorphous Compound 1 relative to the total weight of the first solid dispersion and 20 wt % of polymer relative to the total weight of the first solid dispersion,
  187.5 mg of a second solid dispersion which comprises 80 wt % of amorphous Compound 2 relative to the total weight of the second solid dispersion, 19.5 wt % of polymer relative to the total weight of the second solid dispersion, and 0.5 wt % of sodium lauryl sulfate relative to the total weight of the second solid dispersion,
  30 wt % to 50 wt % filler,
  1 wt % to 10 wt % disintegrant, and
  1 wt % lubricant.

29. The pharmaceutical composition of claim 18, wherein the filler is microcrystalline cellulose, the disintegrant is croscarmellose sodium, and the lubricant is magnesium stearate.

30. A method of treating cystic fibrosis in a patient comprising orally administering to the patient the pharmaceutical composition of claim 1.

31. The method of claim 30, wherein the pharmaceutical composition is administered once per day.

32. The method of claim 30, wherein the pharmaceutical composition is administered once per day followed by the administration of 150 mg of Compound 2 once per day.

33. The method of claim 30, wherein the patient is heterozygous for a ΔF508 cystic fibrosis transmembrane conductance regulator (CFTR) gene mutation and a second CFTR gene mutation.

34. The method of claim 30, wherein the patient is homozygous for the ΔF508 CFTR gene mutation.

35. A method of treating cystic fibrosis in a patient comprising orally administering to the patient a tablet comprising:
  a first solid dispersion which comprises 80 wt % of amorphous Compound 1 relative to the total weight of the first solid dispersion and 20 wt % of polymer relative to the total weight of the first solid dispersion, a second solid dispersion which comprises 80 wt % of amorphous Compound 2 relative to the total weight of the second solid dispersion, 19.5 wt % of polymer relative to the total weight of the second solid dispersion, and 0.5 wt % of sodium lauryl sulfate relative to the total weight of the second solid dispersion, and wherein the tablet comprises 100 mg of Compound 1 and 150 mg of Compound 2.

36. The method of claim 35, wherein the polymer of the first solid dispersion and the polymer of the second solid dispersion are selected from cellulose derivatives, polyvinylpyrrolidones (PVP), polyethylene glycols (PEG), polyvinyl alcohols (PVA), acrylates, cyclodextrins, copolymers thereof, and derivatives thereof.

37. The method of claim 36, wherein the polymer of the first solid dispersion and the polymer of the second solid dispersion are independently selected from cellulose derivatives.

* * * * *

UNITED STATES PATENT AND TRADEMARK OFFICE
CERTIFICATE OF CORRECTION

PATENT NO. : 11,951,212 B2
APPLICATION NO. : 17/204679
DATED : April 9, 2024
INVENTOR(S) : Brian Dean Phenix et al.

Page 1 of 1

It is certified that error appears in the above-identified patent and that said Letters Patent is hereby corrected as shown below:

In the Claims

Claim 10, Column 137, Line 40, "further comprises wt %" should read --further comprises 10 wt %--

Signed and Sealed this
Sixth Day of August, 2024

Katherine Kelly Vidal
*Director of the United States Patent and Trademark Office*